US011976297B2

(12) United States Patent
Kamb

(10) Patent No.: US 11,976,297 B2
(45) Date of Patent: May 7, 2024

(54) ENGINEERED IMMUNE CELLS WITH RECEPTOR CROSS-TALK

(71) Applicant: A2 BIOTHERAPEUTICS, INC., Agoura Hills, CA (US)

(72) Inventor: Alexander Kamb, Agoura Hills, CA (US)

(73) Assignee: A2 BIOTHERAPEUTICS, INC., Agoura Hills, CA (US)

( * ) Notice: Subject to any disclaimer, the term of this patent is extended or adjusted under 35 U.S.C. 154(b) by 140 days.

(21) Appl. No.: 17/480,466

(22) Filed: Sep. 21, 2021

(65) Prior Publication Data

US 2022/0090014 A1 Mar. 24, 2022

Related U.S. Application Data

(60) Provisional application No. 63/081,250, filed on Sep. 21, 2020, provisional application No. 63/081,237, filed on Sep. 21, 2020, provisional application No. 63/081,256, filed on Sep. 21, 2020, provisional application No. 63/081,231, filed on Sep. 21, 2020, provisional application No. 63/081,242, filed on Sep. 21, 2020, provisional application No. 63/081,229, filed on Sep. 21, 2020, provisional application No. 63/081,248, filed on Sep. 21, 2020, provisional application No. 63/081,258, filed on Sep. 21, 2020.

(51) Int. Cl.

| | |
|---|---|
| *C12N 5/0783* | (2010.01) |
| *A61K 35/17* | (2015.01) |
| *C07K 14/47* | (2006.01) |
| *C07K 14/725* | (2006.01) |
| *C12N 15/85* | (2006.01) |

(52) U.S. Cl.

CPC ............ *C12N 5/0637* (2013.01); *A61K 35/17* (2013.01); *C07K 14/4702* (2013.01); *C07K 14/7051* (2013.01); *C12N 15/85* (2013.01); *C07K 2317/53* (2013.01); *C07K 2317/622* (2013.01); *C07K 2319/03* (2013.01); *C07K 2319/715* (2013.01); *C12N 2510/00* (2013.01)

(58) Field of Classification Search

CPC ..... C12N 5/0636; C12N 5/0637; A61K 35/17

See application file for complete search history.

(56) References Cited

U.S. PATENT DOCUMENTS

| | | | |
|---|---|---|---|
| 5,858,358 | A | 1/1999 | June et al. |
| 5,883,223 | A | 3/1999 | Gray |
| 6,352,694 | B1 | 3/2002 | June et al. |
| 6,534,055 | B1 | 3/2003 | June et al. |
| 6,692,964 | B1 | 2/2004 | June et al. |
| 6,797,514 | B2 | 9/2004 | Berenson et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 10,040,846 | B2 | 8/2018 | Frigault et al. |
| 2004/0101519 | A1 | 5/2004 | June et al. |
| 2006/0034810 | A1 | 2/2006 | Riley et al. |
| 2006/0121005 | A1 | 6/2006 | Berenson et al. |
| 2015/0376296 | A1 | 12/2015 | Fedorov et al. |
| 2016/0289294 | A1* | 10/2016 | Pulé .................. C07K 14/7051 |

FOREIGN PATENT DOCUMENTS

| | | | |
|---|---|---|---|
| WO | 2012/138475 | A1 | 10/2012 |

OTHER PUBLICATIONS

Fedorov et al. PD-1- and CTLA-4-based inhibitory chimeric antigen receptors (iCARs) divert off-target immunotherapy responses. Science Translational Medicine 2013, 5;215:1-13. (Year: 2013).*

San Jose et al. Triggering the TCR complex causes the downregulation of nonengaged receptors by a signal transduction-dependent mechanism. Immunity 2000, 12;2:161-170. (Year: 2000).*

Brown et al. The LILR family: modulators of innate and adaptive immune pathways in health and disease. Tissue Antigens 2004, 64:215-225. (Year: 2004).*

Guedan et al. Engineering and design of chimeric antigen receptors. Molecular Therapy: Methods & Clinical Development 2019, 12:145-156. (Year: 2019).*

Arseneault, 2017, Loss of chromosome Y leads to down regulation of KDM5D and KDM6C epigenetic modifiers in clear cell renal cell carcinoma, Sci Rep, 7:44876.

Badran, 2002, Identification of three NFAT binding motifs in the 5'-upstream region of the human CD3gamma gene that differentially bind NFATc1, NFATc2, and NF-kappa B p50, J. Biological Chemistry, 277:47136-47148.

Chen, 2013, Fusion Protein Linkers: Property, Design and Functionality, Adv Drug Deliv Rev, 65(10):1357-1369.

Cheng, 2017, Pan-cancer analysis of homozygous deletions in primary tumours uncovers rare tumour suppressors, Nature Comm, 8:1221, 14 pages.

El-Naggar, 1996, Genotypic analysis of primary head and neck squamous carcinoma by combined flurescence in situ hybridization and DNA flow cytometry, Am J Clin Pathol, 105(1):102-8.

Fedorov, 2013, PD-1- and CTLA-4-Based Inhibitory Chimeric Antigen Receptors (iCARs) Divert Off-Target Immunotherapy Responses, Sci Transl Med., 5(215):215ra172, 25 pages.

Haanen, 1999, Selective expansion of cross-reactive CD8+ memory T cells by viral variants, J. Exp. Med, 190(9):1319-1328.

(Continued)

*Primary Examiner* — Allison M Fox
*Assistant Examiner* — Jennifer S Spence
(74) *Attorney, Agent, or Firm* — Brown Rudnick LLP; Adam M. Schoen

(57) ABSTRACT

The present disclosure provides engineered immune cells and methods for their creation and use. The immune cells comprise activating and blocking receptors, that exhibit cross-talk between the receptors.

20 Claims, 35 Drawing Sheets

Specification includes a Sequence Listing.

(56) References Cited

OTHER PUBLICATIONS

Jury, 2007, Lipid rafts in T cell signalling and disease, Seminars in Cell & Developmental Biology, 18:608-615.
Kagoya, 2018, A novel chimeric antigen receptor containing a JAK-STAT signaling domain mediates superior antitumor effects, Nature Medicine, 24(3):352-359.
Lajoie, 2020, Designed protein logic to target cells with precise combinations of surface antigens, Science, 369(6511):1637-1643.
Passerini, 2008, STAT5-signaling cytokines regulate the expression of FOXP3 in CD4+CD25+ regulatory T cells and CD4+CD25− effector T cells, International Immunology, 20(3):421-431.
Simons, 1997, Functional raft in cell membranes, Nature, 387:569-572.
Tao, 2020, CD19-CAR-T Cells Bearing a KIR/PD-1 Based Inhibitory CAR Eradicate CD19 + HLA-C1− Malignant B Cells While Sparing CD19 + HLA-C1 + Healthy B Cells, Cancers, 12(9):2612, 17 pages.
Ji-Tei, 2000, Sensitive assay of RNA interference in *Drosophila* and Chinese hamster cultured cells using firefly luciferase gene as target, FEBS Letters 479:79-82.
Wong, 2015, TMSB4Y is a candidate tumor suppressor on the Y chromosome and is deleted in male breast cancer, Oncotarget, 6(42):44927-40.

* cited by examiner

| Activator | Blocker | Blocker ESO peptide (uM) |
|---|---|---|
| MP1-CAR | - | 50 |
| MP1-CAR | - | 5 |
| MP1-CAR | - | 0.5 |
| MP1-CAR | - | 0 |
| MP1-CAR | ESO-Tmod | 50 |
| MP1-CAR | ESO-Tmod | 5 |
| MP1-CAR | ESO-Tmod | 0.5 |
| MP1-CAR | ESO-Tmod | 0 |

| Activator | Blocker | Activator MP1 peptide (uM) |
|---|---|---|
| MP1-CAR | - | 50 |
| MP1-CAR | - | 5 |
| MP1-CAR | - | 0.5 |
| MP1-CAR | ESO-Tmod | 50 |
| MP1-CAR | ESO-Tmod | 5 |
| MP1-CAR | ESO-Tmod | 0.5 |

Fold EC50 shift with blocker hinge variants

| Group | | C# | Hinge | Length (aa) | |
|---|---|---|---|---|---|
| Immune gene | | C1765 | 2B1 | 64 | |
| Immune gene | | C3701 | 2B1 trunc | 32 | |
| Immune gene | | C3746 | PD-1 | 26 | |
| Immune gene | | C3747 | CTLA4 | 34 | |
| Immune gene | | C3748 | BTLA | 24 | |
| Synthetic | Rigid | C3698 | A(EAAAK)3A | 17 | SEQ ID NO: 392 |
| Synthetic | Rigid | C3699 | A(EAAAK)5A | 27 | SEQ ID NO: 393 |
| Synthetic | Fflexible | C3749 | (G4Q)2 | 10 | SEQ ID NO: 394 |
| Synthetic | Fflexible | C3750 | (G4Q)5 | 25 | SEQ ID NO: 396 |
| Synthetic | Fflexible | C3751 | (G4Q)10 | 49 | SEQ ID NO: 397 |

| Construct | mAb | Notes |
| --- | --- | --- |
| CT-479 | Zalutumumab | Ph III terminated due to skin rash & no benefit |
| CT-482 | 12D03 | No clinical data |
| CT-486 | Cetuximab (Erbitux) | Treatment for mCRC & HNC |
| CT-487 | Matuzumab | Ph II terminated due to no response |
| CT-488 | Panitumumab (Vectibix) | Treatment for mCRC |

$$\text{Killing } \% = \frac{UTD_{\text{Target cell area}} - CTL_{\text{Target cell area}}}{UTD_{\text{Target cell area}}} \%$$

| Construct | mAb | Notes |
|---|---|---|
| CT-479 | Zalutumumab | Ph III terminated due to skin rash & no benefit |
| CT-482 | 12D03 | No clinical data |
| CT-486 | Cetuximab (Erbitux) | Treatment for mCRC & HNC |
| CT-487 | Matuzumab | Ph II terminated due to no response |
| CT-488 | Panitumumab (Vectibix) | Treatment for mCRC |

$$\text{Killing \%} = \frac{UTD_{\ Target\ cell\ area} - CTL_{\ Target\ cell\ area}}{UTD_{\ Target\ cell\ area}}\ \%$$

SEQUENCE LISTING

<160> NUMBER OF SEQ ID NOS: 391

<210> SEQ ID NO 1
<211> LENGTH: 45
<212> TYPE: PRT
<213> ORGANISM: Artificial Sequence
<220> FEATURE:
<223> OTHER INFORMATION: CD8alpha hinge

<400> SEQUENCE: 1

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

<210> SEQ ID NO 2
<211> LENGTH: 135
<212> TYPE: DNA
<213> ORGANISM: Artificial Sequence
<220> FEATURE:
<223> OTHER INFORMATION: CD8alpha hinge

<400> SEQUENCE: 2

```
accacgacgc cagcgccgcg accaccaaca ccggcgccca ccatcgcgtc gcagcccctg      60

tccctgcgcc cagaggcgtg ccggccagcg gcggggggcg cagtgcacac gagggggctg     120

gacttcgcct gtgat                                                      135
```

<210> SEQ ID NO 3
<211> LENGTH: 41
<212> TYPE: PRT
<213> ORGANISM: Artificial Sequence
<220> FEATURE:
<223> OTHER INFORMATION: CD28 hinge

<400> SEQUENCE: 3

```
Cys Thr Ile Glu Val Met Tyr Pro Pro Pro Tyr Leu Asp Asn Glu Lys
1               5                   10                  15

Ser Asn Gly Thr Ile Ile His Val Lys Gly Lys His Leu Cys Pro Ser
            20                  25                  30

Pro Leu Phe Pro Gly Pro Ser Lys Pro
        35                  40
```

<210> SEQ ID NO 4
<211> LENGTH: 123
<212> TYPE: DNA
<213> ORGANISM: Artificial Sequence
<220> FEATURE:
<223> OTHER INFORMATION: CD28 hinge

<400> SEQUENCE: 4

```
tgtaccattg aagttatgta tcctcctcct tacctagaca atgagaagag caatggaacc      60

attatccatg tgaaagggaa acacctttgt ccaagtcccc tatttcccgg accttctaag     120

ccc                                                                   123
```

<210> SEQ ID NO 5
<211> LENGTH: 27
<212> TYPE: PRT
<213> ORGANISM: Artificial Sequence
<220> FEATURE:
<223> OTHER INFORMATION: CD28 transmembrane domain

<400> SEQUENCE: 5

Phe Trp Val Leu Val Val Val Gly Gly Val Leu Ala Cys Tyr Ser Leu
1 5 10 15

Leu Val Thr Val Ala Phe Ile Ile Phe Trp Val
20 25

<210> SEQ ID NO 6
<211> LENGTH: 81
<212> TYPE: DNA
<213> ORGANISM: Artificial Sequence
<220> FEATURE:
<223> OTHER INFORMATION: CD28 transmembrane domain

<400> SEQUENCE: 6
ttctgggtgc tggtcgttgt gggcggcgtg ctggcctgct acagcctgct ggtgacagtg 60
gccttcatca tcttttgggt g 81

<210> SEQ ID NO 7
<211> LENGTH: 25
<212> TYPE: PRT
<213> ORGANISM: Artificial Sequence
<220> FEATURE:
<223> OTHER INFORMATION: IL-2R beta transmembrane domain

<400> SEQUENCE: 7

Ile Pro Trp Leu Gly His Leu Leu Val Gly Leu Ser Gly Ala Phe Gly
1 5 10 15

Phe Ile Ile Leu Val Tyr Leu Leu Ile
20 25

<210> SEQ ID NO 8
<211> LENGTH: 75
<212> TYPE: DNA
<213> ORGANISM: Artificial Sequence
<220> FEATURE:
<223> OTHER INFORMATION: IL-2R beta transmembrane domain

<400> SEQUENCE: 8
attccgtggc tcggccacct cctcgtgggc ctcagcgggg cttttggctt catcatctta 60
gtgtacttgc tgatc 75

<210> SEQ ID NO 9
<211> LENGTH: 112
<212> TYPE: PRT
<213> ORGANISM: Artificial Sequence
<220> FEATURE:
<223> OTHER INFORMATION: CD3 zeta activation domain

<400> SEQUENCE: 9

Arg Val Lys Phe Ser Arg Ser Ala Asp Ala Pro Ala Tyr Lys Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala

```
                85                  90                  95

Thr Lys Asp Thr Tyr Asp Ala Leu His Met Gln Ala Leu Pro Pro Arg
            100                 105                 110


<210> SEQ ID NO 10
<211> LENGTH: 336
<212> TYPE: DNA
<213> ORGANISM: Artificial Sequence
<220> FEATURE:
<223> OTHER INFORMATION: CD3 zeta activation domain

<400> SEQUENCE: 10

agagtgaagt tcagcaggag cgcagacgcc cccgcgtaca agcagggcca gaaccagctc      60

tataacgagc tcaatctagg acgaagagag gagtacgatg ttttggacaa gcgtagaggc     120

cgggaccctg agatgggggg aaagccgaga aggaagaacc ctcaggaagg cctgtacaat     180

gaactgcaga aagataagat ggcggaggcc tacagtgaga ttgggatgaa aggcgagcgc     240

cggaggggca aggggcacga tggcctttac cagggactca gtacagccac caaggacacc     300

tacgacgccc ttcacatgca ggccctgccc cctcgc                               336


<210> SEQ ID NO 11
<211> LENGTH: 43
<212> TYPE: PRT
<213> ORGANISM: Artificial Sequence
<220> FEATURE:
<223> OTHER INFORMATION: CD3 zeta activation domain

<400> SEQUENCE: 11

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu His Met Gln Ala Leu Pro Pro Arg
        35                  40


<210> SEQ ID NO 12
<211> LENGTH: 129
<212> TYPE: DNA
<213> ORGANISM: Artificial Sequence
<220> FEATURE:
<223> OTHER INFORMATION: CD3 zeta activation domain

<400> SEQUENCE: 12

agagtgaagt tcagcaggag cgcagacgcc cccgcgtacc agcagggcca gaaccagctc      60

tataacgagc tcaatctagg acgaagagag gagtacgatg ttttgcacat gcaggccctg     120

ccccctcgc                                                             129


<210> SEQ ID NO 13
<211> LENGTH: 41
<212> TYPE: PRT
<213> ORGANISM: Artificial Sequence
<220> FEATURE:
<223> OTHER INFORMATION: CD28 co-stimulatory domain

<400> SEQUENCE: 13

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
```

35 40

<210> SEQ ID NO 14
<211> LENGTH: 123
<212> TYPE: DNA
<213> ORGANISM: Artificial Sequence
<220> FEATURE:
<223> OTHER INFORMATION: CD28 co-stimulatory domain

<400> SEQUENCE: 14
aggagcaagc ggagcagact gctgcacagc gactacatga acatgacccc ccggaggcct 60
ggccccaccc ggaagcacta ccagccctac gcccctccca gggatttcgc cgcctaccgg 120
agc 123

<210> SEQ ID NO 15
<211> LENGTH: 94
<212> TYPE: PRT
<213> ORGANISM: Artificial Sequence
<220> FEATURE:
<223> OTHER INFORMATION: IL-2-Rbeta intracellular domain

<400> SEQUENCE: 15

Asn Cys Arg Asn Thr Gly Pro Trp Leu Lys Lys Val Leu Lys Cys Asn
1 5 10 15

Thr Pro Asp Pro Ser Lys Phe Phe Ser Gln Leu Ser Ser Glu His Gly
20 25 30

Gly Asp Val Gln Lys Trp Leu Ser Ser Pro Phe Pro Ser Ser Ser Phe
35 40 45

Ser Pro Gly Gly Leu Ala Pro Glu Ile Ser Pro Leu Glu Val Leu Glu
50 55 60

Arg Asp Lys Val Thr Gln Leu Leu Pro Leu Asn Thr Asp Ala Tyr Leu
65 70 75 80

Ser Leu Gln Glu Leu Gln Gly Gln Asp Pro Thr His Leu Val
85 90

<210> SEQ ID NO 16
<211> LENGTH: 282
<212> TYPE: DNA
<213> ORGANISM: Artificial Sequence
<220> FEATURE:
<223> OTHER INFORMATION: IL-2-Rbeta intracellular domain

<400> SEQUENCE: 16
aactgcagga acaccgggcc atggctgaag aaggtcctga agtgtaacac cccagacccc 60
tcgaagttct tttcccagct gagctcagag catggaggcg acgtccagaa gtggctctct 120
tcgcccttcc cctcatcgtc cttcagccct ggcggcctgg cacctgagat ctcgccacta 180
gaagtgctgg agagggacaa ggtgacgcag ctgctccccc tgaacactga tgcctacttg 240
tctctccaag aactccaggg tcaggaccca actcacttgg tg 282

<210> SEQ ID NO 17
<211> LENGTH: 4
<212> TYPE: PRT
<213> ORGANISM: Artificial Sequence
<220> FEATURE:
<223> OTHER INFORMATION: STAT5 recruitment motif

<400> SEQUENCE: 17

Tyr Leu Ser Leu
1

<210> SEQ ID NO 18
<211> LENGTH: 760
<212> TYPE: PRT
<213> ORGANISM: Homo sapiens

<400> SEQUENCE: 18

```
Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Ser Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380
```

-continued

```
Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760
```

<210> SEQ ID NO 19
<211> LENGTH: 300
<212> TYPE: DNA
<213> ORGANISM: Artificial Sequence
<220> FEATURE:

<223> OTHER INFORMATION: CD3 epsilon intracellular domain

<400> SEQUENCE: 19
aagaatagaa aggccaaggc caagcctgtg acacgaggag cgggtgctgg cggcaggcaa 60
aggggacaaa acaaggagag gccaccacct gttcccaacc cagactatga gcccatccgg 120
aaaggccagc gggacctgta ttctggcctg aatcagcgca gaatcggcgg aagcaggagc 180
aagcggagca gactgctgca cagcgactac atgaacatga ccccccggag gcctggcccc 240
acccggaagc actaccagcc ctacgcccct cccagggatt tcgccgccta ccggagctag 300

<210> SEQ ID NO 20
<211> LENGTH: 69
<212> TYPE: DNA
<213> ORGANISM: Artificial SEquence
<220> FEATURE:
<223> OTHER INFORMATION: TCR beta transmembrane domain

<400> SEQUENCE: 20
accatcctct atgagatctt gctagggaag gccaccttgt atgccgtgct ggtcagtgcc 60
ctcgtgctg 69

<210> SEQ ID NO 21
<211> LENGTH: 4
<212> TYPE: PRT
<213> ORGANISM: Artificial Sequence
<220> FEATURE:
<223> OTHER INFORMATION: ITAM motif
<220> FEATURE:
<221> NAME/KEY: X
<222> LOCATION: (2)..(3)
<223> OTHER INFORMATION: X can be any amino acid

<400> SEQUENCE: 21

Tyr Xaa Xaa Leu
1

<210> SEQ ID NO 22
<211> LENGTH: 270
<212> TYPE: DNA
<213> ORGANISM: Artificial Sequence
<220> FEATURE:
<223> OTHER INFORMATION: CD3 gamma intracellular domain

<400> SEQUENCE: 22
ggacaggatg gagttcgcca gtcgagagct tcagacaagc agactctgtt gcccaatgac 60
cagctctacc agcccctcaa ggatcgagaa gatgaccagt acagccacct tcaaggaaac 120
cagttgagga ggaatggcgg aagcaggagc aagcggagca gactgctgca cagcgactac 180
atgaacatga ccccccggag gcctggcccc acccggaagc actaccagcc ctacgcccct 240
cccagggatt tcgccgccta ccggagctag 270

<210> SEQ ID NO 23
<211> LENGTH: 10
<212> TYPE: PRT
<213> ORGANISM: Artificial Sequence
<220> FEATURE:
<223> OTHER INFORMATION: UTY peptide
<220> FEATURE:
<221> NAME/KEY: X
<222> LOCATION: (1)..(1)
<223> OTHER INFORMATION: X is R or G
<220> FEATURE:
<221> NAME/KEY: X
<222> LOCATION: (6)..(6)

<223> OTHER INFORMATION: X is E or A
<220> FEATURE:
<221> NAME/KEY: X
<222> LOCATION: (8)..(8)
<223> OTHER INFORMATION: X is V or P

<400> SEQUENCE: 23

Xaa Glu Ser Glu Glu Xaa Ser Xaa Ser Leu
1 5 10

<210> SEQ ID NO 24
<211> LENGTH: 9
<212> TYPE: PRT
<213> ORGANISM: Artificial Sequence
<220> FEATURE:
<223> OTHER INFORMATION: RPSY peptide
<220> FEATURE:
<221> NAME/KEY: X
<222> LOCATION: (8)..(8)
<223> OTHER INFORMATION: X is V or L

<400> SEQUENCE: 24

Thr Ile Arg Tyr Pro Asp Pro Xaa Ile
1 5

<210> SEQ ID NO 25
<211> LENGTH: 8
<212> TYPE: PRT
<213> ORGANISM: Artificial Sequence
<220> FEATURE:
<223> OTHER INFORMATION: UTY peptide
<220> FEATURE:
<221> NAME/KEY: X
<222> LOCATION: (5)..(5)
<223> OTHER INFORMATION: X is H or R
<220> FEATURE:
<221> NAME/KEY: X
<222> LOCATION: (7)..(7)
<223> OTHER INFORMATION: X is D or N

<400> SEQUENCE: 25

Leu Pro His Asn Xaa Thr Xaa Leu
1 5

<210> SEQ ID NO 26
<211> LENGTH: 23
<212> TYPE: PRT
<213> ORGANISM: Artificial Sequence
<220> FEATURE:
<223> OTHER INFORMATION: TCR alpha transmembrane domain

<400> SEQUENCE: 26

Val Ile Gly Phe Arg Ile Leu Leu Leu Lys Val Ala Gly Phe Asn Leu
1 5 10 15

Leu Met Thr Leu Arg Leu Trp
20

<210> SEQ ID NO 27
<211> LENGTH: 69
<212> TYPE: DNA
<213> ORGANISM: Artificial Sequence
<220> FEATURE:
<223> OTHER INFORMATION: TCR alpha transmembrane domain

<400> SEQUENCE: 27
gtgattgggt tccgaatcct cctcctgaaa gtggccgggt ttaatctgct catgacgctg 60
cggctgtgg 69

<210> SEQ ID NO 28
<211> LENGTH: 23
<212> TYPE: PRT
<213> ORGANISM: Artificial Sequence
<220> FEATURE:
<223> OTHER INFORMATION: TCR beta transmembrane domain

<400> SEQUENCE: 28

Thr Ile Leu Tyr Glu Ile Leu Leu Gly Lys Ala Thr Leu Tyr Ala Val
1               5                   10                  15

Leu Val Ser Ala Leu Val Leu
            20

<210> SEQ ID NO 29
<211> LENGTH: 21
<212> TYPE: PRT
<213> ORGANISM: Artificial Sequence
<220> FEATURE:
<223> OTHER INFORMATION: CD3 zeta transmembrane domain

<400> SEQUENCE: 29

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 30
<211> LENGTH: 89
<212> TYPE: PRT
<213> ORGANISM: Artificial Sequence
<220> FEATURE:
<223> OTHER INFORMATION: CD3 delta intracellular domain

<400> SEQUENCE: 30

Gly His Glu Thr Gly Arg Leu Ser Gly Ala Ala Asp Thr Gln Ala Leu
1               5                   10                  15

Leu Arg Asn Asp Gln Val Tyr Gln Pro Leu Arg Asp Arg Asp Asp Ala
            20                  25                  30

Gln Tyr Ser His Leu Gly Gly Asn Trp Ala Arg Asn Lys Gly Gly Ser
        35                  40                  45

Arg Ser Lys Arg Ser Arg Leu Leu His Ser Asp Tyr Met Asn Met Thr
    50                  55                  60

Pro Arg Arg Pro Gly Pro Thr Arg Lys His Tyr Gln Pro Tyr Ala Pro
65                  70                  75                  80

Pro Arg Asp Phe Ala Ala Tyr Arg Ser
                85

<210> SEQ ID NO 31
<211> LENGTH: 269
<212> TYPE: DNA
<213> ORGANISM: Artificial Sequence
<220> FEATURE:
<223> OTHER INFORMATION: CD3 delta intracellular domain

<400> SEQUENCE: 31
ggacatgaga ctggaaggct gtctggggct gccgacacac aagctctgtt gaggaatgac      60
caggtctatc agcccctccg agatcgagat gatgctcagt acagccacct tggaggaaac     120
tgggctcgga acaagggcgg aagcaggagc aagcggagca gactgctgca cagcgactac     180
atgaacatga ccccccggag gcctggcccc acccggaagc actaccagcc ctacgcccct     240
cccagggatt tcgccgccta ccggagcta                                       269

<210> SEQ ID NO 32
<211> LENGTH: 99
<212> TYPE: PRT
<213> ORGANISM: Artificial Sequence
<220> FEATURE:
<223> OTHER INFORMATION: CD3 epsilon intracellular domain

<400> SEQUENCE: 32

Lys Asn Arg Lys Ala Lys Ala Lys Pro Val Thr Arg Gly Ala Gly Ala
1 5 10 15

Gly Gly Arg Gln Arg Gly Gln Asn Lys Glu Arg Pro Pro Pro Val Pro
20 25 30

Asn Pro Asp Tyr Glu Pro Ile Arg Lys Gly Gln Arg Asp Leu Tyr Ser
35 40 45

Gly Leu Asn Gln Arg Arg Ile Gly Gly Ser Arg Ser Lys Arg Ser Arg
50 55 60

Leu Leu His Ser Asp Tyr Met Asn Met Thr Pro Arg Arg Pro Gly Pro
65 70 75 80

Thr Arg Lys His Tyr Gln Pro Tyr Ala Pro Pro Arg Asp Phe Ala Ala
85 90 95

Tyr Arg Ser

<210> SEQ ID NO 33
<211> LENGTH: 89
<212> TYPE: PRT
<213> ORGANISM: Artificial Sequence
<220> FEATURE:
<223> OTHER INFORMATION: CD3 gamma intracellular domain

<400> SEQUENCE: 33

Gly Gln Asp Gly Val Arg Gln Ser Arg Ala Ser Asp Lys Gln Thr Leu
1 5 10 15

Leu Pro Asn Asp Gln Leu Tyr Gln Pro Leu Lys Asp Arg Glu Asp Asp
20 25 30

Gln Tyr Ser His Leu Gln Gly Asn Gln Leu Arg Arg Asn Gly Gly Ser
35 40 45

Arg Ser Lys Arg Ser Arg Leu Leu His Ser Asp Tyr Met Asn Met Thr
50 55 60

Pro Arg Arg Pro Gly Pro Thr Arg Lys His Tyr Gln Pro Tyr Ala Pro
65 70 75 80

Pro Arg Asp Phe Ala Ala Tyr Arg Ser
85

<210> SEQ ID NO 34
<211> LENGTH: 11
<212> TYPE: PRT
<213> ORGANISM: Artificial Sequence
<220> FEATURE:
<223> OTHER INFORMATION: SMCY peptide
<220> FEATURE:
<221> NAME/KEY: X
<222> LOCATION: (3)..(3)
<223> OTHER INFORMATION: X is S or A
<220> FEATURE:
<221> NAME/KEY: X
<222> LOCATION: (8)..(8)
<223> OTHER INFORMATION: X is R or Q

<400> SEQUENCE: 34

Ser Pro Xaa Val Asp Lys Ala Xaa Ala Glu Leu
1 5 10

<210> SEQ ID NO 35
<211> LENGTH: 10
<212> TYPE: PRT
<213> ORGANISM: Artificial Sequence
<220> FEATURE:
<223> OTHER INFORMATION: TCR beta intracellular domain

<400> SEQUENCE: 35

Met Ala Met Val Lys Arg Lys Asp Ser Arg
1 5 10

<210> SEQ ID NO 36
<211> LENGTH: 30
<212> TYPE: DNA
<213> ORGANISM: Artificial Sequence
<220> FEATURE:
<223> OTHER INFORMATION: TCR beta intracellular domain

<400> SEQUENCE: 36
atggccatgg tcaagagaaa ggattccaga 30

<210> SEQ ID NO 37
<211> LENGTH: 41
<212> TYPE: PRT
<213> ORGANISM: Artificial Sequence
<220> FEATURE:
<223> OTHER INFORMATION: CD28 intracellular domain

<400> SEQUENCE: 37

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 38
<211> LENGTH: 123
<212> TYPE: DNA
<213> ORGANISM: Artificial Sequence
<220> FEATURE:
<223> OTHER INFORMATION: CD28 intracellular domain

<400> SEQUENCE: 38
aggagcaagc ggagcagact gctgcacagc gactacatga acatgacccc ccggaggcct 60
ggccccaccc ggaagcacta ccagccctac gcccctccca gggatttcgc cgcctaccgg 120
agc 123

<210> SEQ ID NO 39
<211> LENGTH: 42
<212> TYPE: PRT
<213> ORGANISM: Artificial Sequence
<220> FEATURE:
<223> OTHER INFORMATION: 4-1BB intracellular domain

<400> SEQUENCE: 39

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 40
<211> LENGTH: 126
<212> TYPE: DNA
<213> ORGANISM: Artificial Sequence
<220> FEATURE:
<223> OTHER INFORMATION: 4-1BB intracellular domain

<400> SEQUENCE: 40
aaacggggca gaaagaaact cctgtatata ttcaaacaac catttatgag gccagtacaa 60
actactcaag aggaagatgg ctgtagctgc cgatttccag aagaagaaga aggaggatgt 120
gaactg 126

<210> SEQ ID NO 41
<211> LENGTH: 16
<212> TYPE: PRT
<213> ORGANISM: Artificial Sequence
<220> FEATURE:
<223> OTHER INFORMATION: HLA-A*02 CDR-L1

<400> SEQUENCE: 41

Arg Ser Ser Gln Ser Ile Val His Ser Asn Gly Asn Thr Tyr Leu Glu
1 5 10 15

<210> SEQ ID NO 42
<211> LENGTH: 12
<212> TYPE: PRT
<213> ORGANISM: Artificial Sequence
<220> FEATURE:
<223> OTHER INFORMATION: HLA-A*02 CDR-L2

<400> SEQUENCE: 42

Lys Val Ser Asn Arg Phe Ser Gly Val Pro Asp Arg
1 5 10

<210> SEQ ID NO 43
<211> LENGTH: 9
<212> TYPE: PRT
<213> ORGANISM: Artificial Sequence
<220> FEATURE:
<223> OTHER INFORMATION: HLA-A*02 CDR-L3

<400> SEQUENCE: 43

Phe Gln Gly Ser His Val Pro Arg Thr
1 5

<210> SEQ ID NO 44
<211> LENGTH: 12
<212> TYPE: PRT
<213> ORGANISM: Artificial Sequence
<220> FEATURE:
<223> OTHER INFORMATION: HLA-A*02 CDR-H1

<400> SEQUENCE: 44

Ala Ser Gly Tyr Thr Phe Thr Ser Tyr His Ile His
1 5 10

<210> SEQ ID NO 45
<211> LENGTH: 18
<212> TYPE: PRT
<213> ORGANISM: Artificial Sequence
<220> FEATURE:
<223> OTHER INFORMATION: HLA-A*02 CDR-H2

<400> SEQUENCE: 45

Trp Ile Tyr Pro Gly Asn Val Asn Thr Glu Tyr Asn Glu Lys Phe Lys
1 5 10 15

Gly Lys

<210> SEQ ID NO 46
<211> LENGTH: 9
<212> TYPE: PRT
<213> ORGANISM: Artificial Sequence
<220> FEATURE:
<223> OTHER INFORMATION: HLA-A*02 CDR-H3

<400> SEQUENCE: 46

Glu Glu Ile Thr Tyr Ala Met Asp Tyr
1 5

<210> SEQ ID NO 47
<211> LENGTH: 16
<212> TYPE: PRT
<213> ORGANISM: Artificial Sequence
<220> FEATURE:
<223> OTHER INFORMATION: HLA-A*02 CDR-L1

<400> SEQUENCE: 47

Arg Ser Ser Gln Ser Ile Val His Ser Asn Gly Asn Thr Tyr Leu Asp
1 5 10 15

<210> SEQ ID NO 48
<211> LENGTH: 12
<212> TYPE: PRT
<213> ORGANISM: Artificial Sequence
<220> FEATURE:
<223> OTHER INFORMATION: HLA-A*02 CDR-L2

<400> SEQUENCE: 48

Lys Val Ser Asn Arg Phe Ser Gly Val Pro Asp Arg
1 5 10

<210> SEQ ID NO 49
<211> LENGTH: 9
<212> TYPE: PRT
<213> ORGANISM: Artificial Sequence
<220> FEATURE:
<223> OTHER INFORMATION: HLA-A*02 CDR-L3

<400> SEQUENCE: 49

Met Gln Gly Ser His Val Pro Arg Thr
1 5

<210> SEQ ID NO 50
<211> LENGTH: 11
<212> TYPE: PRT
<213> ORGANISM: Artificial Sequence
<220> FEATURE:
<223> OTHER INFORMATION: HLA-A*02 CDR-H1

<400> SEQUENCE: 50

Ser Gly Tyr Thr Phe Thr Ser Tyr His Met His
1 5 10

<210> SEQ ID NO 51
<211> LENGTH: 17
<212> TYPE: PRT
<213> ORGANISM: Artificial Sequence
<220> FEATURE:
<223> OTHER INFORMATION: HLA-A*02 CDR-H2

<400> SEQUENCE: 51

Trp Ile Tyr Pro Gly Asp Gly Ser Thr Gln Tyr Asn Glu Lys Phe Lys
1 5 10 15

Gly

<210> SEQ ID NO 52
<211> LENGTH: 9
<212> TYPE: PRT
<213> ORGANISM: Artificial Sequence
<220> FEATURE:
<223> OTHER INFORMATION: HLA-A*02 CDR-H3

<400> SEQUENCE: 52

Glu Gly Thr Tyr Tyr Ala Met Asp Tyr
1 5

<210> SEQ ID NO 53
<211> LENGTH: 247
<212> TYPE: PRT
<213> ORGANISM: Artificial Sequence
<220> FEATURE:
<223> OTHER INFORMATION: HLA-A*02 ScFv

<400> SEQUENCE: 53

Asp Val Leu Met Thr Gln Thr Pro Leu Ser Leu Pro Val Ser Leu Gly
1 5 10 15

Asp Gln Ala Ser Ile Ser Cys Arg Ser Ser Gln Ser Ile Val His Ser
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser His Val Pro Arg Thr Ser Gly Gly Gly Thr Lys Leu Glu Ile Lys
100 105 110

Gly Gly Gly Gly Ser Gly Gly Gly Gly Ser Gly Gly Gly Gly Ser Gly
115 120 125

Gly Gln Val Gln Leu Gln Gln Ser Gly Pro Glu Leu Val Lys Pro Gly
130 135 140

Ala Ser Val Arg Ile Ser Cys Lys Ala Ser Gly Tyr Thr Phe Thr Ser
145 150 155 160

Tyr His Ile His Trp Val Lys Gln Arg Pro Gly Gln Gly Leu Glu Trp
165 170 175

Ile Gly Trp Ile Tyr Pro Gly Asn Val Asn Thr Glu Tyr Asn Glu Lys
180 185 190

Phe Lys Gly Lys Ala Thr Leu Thr Ala Asp Lys Ser Ser Ser Thr Ala
195 200 205

Tyr Met His Leu Ser Ser Leu Thr Ser Glu Asp Ser Ala Val Tyr Phe
210 215 220

Cys Ala Arg Glu Glu Ile Thr Tyr Ala Met Asp Tyr Trp Gly Gln Gly
225 230 235 240

Thr Ser Val Thr Val Ser Ser
245

<210> SEQ ID NO 54

<211> LENGTH: 247
<212> TYPE: PRT
<213> ORGANISM: Artificial Sequence
<220> FEATURE:
<223> OTHER INFORMATION: HLA-A*02 ScFv

<400> SEQUENCE: 54

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Gly Leu Glu Trp Met
        35                  40                  45

Gly Trp Ile Tyr Pro Gly Asn Val Asn Thr Glu Tyr Asn Glu Lys Phe
    50                  55                  60

Lys Gly Lys Ala Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Ile Thr Tyr Ala Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Glu Ile Val Leu Thr Gln Ser Pro Gly
    130                 135                 140

Thr Leu Ser Leu Ser Pro Gly Glu Arg Ala Thr Leu Ser Cys Arg Ser
145                 150                 155                 160

Ser Gln Ser Ile Val His Ser Asn Gly Asn Thr Tyr Leu Glu Trp Tyr
                165                 170                 175

Gln Gln Lys Pro Gly Gln Ala Pro Arg Leu Leu Ile Tyr Lys Val Ser
            180                 185                 190

Asn Arg Phe Ser Gly Ile Pro Asp Arg Phe Ser Gly Ser Gly Ser Gly
        195                 200                 205

Thr Asp Phe Thr Leu Thr Ile Ser Arg Leu Glu Pro Glu Asp Phe Ala
    210                 215                 220

Val Tyr Tyr Cys Phe Gln Gly Ser His Val Pro Arg Thr Phe Gly Gly
225                 230                 235                 240

Gly Thr Lys Val Glu Ile Lys
                245
```

<210> SEQ ID NO 55
<211> LENGTH: 247
<212> TYPE: PRT
<213> ORGANISM: Artificial Sequence
<220> FEATURE:
<223> OTHER INFORMATION: HLA-A*02 ScFv

<400> SEQUENCE: 55

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Gly Leu Glu Trp Met
        35                  40                  45

Gly Trp Ile Tyr Pro Gly Asn Val Asn Thr Glu Tyr Asn Glu Lys Phe
    50                  55                  60

Lys Gly Lys Ala Thr Ile Thr Ala Asp Lys Ser Thr Ser Thr Ala Tyr
```

```
65                  70                  75                  80

Met Glu Leu Ser Ser Leu Arg Ser Glu Asp Thr Ala Val Tyr Tyr Cys
                85                  90                  95

Ala Arg Glu Glu Ile Thr Tyr Ala Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Asp Ile Val Met Thr Gln Thr Pro Leu
    130                 135                 140

Ser Leu Pro Val Thr Pro Gly Glu Pro Ala Ser Ile Ser Cys Arg Ser
145                 150                 155                 160

Ser Gln Ser Ile Val His Ser Asn Gly Asn Thr Tyr Leu Glu Trp Tyr
                165                 170                 175

Leu Gln Lys Pro Gly Gln Ser Pro Gln Leu Leu Ile Tyr Lys Val Ser
            180                 185                 190

Asn Arg Phe Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Phe Gln Gly Ser His Val Pro Arg Thr Phe Gly Gly
225                 230                 235                 240

Gly Thr Lys Val Glu Ile Lys
                245


<210> SEQ ID NO 56
<211> LENGTH: 247
<212> TYPE: PRT
<213> ORGANISM: Artificial Sequence
<220> FEATURE:
<223> OTHER INFORMATION: HLA-A*02 ScFv

<400> SEQUENCE: 56

Glu Val Gln Leu Val Glu Ser Gly Gly Gly Leu Val Lys Pro Gly Gly
1               5                   10                  15

Ser Leu Arg Leu Ser Cys Ala Ala Ser Gly Tyr Thr Phe Thr Ser Tyr
            20                  25                  30

His Ile His Trp Val Arg Gln Ala Pro Gly Lys Gly Leu Glu Trp Val
        35                  40                  45

Gly Trp Ile Tyr Pro Gly Asn Val Asn Thr Glu Tyr Asn Glu Lys Phe
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Ala Arg Glu Glu Ile Thr Tyr Ala Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Asp Ile Gln Met Thr Gln Ser Pro Ser
    130                 135                 140

Ser Leu Ser Ala Ser Val Gly Asp Arg Val Thr Ile Thr Cys Arg Ser
145                 150                 155                 160

Ser Gln Ser Ile Val His Ser Asn Gly Asn Thr Tyr Leu Glu Trp Tyr
                165                 170                 175

Gln Gln Lys Pro Gly Lys Ala Pro Lys Leu Leu Ile Tyr Lys Val Ser
```

```
            180                 185                 190

Asn Arg Phe Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Phe Gln Gly Ser His Val Pro Arg Thr Phe Gly Gly
225                 230                 235                 240

Gly Thr Lys Val Glu Ile Lys
                245


<210> SEQ ID NO 57
<211> LENGTH: 247
<212> TYPE: PRT
<213> ORGANISM: Artificial Sequence
<220> FEATURE:
<223> OTHER INFORMATION: HLA-A*02 ScFv

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

His Ile His Trp Val Arg Gln Ala Pro Gly Gln Gly Leu Glu Trp Ile
        35                  40                  45

Gly Trp Ile Tyr Pro Gly Asn Val Asn Thr Glu Tyr Asn Glu Lys Phe
    50                  55                  60

Lys Gly Lys Ala Thr Ile Thr Ala Asp Glu Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Ile Thr Tyr Ala Met Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gly Gly Asp Ile Gln Met Thr Gln Ser Pro Ser
    130                 135                 140

Thr Leu Ser Ala Ser Val Gly Asp Arg Val Thr Ile Thr Cys Arg Ser
145                 150                 155                 160

Ser Gln Ser Ile Val His Ser Asn Gly Asn Thr Tyr Leu Glu Trp Tyr
                165                 170                 175

Gln Gln Lys Pro Gly Lys Ala Pro Lys Leu Leu Ile Tyr Lys Val Ser
            180                 185                 190

Asn Arg Phe Ser Gly Val Pro Ala Arg Phe Ser Gly Ser Gly Ser Gly
        195                 200                 205

Thr Glu Phe Thr Leu Thr Ile Ser Ser Leu Gln Pro Asp Asp Phe Ala
    210                 215                 220

Thr Tyr Tyr Cys Phe Gln Gly Ser His Val Pro Arg Thr Phe Gly Gln
225                 230                 235                 240

Gly Thr Lys Val Glu Val Lys
                245


<210> SEQ ID NO 58
<211> LENGTH: 247
<212> TYPE: PRT
<213> ORGANISM: Artificial Sequence
<220> FEATURE:
<223> OTHER INFORMATION: HLA-A*02 ScFv
```

<400> SEQUENCE: 58

Gln Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

His Met His Trp Val Arg Gln Ala Pro Gly Gln Gly Leu Glu Trp Ile
35 40 45

Gly Tyr Ile Tyr Pro Gly Asn Val Asn Thr Glu Tyr Asn Glu Lys Phe
50 55 60

Lys Gly Lys Ala Thr Leu Thr Ala Asp Lys Ser Thr Asn Thr Ala Tyr
65 70 75 80

Met Glu Leu Ser Ser Leu Arg Ser Glu Asp Thr Ala Val Tyr Phe Cys
85 90 95

Ala Arg Glu Glu Ile Thr Tyr Ala Met Asp Tyr Trp Gly Gln Gly Thr
100 105 110

Leu Val Thr Val Ser Ser Gly Gly Gly Gly Ser Gly Gly Gly Gly Ser
115 120 125

Gly Gly Gly Gly Ser Gly Gly Asp Val Gln Met Thr Gln Ser Pro Ser
130 135 140

Thr Leu Ser Ala Ser Val Gly Asp Arg Val Thr Ile Thr Cys Ser Ser
145 150 155 160

Ser Gln Ser Ile Val His Ser Asn Gly Asn Thr Tyr Met Glu Trp Tyr
165 170 175

Gln Gln Lys Pro Gly Lys Ala Pro Lys Leu Leu Ile Tyr Lys Val Ser
180 185 190

Asn Arg Phe Ser Gly Val Pro Asp Arg Phe Ser Gly Ser Gly Ser Gly
195 200 205

Thr Glu Phe Thr Leu Thr Ile Ser Ser Leu Gln Pro Asp Asp Phe Ala
210 215 220

Thr Tyr Tyr Cys His Gln Gly Ser His Val Pro Arg Thr Phe Gly Gln
225 230 235 240

Gly Thr Lys Val Glu Val Lys
245

<210> SEQ ID NO 59
<211> LENGTH: 247
<212> TYPE: PRT
<213> ORGANISM: Artificial Sequence
<220> FEATURE:
<223> OTHER INFORMATION: HLA-A*02 ScFv

<400> SEQUENCE: 59

Gln Val Gln Leu Gln Gln Ser Gly Pro Glu Leu Val Lys Pro Gly Ala
1 5 10 15

Ser Val Lys Met Ser Cys Lys Ala Ser Gly Tyr Thr Phe Thr Ser Tyr
20 25 30

His Ile Gln Trp Val Lys Gln Arg Pro Gly Gln Gly Leu Glu Trp Ile
35 40 45

Gly Trp Ile Tyr Pro Gly Asp Gly Ser Thr Gln Tyr Asn Glu Lys Phe
50 55 60

Lys Gly Lys Thr Thr Leu Thr Ala Asp Lys Ser Ser Ser Thr Ala Tyr
65 70 75 80

Met Leu Leu Ser Ser Leu Thr Ser Glu Asp Ser Ala Ile Tyr Phe Cys
85 90 95

```
Ala Arg Glu Gly Thr Tyr Tyr Ala Met Asp Tyr Trp Gly Gln Gly Thr
            100                 105                 110

Ser Val Thr Val Ser Ser Gly Gly Gly Gly Ser Gly Gly Gly Gly Ser
        115                 120                 125

Gly Gly Gly Gly Ser Gly Gly Asp Val Leu Met Thr Gln Thr Pro Leu
    130                 135                 140

Ser Leu Pro Val Ser Leu Gly Asp Gln Val Ser Ile Ser Cys Arg Ser
145                 150                 155                 160

Ser Gln Ser Ile Val His Ser Asn Gly Asn Thr Tyr Leu Glu Trp Tyr
                165                 170                 175

Leu Gln Lys Pro Gly Gln Ser Pro Lys Leu Leu Ile Tyr Lys Val Ser
            180                 185                 190

Asn Arg Phe Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Leu Gly
    210                 215                 220

Val Tyr Tyr Cys Phe Gln Gly Ser His Val Pro Arg Thr Phe Gly Gly
225                 230                 235                 240

Gly Thr Lys Leu Glu Ile Lys
                245


<210> SEQ ID NO 60
<211> LENGTH: 247
<212> TYPE: PRT
<213> ORGANISM: Artificial Sequence
<220> FEATURE:
<223> OTHER INFORMATION: HLA-A*02 ScFv

<400> SEQUENCE: 60

Gln Leu Gln Leu Gln Glu Ser Gly Pro Gly Leu Val Lys Pro Ser Glu
1               5                   10                  15

Thr Leu Ser Leu Thr Cys Thr Val Ser Gly Tyr Thr Phe Thr Ser Tyr
            20                  25                  30

His Ile Gln Trp Ile Arg Gln Pro Pro Gly Lys Gly Leu Glu Trp Ile
        35                  40                  45

Gly Trp Ile Tyr Pro Gly Asp Gly Ser Thr Gln Tyr Asn Glu Lys Phe
    50                  55                  60

Lys Gly Arg Ala Thr Ile Ser Val Asp Thr Ser Lys Asn Gln Phe Ser
65                  70                  75                  80

Leu Asn Leu Asp Ser Val Ser Ala Ala Asp Thr Ala Ile Tyr Tyr Cys
                85                  90                  95

Ala Arg Glu Gly Thr Tyr Tyr Ala Met Asp Tyr Trp Gly Lys Gly Ser
            100                 105                 110

Thr Val Thr Val Ser Ser Gly Gly Gly Gly Ser Gly Gly Gly Gly Ser
        115                 120                 125

Gly Gly Gly Gly Ser Gly Gly Asp Ile Gln Met Thr Gln Ser Pro Ser
    130                 135                 140

Ser Leu Ser Ala Ser Val Gly Asp Arg Val Thr Ile Thr Cys Arg Ser
145                 150                 155                 160

Ser Gln Ser Ile Val His Ser Asn Gly Asn Thr Tyr Leu Glu Trp Tyr
                165                 170                 175

Gln Gln Lys Pro Gly Lys Ala Pro Lys Leu Leu Ile Tyr Lys Val Ser
            180                 185                 190

Asn Arg Phe Ser Gly Val Pro Ser Arg Phe Ser Gly Ser Gly Ser Gly
        195                 200                 205
```

-continued

```
Thr Asp Phe Thr Phe Thr Ile Ser Ser Leu Gln Pro Glu Asp Ile Ala
    210                 215                 220

Thr Tyr Tyr Cys Phe Gln Gly Ser His Val Pro Arg Thr Phe Gly Pro
225                 230                 235                 240

Gly Thr Lys Val Asp Ile Lys
                245


<210> SEQ ID NO 61
<211> LENGTH: 247
<212> TYPE: PRT
<213> ORGANISM: Artificial Sequence
<220> FEATURE:
<223> OTHER INFORMATION: HLA-A*02 ScFv

<400> SEQUENCE: 61

Glu Val Gln Leu Val Gln Ser Gly Ala Glu Leu Lys Lys Pro Gly Ser
1               5                   10                  15

Ser Val Lys Val Ser Cys Lys Ala Ser Gly Tyr Thr Phe Thr Ser Tyr
            20                  25                  30

His Ile Gln Trp Val Lys Gln Ala Pro Gly Gln Gly Leu Glu Trp Ile
        35                  40                  45

Gly Trp Ile Tyr Pro Gly Asp Gly Ser Thr Gln Tyr Asn Glu Lys Phe
    50                  55                  60

Lys Gly Lys Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gly Gly Asp Ile Gln Met Thr Gln Ser Pro Ser
    130                 135                 140

Thr Leu Ser Ala Ser Val Gly Asp Arg Val Thr Ile Thr Cys Arg Ser
145                 150                 155                 160

Ser Gln Ser Ile Val His Ser Asn Gly Asn Thr Tyr Leu Glu Trp Tyr
                165                 170                 175

Gln Gln Lys Pro Gly Lys Ala Pro Lys Leu Leu Ile Tyr Lys Val Ser
            180                 185                 190

Asn Arg Phe Ser Gly Val Pro Ser Arg Phe Ser Gly Ser Gly Ser Gly
        195                 200                 205

Thr Asp Phe Thr Leu Thr Ile Ser Ser Leu Gln Pro Asp Asp Phe Ala
    210                 215                 220

Thr Tyr Tyr Cys Phe Gln Gly Ser His Val Pro Arg Thr Phe Gly Gln
225                 230                 235                 240

Gly Thr Lys Val Glu Val Lys
                245


<210> SEQ ID NO 62
<211> LENGTH: 247
<212> TYPE: PRT
<213> ORGANISM: Artificial Sequence
<220> FEATURE:
<223> OTHER INFORMATION: HLA-A*02 ScFv

<400> SEQUENCE: 62

Gln Val Gln Leu Val Gln Ser Gly Ala Glu Val Lys Lys Pro Gly Ser
1               5                   10                  15
```

Ser Val Lys Val Ser Cys Lys Ala Ser Gly Tyr Thr Phe Thr Ser Tyr
20 25 30

His Ile Gln Trp Val Arg Gln Ala Pro Gly Gln Gly Leu Glu Trp Met
35 40 45

Gly Trp Ile Tyr Pro Gly Asp Gly Ser Thr Gln Tyr Asn Glu Lys Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Gly Thr Tyr Tyr Ala Met Asp Tyr Trp Gly Gln Gly Thr
100 105 110

Thr Val Thr Val Ser Ser Gly Gly Gly Gly Ser Gly Gly Gly Gly Ser
115 120 125

Gly Gly Gly Gly Ser Gly Gly Glu Ile Val Leu Thr Gln Ser Pro Gly
130 135 140

Thr Leu Ser Leu Ser Pro Gly Glu Arg Ala Thr Leu Ser Cys Arg Ser
145 150 155 160

Ser Gln Ser Ile Val His Ser Asn Gly Asn Thr Tyr Leu Glu Trp Tyr
165 170 175

Gln Gln Lys Pro Gly Gln Ala Pro Arg Leu Leu Ile Tyr Lys Val Ser
180 185 190

Asn Arg Phe Ser Gly Ile Pro Asp Arg Phe Ser Gly Ser Gly Ser Gly
195 200 205

Thr Asp Phe Thr Leu Thr Ile Ser Arg Leu Glu Pro Glu Asp Phe Ala
210 215 220

Val Tyr Tyr Cys Phe Gln Gly Ser His Val Pro Arg Thr Phe Gly Gly
225 230 235 240

Gly Thr Lys Val Glu Ile Lys
245

<210> SEQ ID NO 63
<211> LENGTH: 247
<212> TYPE: PRT
<213> ORGANISM: Artificial Sequence
<220> FEATURE:
<223> OTHER INFORMATION: HLA-A*02 ScFv

<400> SEQUENCE: 63

Gln Val Thr Leu Lys Gln Ser Gly Ala Glu Val Lys Lys Pro Gly Ser
1 5 10 15

Ser Val Lys Val Ser Cys Thr Ala Ser Gly Tyr Thr Phe Thr Ser Tyr
20 25 30

His Val Ser Trp Val Arg Gln Ala Pro Gly Gln Gly Leu Glu Trp Leu
35 40 45

Gly Arg Ile Tyr Pro Gly Asp Gly Ser Thr Gln Tyr Asn Glu Lys Phe
50 55 60

Lys Gly Lys Val Thr Ile Thr Ala Asp Lys Ser Met Asp Thr Ser Phe
65 70 75 80

Met Glu Leu Thr Ser Leu Thr Ser Glu Asp Thr Ala Val Tyr Tyr Cys
85 90 95

Ala Arg Glu Gly Thr Tyr Tyr Ala Met Asp Leu Trp Gly Gln Gly Thr
100 105 110

Leu Val Thr Val Ser Ser Gly Gly Gly Gly Ser Gly Gly Gly Gly Ser
115 120 125

Gly Gly Gly Gly Ser Gly Gly Glu Ile Val Leu Thr Gln Ser Pro Gly
    130                 135                 140

Thr Leu Ser Leu Ser Pro Gly Glu Arg Ala Thr Leu Ser Cys Arg Ser
145                 150                 155                 160

Ser Gln Ser Ile Val His Ser Asn Gly Asn Thr Tyr Leu Ala Trp Tyr
                165                 170                 175

Gln Gln Lys Pro Gly Gln Ala Pro Arg Leu Leu Ile Ser Lys Val Ser
            180                 185                 190

Asn Arg Phe Ser Gly Val Pro Asp Arg Phe Ser Gly Ser Gly Ser Gly
        195                 200                 205

Thr Asp Phe Thr Leu Thr Ile Ser Arg Leu Glu Pro Glu Asp Phe Ala
    210                 215                 220

Val Tyr Tyr Cys Gln Gln Gly Ser His Val Pro Arg Thr Phe Gly Gly
225                 230                 235                 240

Gly Thr Lys Val Glu Ile Lys
                245

<210> SEQ ID NO 64
<211> LENGTH: 247
<212> TYPE: PRT
<213> ORGANISM: Artificial Sequence
<220> FEATURE:
<223> OTHER INFORMATION: HLA-A*02 ScFv

<400> SEQUENCE: 64

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

His Met His Trp Val Arg Gln Ala Pro Gly Gln Arg Leu Glu Trp Met
        35                  40                  45

Gly Trp Ile Tyr Pro Gly Asp Gly Ser Thr Gln Tyr Asn Glu Lys Phe
    50                  55                  60

Lys Gly Lys Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Thr Tyr Tyr Ala Met Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gly Gly Asp Ile Val Met Thr Gln Thr Pro Leu
    130                 135                 140

Ser Leu Pro Val Thr Pro Gly Glu Pro Ala Ser Ile Ser Cys Arg Ser
145                 150                 155                 160

Ser Gln Ser Ile Val His Ser Asn Gly Asn Thr Tyr Leu Asp Trp Tyr
                165                 170                 175

Leu Gln Lys Pro Gly Gln Ser Pro Gln Leu Leu Ile Tyr Lys Val Ser
            180                 185                 190

Asn Arg Phe Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Met Gln Gly Ser His Val Pro Arg Thr Phe Gly Gly
225                 230                 235                 240

```
Gly Thr Lys Val Glu Ile Lys
                245


<210> SEQ ID NO 65
<211> LENGTH: 670
<212> TYPE: PRT
<213> ORGANISM: Homo sapiens

<400> SEQUENCE: 65

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Leu Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
        115                 120                 125

Ala Gln Pro Ser Pro Val Val Asn Ser Gly Gly Asn Val Ile Leu Gln
    130                 135                 140

Cys Asp Ser Gln Val Ala Phe Asp Gly Phe Ser Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
    290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
```

```
        355                 360                 365

Leu Arg Ser Thr Tyr Gln Ser Gln Lys Tyr Gln Ala Glu Phe Pro Met
    370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Gly Pro Ser Ser Pro Thr Thr Gly
            420                 425                 430

Pro Thr Ser Thr Ser Gly Pro Glu Asp Gln Pro Leu Thr Pro Thr Gly
        435                 440                 445

Ser Asp Pro Gln Ser Gly Leu Gly Arg His Leu Gly Val Val Ile Gly
    450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
        515                 520                 525

Glu Glu Asn Leu Tyr Ala Ala Val Lys His Thr Gln Pro Glu Asp Gly
    530                 535                 540

Val Glu Met Asp Thr Arg Ser Pro His Asp Glu Asp Pro Gln Ala Val
545                 550                 555                 560

Thr Tyr Ala Glu Val Lys His Ser Arg Pro Arg Arg Glu Met Ala Ser
                565                 570                 575

Pro Pro Ser Pro Leu Ser Gly Glu Phe Leu Asp Thr Lys Asp Arg Gln
            580                 585                 590

Ala Glu Glu Asp Arg Gln Met Asp Thr Glu Ala Ala Ala Ser Glu Ala
        595                 600                 605

Pro Gln Asp Val Thr Tyr Ala Gln Leu His Ser Leu Thr Leu Arg Arg
    610                 615                 620

Glu Ala Thr Glu Pro Pro Pro Ser Gln Glu Gly Pro Ser Pro Ala Val
625                 630                 635                 640

Pro Ser Ile Tyr Ala Thr Leu Ala Ile His Pro Ser Gln Glu Gly Pro
                645                 650                 655

Ser Pro Ala Val Pro Ser Ile Tyr Ala Thr Leu Ala Ile His
            660                 665                 670
```

<210> SEQ ID NO 66
<211> LENGTH: 3229
<212> TYPE: DNA
<213> ORGANISM: Homo sapiens

<400> SEQUENCE: 66

```
aaatgagttt taaaaaggct tgtccaggaa gcacatatgg gagctggtca ctctgcattt     60

tgggccctcc tggaggtgtt tagaccttcc gagagagaaa ctgagacaca tgagagggaa    120

gaaatgactc agtggtgaga ccctgtggag tcccacccac aaccagcaca ctgtgaccca    180

ctgcacaaac ctctagccca cagctcactt cctcctttaa gaagagaaga gaaaagagga    240

gaggagagga ggaacagaaa agaaaagaaa agaaaaagtg ggaaacaaat aatctaagaa    300

tgaggagaaa gcaagaagag tgaccccctt gtgggcactc cattggtttt atggcgcctc    360
```

-continued

```
tactttctgg agtttgtgta aaacaaaaat attatggtct ttgtgcacat ttacatcaag    420
ctcagcctgg gcggcacagc cagatgcgag atgcgtctct gctgatctga gtctgcctgc    480
agcatggacc tgggtcttcc ctgaagcatc tccagggctg gagggacgac tgccatgcac    540
cgagggctca tccatccaca gagcagggca gtgggaggag acgccatgac cccatcctc    600
acggtcctga tctgtctcgg gctgagtctg ggcccccgga cccacgtgca ggcagggcac    660
ctccccaagc ccaccctctg ggctgaacca ggctctgtga tcacccaggg gagtcctgtg    720
accctcaggt gtcagggggg ccaggagacc caggagtacc gtctatatag agaaaagaaa    780
acagcaccct ggattacacg gatcccacag gagcttgtga agaagggcca gttccccatc    840
ccatccatca cctgggaaca cacagggcgg tatcgctgtt actatggtag cgacactgca    900
ggccgctcag agagcagtga ccccctggag ctggtggtga caggagccta catcaaaccc    960
accctctcag cccagcccag ccccgtggtg aactcaggag ggaatgtaac cctccagtgt   1020
gactcacagg tggcatttga tggcttcatt ctgtgtaagg aaggagaaga tgaacaccca   1080
caatgcctga actcccagcc ccatgcccgt gggtcgtccc gcgccatctt ctccgtgggc   1140
cccgtgagcc cgagtcgcag gtggtggtac aggtgctatg cttatgactc gaactctccc   1200
tatgagtggt ctctacccag tgatctcctg gagctcctgg tcctaggtgt ttctaagaag   1260
ccatcactct cagtgcagcc aggtcctatc gtggcccctg aggagaccct gactctgcag   1320
tgtggctctg atgctggcta caacagattt gttctgtata aggacgggga acgtgacttc   1380
cttcagctcg ctggcgcaca gccccaggct gggctctccc aggccaactt caccctgggc   1440
cctgtgagcc gctcctacgg gggccagtac agatgctacg gtgcacacaa cctctcctcc   1500
gagtggtcgg cccccagcga ccccctggac atcctgatcg caggacagtt ctatgacaga   1560
gtctccctct cggtgcagcc gggccccacg gtggcctcag gagagaacgt gaccctgctg   1620
tgtcagtcac agggatggat gcaaactttc cttctgacca aggagggggc agctgatgac   1680
ccatggcgtc taagatcaac gtaccaatct caaaaatacc aggctgaatt ccccatgggt   1740
cctgtgacct cagcccatgc ggggacctac aggtgctacg gctcacagag ctccaaaccc   1800
tacctgctga ctcaccccag tgacccccctg gagctcgtgg tctcaggacc gtctgggggc   1860
cccagctccc cgacaacagg ccccacctcc acatctggcc ctgaggacca gcccctcacc   1920
cccaccgggt cggatcccca gagtggtctg ggaaggcacc tgggggttgt gatcggcatc   1980
ttggtggccg tcatcctact gctcctcctc ctcctcctcc tcttcctcat cctccgacat   2040
cgacgtcagg gcaaacactg gacatcgacc cagagaaagg ctgatttcca acatcctgca   2100
ggggctgtgg ggccagagcc cacagacaga ggcctgcagt ggaggtccag cccagctgcc   2160
gatgcccagg aagaaaacct ctatgctgcc gtgaagcaca cacagcctga ggatggggtg   2220
gagatggaca ctcggagccc acacgatgaa gacccccagg cagtgacgta tgccgaggtg   2280
aaacactcca gacctaggag agaaatggcc tctcctcctt ccccactgtc tggggaattc   2340
ctggacacaa aggacagaca ggcggaagag gacaggcaga tggacactga ggctgctgca   2400
tctgaagccc cccaggatgt gacctacgcc cagctgcaca gcttgaccct cagacgggag   2460
gcaactgagc ctcctccatc ccaggaaggg ccctctccag ctgtgcccag catctacgcc   2520
actctggcca tccactagcc caggggggga cgcagacccc acactccatg gagtctggaa   2580
tgcatgggag ctgccccccc agtggacacc attggacccc acccagcctg gatctacccc   2640
aggagactct gggaactttt aggggtcact caattctgca gtataaataa ctaatgtctc   2700
tacaattttg aaataaagca acagacttct caataatcaa tgaagtagct gagaaaacta   2760
```

```
agtcagaaag tgcattaaac tgaatcacaa tgtaaatatt acacatcaag cgatgaaact   2820

ggaaaactac aagccacgaa tgaatgaatt aggaaagaaa aaaagtagga aatgaatgat   2880

cttggctttc ctataagaaa tttagggcag ggcacggtgg ctcacgcctg taattccagc   2940

actttgggag gccgaggcgg gcagatcacg agttcaggag atcgagacca tcttggccaa   3000

catggtgaaa ccctgtctct cctaaaaata caaaaattag ctggatgtgg tggcagtgcc   3060

tgtaatccca gctatttggg aggctgaggc aggagaatcg cttgaaccag ggagtcagag   3120

gtttcagtga gccaagatcg caccactgct ctccagcctg gcgacagagg gagactccat   3180

ctcaaattaa aaaaaaaaaa aaaaaagaaa gaaaaaaaaa aaaaaaaaa               3229
```

<210> SEQ ID NO 67
<211> LENGTH: 6
<212> TYPE: PRT
<213> ORGANISM: Artificial Sequence
<220> FEATURE:
<223> OTHER INFORMATION: ITIM

<400> SEQUENCE: 67

Asn Leu Tyr Ala Ala Val
1               5

<210> SEQ ID NO 68
<211> LENGTH: 6
<212> TYPE: PRT
<213> ORGANISM: Artificial Sequence
<220> FEATURE:
<223> OTHER INFORMATION: ITIM

<400> SEQUENCE: 68

Val Thr Tyr Ala Glu Val
1               5

<210> SEQ ID NO 69
<211> LENGTH: 6
<212> TYPE: PRT
<213> ORGANISM: Artificial Sequence
<220> FEATURE:
<223> OTHER INFORMATION: ITIM

<400> SEQUENCE: 69

Val Thr Tyr Ala Gln Leu
1               5

<210> SEQ ID NO 70
<211> LENGTH: 6
<212> TYPE: PRT
<213> ORGANISM: Artificial Sequence
<220> FEATURE:
<223> OTHER INFORMATION: ITIM

<400> SEQUENCE: 70

Ser Ile Tyr Ala Thr Leu
1               5

<210> SEQ ID NO 71
<211> LENGTH: 35
<212> TYPE: PRT
<213> ORGANISM: Artificial Sequence
<220> FEATURE:
<223> OTHER INFORMATION: ITIM 1-2

<400> SEQUENCE: 71

```
Asn Leu Tyr Ala Ala Val Lys His Thr Gln Pro Glu Asp Gly Val Glu
1               5                   10                  15

Met Asp Thr Arg Ser Pro His Asp Glu Asp Pro Gln Ala Val Thr Tyr
            20                  25                  30

Ala Glu Val
        35


<210> SEQ ID NO 72
<211> LENGTH: 58
<212> TYPE: PRT
<213> ORGANISM: Artificial Sequence
<220> FEATURE:
<223> OTHER INFORMATION: ITIM 2-3

<400> SEQUENCE: 72

Val Thr Tyr Ala Glu Val Lys His Ser Arg Pro Arg Arg Glu Met Ala
1               5                   10                  15

Ser Pro Pro Ser Pro Leu Ser Gly Glu Phe Leu Asp Thr Lys Asp Arg
            20                  25                  30

Gln Ala Glu Glu Asp Arg Gln Met Asp Thr Glu Ala Ala Ala Ser Glu
        35                  40                  45

Ala Pro Gln Asp Val Thr Tyr Ala Gln Leu
    50                  55


<210> SEQ ID NO 73
<211> LENGTH: 36
<212> TYPE: PRT
<213> ORGANISM: Artificial Sequence
<220> FEATURE:
<223> OTHER INFORMATION: ITIM 3-4

<400> SEQUENCE: 73

Val Thr Tyr Ala Gln Leu His Ser Leu Thr Leu Arg Arg Glu Ala Thr
1               5                   10                  15

Glu Pro Pro Pro Ser Gln Glu Gly Pro Ser Pro Ala Val Pro Ser Ile
            20                  25                  30

Tyr Ala Thr Leu
        35


<210> SEQ ID NO 74
<211> LENGTH: 87
<212> TYPE: PRT
<213> ORGANISM: Artificial Sequence
<220> FEATURE:
<223> OTHER INFORMATION: ITIM 1-3

<400> SEQUENCE: 74

Asn Leu Tyr Ala Ala Val Lys His Thr Gln Pro Glu Asp Gly Val Glu
1               5                   10                  15

Met Asp Thr Arg Ser Pro His Asp Glu Asp Pro Gln Ala Val Thr Tyr
            20                  25                  30

Ala Glu Val Lys His Ser Arg Pro Arg Arg Glu Met Ala Ser Pro Pro
        35                  40                  45

Ser Pro Leu Ser Gly Glu Phe Leu Asp Thr Lys Asp Arg Gln Ala Glu
    50                  55                  60

Glu Asp Arg Gln Met Asp Thr Glu Ala Ala Ala Ser Glu Ala Pro Gln
65                  70                  75                  80

Asp Val Thr Tyr Ala Gln Leu
                85
```

<210> SEQ ID NO 75
<211> LENGTH: 88
<212> TYPE: PRT
<213> ORGANISM: Artificial Sequence
<220> FEATURE:
<223> OTHER INFORMATION: ITIM 2-4

<400> SEQUENCE: 75

Val Thr Tyr Ala Glu Val Lys His Ser Arg Pro Arg Arg Glu Met Ala
1 5 10 15

Ser Pro Pro Ser Pro Leu Ser Gly Glu Phe Leu Asp Thr Lys Asp Arg
20 25 30

Gln Ala Glu Glu Asp Arg Gln Met Asp Thr Glu Ala Ala Ala Ser Glu
35 40 45

Ala Pro Gln Asp Val Thr Tyr Ala Gln Leu His Ser Leu Thr Leu Arg
50 55 60

Arg Glu Ala Thr Glu Pro Pro Pro Ser Gln Glu Gly Pro Ser Pro Ala
65 70 75 80

Val Pro Ser Ile Tyr Ala Thr Leu
85

<210> SEQ ID NO 76
<211> LENGTH: 117
<212> TYPE: PRT
<213> ORGANISM: Artificial Sequence
<220> FEATURE:
<223> OTHER INFORMATION: ITIM 1-4

<400> SEQUENCE: 76

Asn Leu Tyr Ala Ala Val Lys His Thr Gln Pro Glu Asp Gly Val Glu
1 5 10 15

Met Asp Thr Arg Ser Pro His Asp Glu Asp Pro Gln Ala Val Thr Tyr
20 25 30

Ala Glu Val Lys His Ser Arg Pro Arg Arg Glu Met Ala Ser Pro Pro
35 40 45

Ser Pro Leu Ser Gly Glu Phe Leu Asp Thr Lys Asp Arg Gln Ala Glu
50 55 60

Glu Asp Arg Gln Met Asp Thr Glu Ala Ala Ala Ser Glu Ala Pro Gln
65 70 75 80

Asp Val Thr Tyr Ala Gln Leu His Ser Leu Thr Leu Arg Arg Glu Ala
85 90 95

Thr Glu Pro Pro Pro Ser Gln Glu Gly Pro Ser Pro Ala Val Pro Ser
100 105 110

Ile Tyr Ala Thr Leu
115

<210> SEQ ID NO 77
<211> LENGTH: 20
<212> TYPE: PRT
<213> ORGANISM: Artificial Sequence
<220> FEATURE:
<223> OTHER INFORMATION: D3D4 domain

<400> SEQUENCE: 77

Tyr Gly Ser Gln Ser Ser Lys Pro Tyr Leu Leu Thr His Pro Ser Asp
1 5 10 15

Pro Leu Glu Leu
20

<210> SEQ ID NO 78

<211> LENGTH: 43
<212> TYPE: PRT
<213> ORGANISM: Artificial Sequence
<220> FEATURE:
<223> OTHER INFORMATION: short hinge

<400> SEQUENCE: 78

```
Val Val Ser Gly Pro Ser Gly Gly Pro Ser Ser Pro Thr Thr Gly Pro
1               5                   10                  15

Thr Ser Thr Ser Gly Pro Glu Asp Gln Pro Leu Thr Pro Thr Gly Ser
            20                  25                  30

Asp Pro Gln Ser Gly Leu Gly Arg His Leu Gly
        35                  40
```

<210> SEQ ID NO 79
<211> LENGTH: 86
<212> TYPE: PRT
<213> ORGANISM: Artificial Sequence
<220> FEATURE:
<223> OTHER INFORMATION: hinge- transmembrane

<400> SEQUENCE: 79

```
Tyr Gly Ser Gln Ser Ser Lys Pro Tyr Leu Leu Thr His Pro Ser Asp
1               5                   10                  15

Pro Leu Glu Leu Val Val Ser Gly Pro Ser Gly Gly Pro Ser Ser Pro
            20                  25                  30

Thr Thr Gly Pro Thr Ser Thr Ser Gly Pro Glu Asp Gln Pro Leu Thr
        35                  40                  45

Pro Thr Gly Ser Asp Pro Gln Ser Gly Leu Gly Arg His Leu Gly Val
    50                  55                  60

Val Ile Gly Ile Leu Val Ala Val Ile Leu Leu Leu Leu Leu Leu Leu
65                  70                  75                  80

Leu Leu Phe Leu Ile Leu
                85
```

<210> SEQ ID NO 80
<211> LENGTH: 190
<212> TYPE: PRT
<213> ORGANISM: Artificial Sequence
<220> FEATURE:
<223> OTHER INFORMATION: hinge-transmembrane-intracellular domain

<400> SEQUENCE: 80

```
Val Val Ile Gly Ile Leu Val Ala Val Ile Leu Leu Leu Leu Leu Leu
1               5                   10                  15

Leu Leu Leu Phe Leu Ile Leu Arg His Arg Arg Gln Gly Lys His Trp
            20                  25                  30

Thr Ser Thr Gln Arg Lys Ala Asp Phe Gln His Pro Ala Gly Ala Val
        35                  40                  45

Gly Pro Glu Pro Thr Asp Arg Gly Leu Gln Trp Arg Ser Ser Pro Ala
    50                  55                  60

Ala Asp Ala Gln Glu Glu Asn Leu Tyr Ala Ala Val Lys His Thr Gln
65                  70                  75                  80

Pro Glu Asp Gly Val Glu Met Asp Thr Arg Ser Pro His Asp Glu Asp
                85                  90                  95

Pro Gln Ala Val Thr Tyr Ala Glu Val Lys His Ser Arg Pro Arg Arg
            100                 105                 110

Glu Met Ala Ser Pro Pro Ser Pro Leu Ser Gly Glu Phe Leu Asp Thr
        115                 120                 125
```

-continued

```
Lys Asp Arg Gln Ala Glu Glu Asp Arg Gln Met Asp Thr Glu Ala Ala
    130                 135                 140

Ala Ser Glu Ala Pro Gln Asp Val Thr Tyr Ala Gln Leu His Ser Leu
145                 150                 155                 160

Thr Leu Arg Arg Glu Ala Thr Glu Pro Pro Pro Ser Gln Glu Gly Pro
                165                 170                 175

Ser Pro Ala Val Pro Ser Ile Tyr Ala Thr Leu Ala Ile His
            180                 185                 190


<210> SEQ ID NO 81
<211> LENGTH: 167
<212> TYPE: PRT
<213> ORGANISM: Artificial Sequence
<220> FEATURE:
<223> OTHER INFORMATION: LILRB1 intracellular domain

<400> SEQUENCE: 81

Arg His Arg Arg Gln Gly Lys His Trp Thr Ser Thr Gln Arg Lys Ala
1               5                   10                  15

Asp Phe Gln His Pro Ala Gly Ala Val Gly Pro Glu Pro Thr Asp Arg
            20                  25                  30

Gly Leu Gln Trp Arg Ser Ser Pro Ala Ala Asp Ala Gln Glu Glu Asn
        35                  40                  45

Leu Tyr Ala Ala Val Lys His Thr Gln Pro Glu Asp Gly Val Glu Met
    50                  55                  60

Asp Thr Arg Ser Pro His Asp Glu Asp Pro Gln Ala Val Thr Tyr Ala
65                  70                  75                  80

Glu Val Lys His Ser Arg Pro Arg Arg Glu Met Ala Ser Pro Pro Ser
                85                  90                  95

Pro Leu Ser Gly Glu Phe Leu Asp Thr Lys Asp Arg Gln Ala Glu Glu
            100                 105                 110

Asp Arg Gln Met Asp Thr Glu Ala Ala Ala Ser Glu Ala Pro Gln Asp
        115                 120                 125

Val Thr Tyr Ala Gln Leu His Ser Leu Thr Leu Arg Arg Glu Ala Thr
    130                 135                 140

Glu Pro Pro Pro Ser Gln Glu Gly Pro Ser Pro Ala Val Pro Ser Ile
145                 150                 155                 160

Tyr Ala Thr Leu Ala Ile His
                165


<210> SEQ ID NO 82
<211> LENGTH: 253
<212> TYPE: PRT
<213> ORGANISM: Artificial Sequence
<220> FEATURE:
<223> OTHER INFORMATION: LILRB1 hinge-transmemebrane-intracellular
      domain

<400> SEQUENCE: 82

Tyr Gly Ser Gln Ser Ser Lys Pro Tyr Leu Leu Thr His Pro Ser Asp
1               5                   10                  15

Pro Leu Glu Leu Val Val Ser Gly Pro Ser Gly Gly Pro Ser Ser Pro
            20                  25                  30

Thr Thr Gly Pro Thr Ser Thr Ser Gly Pro Glu Asp Gln Pro Leu Thr
        35                  40                  45

Pro Thr Gly Ser Asp Pro Gln Ser Gly Leu Gly Arg His Leu Gly Val
    50                  55                  60

Val Ile Gly Ile Leu Val Ala Val Ile Leu Leu Leu Leu Leu Leu Leu
```

```
65                  70                  75                  80

Leu Leu Phe Leu Ile Leu Arg His Arg Arg Gln Gly Lys His Trp Thr
                85                  90                  95

Ser Thr Gln Arg Lys Ala Asp Phe Gln His Pro Ala Gly Ala Val Gly
            100                 105                 110

Pro Glu Pro Thr Asp Arg Gly Leu Gln Trp Arg Ser Ser Pro Ala Ala
        115                 120                 125

Asp Ala Gln Glu Glu Asn Leu Tyr Ala Ala Val Lys His Thr Gln Pro
    130                 135                 140

Glu Asp Gly Val Glu Met Asp Thr Arg Ser Pro His Asp Glu Asp Pro
145                 150                 155                 160

Gln Ala Val Thr Tyr Ala Glu Val Lys His Ser Arg Pro Arg Arg Glu
                165                 170                 175

Met Ala Ser Pro Pro Ser Pro Leu Ser Gly Glu Phe Leu Asp Thr Lys
            180                 185                 190

Asp Arg Gln Ala Glu Glu Asp Arg Gln Met Asp Thr Glu Ala Ala Ala
        195                 200                 205

Ser Glu Ala Pro Gln Asp Val Thr Tyr Ala Gln Leu His Ser Leu Thr
    210                 215                 220

Leu Arg Arg Glu Ala Thr Glu Pro Pro Pro Ser Gln Glu Gly Pro Ser
225                 230                 235                 240

Pro Ala Val Pro Ser Ile Tyr Ala Thr Leu Ala Ile His
                245                 250


<210> SEQ ID NO 83
<211> LENGTH: 233
<212> TYPE: PRT
<213> ORGANISM: Artificial Sequence
<220> FEATURE:
<223> OTHER INFORMATION: LILRB1 hinge-TM-intracellular domain

<400> SEQUENCE: 83

Val Val Ser Gly Pro Ser Gly Gly Pro Ser Ser Pro Thr Thr Gly Pro
1               5                   10                  15

Thr Ser Thr Ser Gly Pro Glu Asp Gln Pro Leu Thr Pro Thr Gly Ser
            20                  25                  30

Asp Pro Gln Ser Gly Leu Gly Arg His Leu Gly Val Val Ile Gly Ile
        35                  40                  45

Leu Val Ala Val Ile Leu Leu Leu Leu Leu Leu Leu Leu Leu Phe Leu
    50                  55                  60

Ile Leu Arg His Arg Arg Gln Gly Lys His Trp Thr Ser Thr Gln Arg
65                  70                  75                  80

Lys Ala Asp Phe Gln His Pro Ala Gly Ala Val Gly Pro Glu Pro Thr
                85                  90                  95

Asp Arg Gly Leu Gln Trp Arg Ser Ser Pro Ala Ala Asp Ala Gln Glu
            100                 105                 110

Glu Asn Leu Tyr Ala Ala Val Lys His Thr Gln Pro Glu Asp Gly Val
        115                 120                 125

Glu Met Asp Thr Arg Ser Pro His Asp Glu Asp Pro Gln Ala Val Thr
    130                 135                 140

Tyr Ala Glu Val Lys His Ser Arg Pro Arg Arg Glu Met Ala Ser Pro
145                 150                 155                 160

Pro Ser Pro Leu Ser Gly Glu Phe Leu Asp Thr Lys Asp Arg Gln Ala
                165                 170                 175

Glu Glu Asp Arg Gln Met Asp Thr Glu Ala Ala Ala Ser Glu Ala Pro
```

-continued

```
            180                 185                 190

Gln Asp Val Thr Tyr Ala Gln Leu His Ser Leu Thr Leu Arg Arg Glu
        195                 200                 205

Ala Thr Glu Pro Pro Pro Ser Gln Glu Gly Pro Ser Pro Ala Val Pro
    210                 215                 220

Ser Ile Tyr Ala Thr Leu Ala Ile His
225                 230


<210> SEQ ID NO 84
<211> LENGTH: 63
<212> TYPE: PRT
<213> ORGANISM: Artificial Sequence
<220> FEATURE:
<223> OTHER INFORMATION: LILRB1 hinge domain

<400> SEQUENCE: 84

Tyr Gly Ser Gln Ser Ser Lys Pro Tyr Leu Leu Thr His Pro Ser Asp
1               5                   10                  15

Pro Leu Glu Leu Val Val Ser Gly Pro Ser Gly Gly Pro Ser Ser Pro
            20                  25                  30

Thr Thr Gly Pro Thr Ser Thr Ser Gly Pro Glu Asp Gln Pro Leu Thr
        35                  40                  45

Pro Thr Gly Ser Asp Pro Gln Ser Gly Leu Gly Arg His Leu Gly
    50                  55                  60


<210> SEQ ID NO 85
<211> LENGTH: 23
<212> TYPE: PRT
<213> ORGANISM: Artificial Sequence
<220> FEATURE:
<223> OTHER INFORMATION: LILRB1 transmembrane domain

<400> SEQUENCE: 85

Val Val Ile Gly Ile Leu Val Ala Val Ile Leu Leu Leu Leu Leu Leu
1               5                   10                  15

Leu Leu Leu Phe Leu Ile Leu
            20


<210> SEQ ID NO 86
<211> LENGTH: 237
<212> TYPE: PRT
<213> ORGANISM: Artificial Sequence
<220> FEATURE:
<223> OTHER INFORMATION: MSLN binding domain

<400> SEQUENCE: 86

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Gly Trp Asp Phe Asp Tyr Trp Gly Gln Gly Thr Leu Val Thr
            100                 105                 110
```

```
Val Ser Ser Gly Gly Gly Gly Ser Gly Gly Gly Gly Ser Gly Gly Gly
        115                 120                 125

Gly Ser Gly Gly Asp Ile Val Met Thr Gln Ser Ser Ser Leu Ser Ala
    130                 135                 140

Ser Val Gly Asp Arg Val Thr Ile Thr Cys Arg Ala Ser Gln Ser Ile
145                 150                 155                 160

Arg Tyr Tyr Leu Ser Trp Tyr Gln Gln Lys Pro Gly Lys Ala Pro Lys
                165                 170                 175

Leu Leu Ile Tyr Thr Ala Ser Ile Leu Gln Asn Gly Val Pro Ser Arg
            180                 185                 190

Phe Ser Gly Ser Gly Ser Gly Thr Asp Phe Thr Leu Thr Ile Ser Ser
        195                 200                 205

Leu Gln Pro Glu Asp Phe Ala Thr Tyr Tyr Cys Leu Gln Thr Tyr Thr
    210                 215                 220

Thr Pro Asp Phe Gly Pro Gly Thr Lys Val Glu Ile Lys
225                 230                 235
```

<210> SEQ ID NO 87
<211> LENGTH: 711
<212> TYPE: DNA
<213> ORGANISM: Artificial Sequence
<220> FEATURE:
<223> OTHER INFORMATION: MSLN binding domain

<400> SEQUENCE: 87

```
caggtgcagc tggtgcagtc tggggctgag gtggagaagc ctggggcctc agtgaaggtc     60

tcctgcaagg cttctggata caccttcacc gactactata tgcactgggt gcgacaggcc    120

cctggacaag ggcttgagtg gatgggatgg atcaacccta acagtggtgg cacaaactat    180

gcacagaagt ttcagggcag ggtcaccatg accagggaca cgtccatcag cacagcctac    240

atggagctga gcaggctgag atctgacgac acggccgtgt attactgtgc gtctggctgg    300

gactttgact actggggcca gggaaccctg gtcaccgtgt cctcaggcgg aggtggaagc    360

ggagggggag gatctggcgg cggaggaagc ggaggcgaca tcgtgatgac ccagtcttcc    420

tccctgtctg catctgtcgg agacagagtc accatcactt gccgggccag tcagagcatt    480

aggtactatt taagttggta tcagcagaaa ccaggaaaag cccctaagct cctgatctat    540

actgcatcca ttttacaaaa tggggtccca tcaaggttca gtggcagtgg atctgggaca    600

gatttcactc tcaccatcag cagcctgcaa cctgaggatt ttgcaactta ttactgcctc    660

cagacttaca ctactccgga ctttggccca gggaccaagg tggaaatcaa a             711
```

<210> SEQ ID NO 88
<211> LENGTH: 246
<212> TYPE: PRT
<213> ORGANISM: Artificial Sequence
<220> FEATURE:
<223> OTHER INFORMATION: MSLN binding domain

<400> SEQUENCE: 88

```
Gln Val Gln Leu Val Gln Ser Gly Ala Glu Val Arg Ala Pro Gly Ala
1               5                   10                  15

Ser Val Lys Ile Ser Cys Lys Ala Ser Gly Phe Thr Phe Arg Gly Tyr
            20                  25                  30

Tyr Ile His Trp Val Arg Gln Ala Pro Gly Gln Gly Leu Glu Trp Met
        35                  40                  45

Gly Ile Ile Asn Pro Ser Gly Gly Ser Arg Ala Tyr Ala Gln Lys Phe
```

```
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Met Tyr Tyr Cys
                85                  90                  95

Ala Arg Thr Ala Ser Cys Gly Gly Asp Cys Tyr Tyr Leu Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gly Gly Asp Ile Gln Met Thr
    130                 135                 140

Gln Ser Pro Pro Thr Leu Ser Ala Ser Val Gly Asp Arg Val Thr Ile
145                 150                 155                 160

Thr Cys Arg Ala Ser Glu Asn Val Asn Ile Trp Leu Ala Trp Tyr Gln
                165                 170                 175

Gln Lys Pro Gly Lys Ala Pro Lys Leu Leu Ile Tyr Lys Ser Ser Ser
            180                 185                 190

Leu Ala Ser Gly Val Pro Ser Arg Phe Ser Gly Ser Gly Ser Gly Ala
        195                 200                 205

Glu Phe Thr Leu Thr Ile Ser Ser Leu Gln Pro Asp Asp Phe Ala Thr
    210                 215                 220

Tyr Tyr Cys Gln Gln Tyr Gln Ser Tyr Pro Leu Thr Phe Gly Gly Gly
225                 230                 235                 240

Thr Lys Val Glu Ile Lys
                245


<210> SEQ ID NO 89
<211> LENGTH: 738
<212> TYPE: DNA
<213> ORGANISM: Artificial Sequence
<220> FEATURE:
<223> OTHER INFORMATION: MSLN binding domain

<400> SEQUENCE: 89

caggtgcagc tggtgcagtc tggggctgag gtgagggcac ctggggcctc agtgaagatt     60

tcctgcaagg cttctggatt caccttcaga ggctactata tccactgggt gcgacaggcc    120

cctggacaag ggcttgagtg gatgggaatc atcaacccta gtggtggtag cagagcctac    180

gcacagaagt tccagggcag ggtcaccatg accagggaca cttccacgag cacagtctac    240

atggagctga gcagcctgag atctgacgac acggccatgt attactgtgc gagaaccgca    300

agttgtggtg gtgactgcta ctaccttgac tactggggcc agggaaccct ggtcaccgtg    360

tcctcaggcg gaggtggaag cggaggggga ggatctggcg gcggaggaag cggaggcgac    420

atccagatga cccagtctcc tcccaccctg tctgcatctg taggagacag agtcaccatc    480

acttgccggg ccagtgagaa tgttaatatc tggttggcct ggtatcagca gaaaccaggg    540

aaagccccta agctcctgat ctataagtca tccagtttag caagtggggt cccatcaagg    600

ttcagtggca gtggatctgg ggcagaattc actctcacca tcagcagcct gcagcctgat    660

gattttgcaa cttattactg ccaacagtat caaagttacc ccctcacttt cggcggaggg    720

accaaggtgg aaatcaaa                                                  738


<210> SEQ ID NO 90
<211> LENGTH: 242
<212> TYPE: PRT
<213> ORGANISM: Artificial Sequence
```

<220> FEATURE:
<223> OTHER INFORMATION: MSLN binding domain

<400> SEQUENCE: 90

Gln Val Gln Leu Val Gln Ser Gly Ala Glu Val Lys Lys Pro Gly Ala
1 5 10 15

Ser Val Lys Val Ser Cys Lys Ala Ser Gly Tyr Ser Phe Thr Gly Tyr
20 25 30

Thr Met Asn Trp Val Arg Gln Ala Pro Gly Gln Arg Leu Glu Trp Met
35 40 45

Gly Leu Ile Thr Pro Tyr Asn Gly Ala Ser Ser Tyr Asn Gln Lys Phe
50 55 60

Arg Gly Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Gly Gly Tyr Asp Gly Arg Gly Phe Asp Tyr Trp Gly Gln Gly
100 105 110

Thr Thr Val Thr Val Ser Ser Gly Gly Gly Gly Ser Gly Gly Gly Gly
115 120 125

Ser Gly Gly Gly Gly Ser Gly Gly Asp Ile Gln Met Thr Gln Ser Pro
130 135 140

Ser Ser Leu Ser Ala Ser Val Gly Asp Arg Val Thr Ile Thr Cys Ser
145 150 155 160

Ala Ser Ser Ser Val Ser Tyr Met His Trp Tyr Gln Gln Lys Pro Gly
165 170 175

Lys Ala Pro Lys Arg Leu Ile Tyr Asp Thr Ser Lys Leu Ala Ser Gly
180 185 190

Val Pro Ser Arg Phe Ser Gly Ser Gly Ser Gly Thr Glu Phe Thr Leu
195 200 205

Thr Ile Ser Ser Leu Gln Pro Glu Asp Phe Ala Thr Tyr Tyr Cys Gln
210 215 220

Gln Trp Ser Gly Tyr Pro Leu Thr Phe Gly Gln Gly Thr Lys Leu Glu
225 230 235 240

Ile Lys

<210> SEQ ID NO 91
<211> LENGTH: 726
<212> TYPE: DNA
<213> ORGANISM: Artificial Sequence
<220> FEATURE:
<223> OTHER INFORMATION: MSLN binding domain

<400> SEQUENCE: 91
caggtgcagc tggtgcagtc tggggctgag gtgaagaagc ctggggcctc agtgaaggtt 60
tcctgcaagg cttctggata ctcattcacc ggctacacca tgaactgggt gaggcaggcc 120
cctggacaaa gacttgagtg gatgggactt atcacccctt acaatggtgc ttctagctac 180
aaccagaagt tcaggggcag ggtcacaatc actagagaca cgtcagccag cacagcctac 240
atggagctct ccagcctgag atctgaagac actgcagtct attactgtgc aagggggggt 300
tacgacggga ggggttttga ctactggggc cagggaacca cggtcaccgt gtcctcaggc 360
ggaggtggaa gcggaggggg aggatctggc ggcggaggaa gcggaggcga catccagatg 420
acccagtctc cttcaagctt gtctgcatct gtaggagaca gggtcaccat cacttgcagt 480
gccagctcaa gtgtaagtta catgcactgg tatcagcaga aaccaggcaa ggcccctaag 540

```
agattgatct atgacacatc caaattagca agtggggtcc caagtcgctt cagtggcagt    600

ggatctggga ccgaattcac tctcaccatc agcagcttgc agcctgagga ttttgcaact    660

tattactgcc agcagtggag tggttaccct ctcacgttcg gtcaggggac aaagttggaa    720

atcaaa                                                               726
```

<210> SEQ ID NO 92
<211> LENGTH: 242
<212> TYPE: PRT
<213> ORGANISM: Artificial Sequence
<220> FEATURE:
<223> OTHER INFORMATION: MSLN binding domain

<400> SEQUENCE: 92

```
Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95

Ala Arg Gly Gly Tyr Asp Gly Arg Gly Phe Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Gly Gly Asp Ile Glu Leu Thr Gln Ser Pro
    130                 135                 140

Ala Ile Met Ser Ala Ser Pro Gly Glu Lys Val Thr Met Thr Cys Ser
145                 150                 155                 160

Ala Ser Ser Ser Val Ser Tyr Met His Trp Tyr Gln Gln Lys Ser Gly
                165                 170                 175

Thr Ser Pro Lys Arg Trp Ile Tyr Asp Thr Ser Lys Leu Ala Ser Gly
            180                 185                 190

Val Pro Gly Arg Phe Ser Gly Ser Gly Ser Gly Asn Ser Tyr Ser Leu
        195                 200                 205

Thr Ile Ser Ser Val Glu Ala Glu Asp Asp Ala Thr Tyr Tyr Cys Gln
    210                 215                 220

Gln Trp Ser Gly Tyr Pro Leu Thr Phe Gly Ala Gly Thr Lys Leu Glu
225                 230                 235                 240

Ile Lys
```

<210> SEQ ID NO 93
<211> LENGTH: 726
<212> TYPE: DNA
<213> ORGANISM: Artificial Sequence
<220> FEATURE:
<223> OTHER INFORMATION: MSLN binding domain

<400> SEQUENCE: 93

```
caggtgcagc tgcagcagtc tgggcctgag ctggagaagc ctggggcctc agtgaagatt     60

tcctgcaagg cttctggata ctcattcacc ggctacacca tgaactgggt gaagcagagc    120
```

-continued

```
catggaaaaa gccttgagtg gattggactt atcacccctt acaatggtgc ttctagctac    180

aaccagaagt tcaggggcaa ggccacatta actgtagaca agtcatccag cacagcctac    240

atggacctcc tcagcctgac atctgaagac tctgcagtct atttctgtgc aagggggggt    300

tacgacggga ggggttttga ctactggggc cagggaacca cggtcaccgt gtcctcaggc    360

ggaggtggaa gcggaggggg aggatctggc ggcggaggaa gcggaggcga catcgagctc    420

acccagtctc ctgcaatcat gtctgcatct ccaggagaga aggtcaccat gacttgcagt    480

gccagctcaa gtgtaagtta catgcactgg tatcagcaga aatcaggcac ctcccctaag    540

agatggatct atgacacatc caaattggca agtggggtcc caggtcgctt cagtggcagt    600

ggatctggga actcttactc tctcaccatc agcagcgtgg aggctgagga tgatgcaact    660

tattactgcc agcagtggag tggttaccct ctcacgttcg gtgctgggac aaagttggaa    720

atcaaa                                                               726


<210> SEQ ID NO 94
<211> LENGTH: 243
<212> TYPE: PRT
<213> ORGANISM: Artificial Sequence
<220> FEATURE:
<223> OTHER INFORMATION: CEA binding domain

<400> SEQUENCE: 94

Gln Val Gln Leu Gln Gln Ser Gly Ala Glu Leu Val Arg Ser Gly Thr
1               5                   10                  15

Ser Val Lys Leu Ser Cys Thr Ala Ser Gly Phe Asn Ile Lys Asp Ser
            20                  25                  30

Tyr Met His Trp Leu Arg Gln Gly Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Thr Val Thr Val Ser Ser Gly Gly Gly Gly Ser Gly Gly Gly
        115                 120                 125

Gly Ser Gly Gly Gly Gly Ser Gly Gly Glu Asn Val Leu Thr Gln Ser
    130                 135                 140

Pro Ala Ile Met Ser Ala Ser Pro Gly Glu Lys Val Thr Ile Thr Cys
145                 150                 155                 160

Ser Ala Ser Ser Ser Val Ser Tyr Met His Trp Phe Gln Gln Lys Pro
                165                 170                 175

Gly Thr Ser Pro Lys Leu Trp Ile Tyr Ser Thr Ser Asn Leu Ala Ser
            180                 185                 190

Gly Val Pro Ala Arg Phe Ser Gly Ser Gly Ser Gly Thr Ser Tyr Ser
        195                 200                 205

Leu Thr Ile Ser Arg Met Glu Ala Glu Asp Ala Ala Thr Tyr Tyr Cys
    210                 215                 220

Gln Gln Arg Ser Ser Tyr Pro Leu Thr Phe Gly Ala Gly Thr Lys Leu
225                 230                 235                 240

Glu Leu Lys
```

<210> SEQ ID NO 95
<211> LENGTH: 729
<212> TYPE: DNA
<213> ORGANISM: Artificial Sequence
<220> FEATURE:
<223> OTHER INFORMATION: CEA binding domain

<400> SEQUENCE: 95
caggtccagc tgcagcagtc tggggcagag cttgtgaggt cagggacctc agtcaagttg 60
tcctgcacag cttctggctt caacattaaa gactcctata tgcactggtt gaggcagggg 120
cctgaacagg gcctggagtg gattggatgg attgatcctg agaatggtga tactgaatat 180
gccccgaagt tccagggcaa ggccactttt actacagaca catcctccaa cacagcctac 240
ctgcagctca gcagcctgac atctgaggac actgccgtct attactgtaa tgaagggaca 300
ccgacagggc catactattt tgactactgg ggtcaaggaa ccacagtcac cgtgtcctca 360
ggcggaggtg gaagcggagg gggaggatct ggcggcggag gaagcggagg cgagaacgtt 420
ctcacccagt ctccagcaat catgtctgca tctccagggg agaaggtcac cataacctgc 480
agtgccagct caagtgtaag ttacatgcac tggttccagc agaagccagg cacttctccc 540
aaactctgga tttatagcac atccaacctg gcttctggag tccctgctcg cttcagtggc 600
agtggatctg ggacctctta ctctctcaca atcagccgaa tggaggctga agatgctgcc 660
acttattact gccagcaaag gagtagttac ccgctcacgt tcggtgctgg gaccaagctg 720
gagctgaaa 729

<210> SEQ ID NO 96
<211> LENGTH: 243
<212> TYPE: PRT
<213> ORGANISM: Artificial Sequence
<220> FEATURE:
<223> OTHER INFORMATION: CEA binding domain

<400> SEQUENCE: 96

Gln Val Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Ser
20 25 30

Tyr Met His Trp Val Arg Gln Ala Pro Gly Gln Gly Leu Glu Trp Met
35 40 45

Gly Trp Ile Asp Pro Glu Asn Gly Asp Thr Glu Tyr Ala Pro Lys Phe
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Asn Glu Gly Thr Pro Thr Gly Pro Tyr Tyr Phe Asp Tyr Trp Gly Gln
100 105 110

Gly Thr Thr Val Thr Val Ser Ser Gly Gly Gly Gly Ser Gly Gly Gly
115 120 125

Gly Ser Gly Gly Gly Gly Ser Gly Gly Glu Ile Val Leu Thr Gln Ser
130 135 140

Pro Ala Thr Leu Ser Leu Ser Pro Gly Glu Arg Ala Thr Leu Ser Cys
145 150 155 160

Ser Ala Ser Ser Ser Val Ser Tyr Met His Trp Tyr Gln Gln Lys Pro
165 170 175

```
Gly Leu Ala Pro Arg Leu Leu Ile Tyr Ser Thr Ser Asn Leu Ala Ser
            180                 185                 190

Gly Ile Pro Asp Arg Phe Ser Gly Ser Gly Ser Gly Thr Asp Phe Thr
        195                 200                 205

Leu Thr Ile Ser Arg Leu Glu Pro Glu Asp Phe Ala Val Tyr Tyr Cys
    210                 215                 220

Gln Gln Arg Ser Ser Tyr Pro Leu Thr Phe Gly Gln Gly Thr Lys Leu
225                 230                 235                 240

Glu Ile Lys
```

<210> SEQ ID NO 97
<211> LENGTH: 729
<212> TYPE: DNA
<213> ORGANISM: Artificial Sequence
<220> FEATURE:
<223> OTHER INFORMATION: CEA binding domain

<400> SEQUENCE: 97

```
caggtccagc tggtgcagtc tggggcagag gtgaagaaac caggggcctc agtcaaggtg     60

tcctgcaaag cttctggctt caacattaaa gactcctata tgcactgggt gaggcaggcg    120

cctggacagg gcctggagtg gatgggatgg attgatcctg agaatggtga tactgaatat    180

gccccgaagt tccagggcag ggtcactatg actacagaca catccacctc cacagcctac    240

atggagctca ggagcctgag atctgacgac actgccgtct attactgtaa tgaagggaca    300

ccgacagggc catactattt tgactactgg ggtcaaggaa ccacagtcac cgtgtcctca    360

ggcggaggtg gaagcggagg gggaggatct ggcggcggag gaagcggagg cgagatcgtt    420

ctcacccagt ctccagcaac cttgtctctg tctccagggg agagggccac cctaagctgc    480

agtgccagct caagtgtaag ttacatgcac tggtaccagc agaagccagg ccttgctccc    540

agactcctga tttatagcac atccaacctg gcttctggaa tccctgatcg cttcagtggc    600

agtggatctg ggaccgattt cactctcaca atcagccgac tggagcctga agatttcgcc    660

gtttattact gccagcaaag gagtagttac ccgctcacgt tcggtcaggg gaccaagctg    720

gagatcaaa                                                            729
```

<210> SEQ ID NO 98
<211> LENGTH: 243
<212> TYPE: PRT
<213> ORGANISM: Artificial Sequence
<220> FEATURE:
<223> OTHER INFORMATION: CEA binding domain

<400> SEQUENCE: 98

```
Glu Val Gln Leu Ala Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asp
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

-continued

Ala Lys Ser Asn Glu Phe Leu Phe Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gly Gly Ser Ser Glu Leu Thr Gln Asp Pro Ala Val
    130                 135                 140

Ser Val Ala Leu Gly Gln Thr Val Arg Ile Thr Cys Gln Gly Asp Ser
145                 150                 155                 160

Leu Arg Ser Ser Tyr Ala Ser Trp Tyr Arg Gln Arg Pro Gly Gln Ala
                165                 170                 175

Pro Val Leu Val Ile Tyr Gly Lys Asn Asn Arg Pro Ser Gly Ile Pro
            180                 185                 190

Asp Arg Phe Ser Gly Ser Ser Ser Gly Asn Thr Ala Ser Leu Thr Ile
        195                 200                 205

Thr Gly Ala Gln Ala Glu Asp Glu Ala Asp Tyr Tyr Trp Asn Ser Ser
    210                 215                 220

Tyr Ala Trp Leu Pro Tyr Val Val Phe Gly Gly Gly Thr Lys Leu Thr
225                 230                 235                 240

Val Leu Gly

<210> SEQ ID NO 99
<211> LENGTH: 729
<212> TYPE: DNA
<213> ORGANISM: Artificial Sequence
<220> FEATURE:
<223> OTHER INFORMATION: CEA binding domain

<400> SEQUENCE: 99
gaggtgcagc tggcggagtc tgggggaggc ttggtacagc ctgggggtc cctgagactc 60 tcctgtgcag cctctggatt cacctttagc agcgatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaggac acggccgtgt attactgtgc aaagtctaat 300
gagtttcttt ttgactactg gggccaaggt accctggtca ccgtgtcgag tggcggaggt 360
ggaagcggag gggaggatc tggcggcgga ggaagcggag gctcttctga gctgactcag 420
gaccctgctg tgtctgtggc cttgggacag acagtcagga tcacatgcca aggagacagc 480
ctcagaagct cttatgcaag ctggtaccgg cagaggccag gacaggcccc tgtacttgtc 540
atctatggta aaaacaaccg gccctcaggg atcccagacc gattctctgg ctccagctca 600
ggaaacacag cttccttgac catcactggg gctcaggcgg aagatgaggc tgactattac 660
tggaactcca gctacgcttg gctgccctac gtggtattcg gcggagggac caagctgacc 720
gtcctaggt 729

<210> SEQ ID NO 100
<211> LENGTH: 243
<212> TYPE: PRT
<213> ORGANISM: Artificial Sequence
<220> FEATURE:
<223> OTHER INFORMATION: CEA binding domain

<400> SEQUENCE: 100

Gln Val Gln Leu Glu Gln Ser Gly Ala Gly Val Val Lys Pro Gly Ala
1               5                   10                  15

Ser Val Lys Leu Ser Cys Lys Ala Ser Gly Phe Asn Ile Lys Asp Ser

-continued

```
            20                  25                  30

Tyr Met His Trp Leu Arg Gln Gly Pro Gly Gln Arg Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ala Asn Thr Ala Tyr
65                  70                  75                  80

Leu Gly Leu Ser Ser Leu Arg Pro Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Glu Asn Val Leu Thr Gln Ser
    130                 135                 140

Pro Ser Ser Met Ser Val Ser Val Gly Asp Arg Val Asn Ile Ala Cys
145                 150                 155                 160

Ser Ala Ser Ser Ser Val Pro Tyr Met His Trp Leu Gln Gln Lys Pro
                165                 170                 175

Gly Lys Ser Pro Lys Leu Leu Ile Tyr Leu Thr Ser Asn Leu Ala Ser
            180                 185                 190

Gly Val Pro Ser Arg Phe Ser Gly Ser Gly Ser Gly Thr Asp Tyr Ser
        195                 200                 205

Leu Thr Ile Ser Ser Val Gln Pro Glu Asp Ala Ala Thr Tyr Tyr Cys
    210                 215                 220

Gln Gln Arg Ser Ser Tyr Pro Leu Thr Phe Gly Gly Gly Thr Lys Leu
225                 230                 235                 240

Glu Ile Lys
```

<210> SEQ ID NO 101
<211> LENGTH: 729
<212> TYPE: DNA
<213> ORGANISM: Artificial Sequence
<220> FEATURE:
<223> OTHER INFORMATION: CEA binding domain

<400> SEQUENCE: 101

```
caggtccagc tggagcagtc tggggcaggg gttgtgaagc caggggcctc agtcaagttg     60

tcctgcaaag cttctggctt caacattaaa gactcctata tgcactggtt gaggcagggg    120

cctggacagc gcctggagtg gattggatgg attgatcctg agaatggtga tactgaatat    180

gccccgaagt tccagggcaa ggccactttt actacagaca catccgccaa cacagcctac    240

ctggggctca gcagcctgag acctgaggac actgccgtct attactgtaa tgaagggaca    300

ccgacagggc catactattt tgactactgg ggtcaaggaa ccctagtcac cgtgtcctca    360

ggcggaggtg gaagcggagg gggaggatct ggcggcggag gaagcggagg cgagaacgtt    420

ctcacccagt ctccaagctc tatgtctgta tctgtcgggg acagggtcaa catcgcctgc    480

agtgccagct caagtgtacc ttacatgcac tggctccagc agaagccagg caaatctccc    540

aaactcctga tttatctcac atccaacctg gcttctggag tccctagccg cttcagtggc    600

agtggatctg ggaccgatta ctctctcaca atcagctcag tgcagcctga agatgctgcc    660

acttattact gccagcaaag gagtagttac ccgctcacgt tcggtggtgg gaccaagctg    720

gagatcaaa                                                            729
```

<210> SEQ ID NO 102
<211> LENGTH: 249
<212> TYPE: PRT
<213> ORGANISM: Artificial Sequence
<220> FEATURE:
<223> OTHER INFORMATION: EGFR ScFv

<400> SEQUENCE: 102

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Thr Met Val Arg Gly Val Met Lys Asp Tyr Phe
            100                 105                 110

Asp Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gly Gly Ala Ile
    130                 135                 140

Gln Leu Thr Gln Ser Pro Ser Ser Leu Ser Ala Ser Val Gly Asp Arg
145                 150                 155                 160

Val Thr Ile Thr Cys Arg Ala Ser Gln Asp Ile Ser Ser Ala Leu Val
                165                 170                 175

Trp Tyr Gln Gln Lys Pro Gly Lys Ala Pro Lys Leu Leu Ile Tyr Asp
            180                 185                 190

Ala Ser Ser Leu Glu Ser Gly Val Pro Ser Arg Phe Ser Gly Ser Glu
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gln Gln Phe Asn Ser Tyr Pro Leu Thr Phe
225                 230                 235                 240

Gly Gly Gly Thr Lys Val Glu Ile Lys
                245
```

<210> SEQ ID NO 103
<211> LENGTH: 747
<212> TYPE: DNA
<213> ORGANISM: Artificial Sequence
<220> FEATURE:
<223> OTHER INFORMATION: EGFR ScFv

<400> SEQUENCE: 103

```
caggtgcagc tggtggagtc tgggggaggc gtggtccagc ctgggaggtc cctgagactc     60

tcctgtgcag cgtctggatt caccttcagt acctatggca tgcactgggt ccgccaggct    120

ccaggcaagg ggctggagtg ggtggcagtt atatgggatg atggaagtta taaatactat    180

ggagactccg tgaagggccg attcaccatc tccagagaca attccaagaa cacgctgtat    240

ctgcaaatga acagcctgag agccgaggac acggctgtgt attactgtgc gagagatggt    300

attactatgg ttcggggagt tatgaaggac tactttgact actggggcca gggaaccctg    360
```

```
gtcaccgtct cctcaggcgg aggtggaagc ggagggggag gatctggcgg cggaggaagc    420

ggaggcgcca tccagttgac ccagtctcca tcctccctgt ctgcatctgt aggagacaga    480

gtcaccatca cttgccgggc aagtcaggac attagcagtg ctttagtctg gtatcagcag    540

aaaccaggga aagctcctaa gctcctgatc tatgatgcct ccagtttgga aagtggggtc    600

ccatcaaggt tcagcggcag tgaatctggg acagatttca ctctcaccat cagcagcctg    660

cagcctgaag attttgcaac ttattactgt caacagttta atagttaccc gctcactttc    720

ggcggaggga ccaaggtgga gatcaaa                                         747
```

<210> SEQ ID NO 104
<211> LENGTH: 249
<212> TYPE: PRT
<213> ORGANISM: Artificial Sequence
<220> FEATURE:
<223> OTHER INFORMATION: EGFR ScFv

<400> SEQUENCE: 104

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Ala
            20                  25                  30

Leu Val Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Glu Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gly Gly Gln Val Gln Leu
        115                 120                 125

Val Glu Ser Gly Gly Gly Val Val Gln Pro Gly Arg Ser Leu Arg Leu
    130                 135                 140

Ser Cys Ala Ala Ser Gly Phe Thr Phe Ser Thr Tyr Gly Met His Trp
145                 150                 155                 160

Val Arg Gln Ala Pro Gly Lys Gly Leu Glu Trp Val Ala Val Ile Trp
                165                 170                 175

Asp Asp Gly Ser Tyr Lys Tyr Tyr Gly Asp Ser Val Lys Gly Arg Phe
            180                 185                 190

Thr Ile Ser Arg Asp Asn Ser Lys Asn Thr Leu Tyr Leu Gln Met Asn
        195                 200                 205

Ser Leu Arg Ala Glu Asp Thr Ala Val Tyr Tyr Cys Ala Arg Asp Gly
    210                 215                 220

Ile Thr Met Val Arg Gly Val Met Lys Asp Tyr Phe Asp Tyr Trp Gly
225                 230                 235                 240

Gln Gly Thr Leu Val Thr Val Ser Ser
                245
```

<210> SEQ ID NO 105
<211> LENGTH: 747
<212> TYPE: DNA
<213> ORGANISM: Artificial Sequence
<220> FEATURE:

<223> OTHER INFORMATION: EGFR ScFv

<400> SEQUENCE: 105

```
gccatccagt tgacccagtc tccatcctcc ctgtctgcat ctgtaggaga cagagtcacc     60
atcacttgcc gggcaagtca ggacattagc agtgctttag tctggtatca gcagaaacca    120
gggaaagctc ctaagctcct gatctatgat gcctccagtt tggaaagtgg ggtcccatca    180
aggttcagcg gcagtgaatc tgggacagat ttcactctca ccatcagcag cctgcagcct    240
gaagattttg caacttatta ctgtcaacag tttaatagtt acccgctcac tttcggcgga    300
gggaccaagg tggagatcaa aggcggaggt ggaagcggag ggggaggatc tggcggcgga    360
ggaagcggag gccaggtgca gctggtggag tctgggggag gcgtggtcca gcctgggagg    420
tccctgagac tctcctgtgc agcgtctgga ttcaccttca gtacctatgg catgcactgg    480
gtccgccagg ctccaggcaa ggggctggag tgggtggcag ttatatggga tgatggaagt    540
tataaatact atggagactc cgtgaagggc cgattcacca tctccagaga caattccaag    600
aacacgctgt atctgcaaat gaacagcctg agagccgagg acacggctgt gtattactgt    660
gcgagagatg gtattactat ggttcgggga gttatgaagg actactttga ctactggggc    720
cagggaaccc tggtcaccgt ctcctca                                        747
```

<210> SEQ ID NO 106
<211> LENGTH: 247
<212> TYPE: PRT
<213> ORGANISM: Artificial Sequence
<220> FEATURE:
<223> OTHER INFORMATION: EGFR ScFv

<400> SEQUENCE: 106

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Glu Tyr
            20                  25                  30

Pro Ile His Trp Val Lys Gln Ala Pro Gly Lys Gly Phe Lys Trp Met
        35                  40                  45

Gly Met Ile Tyr Thr Asp Ile Gly Lys Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Val Arg Asp Arg Tyr Asp Ser Leu Phe Asp Tyr Trp Gly Gln Gly Thr
            100                 105                 110

Thr Leu Thr Val Ser Ser Gly Gly Gly Gly Ser Gly Gly Gly Gly Ser
        115                 120                 125

Gly Gly Gly Gly Ser Gly Gly Asp Val Val Met Thr Gln Thr Pro Leu
    130                 135                 140

Ser Leu Pro Val Ser Leu Gly Asp Gln Ala Ser Ile Ser Cys Arg Ser
145                 150                 155                 160

Ser Gln Ser Leu Val His Ser Asn Gly Asn Thr Tyr Leu His Trp Tyr
                165                 170                 175

Leu Gln Lys Pro Gly Gln Ser Pro Lys Leu Leu Ile Tyr Lys Val Ser
            180                 185                 190

Asn Arg Phe Ser Gly Val Pro Asp Arg Phe Ser Gly Ser Gly Ser Gly
        195                 200                 205
```

```
Thr Asp Phe Thr Leu Lys Ile Ser Arg Val Glu Ala Glu Asp Leu Gly
    210                 215                 220

Val Tyr Phe Cys Ser Gln Ser Thr His Val Pro Trp Thr Phe Gly Gly
225                 230                 235                 240

Gly Thr Lys Leu Glu Ile Lys
                245


<210> SEQ ID NO 107
<211> LENGTH: 741
<212> TYPE: DNA
<213> ORGANISM: Artificial Sequence
<220> FEATURE:
<223> OTHER INFORMATION: EGFR ScFv

<400> SEQUENCE: 107

cagatccagt tggtgcagtc tggacctgag ctgaagaagc ctggagagac agtcaagatc      60

tcctgcaagg cctctgggta taccttcaca gaatatccaa tacactgggt gaagcaggct     120

ccaggaaagg gtttcaagtg gatgggcatg atatacaccg acattggaaa gccaacatat     180

gctgaagagt tcaagggacg gtttgccttc tctttggaga cctctgccag cactgcctat     240

ttgcagatca acaacctcaa gaatgaggac acggctacat atttctgtgt aagagatcga     300

tatgattccc tctttgacta ctggggccaa ggcaccactc tcacagtctc ctcaggcgga     360

ggtggaagcg gagggggagg atctggcggc ggaggaagcg gaggcgatgt tgtgatgacc     420

caaactccac tctccctgcc tgtcagtctt ggagatcaag cctccatctc ttgcagatct     480

agtcagagcc ttgtacacag taatggaaac acctatttac attggtacct gcagaagcca     540

ggccagtctc caaagctcct gatctacaaa gtttccaacc gattttctgg ggtcccagac     600

aggttcagtg gcagtggatc agggacagat ttcacactca agatcagcag agtggaggct     660

gaggatctgg gagtttattt ctgctctcaa agtacacatg ttccgtggac gttcggtgga     720

ggcaccaagc tggaaatcaa a                                               741


<210> SEQ ID NO 108
<211> LENGTH: 247
<212> TYPE: PRT
<213> ORGANISM: Artificial Sequence
<220> FEATURE:
<223> OTHER INFORMATION: EGFR ScFv

<400> SEQUENCE: 108

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Gly Gly Gly Gly Ser Gly Gly Gly Gly Ser Gly Gly Gly Gly Ser Gly
        115                 120                 125
```

-continued

```
Gly Gln Ile Gln Leu Val Gln Ser Gly Pro Glu Leu Lys Lys Pro Gly
    130                 135                 140

Glu Thr Val Lys Ile Ser Cys Lys Ala Ser Gly Tyr Thr Phe Thr Glu
145                 150                 155                 160

Tyr Pro Ile His Trp Val Lys Gln Ala Pro Gly Lys Gly Phe Lys Trp
                165                 170                 175

Met Gly Met Ile Tyr Thr Asp Ile Gly Lys Pro Thr Tyr Ala Glu Glu
            180                 185                 190

Phe Lys Gly Arg Phe Ala Phe Ser Leu Glu Thr Ser Ala Ser Thr Ala
        195                 200                 205

Tyr Leu Gln Ile Asn Asn Leu Lys Asn Glu Asp Thr Ala Thr Tyr Phe
    210                 215                 220

Cys Val Arg Asp Arg Tyr Asp Ser Leu Phe Asp Tyr Trp Gly Gln Gly
225                 230                 235                 240

Thr Thr Leu Thr Val Ser Ser
                245
```

<210> SEQ ID NO 109
<211> LENGTH: 741
<212> TYPE: DNA
<213> ORGANISM: Artificial Sequence
<220> FEATURE:
<223> OTHER INFORMATION: EGFR ScFv

<400> SEQUENCE: 109

```
gatgttgtga tgacccaaac tccactctcc ctgcctgtca gtcttggaga tcaagcctcc      60

atctcttgca gatctagtca gagccttgta cacagtaatg gaaacaccta tttacattgg     120

tacctgcaga agccaggcca gtctccaaag ctcctgatct acaaagtttc caaccgattt     180

tctggggtcc cagacaggtt cagtggcagt ggatcaggga cagatttcac actcaagatc     240

agcagagtgg aggctgagga tctgggagtt tatttctgct ctcaaagtac acatgttccg     300

tggacgttcg gtggaggcac caagctggaa atcaaaggcg gaggtggaag cggaggggga     360

ggatctggcg gcggaggaag cggaggccag atccagttgg tgcagtctgg acctgagctg     420

aagaagcctg gagagacagt caagatctcc tgcaaggcct ctgggtatac cttcacagaa     480

tatccaatac actgggtgaa gcaggctcca ggaaagggtt tcaagtggat gggcatgata     540

tacaccgaca ttggaaagcc aacatatgct gaagagttca agggacggtt tgccttctct     600

ttggagacct ctgccagcac tgcctatttg cagatcaaca acctcaagaa tgaggacacg     660

gctacatatt tctgtgtaag agatcgatat gattccctct ttgactactg gggccaaggc     720

accactctca cagtctcctc a                                               741
```

<210> SEQ ID NO 110
<211> LENGTH: 249
<212> TYPE: PRT
<213> ORGANISM: Artificial Sequence
<220> FEATURE:
<223> OTHER INFORMATION: EGFR ScFv

<400> SEQUENCE: 110

```
Glu Met Gln Leu Val Glu Ser Gly Gly Gly Phe Val Lys Pro Gly Gly
1               5                   10                  15

Ser Leu Lys Leu Ser Cys Ala Ala Ser Gly Phe Ala Phe Ser His Tyr
            20                  25                  30

Asp Met Ser Trp Val Arg Gln Thr Pro Lys Gln Arg Leu Glu Trp Val
        35                  40                  45
```

```
Ala Tyr Ile Ala Ser Gly Gly Asp Ile Thr Tyr Tyr Ala Asp Thr Val
    50                  55                  60

Lys Gly Arg Phe Thr Ile Ser Arg Asp Asn Ala Gln Asn Thr Leu Tyr
65                  70                  75                  80

Leu Gln Met Ser Ser Leu Lys Ser Glu Asp Thr Ala Met Phe Tyr Cys
                85                  90                  95

Ser Arg Ser Ser Tyr Gly Asn Asn Gly Asp Ala Leu Asp Phe Trp Gly
            100                 105                 110

Gln Gly Thr Ser Val Thr Val Ser Ser Gly Gly Gly Gly Ser Gly Gly
        115                 120                 125

Gly Gly Ser Gly Gly Gly Gly Ser Gly Gly Asp Val Val Met Thr Gln
    130                 135                 140

Thr Pro Leu Ser Leu Pro Val Ser Leu Gly Asp Gln Ala Ser Ile Ser
145                 150                 155                 160

Cys Arg Ser Ser Gln Ser Leu Val His Ser Asn Gly Asn Thr Tyr Leu
                165                 170                 175

His Trp Tyr Leu Gln Lys Pro Gly Gln Ser Pro Lys Leu Leu Ile Tyr
            180                 185                 190

Lys Val Ser Asn Arg Phe Ser Gly Val Pro Asp Arg Phe Ser Gly Ser
        195                 200                 205

Gly Ser Gly Thr Asp Phe Thr Leu Lys Ile Ser Arg Val Glu Ala Glu
    210                 215                 220

Asp Leu Gly Val Tyr Phe Cys Ser Gln Ser Thr His Val Leu Thr Phe
225                 230                 235                 240

Gly Ser Gly Thr Lys Leu Glu Ile Lys
                245
```

```
<210> SEQ ID NO 111
<211> LENGTH: 747
<212> TYPE: DNA
<213> ORGANISM: Artificial Sequence
<220> FEATURE:
<223> OTHER INFORMATION: EGFR ScFv

<400> SEQUENCE: 111

gaaatgcagc tggtggagtc tgggggaggc ttcgtgaagc ctggagggtc cctgaaactc      60

tcatgtgcag cctctggatt cgctttcagt cactatgaca tgtcttgggt tcgccagact     120

ccgaagcaga ggctggagtg ggtcgcatac attgctagtg gtggtgatat cacctactat     180

gcagacactg tgaagggccg attcaccatc tccagagaca atgcccagaa caccctgtac     240

ctgcaaatga gcagtctgaa gtctgaggac acagccatgt tttactgttc acgatcctcc     300

tatggtaaca acggagatgc cctggacttc tggggtcaag gtacctcagt caccgtctcc     360

tcaggcggag gtggaagcgg agggggagga tctggcggcg gaggaagcgg aggcgatgtt     420

gtgatgaccc aaactccact ctccctgcct gtcagtcttg gagatcaagc ctccatctct     480

tgcagatcta gtcagagcct tgttcacagt aatggaaaca cctatttaca ttggtacctg     540

cagaagccag gccagtctcc aaagctcctg atctacaaag tttccaaccg attttctggg     600

gtcccagaca ggttcagtgg cagtggatca gggacagatt tcacactcaa gatcagcaga     660

gtggaggctg aggatctggg agtttatttc tgctctcaaa gtacacatgt tctcacgttc     720

ggctcgggga caaagttgga aataaaa                                         747

<210> SEQ ID NO 112
<211> LENGTH: 249
<212> TYPE: PRT
```

<213> ORGANISM: Artificial Sequence
<220> FEATURE:
<223> OTHER INFORMATION: EGFR ScFv

<400> SEQUENCE: 112

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Leu Thr Phe Gly Ser Gly Thr Lys Leu Glu Ile Lys Gly
            100                 105                 110

Gly Gly Gly Ser Gly Gly Gly Gly Ser Gly Gly Gly Gly Ser Gly Gly
        115                 120                 125

Glu Met Gln Leu Val Glu Ser Gly Gly Gly Phe Val Lys Pro Gly Gly
    130                 135                 140

Ser Leu Lys Leu Ser Cys Ala Ala Ser Gly Phe Ala Phe Ser His Tyr
145                 150                 155                 160

Asp Met Ser Trp Val Arg Gln Thr Pro Lys Gln Arg Leu Glu Trp Val
                165                 170                 175

Ala Tyr Ile Ala Ser Gly Gly Asp Ile Thr Tyr Tyr Ala Asp Thr Val
            180                 185                 190

Lys Gly Arg Phe Thr Ile Ser Arg Asp Asn Ala Gln Asn Thr Leu Tyr
        195                 200                 205

Leu Gln Met Ser Ser Leu Lys Ser Glu Asp Thr Ala Met Phe Tyr Cys
    210                 215                 220

Ser Arg Ser Ser Tyr Gly Asn Asn Gly Asp Ala Leu Asp Phe Trp Gly
225                 230                 235                 240

Gln Gly Thr Ser Val Thr Val Ser Ser
                245
```

<210> SEQ ID NO 113
<211> LENGTH: 747
<212> TYPE: DNA
<213> ORGANISM: Artificial Sequence
<220> FEATURE:
<223> OTHER INFORMATION: EGFR ScFv

<400> SEQUENCE: 113

```
gatgttgtga tgacccaaac tccactctcc ctgcctgtca gtcttggaga tcaagcctcc      60

atctcttgca gatctagtca gagccttgtt cacagtaatg gaaacaccta tttacattgg     120

tacctgcaga agccaggcca gtctccaaag ctcctgatct acaaagtttc caaccgattt     180

tctggggtcc cagacaggtt cagtggcagt ggatcaggga cagatttcac actcaagatc     240

agcagagtgg aggctgagga tctgggagtt tatttctgct ctcaaagtac acatgttctc     300

acgttcggct cggggacaaa gttggaaata aaaggcggag gtggaagcgg agggggagga     360

tctggcggcg gaggaagcgg aggcgaaatg cagctggtgg agtctggggg aggcttcgtg     420

aagcctggag ggtccctgaa actctcatgt gcagcctctg gattcgcttt cagtcactat     480
```

```
gacatgtctt gggttcgcca gactccgaag cagaggctgg agtgggtcgc atacattgct    540

agtggtggtg atatcaccta ctatgcagac actgtgaagg gccgattcac catctccaga    600

gacaatgccc agaacaccct gtacctgcaa atgagcagtc tgaagtctga ggacacagcc    660

atgttttact gttcacgatc ctcctatggt aacaacggag atgccctgga cttctggggt    720

caaggtacct cagtcaccgt ctcctca                                        747
```

```
<210> SEQ ID NO 114
<211> LENGTH: 243
<212> TYPE: PRT
<213> ORGANISM: Artificial Sequence
<220> FEATURE:
<223> OTHER INFORMATION: EGFR ScFv

<400> SEQUENCE: 114

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Gly Gly Gly Gly Ser Gly Gly Gly Gly
        115                 120                 125

Ser Gly Gly Gly Gly Ser Gly Gly Asp Ile Leu Leu Thr Gln Ser Pro
    130                 135                 140

Val Ile Leu Ser Val Ser Pro Gly Glu Arg Val Ser Phe Ser Cys Arg
145                 150                 155                 160

Ala Ser Gln Ser Ile Gly Thr Asn Ile His Trp Tyr Gln Gln Arg Thr
                165                 170                 175

Asn Gly Ser Pro Arg Leu Leu Ile Lys Tyr Ala Ser Glu Ser Ile Ser
            180                 185                 190

Gly Ile Pro Ser Arg Phe Ser Gly Ser Gly Ser Gly Thr Asp Phe Thr
        195                 200                 205

Leu Ser Ile Asn Ser Val Glu Ser Glu Asp Ile Ala Asp Tyr Tyr Cys
    210                 215                 220

Gln Gln Asn Asn Asn Trp Pro Thr Thr Phe Gly Ala Gly Thr Lys Leu
225                 230                 235                 240

Glu Leu Lys


<210> SEQ ID NO 115
<211> LENGTH: 729
<212> TYPE: DNA
<213> ORGANISM: Artificial Sequence
<220> FEATURE:
<223> OTHER INFORMATION: EGFR ScFv

<400> SEQUENCE: 115

caggtgcagc tgaagcagtc cggccccggc ctggtgcagc cctcccagtc cctgtccatc     60
```

acctgcaccg tgtccggctt ctccctgacc aactacggcg tgcactgggt gcggcagtcc 120
cccggcaagg gcctggagtg gctgggcgtg atctggtccg gcggcaacac cgactacaac 180 accccccttca cctcccggct gtccatcaac aaggacaact ccaagtccca ggtgttcttc 240
aagatgaact ccctgcagtc caacgacacc gccatctact actgcgcccg ggccctgacc 300
tactacgact acgagttcgc ctactggggc cagggcaccc tggtgaccgt gtccgccggc 360
ggaggtggaa gcggaggggg aggatctggc ggcggaggaa gcggaggcga catcctgctg 420
acccagtccc ccgtgatcct gtccgtgtcc cccggcgagc gggtgtcctt ctcctgccgg 480
gcctcccagt ccatcggcac caacatccac tggtaccagc agcggaccaa cggctccccc 540
cggctgctga tcaagtacgc ctccgagtcc atctccggca tcccctcccg gttctccggc 600
tccggctccg gcaccgactt caccctgtcc atcaactccg tggagtccga ggacatcgcc 660
gactactact gccagcagaa caacaactgg cccaccacct tcggcgccgg caccaagctg 720
gagctgaag 729

<210> SEQ ID NO 116
<211> LENGTH: 244
<212> TYPE: PRT
<213> ORGANISM: Artificial Sequence
<220> FEATURE:
<223> OTHER INFORMATION: EGFR ScFv

<400> SEQUENCE: 116

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser His
20 25 30

Trp Met His Trp Val Arg Gln Ala Pro Gly Gln Gly Leu Glu Trp Ile
35 40 45

Gly Glu Phe Asn Pro Ser Asn Gly Arg Thr Asn Tyr Asn Glu Lys Phe
50 55 60

Lys Ser Lys Ala Thr Met Thr Val Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Ala Ser Arg Asp Tyr Asp Tyr Asp Gly Arg Tyr Phe Asp Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gly Gly Asp Ile Gln Met Thr Gln
130 135 140

Ser Pro Ser Ser Leu Ser Ala Ser Val Gly Asp Arg Val Thr Ile Thr
145 150 155 160

Cys Ser Ala Ser Ser Ser Val Thr Tyr Met Tyr Trp Tyr Gln Gln Lys
165 170 175

Pro Gly Lys Ala Pro Lys Leu Leu Ile Tyr Asp Thr Ser Asn Leu Ala
180 185 190

Ser Gly Val Pro Ser Arg Phe Ser Gly Ser Gly Ser Gly Thr Asp Tyr
195 200 205

Thr Phe Thr Ile Ser Ser Leu Gln Pro Glu Asp Ile Ala Thr Tyr Tyr
210 215 220

Cys Gln Gln Trp Ser Ser His Ile Phe Thr Phe Gly Gln Gly Thr Lys
225 230 235 240

Val Glu Ile Lys

<210> SEQ ID NO 117
<211> LENGTH: 731
<212> TYPE: DNA
<213> ORGANISM: Artificial Sequence
<220> FEATURE:
<223> OTHER INFORMATION: EGFR ScFv

<400> SEQUENCE: 117
aggtgcagct ggtgcagtcc ggcgccgagg tgaagaagcc cggcgcctcc gtgaaggtgt 60
cctgcaaggc ctccggctac accttcacct cccactggat gcactgggtg cggcaggccc 120
ccggccaggg cctggagtgg atcggcgagt tcaacccctc caacggccgg accaactaca 180
acgagaagtt caagtccaag gccaccatga ccgtggacac ctccaccaac accgcctaca 240
tggagctgtc ctccctgcgg tccgaggaca ccgccgtgta ctactgcgcc tcccgggact 300
acgactacga cggccggtac ttcgactact ggggccaggg caccctggtg accgtgtcct 360
ccggcggagg tggaagcgga gggggaggat ctggcggcgg aggaagcgga ggcgacatcc 420
agatgaccca gtcccctcc tccctgtccg cctccgtggg cgaccgggtg accatcacct 480
gctccgcctc ctcctccgtg acctacatgt actggtacca gcagaagccc ggcaaggccc 540
ccaagctgct gatctacgac acctccaacc tggcctccgg cgtgccctcc cggttctccg 600
gctccggctc cggcaccgac tacaccttca ccatctcctc cctgcagccc gaggacatcg 660
ccacctacta ctgccagcag tggtcctccc acatcttcac cttcggccag ggcaccaagg 720
tggagatcaa g 731

<210> SEQ ID NO 118
<211> LENGTH: 243
<212> TYPE: PRT
<213> ORGANISM: Artificial Sequence
<220> FEATURE:
<223> OTHER INFORMATION: EGFR ScFv

<400> SEQUENCE: 118

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Val Ser Ser Gly
20 25 30

Asp Tyr Tyr Trp Thr Trp Ile Arg Gln Ser Pro Gly Lys Gly Leu Glu
35 40 45

Trp Ile Gly His Ile Tyr Tyr Ser Gly Asn Thr Asn Tyr Asn Pro Ser
50 55 60

Leu Lys Ser Arg Leu Thr Ile Ser Ile Asp Thr Ser Lys Thr Gln Phe
65 70 75 80

Ser Leu Lys Leu Ser Ser Val Thr Ala Ala Asp Thr Ala Ile Tyr Tyr
85 90 95

Cys Val Arg Asp Arg Val Thr Gly Ala Phe Asp Ile Trp Gly Gln Gly
100 105 110

Thr Met Val Thr Val Ser Ser Gly Gly Gly Gly Ser Gly Gly Gly Gly
115 120 125

Ser Gly Gly Gly Gly Ser Gly Gly Asp Ile Gln Met Thr Gln Ser Pro
130 135 140

Ser Ser Leu Ser Ala Ser Val Gly Asp Arg Val Thr Ile Thr Cys Gln
145 150 155 160

-continued

```
Ala Ser Gln Asp Ile Ser Asn Tyr Leu Asn Trp Tyr Gln Gln Lys Pro
                165                 170                 175

Gly Lys Ala Pro Lys Leu Leu Ile Tyr Asp Ala Ser Asn Leu Glu Thr
            180                 185                 190

Gly Val Pro Ser Arg Phe Ser Gly Ser Gly Ser Gly Thr Asp Phe Thr
        195                 200                 205

Phe Thr Ile Ser Ser Leu Gln Pro Glu Asp Ile Ala Thr Tyr Phe Cys
    210                 215                 220

Gln His Phe Asp His Leu Pro Leu Ala Phe Gly Gly Gly Thr Lys Val
225                 230                 235                 240

Glu Ile Lys
```

<210> SEQ ID NO 119
<211> LENGTH: 729
<212> TYPE: DNA
<213> ORGANISM: Artificial Sequence
<220> FEATURE:
<223> OTHER INFORMATION: EGFR ScFv

<400> SEQUENCE: 119

```
caggtgcagc tgcaggagtc cggccccggc ctggtgaagc cctccgagac cctgtccctg      60

acctgcaccg tgtccggcgg ctccgtgtcc tccggcgact actactggac ctggatccgg     120

cagtcccccg gcaagggcct ggagtggatc ggccacatct actactccgg caacaccaac     180

tacaacccct ccctgaagtc ccggctgacc atctccatcg acacctccaa gacccagttc     240

tccctgaagc tgtcctccgt gaccgccgcc gacaccgcca tctactactg cgtgcgggac     300

cgggtgaccg gcgccttcga catctggggc cagggcacca tggtgaccgt gtcctccggc     360

ggaggtggaa gcggaggggg aggatctggc ggcggaggaa gcggaggcga catccagatg     420

acccagtccc cctcctccct gtccgcctcc gtgggcgacc gggtgaccat cacctgccag     480

gcctcccagg acatctccaa ctacctgaac tggtaccagc agaagcccgg caaggccccc     540

aagctgctga tctacgacgc ctccaacctg gagaccggcg tgccctcccg gttctccggc     600

tccggctccg gcaccgactt caccttcacc atctcctccc tgcagcccga ggacatcgcc     660

acctacttct gccagcactt cgaccacctg cccctggcct tcggcggcgg caccaaggtg     720

gagatcaag                                                             729
```

<210> SEQ ID NO 120
<211> LENGTH: 125
<212> TYPE: PRT
<213> ORGANISM: Artificial Sequence
<220> FEATURE:
<223> OTHER INFORMATION: EGFR VH

<400> SEQUENCE: 120

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Asp Asp Gly Ser Tyr Lys Tyr Tyr Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

-continued 85 90 95

Ala Arg Asp Gly Ile Thr Met Val Arg Gly Val Met Lys Asp Tyr Phe
100 105 110

Asp Tyr Trp Gly Gln Gly Thr Leu Val Thr Val Ser Ser
115 120 125

<210> SEQ ID NO 121
<211> LENGTH: 107
<212> TYPE: PRT
<213> ORGANISM: Artificial Sequence
<220> FEATURE:
<223> OTHER INFORMATION: EGFR VL

<400> SEQUENCE: 121

Ala Ile Gln Leu Thr Gln Ser Pro Ser Ser Leu Ser Ala Ser Val Gly
1 5 10 15

Asp Arg Val Thr Ile Thr Cys Arg Ala Ser Gln Asp Ile Ser Ser Ala
20 25 30

Leu Val Trp Tyr Gln Gln Lys Pro Gly Lys Ala Pro Lys Leu Leu Ile
35 40 45

Tyr Asp Ala Ser Ser Leu Glu Ser Gly Val Pro Ser Arg Phe Ser Gly
50 55 60

Ser Glu Ser Gly Thr Asp Phe Thr Leu Thr Ile Ser Ser Leu Gln Pro
65 70 75 80

Glu Asp Phe Ala Thr Tyr Tyr Cys Gln Gln Phe Asn Ser Tyr Pro Leu
85 90 95

Thr Phe Gly Gly Gly Thr Lys Val Glu Ile Lys
100 105

<210> SEQ ID NO 122
<211> LENGTH: 118
<212> TYPE: PRT
<213> ORGANISM: Artificial Sequence
<220> FEATURE:
<223> OTHER INFORMATION: EGFR VH

<400> SEQUENCE: 122

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Thr Phe Thr Glu Tyr
20 25 30

Pro Ile His Trp Val Lys Gln Ala Pro Gly Lys Gly Phe Lys Trp Met
35 40 45

Gly Met Ile Tyr Thr Asp Ile Gly Lys Pro Thr Tyr Ala Glu Glu Phe
50 55 60

Lys Gly Arg Phe Ala Phe Ser Leu Glu Thr Ser Ala Ser Thr Ala Tyr
65 70 75 80

Leu Gln Ile Asn Asn Leu Lys Asn Glu Asp Thr Ala Thr Tyr Phe Cys
85 90 95

Val Arg Asp Arg Tyr Asp Ser Leu Phe Asp Tyr Trp Gly Gln Gly Thr
100 105 110

Thr Leu Thr Val Ser Ser
115

<210> SEQ ID NO 123
<211> LENGTH: 112
<212> TYPE: PRT
<213> ORGANISM: Artificial Sequence
<220> FEATURE:

<223> OTHER INFORMATION: EGFR VL

<400> SEQUENCE: 123

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Leu Gly Val Tyr Phe Cys Ser Gln Ser
85 90 95

Thr His Val Pro Trp Thr Phe Gly Gly Gly Thr Lys Leu Glu Ile Lys
100 105 110

<210> SEQ ID NO 124
<211> LENGTH: 121
<212> TYPE: PRT
<213> ORGANISM: Artificial Sequence
<220> FEATURE:
<223> OTHER INFORMATION: EGFR VH

<400> SEQUENCE: 124

Glu Met Gln Leu Val Glu Ser Gly Gly Gly Phe Val Lys Pro Gly Gly
1 5 10 15

Ser Leu Lys Leu Ser Cys Ala Ala Ser Gly Phe Ala Phe Ser His Tyr
20 25 30

Asp Met Ser Trp Val Arg Gln Thr Pro Lys Gln Arg Leu Glu Trp Val
35 40 45

Ala Tyr Ile Ala Ser Gly Gly Asp Ile Thr Tyr Tyr Ala Asp Thr Val
50 55 60

Lys Gly Arg Phe Thr Ile Ser Arg Asp Asn Ala Gln Asn Thr Leu Tyr
65 70 75 80

Leu Gln Met Ser Ser Leu Lys Ser Glu Asp Thr Ala Met Phe Tyr Cys
85 90 95

Ser Arg Ser Ser Tyr Gly Asn Asn Gly Asp Ala Leu Asp Phe Trp Gly
100 105 110

Gln Gly Thr Ser Val Thr Val Ser Ser
115 120

<210> SEQ ID NO 125
<211> LENGTH: 111
<212> TYPE: PRT
<213> ORGANISM: Artificial Sequence
<220> FEATURE:
<223> OTHER INFORMATION: EGFR VL

<400> SEQUENCE: 125

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Lys Leu Leu Ile Tyr Lys Val Ser Asn Arg Phe Ser Gly Val Pro

```
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Leu Thr Phe Gly Ser Gly Thr Lys Leu Glu Ile Lys
            100                 105                 110


<210> SEQ ID NO 126
<211> LENGTH: 119
<212> TYPE: PRT
<213> ORGANISM: Artificial Sequence
<220> FEATURE:
<223> OTHER INFORMATION: EGR VH

<400> SEQUENCE: 126

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115


<210> SEQ ID NO 127
<211> LENGTH: 107
<212> TYPE: PRT
<213> ORGANISM: Artificial Sequence
<220> FEATURE:
<223> OTHER INFORMATION: EGFR VL

<400> SEQUENCE: 127

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105


<210> SEQ ID NO 128
<211> LENGTH: 121
```

<212> TYPE: PRT
<213> ORGANISM: Artificial Sequence
<220> FEATURE:
<223> OTHER INFORMATION: EGFR VH

<400> SEQUENCE: 128

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser His
20 25 30

Trp Met His Trp Val Arg Gln Ala Pro Gly Gln Gly Leu Glu Trp Ile
35 40 45

Gly Glu Phe Asn Pro Ser Asn Gly Arg Thr Asn Tyr Asn Glu Lys Phe
50 55 60

Lys Ser Lys Ala Thr Met Thr Val Asp Thr Ser Thr Asn Thr Ala Tyr
65 70 75 80

Met Glu Leu Ser Ser Leu Arg Ser Glu Asp Thr Ala Val Tyr Tyr Cys
85 90 95

Ala Ser Arg Asp Tyr Asp Tyr Asp Gly Arg Tyr Phe Asp Tyr Trp Gly
100 105 110

Gln Gly Thr Leu Val Thr Val Ser Ser
115 120

<210> SEQ ID NO 129
<211> LENGTH: 106
<212> TYPE: PRT
<213> ORGANISM: Artificial Sequence
<220> FEATURE:
<223> OTHER INFORMATION: EGFR VL

<400> SEQUENCE: 129

Asp Ile Gln Met Thr Gln Ser Pro Ser Ser Leu Ser Ala Ser Val Gly
1 5 10 15

Asp Arg Val Thr Ile Thr Cys Ser Ala Ser Ser Ser Val Thr Tyr Met
20 25 30

Tyr Trp Tyr Gln Gln Lys Pro Gly Lys Ala Pro Lys Leu Leu Ile Tyr
35 40 45

Asp Thr Ser Asn Leu Ala Ser Gly Val Pro Ser Arg Phe Ser Gly Ser
50 55 60

Gly Ser Gly Thr Asp Tyr Thr Phe Thr Ile Ser Ser Leu Gln Pro Glu
65 70 75 80

Asp Ile Ala Thr Tyr Tyr Cys Gln Gln Trp Ser Ser His Ile Phe Thr
85 90 95

Phe Gly Gln Gly Thr Lys Val Glu Ile Lys
100 105

<210> SEQ ID NO 130
<211> LENGTH: 119
<212> TYPE: PRT
<213> ORGANISM: Artificial Sequence
<220> FEATURE:
<223> OTHER INFORMATION: EGFR VH

<400> SEQUENCE: 130

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Val Ser Ser Gly
20 25 30

Asp Tyr Tyr Trp Thr Trp Ile Arg Gln Ser Pro Gly Lys Gly Leu Glu

```
        35                  40                  45

Trp Ile Gly His Ile Tyr Tyr Ser Gly Asn Thr Asn Tyr Asn Pro Ser
    50                  55                  60

Leu Lys Ser Arg Leu Thr Ile Ser Ile Asp Thr Ser Lys Thr Gln Phe
65                  70                  75                  80

Ser Leu Lys Leu Ser Ser Val Thr Ala Ala Asp Thr Ala Ile Tyr Tyr
                85                  90                  95

Cys Val Arg Asp Arg Val Thr Gly Ala Phe Asp Ile Trp Gly Gln Gly
            100                 105                 110

Thr Met Val Thr Val Ser Ser
        115


<210> SEQ ID NO 131
<211> LENGTH: 107
<212> TYPE: PRT
<213> ORGANISM: Artificial Sequence
<220> FEATURE:
<223> OTHER INFORMATION: EGFR VL

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Phe Asp His Leu Pro Leu
                85                  90                  95

Ala Phe Gly Gly Gly Thr Lys Val Glu Ile Lys
            100                 105


<210> SEQ ID NO 132
<211> LENGTH: 5
<212> TYPE: PRT
<213> ORGANISM: Artificial Sequence
<220> FEATURE:
<223> OTHER INFORMATION: EGFR CDR-H1

<400> SEQUENCE: 132

Thr Tyr Gly Met His
1               5


<210> SEQ ID NO 133
<211> LENGTH: 5
<212> TYPE: PRT
<213> ORGANISM: Artificial Sequence
<220> FEATURE:
<223> OTHER INFORMATION: EGFR CDR-H1

<400> SEQUENCE: 133

Glu Tyr Pro Ile His
1               5


<210> SEQ ID NO 134
<211> LENGTH: 5
<212> TYPE: PRT
<213> ORGANISM: Artificial SEquence
```

<220> FEATURE:
<223> OTHER INFORMATION: EGFR CDR-H1

<400> SEQUENCE: 134

His Tyr Asp Met Ser
1 5

<210> SEQ ID NO 135
<211> LENGTH: 5
<212> TYPE: PRT
<213> ORGANISM: Artificial Sequence
<220> FEATURE:
<223> OTHER INFORMATION: EGFR CDR-H1

<400> SEQUENCE: 135

Asn Tyr Gly Val His
1 5

<210> SEQ ID NO 136
<211> LENGTH: 5
<212> TYPE: PRT
<213> ORGANISM: Artificial Sequence
<220> FEATURE:
<223> OTHER INFORMATION: EGFR CDR-H1

<400> SEQUENCE: 136

Ser His Trp Met His
1 5

<210> SEQ ID NO 137
<211> LENGTH: 7
<212> TYPE: PRT
<213> ORGANISM: Artificial Sequence
<220> FEATURE:
<223> OTHER INFORMATION: EGFR CDR-H1

<400> SEQUENCE: 137

Ser Gly Asp Tyr Tyr Trp Thr
1 5

<210> SEQ ID NO 138
<211> LENGTH: 17
<212> TYPE: PRT
<213> ORGANISM: Artificial Sequence
<220> FEATURE:
<223> OTHER INFORMATION: EGFR CDR-H2

<400> SEQUENCE: 138

Val Ile Trp Asp Asp Gly Ser Tyr Lys Tyr Tyr Gly Asp Ser Val Lys
1 5 10 15

Gly

<210> SEQ ID NO 139
<211> LENGTH: 17
<212> TYPE: PRT
<213> ORGANISM: Artificial Sequence
<220> FEATURE:
<223> OTHER INFORMATION: EGFR CDR-H2

<400> SEQUENCE: 139

Met Ile Tyr Thr Asp Ile Gly Lys Pro Thr Tyr Ala Glu Glu Phe Lys
1 5 10 15

Gly

<210> SEQ ID NO 140

<211> LENGTH: 17
<212> TYPE: PRT
<213> ORGANISM: Artificial Sequence
<220> FEATURE:
<223> OTHER INFORMATION: EGFR CDR-H2

<400> SEQUENCE: 140

Tyr Ile Ala Ser Gly Gly Asp Ile Thr Tyr Tyr Ala Asp Thr Val Lys
1 5 10 15

Gly

<210> SEQ ID NO 141
<211> LENGTH: 16
<212> TYPE: PRT
<213> ORGANISM: Artificial Sequence
<220> FEATURE:
<223> OTHER INFORMATION: EGFR CDR-H2

<400> SEQUENCE: 141

Val Ile Trp Ser Gly Gly Asn Thr Asp Tyr Asn Thr Pro Phe Thr Ser
1 5 10 15

<210> SEQ ID NO 142
<211> LENGTH: 17
<212> TYPE: PRT
<213> ORGANISM: Artificial Sequence
<220> FEATURE:
<223> OTHER INFORMATION: EGFR CDR-H2

<400> SEQUENCE: 142

Glu Phe Asn Pro Ser Asn Gly Arg Thr Asn Tyr Asn Glu Lys Phe Lys
1 5 10 15

Ser

<210> SEQ ID NO 143
<211> LENGTH: 16
<212> TYPE: PRT
<213> ORGANISM: Artificial Sequence
<220> FEATURE:
<223> OTHER INFORMATION: EGFR CDR-H2

<400> SEQUENCE: 143

His Ile Tyr Tyr Ser Gly Asn Thr Asn Tyr Asn Pro Ser Leu Lys Ser
1 5 10 15

<210> SEQ ID NO 144
<211> LENGTH: 16
<212> TYPE: PRT
<213> ORGANISM: Artificial Sequence
<220> FEATURE:
<223> OTHER INFORMATION: EGFR CDR-H3

<400> SEQUENCE: 144

Asp Gly Ile Thr Met Val Arg Gly Val Met Lys Asp Tyr Phe Asp Tyr
1 5 10 15

<210> SEQ ID NO 145
<211> LENGTH: 9
<212> TYPE: PRT
<213> ORGANISM: Artificial Sequence
<220> FEATURE:
<223> OTHER INFORMATION: EGFR CDR-H3

<400> SEQUENCE: 145

Asp Arg Tyr Asp Ser Leu Phe Asp Tyr
1 5

<210> SEQ ID NO 146
<211> LENGTH: 12
<212> TYPE: PRT
<213> ORGANISM: Artificial Sequence
<220> FEATURE:
<223> OTHER INFORMATION: EGFR CDR-H3

<400> SEQUENCE: 146

Ser Ser Tyr Gly Asn Asn Gly Asp Ala Leu Asp Phe
1               5                   10

<210> SEQ ID NO 147
<211> LENGTH: 11
<212> TYPE: PRT
<213> ORGANISM: Artificial Sequence
<220> FEATURE:
<223> OTHER INFORMATION: EGFR CDR-H3

<400> SEQUENCE: 147

Ala Leu Thr Tyr Tyr Asp Tyr Glu Phe Ala Tyr
1               5                   10

<210> SEQ ID NO 148
<211> LENGTH: 12
<212> TYPE: PRT
<213> ORGANISM: Artificial Sequence
<220> FEATURE:
<223> OTHER INFORMATION: EGFR CDR-H3

<400> SEQUENCE: 148

Arg Asp Tyr Asp Tyr Asp Gly Arg Tyr Phe Asp Tyr
1               5                   10

<210> SEQ ID NO 149
<211> LENGTH: 9
<212> TYPE: PRT
<213> ORGANISM: Artificial Sequence
<220> FEATURE:
<223> OTHER INFORMATION: EGFR CDR-H3

<400> SEQUENCE: 149

Asp Arg Val Thr Gly Ala Phe Asp Ile
1               5

<210> SEQ ID NO 150
<211> LENGTH: 11
<212> TYPE: PRT
<213> ORGANISM: Artificial Sequence
<220> FEATURE:
<223> OTHER INFORMATION: EGFR CDR-L1

<400> SEQUENCE: 150

Arg Ala Ser Gln Asp Ile Ser Ser Ala Leu Val
1               5                   10

<210> SEQ ID NO 151
<211> LENGTH: 16
<212> TYPE: PRT
<213> ORGANISM: Artificial Sequence
<220> FEATURE:
<223> OTHER INFORMATION: EGFR CDR-L1

<400> SEQUENCE: 151

Arg Ser Ser Gln Ser Leu Val His Ser Asn Gly Asn Thr Tyr Leu His
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: EGFRR CDR-L1

<400> SEQUENCE: 152

Arg Ser Ser Gln Ser Leu Val His Ser Asn Gly Asn Thr Tyr Leu His
1 5 10 15

<210> SEQ ID NO 153
<211> LENGTH: 11
<212> TYPE: PRT
<213> ORGANISM: Artificial Sequence
<220> FEATURE:
<223> OTHER INFORMATION: EGFR CDR-L1

<400> SEQUENCE: 153

Arg Ala Ser Gln Ser Ile Gly Thr Asn Ile His
1 5 10

<210> SEQ ID NO 154
<211> LENGTH: 10
<212> TYPE: PRT
<213> ORGANISM: Artificial Sequence
<220> FEATURE:
<223> OTHER INFORMATION: EGFR CDR-L1

<400> SEQUENCE: 154

Ser Ala Ser Ser Ser Val Thr Tyr Met Tyr
1 5 10

<210> SEQ ID NO 155
<211> LENGTH: 11
<212> TYPE: PRT
<213> ORGANISM: Artificial Sequence
<220> FEATURE:
<223> OTHER INFORMATION: EGFR CDR-L1

<400> SEQUENCE: 155

Gln Ala Ser Gln Asp Ile Ser Asn Tyr Leu Asn
1 5 10

<210> SEQ ID NO 156
<211> LENGTH: 7
<212> TYPE: PRT
<213> ORGANISM: Artificial Sequence
<220> FEATURE:
<223> OTHER INFORMATION: EGFR CDR-L2

<400> SEQUENCE: 156

Asp Ala Ser Ser Leu Glu Ser
1 5

<210> SEQ ID NO 157
<211> LENGTH: 7
<212> TYPE: PRT
<213> ORGANISM: Artificial Sequence
<220> FEATURE:
<223> OTHER INFORMATION: EGFR CDR-L2

<400> SEQUENCE: 157

Lys Val Ser Asn Arg Phe Ser
1 5

<210> SEQ ID NO 158
<211> LENGTH: 7
<212> TYPE: PRT
<213> ORGANISM: Artificial Sequence
<220> FEATURE:
<223> OTHER INFORMATION: EGFR CDR-L2

<400> SEQUENCE: 158

Tyr Ala Ser Glu Ser Ile Ser
1 5

<210> SEQ ID NO 159
<211> LENGTH: 7
<212> TYPE: PRT
<213> ORGANISM: Artificial Sequence
<220> FEATURE:
<223> OTHER INFORMATION: EGFR CDR-L2

<400> SEQUENCE: 159

Asp Thr Ser Asn Leu Ala Ser
1 5

<210> SEQ ID NO 160
<211> LENGTH: 7
<212> TYPE: PRT
<213> ORGANISM: Artificial Sequence
<220> FEATURE:
<223> OTHER INFORMATION: EGFR CDR-L2

<400> SEQUENCE: 160

Asp Ala Ser Asn Leu Glu Thr
1 5

<210> SEQ ID NO 161
<211> LENGTH: 9
<212> TYPE: PRT
<213> ORGANISM: Artificial Sequence
<220> FEATURE:
<223> OTHER INFORMATION: EGFR CDR-L3

<400> SEQUENCE: 161

Gln Gln Phe Asn Ser Tyr Pro Leu Thr
1 5

<210> SEQ ID NO 162
<211> LENGTH: 9
<212> TYPE: PRT
<213> ORGANISM: Artificial Sequence
<220> FEATURE:
<223> OTHER INFORMATION: EGFR CDR-L3

<400> SEQUENCE: 162

Ser Gln Ser Thr His Val Pro Trp Thr
1 5

<210> SEQ ID NO 163
<211> LENGTH: 8
<212> TYPE: PRT
<213> ORGANISM: Artificial Sequence
<220> FEATURE:
<223> OTHER INFORMATION: EGFR CDR-L3

<400> SEQUENCE: 163

Ser Gln Ser Thr His Val Leu Thr
1 5

<210> SEQ ID NO 164

<211> LENGTH: 9
<212> TYPE: PRT
<213> ORGANISM: Artificial Sequence
<220> FEATURE:
<223> OTHER INFORMATION: EGFR CDR-L3

<400> SEQUENCE: 164

Gln Gln Asn Asn Asn Trp Pro Thr Thr
1               5

<210> SEQ ID NO 165
<211> LENGTH: 9
<212> TYPE: PRT
<213> ORGANISM: Artificial Sequence
<220> FEATURE:
<223> OTHER INFORMATION: EGFR CDR-L3

<400> SEQUENCE: 165

Gln Gln Trp Ser Ser His Ile Phe Thr
1               5

<210> SEQ ID NO 166
<211> LENGTH: 9
<212> TYPE: PRT
<213> ORGANISM: Artificial Sequence
<220> FEATURE:
<223> OTHER INFORMATION: EGFR CDR-L3

<400> SEQUENCE: 166

Gln His Phe Asp His Leu Pro Leu Ala
1               5

<210> SEQ ID NO 167
<211> LENGTH: 246
<212> TYPE: PRT
<213> ORGANISM: Artificial Sequence
<220> FEATURE:
<223> OTHER INFORMATION: pan-HLA ScFv

<400> SEQUENCE: 167

Gln Val Gln Leu Lys Gln Ser Gly Pro Gly Leu Val Gln Pro Ser Gln
1               5                   10                  15

Ser Leu Ser Leu Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Arg Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Thr Phe Thr Thr Ser Thr Ser Ala Trp Phe Ala Tyr Trp Gly Gln
            100                 105                 110

Gly Thr Leu Val Thr Val Ser Ala Gly Gly Gly Gly Ser Gly Gly Gly
        115                 120                 125

Gly Ser Gly Gly Gly Gly Ser Gly Gly Ser Ile Val Met Thr Gln Thr
    130                 135                 140

Pro Lys Phe Leu Leu Val Ser Ala Gly Asp Arg Val Thr Ile Thr Cys
145                 150                 155                 160

Lys Ala Ser Gln Ser Val Ser Asn Asp Val Ala Trp Tyr Gln Gln Lys
                165                 170                 175

```
Pro Gly Gln Ser Pro Ile Cys Leu Leu Ile Tyr Tyr Ala Ser Asn Arg
            180                 185                 190

Tyr Thr Gly Val Pro Asp Arg Phe Thr Gly Ser Gly Tyr Gly Thr Asp
        195                 200                 205

Phe Thr Phe Thr Ile Ser Thr Val Gln Ala Glu Asp Leu Ala Val Tyr
    210                 215                 220

Phe Cys Gln Gln Asp Tyr Ser Ser Pro Pro Trp Thr Phe Gly Gly Gly
225                 230                 235                 240

Thr Lys Leu Glu Ile Arg
                245


<210> SEQ ID NO 168
<211> LENGTH: 738
<212> TYPE: DNA
<213> ORGANISM: Artificial Sequence
<220> FEATURE:
<223> OTHER INFORMATION: pan-HLA ScFv

<400> SEQUENCE: 168

caggtgcagc tgaagcagtc aggacctggc ctagtgcagc cctcacagag cctgtccctg      60

acctgcacag tctctggttt ctcattaact agttatggcg tacactgggt tcgccagcct     120

ccaggaaagg gtctggagtg gctgggagtg atctggagtg gtggaagcac agactataat     180

gctgctttca tatccagact gagcatcagg aaggacaact ccaagagcca agtcttcttt     240

aaaatgaaca gtctgcaagc tgatgacaca gccatatact actgtgccag aacctttact     300

acgtctacct cggcctggtt tgcttactgg ggccaaggga ctctggtcac tgtctctgca     360

ggcggaggtg gaagcggagg gggaggatct ggcggcggag gaagcggagg cagcatcgtg     420

atgacccaga ctccaaaatt cctgcttgtg tctgcgggag acagagtcac catcacttgc     480

aaggcgagtc agtctgtgag caacgacgta gcttggtatc agcagaaacc agggcaatct     540

cctatctgtc tcctgatcta ctatgcatct aatcggtata caggggtccc tgataggttc     600

accggaagtg gatatgggac agatttcact ttcaccatca gcaccgtgca ggctgaagat     660

cttgcagtat atttctgtca acaggattat agtagtcctc cgtggacttt cggcggaggg     720

accaagttgg agatcaga                                                   738


<210> SEQ ID NO 169
<211> LENGTH: 245
<212> TYPE: PRT
<213> ORGANISM: Artificial Sequence
<220> FEATURE:
<223> OTHER INFORMATION: pan-HLA ScFv

<400> SEQUENCE: 169

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ser Gly Gly Ser Thr Asp Tyr Asn Ala Ala Phe Ile
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

```
Arg Thr Phe Thr Thr Ser Thr Ser Ala Trp Phe Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Asp Ile Val Met Thr Gln Ser
    130                 135                 140

Pro Asp Ser Leu Ala Val Ser Leu Gly Glu Arg Ala Thr Ile Asn Cys
145                 150                 155                 160

Lys Ala Ser Gln Ser Val Ser Asn Asp Val Ala Trp Tyr Gln Gln Lys
                165                 170                 175

Pro Gly Gln Pro Pro Lys Leu Leu Ile Tyr Tyr Ala Ser Asn Arg Tyr
            180                 185                 190

Thr Gly Val Pro Asp Arg Phe Ser Gly Ser Gly Ser Gly Thr Asp Phe
        195                 200                 205

Thr Leu Thr Ile Ser Ser Leu Gln Ala Glu Asp Val Ala Val Tyr Tyr
    210                 215                 220

Cys Gln Gln Asp Tyr Ser Ser Pro Pro Trp Thr Phe Gly Gly Gly Thr
225                 230                 235                 240

Lys Val Glu Ile Lys
                245


<210> SEQ ID NO 170
<211> LENGTH: 735
<212> TYPE: DNA
<213> ORGANISM: Artificial Sequence
<220> FEATURE:
<223> OTHER INFORMATION: pan-HLA ScFv

<400> SEQUENCE: 170

caggtgcagc tgcaggagtc cggacctggc ctagtgaagc cctcacagac cctgtccctg      60

acctgcacag tctctggttt ctcattaact agctatggtg tacactggat tagacagcct     120

ccaggaaagg gtctggagtg gattggagtg atctggagtg gtggaagcac agactataat     180

gctgctttca tatccagagt gaccatcagc gtggacacct ccaagaacca attctccctt     240

aaactgagca gtgtgacagc tgccgacaca gccgtatact actgtgccag aacctttact     300

acgtctacct cggcctggtt tgcttactgg ggccaaggga ctctggtcac tgtctcttca     360

ggcggaggtg gaagcggagg gggaggatct ggcggcggag gaagcggagg cgacatcgtg     420

atgacccaga gtccagattc cctggctgtg tctctgggag agagagccac catcaattgc     480

aaggcgagtc agtctgtgag caacgacgta gcttggtatc agcagaaacc agggcaacct     540

cctaaactcc tgatctacta tgcatctaat cggtatacag gggtccctga taggttcagc     600

ggaagtggat ctgggacaga tttcactctc accatcagca gcctgcaggc tgaagatgtt     660

gcagtatatt actgtcaaca ggattatagt agtcctccgt ggactttcgg cggagggacc     720

aaggtggaga tcaaa                                                      735


<210> SEQ ID NO 171
<211> LENGTH: 245
<212> TYPE: PRT
<213> ORGANISM: Artificial Sequence
<220> FEATURE:
<223> OTHER INFORMATION: pan-HLA ScFv

<400> SEQUENCE: 171

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Ser Leu Thr Ser Tyr
            20                  25                  30

Gly Val His Trp Val Arg Gln Ala Pro Gly Lys Gly Leu Glu Trp Val
            35                  40                  45

Ser Val Ile Trp Ser Gly Gly Ser Thr Asp Tyr Asn Ala Ala Phe Ile
 50                  55                  60

Ser Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Arg Thr Phe Thr Thr Ser Thr Ser Ala Trp Phe Ala Tyr Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Asp Ile Gln Met Thr Gln Ser
130                 135                 140

Pro Ser Ser Leu Ser Ala Ser Val Gly Asp Arg Val Thr Ile Thr Cys
145                 150                 155                 160

Lys Ala Ser Gln Ser Val Ser Asn Asp Val Ala Trp Tyr Gln Gln Lys
                165                 170                 175

Pro Gly Lys Ala Pro Lys Leu Leu Ile Tyr Tyr Ala Ser Asn Arg Tyr
            180                 185                 190

Thr Gly Val Pro Ser Arg Phe Ser Gly Ser Gly Ser Gly Thr Asp Phe
            195                 200                 205

Thr Phe Thr Ile Ser Ser Leu Gln Pro Glu Asp Ile Ala Thr Tyr Tyr
            210                 215                 220

Cys Gln Gln Asp Tyr Ser Ser Pro Pro Trp Thr Phe Gly Gly Gly Thr
225                 230                 235                 240

Lys Val Glu Ile Lys
            245

<210> SEQ ID NO 172
<211> LENGTH: 735
<212> TYPE: DNA
<213> ORGANISM: Artificial Sequence
<220> FEATURE:
<223> OTHER INFORMATION: pan-HLA ScFv

<400> SEQUENCE: 172
gaggtgcagc tgctggagtc cggaggtggc ctagtgcagc ccggagggag cctgcgcctg      60
agctgcgcag cctctggttt ctcattaact agctatggtg tacactgggt tagacaggct     120
ccaggaaagg gtctggagtg ggttagcgtg atctggagtg gtggaagcac agactataat     180
gctgctttca tatccagatt taccatcagc cgggacaact ccaagaacac actctacctt     240
caaatgaaca gtttgagagc tgaagacaca gccgtatact actgtgccag aacctttact     300
acgtctacct cggcctggtt tgcttactgg ggccaaggga ctctggtcac tgtctcttca     360
ggcggaggtg gaagcggagg gggaggatct ggcggcggag gaagcggagg cgacatccag     420
atgacccaga gtccaagctc cctgtctgcg tctgtgggag acagagtcac catcacttgc     480
aaggcgagtc agtctgtgag caacgacgta gcttggtatc agcagaaacc agggaaagct     540
cctaaactcc tgatctacta tgcatctaat cggtatacag gggtccctag taggttcagc     600
ggaagtggat ctgggacaga tttcactttc accatcagca gcctgcagcc tgaagatatt     660
gcaacatatt actgtcaaca ggattatagt agtcctccgt ggactttcgg cggagggacc     720
aaggtggaga tcaaa 735

<210> SEQ ID NO 173
<211> LENGTH: 245
<212> TYPE: PRT
<213> ORGANISM: Artificial Sequence
<220> FEATURE:
<223> OTHER INFORMATION: pan-HLA ScFv

<400> SEQUENCE: 173

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ser Gly Gly Ser Thr Asp Tyr Asn Ala Ala Phe Ile
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr Phe Thr Thr Ser Thr Ser Ala Trp Phe Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Asp Ile Val Met Thr Gln Thr
    130                 135                 140

Pro Leu Ser Leu Ser Val Thr Pro Gly Gln Pro Ala Ser Ile Ser Cys
145                 150                 155                 160

Lys Ala Ser Gln Ser Val Ser Asn Asp Val Ala Trp Tyr Leu Gln Lys
                165                 170                 175

Pro Gly Gln Ser Pro Gln Leu Leu Ile Tyr Tyr Ala Ser Asn Arg Tyr
            180                 185                 190

Thr Gly Val Pro Asp Arg Phe Ser Gly Ser Gly Ser Gly Thr Asp Phe
        195                 200                 205

Thr Leu Lys Ile Ser Arg Val Glu Ala Glu Asp Val Gly Val Tyr Tyr
    210                 215                 220

Cys Gln Gln Asp Tyr Ser Ser Pro Pro Trp Thr Phe Gly Gly Gly Thr
225                 230                 235                 240

Lys Val Glu Ile Lys
                245
```

<210> SEQ ID NO 174
<211> LENGTH: 735
<212> TYPE: DNA
<213> ORGANISM: Artificial Sequence
<220> FEATURE:
<223> OTHER INFORMATION: pan-HLA ScFv

<400> SEQUENCE: 174

```
caggtgcagc tgcaggagtc cggacctggc ctagtgaagc cctcagaaac cctgtccctg     60

acctgcacag tctctggttt ctcattaact agctatggtg tacactggat tagacagcct    120

ccaggaaagg gtctggagtg gattggagtg atctggagtg gtggaagcac agactataat    180

gctgctttca tatccagagt gaccatcagc agggacacct ccaagaacca attctccctt    240
```

```
aaactgagca gtgtgacagc tgccgacaca gccgtatact actgtgccag aacctttact    300

acgtctacct cggcctggtt tgcttactgg ggccaaggga ctctggtcac tgtctcttca    360

ggcggaggtg gaagcggagg gggaggatct ggcggcggag gaagcggagg cgacatcgtg    420

atgacccaga ctccactttc cctgtctgtg actccgggac agccagccag catcagttgc    480

aaggcgagtc agtctgtgag caacgacgta gcttggtatc tgcagaaacc agggcaatct    540

cctcaactcc tgatctacta tgcatctaat cggtatacag gggtccctga taggttcagc    600

ggaagtggat ctgggacaga tttcactttg aagatcagca gggtggaggc tgaagatgtt    660

ggagtatatt actgtcaaca ggattatagt agtcctccgt ggactttcgg cggagggacc    720

aaggtggaga tcaaa                                                     735
```

<210> SEQ ID NO 175
<211> LENGTH: 245
<212> TYPE: PRT
<213> ORGANISM: Artificial Sequence
<220> FEATURE:
<223> OTHER INFORMATION: pan-HLA ScFv

<400> SEQUENCE: 175

```
Gln Val Gln Leu Val Glu Ser Gly Gly Gly Val Val Gln Pro Gly Arg
1               5                   10                  15

Ser Leu Arg Leu Ser Cys Ala Val Ser Gly Phe Ser Leu Thr Ser Tyr
            20                  25                  30

Gly Met His Trp Val Arg Gln Ala Pro Gly Lys Gly Leu Glu Trp Val
        35                  40                  45

Ala Val Ile Trp Ser Gly Gly Ser Thr Asp Tyr Asn Ala Ala Phe Ile
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Thr Phe Thr Thr Ser Thr Ser Ala Trp Phe Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Glu Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Asn Asp Leu Ala Trp Tyr Gln Gln Lys
                165                 170                 175

Pro Gly Gln Ala Pro Arg Leu Leu Ile Tyr Tyr Ala Ser Asn Arg Tyr
            180                 185                 190

Thr Gly Val Pro Asp Arg Phe Ser Gly Ser Gly Ser Gly Thr Asp Phe
        195                 200                 205

Thr Leu Thr Ile Ser Ser Leu Glu Pro Glu Asp Phe Ala Val Tyr Tyr
    210                 215                 220

Cys Gln Gln Asp Tyr Ser Ser Pro Pro Trp Thr Phe Gly Gln Gly Thr
225                 230                 235                 240

Lys Val Glu Ile Lys
                245
```

<210> SEQ ID NO 176
<211> LENGTH: 735

<212> TYPE: DNA
<213> ORGANISM: Artificial Sequence
<220> FEATURE:
<223> OTHER INFORMATION: pan-HLA ScFv

<400> SEQUENCE: 176

```
caggtgcagc tggtggagtc cggaggtggc gtagtgcagc ccggaaggag cctgcgcctg     60

agctgcgcag tctctggttt ctcattaact agctatggta tgcactgggt tagacaggct    120

ccaggaaagg gtctggagtg ggttgcagtg atctggagtg gtggaagcac agactataat    180

gctgctttca tatccagatt taccatcagc cgggacaact ccaagaacac actctacctt    240

caaatgaaca gtttgagagc tgaagacaca gccgtatact actgtgccaa aacctttact    300

acgtctacct cggcctggtt tgcttactgg ggccaaggga ctctggtcac tgtctcttca    360

ggcggaggtg gaagcggagg gggaggatct ggcggcggag gaagcggagg cgagatcgtg    420

ctgacccaga gtccagctac cctgtctctg tctccgggag agagagccac cctcagttgc    480

agggcgagtc agtctgtgag caacgaccta gcttggtatc agcagaaacc agggcaagct    540

cctagactcc tgatctacta tgcatctaat cggtatacag gggtccctga taggttcagc    600

ggaagtggat ctgggacaga tttcactctc accatcagca gcctggagcc tgaagatttt    660

gcagtatatt actgtcaaca ggattatagt agtcctccgt ggactttcgg ccaagggacc    720

aaggtggaga tcaaa                                                     735
```

<210> SEQ ID NO 177
<211> LENGTH: 245
<212> TYPE: PRT
<213> ORGANISM: Artificial Sequence
<220> FEATURE:
<223> OTHER INFORMATION: pan-HLA ScFv

<400> SEQUENCE: 177

```
Gln Val Gln Leu Val Glu Ser Gly Gly Gly Val Val Gln Pro Gly Arg
1               5                   10                  15

Ser Leu Arg Leu Ser Cys Ala Val Ser Gly Phe Ser Leu Thr Ser Tyr
            20                  25                  30

Gly Met His Trp Val Arg Gln Ala Pro Gly Lys Gly Leu Glu Trp Val
        35                  40                  45

Ala Val Ile Trp Ser Gly Gly Ser Thr Asp Tyr Asn Ala Ala Phe Ile
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Thr Phe Thr Thr Ser Thr Ser Ala Trp Phe Ala Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Gln Ala Ser Gln Ser Val Ser Asn Asp Leu Asn Trp Tyr Gln Gln Lys
                165                 170                 175

Pro Gly Lys Ala Pro Lys Leu Leu Ile Tyr Tyr Ala Ser Asn Arg Tyr
            180                 185                 190
```

```
Thr Gly Val Pro Asp Arg Phe Ser Gly Ser Gly Ser Gly Thr Asp Phe
        195                 200                 205

Thr Phe Thr Ile Ser Ser Leu Gln Pro Glu Asp Ile Ala Thr Tyr Tyr
    210                 215                 220

Cys Gln Gln Asp Tyr Ser Ser Pro Pro Trp Thr Phe Gly Gly Gly Thr
225                 230                 235                 240

Lys Val Glu Ile Lys
                245


<210> SEQ ID NO 178
<211> LENGTH: 735
<212> TYPE: DNA
<213> ORGANISM: Artificial Sequence
<220> FEATURE:
<223> OTHER INFORMATION: pan-HLA ScFv

<400> SEQUENCE: 178

caggtgcagc tggtggagtc cggaggtggc gtagtgcagc ccggaaggag cctgcgcctg     60

agctgcgcag tctctggttt ctcattaact agctatggta tgcactgggt tagacaggct    120

ccaggaaagg gtctggagtg ggttgcagtg atctggagtg gtggaagcac agactataat    180

gctgctttca tatccagatt taccatcagc cgggacaact ccaagaacac actctacctt    240

caaatgaaca gtttgagagc tgaagacaca gccgtatact actgtgccag aacctttact    300

acgtctacct cggcctggtt tgcttactgg ggccaaggga ctctggtcac tgtctcttca    360

ggcggaggtg gaagcggagg gggaggatct ggcggcggag gaagcggagg cgacatccag    420

atgacccaga gtccaagctc cctgtctgcg tctgtgggag acagagtcac catcacttgc    480

caggcgagtc agtctgtgag caacgaccta aattggtatc agcagaaacc agggaaagct    540

cctaaactcc tgatctacta tgcatctaat cggtatacag ggtccctga taggttcagc    600

ggaagtggat ctgggacaga tttcactttc accatcagca gcctgcagcc tgaagatatt    660

gcaacatatt actgtcaaca ggattatagt agtcctccgt ggactttcgg cggagggacc    720

aaggtggaga tcaaa                                                     735


<210> SEQ ID NO 179
<211> LENGTH: 741
<212> TYPE: DNA
<213> ORGANISM: Artificial Sequence
<220> FEATURE:
<223> OTHER INFORMATION: HLA-A*02 antigen binding domain

<400> SEQUENCE: 179

gatgttttga tgacccaaac tccactctcc ctgcctgtca gtcttggaga tcaagcctcc     60

atctcttgca gatctagtca gagcattgta catagtaatg gaaacaccta tttagaatgg    120

tacctgcaga aaccaggcca gtctccaaag ctcctgatct acaaagtttc caaccgattt    180

tctggggtcc cagacaggtt cagtggcagt ggatcaggga cagatttcac actcaagatc    240

agtagagtgg aggctgagga tctgggagtt tattactgct ttcaaggttc acatgttcct    300

cggacgtccg gtggaggcac caagctggaa atcaaaggcg gaggtggaag cggagggggga    360

ggatctggcg gcggaggaag cggaggccag gtccagctgc agcagtctgg acctgagctg    420

gtgaagcctg gggcttcagt gaggatatcc tgcaaggctt ctggctacac cttcacaagt    480

taccatatac attgggtgaa gcagaggcct ggacagggac ttgagtggat tggatggatt    540

tatcctggaa atgttaatac tgagtacaat gagaagttca agggcaaggc cacactgact    600

gcagacaaat cgtccagcac agcctacatg cacctcagca gcctgacctc tgaggactct    660
```

gcggtctatt tctgtgccag agaggagatt acctatgcta tggactactg gggtcaagga 720
acctcagtca ccgtgtcctc a 741

<210> SEQ ID NO 180
<211> LENGTH: 741
<212> TYPE: DNA
<213> ORGANISM: Artificial Sequence
<220> FEATURE:
<223> OTHER INFORMATION: HLA-A*02 antigen binding domain

<400> SEQUENCE: 180
caggtgcagc tggtgcagtc tggggctgag gtgaagaagc ctgggtcctc agtgaaggtt 60
tcctgcaagg cttctggata caccttcact agctatcata tacattgggt gcgccaggcc 120
cccggacaag ggcttgagtg gatgggatgg atctaccctg gcaatgttaa cacagaatat 180
aatgagaagt tcaagggcaa agccaccatt accgcggaca aatccacgag cacagcctac 240
atggagctga gcagcctgag atctgaagac acggctgtgt attactgtgc gagggaggaa 300
attacctacg ctatggacta ctggggccag ggaaccacag tcaccgtgtc ctcaggcgga 360
ggtggaagcg gagggggagg atctggcggc ggaggaagcg gaggcgagat tgtattgacc 420
cagagcccag gcaccctgag cctctctcca ggagagcggg ccaccctcag ttgtagatcc 480
agtcagagta ttgtacacag taatgggaac acctatttgg aatggtatca gcagaaacca 540
ggtcaagccc caagattgct catctacaaa gtctctaaca gatttagtgg tattccagac 600
aggttcagcg gttccggaag tggtactgat ttcaccctca cgatctccag gctcgagcca 660
gaagatttcg ccgtttatta ctgttttcaa ggttcacatg tgccgcgcac attcggtggg 720
ggtactaaag tagaaatcaa a 741

<210> SEQ ID NO 181
<211> LENGTH: 741
<212> TYPE: DNA
<213> ORGANISM: Artificial Sequence
<220> FEATURE:
<223> OTHER INFORMATION: HLA-A*02 antigen binding domain

<400> SEQUENCE: 181
caggtgcagc tggtgcagtc tggggctgag gtgaagaagc ctgggtcctc agtgaaggtt 60
tcctgcaagg cttctggata caccttcact agctatcata tacattgggt gcgccaggcc 120
cccggacaag ggcttgagtg gatgggatgg atctaccctg gcaatgttaa cacagaatat 180
aatgagaagt tcaagggcaa agccaccatt accgcggaca aatccacgag cacagcctac 240
atggagctga gcagcctgag atctgaagac acggctgtgt attactgtgc gagggaggaa 300
attacctacg ctatggacta ctggggccag ggaaccacag tcaccgtgtc ctcaggcgga 360
ggtggaagcg gagggggagg atctggcggc ggaggaagcg gaggcgacat tgtaatgacc 420
cagaccccac tcagcctgcc cgtcactcca ggagagccgg ccagcatcag ttgtagatcc 480
agtcagagta ttgtacacag taatgggaac acctatttgg aatggtatct gcagaaacca 540
ggtcaatccc cacaattgct catctacaaa gtctctaaca gatttagtgg tgtaccagac 600
aggttcagcg gttccggaag tggtactgat ttcaccctca agatctccag ggtcgaggca 660
gaagatgtcg gcgtttatta ctgttttcaa ggttcacatg tgccgcgcac attcggtggg 720
ggtactaaag tagaaatcaa a 741

<210> SEQ ID NO 182

<211> LENGTH: 741
<212> TYPE: DNA
<213> ORGANISM: Artificial Sequence
<220> FEATURE:
<223> OTHER INFORMATION: HLA-A*02 antigen binding domain

<400> SEQUENCE: 182
gaggtgcagc tggtggagtc tgggggtggg ctggtgaagc ctgggggctc actgaggctt 60
tcctgcgcgg cttctggata caccttcact agctatcata tacattgggt gcgccaggcc 120
cccggaaaag ggcttgagtg ggtgggatgg atctaccctg gcaatgttaa cacagaatat 180
aatgagaagt tcaagggcag attcaccatt agcagggacg attccaagaa cacactctac 240
ctgcagatga acagcctgaa aactgaagac acggctgtgt attactgtgc gagggaggaa 300
attacctacg ctatggacta ctggggccag ggaaccacag tcaccgtgtc ctcaggcgga 360
ggtggaagcg gagggggagg atctggcggc ggaggaagcg gaggcgacat tcaaatgacc 420
cagagcccat ccagcctgag cgcatctgta ggtgaccggg tcaccatcac ttgtagatcc 480
agtcagagta ttgtacacag taatgggaac acctatttgg aatggtatca gcagaaacca 540
ggtaaagccc caaaattgct catctacaaa gtctctaaca gatttagtgg tgtaccaagc 600
aggttcagcg gttccggaag tggtactgat ttcaccctca cgatctcctc tctccagcca 660
gaagatttcg ccacttatta ctgttttcaa ggttcacatg tgccgcgcac attcggtggg 720
ggtactaaag tagaaatcaa a 741

<210> SEQ ID NO 183
<211> LENGTH: 741
<212> TYPE: DNA
<213> ORGANISM: Artificial Sequence
<220> FEATURE:
<223> OTHER INFORMATION: HLA-A*02 antigen binding domain

<400> SEQUENCE: 183
caggtgcagc tggtgcagtc tggggctgag gtgaagaagc ctgggtcctc agtgaaggtt 60
tcctgcaagg cttctggata caccttcact agctatcata tacattgggt gcgccaggcc 120
cccggacaag ggcttgagtg gatcggatgg atctaccctg gcaatgttaa cacagaatat 180
aatgagaagt tcaagggcaa agccaccatt accgcggacg aatccacgaa cacagcctac 240
atggagctga gcagcctgag atctgaagac acggctgtgt attactgtgc gagggaggaa 300
attacctacg ctatggacta ctggggccag ggaaccctgg tcaccgtgtc ctcaggcgga 360
ggtggaagcg gagggggagg atctggcggc ggaggaagcg gaggcgacat tcaaatgacc 420
cagagcccat ccaccctgag cgcatctgta ggtgaccggg tcaccatcac ttgtagatcc 480
agtcagagta ttgtacacag taatgggaac acctatttgg aatggtatca gcagaaacca 540
ggtaaagccc caaaattgct catctacaaa gtctctaaca gatttagtgg tgtaccagcc 600
aggttcagcg gttccggaag tggtactgaa ttcaccctca cgatctcctc tctccagcca 660
gatgatttcg ccacttatta ctgttttcaa ggttcacatg tgccgcgcac attcggtcag 720
ggtactaaag tagaagtcaa a 741

<210> SEQ ID NO 184
<211> LENGTH: 741
<212> TYPE: DNA
<213> ORGANISM: Artificial Sequence
<220> FEATURE:
<223> OTHER INFORMATION: HLA-A*02 antigen binding domain

<400> SEQUENCE: 184

```
caggtgcagc tggtgcagtc tggggctgag gtgaagaagc ctgggtcctc agtgaaggtt     60

tcctgcaagg cttctggata caccttcact agctatcata tgcattgggt gcgccaggcc    120

cccggacaag ggcttgagtg gatcggatac atctaccctg gcaatgttaa cacagaatat    180

aatgagaagt tcaagggcaa agccaccctt accgcggaca aatccacgaa cacagcctac    240

atggagctga gcagcctgag atctgaagac acggctgtgt atttctgtgc gagggaggaa    300

attacctacg ctatggacta ctggggccag ggaaccctgg tcaccgtgtc ctcaggcgga    360

ggtggaagcg gagggggagg atctggcggc ggaggaagcg gaggcgacgt tcaaatgacc    420

cagagcccat ccaccctgag cgcatctgta ggtgaccggg tcaccatcac ttgtagctcc    480

agtcagagta ttgtacacag taatgggaac acctatatgg aatggtatca gcagaaacca    540

ggtaaagccc caaaattgct catctacaaa gtctctaaca gatttagtgg tgtaccagac    600

aggttcagcg gttccggaag tggtactgaa ttcaccctca cgatctcctc tctccagcca    660

gatgatttcg ccacttatta ctgtcatcaa ggttcacatg tgccgcgcac attcggtcag    720

ggtactaaag tagaagtcaa a                                              741
```

<210> SEQ ID NO 185
<211> LENGTH: 741
<212> TYPE: DNA
<213> ORGANISM: Artificial Sequence
<220> FEATURE:
<223> OTHER INFORMATION: HLA-A*02 antigen binding domain

<400> SEQUENCE: 185

```
caggtgcagc tgcagcagtc tgggcctgag ctggtgaagc ctggggcctc agtgaagatg     60

tcctgcaagg cttctggata caccttcact agctatcata tccagtgggt gaagcagagg    120

cctggacaag ggcttgagtg gatcggatgg atctaccctg gcgatggtag tacacagtat    180

aatgagaagt tcaagggcaa aaccaccctt accgcggaca aatcctccag cacagcctac    240

atgttgctga gcagcctgac ctctgaagac tctgctatct atttctgtgc gagggagggg    300

acctactacg ctatggacta ctggggccag ggaacctcag tcaccgtgtc ctcaggcgga    360

ggtggaagcg gagggggagg atctggcggc ggaggaagcg gaggcgatgt tttgatgacc    420

cagactccac tctccctgcc tgtctctctt ggagaccaag tctccatctc ttgtagatcc    480

agtcagagta ttgtacacag taatgggaac acctatttag aatggtatct gcagaaacca    540

ggtcagtctc caaagttgct catctacaaa gtctctaaca gatttagtgg tgtaccagac    600

aggttcagcg gttccggaag tggtactgat ttcaccctca agatctcgag agtggaggct    660

gaggatctgg gagtttatta ctgttttcaa ggttcacatg tgccgcgcac attcggtgga    720

ggtactaaac tggaaatcaa a                                              741
```

<210> SEQ ID NO 186
<211> LENGTH: 741
<212> TYPE: DNA
<213> ORGANISM: Artificial Sequence
<220> FEATURE:
<223> OTHER INFORMATION: HLA-A*02 antigen binding domain

<400> SEQUENCE: 186

```
cagctgcagc tgcaggagtc tgggcccggg ctggtgaagc cttcggaaac gctgagcctc     60

acctgcacgg tttctggata caccttcacc agctatcata tccagtggat ccgacagccc    120

cctggaaaag ggcttgagtg gatcggatgg atctaccctg gcgatggttc aacacagtac    180
```

-continued

```
aatgagaagt tcaagggcag agccacgatt agcgtggaca catccaagaa ccaattctcc    240

ctgaacctgg acagcgtgag tgctgcggac acggccattt attactgtgc gagagaggga    300

acttactacg ctatggacta ctggggcaaa gggagcacgg tcaccgtgtc ctcaggcgga    360

ggtggaagcg gagggggagg atctggcggc ggaggaagcg gaggcgacat ccagatgacc    420

cagagcccaa gctccctgag tgcgtccgtg ggcgaccgcg tgaccatcac ttgcagatcc    480

tctcagtcca tcgtgcactc caacggcaac acgtacctcg agtggtacca gcagaagccc    540

gggaaggccc cgaaactgct catctacaag gtgagcaacc ggttctccgg cgtccccagc    600

cgcttctcag ggtccggctc ggggacggat ttcaccttca cgattagcag cttgcagccc    660

gaagacatcg ccacgtacta ctgctttcag ggaagtcacg tgccgcgtac cttcgggccg    720

ggcacgaaag tggatattaa g                                               741
```

<210> SEQ ID NO 187
<211> LENGTH: 741
<212> TYPE: DNA
<213> ORGANISM: Artificial Sequence
<220> FEATURE:
<223> OTHER INFORMATION: HLA-A*02 antigen binding domain

<400> SEQUENCE: 187

```
gaggtgcagc tggtgcagtc tggggccgag ctgaagaagc ctgggtcctc ggtgaaggtg     60

tcctgcaagg cttctggata caccttcacc agctatcata tccagtgggt aaaacaggcc    120

cctggacaag ggcttgagtg gatcggatgg atctaccctg gcgatggttc aacacagtac    180

aatgagaagt tcaagggcaa agccacgctt accgtggaca aatccacgaa cacagcctac    240

atggagctga gcagcctgag atctgaggac acggccgtat attactgtgc gagagaggga    300

acttactacg ctatggacta ctggggccaa gggaccctgg tcaccgtgtc ctcaggcgga    360

ggtggaagcg gagggggagg atctggcggc ggaggaagcg gaggcgacat ccagatgacc    420

cagagcccat ccaccctgag tgcgtccgtg ggcgaccgcg tgaccatcac ttgcagatcc    480

tctcagtcca tcgtgcactc caacggcaac acgtacctcg agtggtacca gcagaagccc    540

gggaaggccc cgaaactgct catctacaag gtgagcaacc ggttctccgg cgtccccagc    600

cgcttctcag ggtccggctc ggggacggat ttcaccctca cgattagcag cttgcagccc    660

gatgacttcg ccacgtacta ctgctttcag ggaagtcacg tgccgcgtac cttcgggcag    720

ggcacgaaag tggaagttaa g                                               741
```

<210> SEQ ID NO 188
<211> LENGTH: 741
<212> TYPE: DNA
<213> ORGANISM: Artificial Sequence
<220> FEATURE:
<223> OTHER INFORMATION: HLA-A*02 antigen binding domain

<400> SEQUENCE: 188

```
caggtgcagc tggtgcagtc tggggccgag gtgaagaagc ctgggtcctc ggtgaaggtg     60

tcctgcaagg cttctggata caccttcacc agctatcata tccagtgggt acgacaggcc    120

cctggacaag ggcttgagtg gatgggatgg atctaccctg gcgatggttc aacacagtac    180

aatgagaagt tcaagggcag agtcacgatt accgcggaca aatccacgag cacagcctac    240

atggagctga gcagcctgag atctgaggac acggccgtat attactgtgc gagagaggga    300

acttactacg ctatggacta ctggggccaa gggaccacgg tcaccgtgtc ctcaggcgga    360

ggtggaagcg gagggggagg atctggcggc ggaggaagcg gaggcgagat cgtcctgacc    420
```

```
cagagcccag ggaccctgag tttgtccccg ggcgagcgcg cgaccctcag ttgcagatcc    480

tctcagtcca tcgtgcactc caacggcaac acgtacctcg agtggtacca gcagaagccc    540

gggcaggccc cgcgactgct catctacaag gtgagcaacc ggttctccgg catccccgac    600

cgcttctcag ggtccggctc ggggacggat ttcaccctca cgattagccg cttggagccc    660

gaagacttcg ccgtgtacta ctgctttcag ggaagtcacg tgccgcgtac cttcgggggg    720

ggcacgaaag tggaaattaa g                                              741
```

<210> SEQ ID NO 189
<211> LENGTH: 741
<212> TYPE: DNA
<213> ORGANISM: Artificial Sequence
<220> FEATURE:
<223> OTHER INFORMATION: HLA-A*02 antigen binding domain

<400> SEQUENCE: 189

```
caggtgaccc tgaagcagtc tggggccgag gtgaagaagc ctgggtcctc ggtgaaggtg     60

tcctgcacgg cttctggata caccttcacc agctatcatg tcagctgggt acgacaggcc    120

cctggacaag ggcttgagtg gttgggaagg atctaccctg gcgatggttc aacacagtac    180

aatgagaagt tcaagggcaa agtcacgatt accgcggaca aatccatgga cacatccttc    240

atggagctga ccagcctgac atctgaggac acggccgtat attactgtgc gagagaggga    300

acttactacg ctatggacct ctggggccaa gggaccctgg tcaccgtgtc ctcaggcgga    360

ggtggaagcg gagggggagg atctggcggc ggaggaagcg gaggcgagat cgtcctgacc    420

cagagcccag ggaccctgag tttgtccccg ggcgagcgcg cgaccctcag ttgcagatcc    480

tctcagtcca tcgtgcactc caacggcaac acgtacctcg cgtggtacca gcagaagccc    540

gggcaggccc cgcgactgct catctccaag gtgagcaacc ggttctccgg cgtccccgac    600

cgcttctcag ggtccggctc ggggacggat ttcaccctca cgattagccg cttggagccc    660

gaagacttcg ccgtgtacta ctgccaacag ggaagtcacg tgccgcgtac cttcgggggg    720

ggcacgaaag tggaaattaa g                                              741
```

<210> SEQ ID NO 190
<211> LENGTH: 741
<212> TYPE: DNA
<213> ORGANISM: Artificial Sequence
<220> FEATURE:
<223> OTHER INFORMATION: HLA-A*02 antigen binding domain

<400> SEQUENCE: 190

```
caggtgcagc tggtgcagtc tggggccgag gtgaagaagc ctggggcctc ggtgaaggtg     60

tcctgcaagg cttctggata caccttcacc agctatcata tgcactgggt acgacaggcc    120

cctggacaaa ggcttgagtg gatgggatgg atctaccctg gcgatggttc aacacagtac    180

aatgagaagt tcaagggcaa agtcacgatt acccgggaca catccgcgag cacagcctac    240

atggagctga gcagcctgag atctgaggac acggccgtat attactgtgc gagagaggga    300

acttactacg ctatggacta ctggggccaa gggaccctgg tcaccgtgtc ctcaggcgga    360

ggtggaagcg gagggggagg atctggcggc ggaggaagcg gaggcgacat cgtcatgacc    420

cagaccccac tgtccctgcc tgtgaccccg ggcgagcccg cgagcatcag ttgcagatcc    480

tctcagtcca tcgtgcactc caacggcaac acgtacctcg actggtacct gcagaagccc    540

gggcagtccc cgcaactgct catctacaag gtgagcaacc ggttctccgg cgtccccgac    600
```

```
cgcttctcag ggtccggctc ggggacggat ttcaccctca agattagccg cgtggaggcc    660

gaagacgtcg gcgtgtacta ctgcatgcag ggaagtcacg tgccgcgtac cttcgggggg    720

ggcacgaaag tggaaattaa g                                              741


<210> SEQ ID NO 191
<211> LENGTH: 9
<212> TYPE: PRT
<213> ORGANISM: Artificial Sequence
<220> FEATURE:
<223> OTHER INFORMATION: HA-1 variant H peptide

<400> SEQUENCE: 191

Val Leu His Asp Asp Leu Leu Glu Ala
1               5


<210> SEQ ID NO 192
<211> LENGTH: 19
<212> TYPE: PRT
<213> ORGANISM: Artificial Sequence
<220> FEATURE:
<223> OTHER INFORMATION: P2A self cleaving peptide

<400> SEQUENCE: 192

Ala Thr Asn Phe Ser Leu Leu Lys Gln Ala Gly Asp Val Glu Glu Asn
1               5                   10                  15

Pro Gly Pro


<210> SEQ ID NO 193
<211> LENGTH: 608
<212> TYPE: PRT
<213> ORGANISM: Artificial Sequence
<220> FEATURE:
<223> OTHER INFORMATION: HA-1H TCR alpha and beta

<400> SEQUENCE: 193

Met Val Lys Ile Arg Gln Phe Leu Leu Ala Ile Leu Trp Leu Gln Leu
1               5                   10                  15

Ser Cys Val Ser Ala Ala Lys Asn Glu Val Glu Gln Ser Pro Gln Asn
            20                  25                  30

Leu Thr Ala Gln Glu Gly Glu Phe Ile Thr Ile Asn Cys Ser Tyr Ser
        35                  40                  45

Val Gly Ile Ser Ala Leu His Trp Leu Gln Gln His Pro Gly Gly Gly
    50                  55                  60

Ile Val Ser Leu Phe Met Leu Ser Ser Gly Lys Lys Lys His Gly Arg
65                  70                  75                  80

Leu Ile Ala Thr Ile Asn Ile Gln Glu Lys His Ser Ser Leu His Ile
                85                  90                  95

Thr Ala Ser His Pro Arg Asp Ser Ala Val Tyr Ile Cys Ala Val Arg
            100                 105                 110

Ser Val Ser Gly Ala Gly Ser Tyr Gln Leu Thr Phe Gly Lys Gly Thr
        115                 120                 125

Lys Leu Ser Val Ile Pro Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Cys Val Leu Asp Met Arg Ser Met Asp Phe Lys
            180                 185                 190
```

-continued

```
Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
            260                 265                 270

Trp Ser Ser Gly Ser Gly Ala Thr Asn Phe Ser Leu Leu Lys Gln Ala
        275                 280                 285

Gly Asp Val Glu Glu Asn Pro Gly Pro Met Gly Thr Ser Leu Leu Cys
    290                 295                 300

Trp Met Ala Leu Cys Leu Leu Gly Ala Asp His Ala Asp Thr Gly Val
305                 310                 315                 320

Ser Gln Asn Pro Arg His Lys Ile Thr Lys Arg Gly Gln Asn Val Thr
                325                 330                 335

Phe Arg Cys Asp Pro Ile Ser Glu His Asn Arg Leu Tyr Trp Tyr Arg
            340                 345                 350

Gln Thr Leu Gly Gln Gly Pro Glu Phe Leu Thr Tyr Phe Gln Asn Glu
        355                 360                 365

Ala Gln Leu Glu Lys Ser Arg Leu Leu Ser Asp Arg Phe Ser Ala Glu
    370                 375                 380

Arg Pro Lys Gly Ser Phe Ser Thr Leu Glu Ile Gln Arg Thr Glu Gln
385                 390                 395                 400

Gly Asp Ser Ala Met Tyr Leu Cys Ala Ser Ser Ile Asp Ser Phe Asn
                405                 410                 415

Glu Gln Phe Phe Gly Pro Gly Thr Arg Leu Thr Val Leu Glu Asp Leu
            420                 425                 430

Lys Asn Val Phe Pro Pro Glu Val Ala Val Phe Glu Pro Ser Glu Ala
        435                 440                 445

Glu Ile Ser His Thr Gln Lys Ala Thr Leu Val Cys Leu Ala Thr Gly
    450                 455                 460

Phe Tyr Pro Asp His Val Glu Leu Ser Trp Trp Val Asn Gly Lys Glu
465                 470                 475                 480

Val His Ser Gly Val Cys Thr Asp Pro Gln Pro Leu Lys Glu Gln Pro
                485                 490                 495

Ala Leu Asn Asp Ser Arg Tyr Cys Leu Ser Ser Arg Leu Arg Val Ser
            500                 505                 510

Ala Thr Phe Trp Gln Asn Pro Arg Asn His Phe Arg Cys Gln Val Gln
        515                 520                 525

Phe Tyr Gly Leu Ser Glu Asn Asp Glu Trp Thr Gln Asp Arg Ala Lys
    530                 535                 540

Pro Val Thr Gln Ile Val Ser Ala Glu Ala Trp Gly Arg Ala Asp Cys
545                 550                 555                 560

Gly Phe Thr Ser Glu Ser Tyr Gln Gln Gly Val Leu Ser Ala Thr Ile
                565                 570                 575

Leu Tyr Glu Ile Leu Leu Gly Lys Ala Thr Leu Tyr Ala Val Leu Val
            580                 585                 590

Ser Ala Leu Val Leu Met Ala Met Val Lys Arg Lys Asp Ser Arg Gly
        595                 600                 605
```

<210> SEQ ID NO 194
<211> LENGTH: 1827
<212> TYPE: DNA
<213> ORGANISM: Artificial Sequence
<220> FEATURE:
<223> OTHER INFORMATION: HA-1(H) TCR alpha and beta

<400> SEQUENCE: 194
atggtgaaga tccggcaatt tttgttggct attttgtggc ttcagctaag ctgtgtaagt 60
gccgccaaaa atgaagtgga gcagagtcct cagaacctga ctgcccagga aggagaattt 120
atcacaatca actgcagtta ctcggtagga ataagtgcct tacactggct gcaacagcat 180
ccaggaggag gcattgtttc cttgtttatg ctgagctcag ggaagaagaa gcatggaaga 240
ttaattgcca caataaacat acaggaaaag cacagctccc tgcacatcac agcctcccat 300
cccagagact ctgccgtcta catctgtgct gtcagaagcg tgtccggggc cggctcctac 360
cagctcacct ttgggaaggg gaccaaatta tcagtcattc caaatatcca gaaccctgac 420
cctgccgtgt accagctgag agactctaaa tccagtgaca agtctgtctg cctattcacc 480
gattttgatt ctcaaacaaa tgtgtcacaa agtaaggatt ctgatgtgta tatcacagac 540
aaatgtgtgc tagacatgag gtctatggac ttcaagagca acagtgctgt ggcctggagc 600
aacaaatctg actttgcatg tgcaaacgcc ttcaacaaca gcattattcc agaagacacc 660
ttcttcccca gcccagaaag ttcctgtgat gtcaagctgg tcgagaaaag ctttgaaaca 720
gatacgaacc taaactttca aaacctgtca gtgattgggt tccgaatcct cctcctgaaa 780
gtggccgggt ttaatctgct catgacgctg cggctgtggt ccagcggatc cggagccacc 840
aacttcagcc tgctgaagca ggccggcgac gtggaggaga accccggccc catgggcacc 900
agcctcctct gctggatggc cctgtgtctc ctgggggcag atcacgcaga tactggagtc 960
tcccagaacc ccagacacaa gatcacaaag aggggacaga atgtaacttt caggtgtgat 1020
ccaatttctg aacacaaccg cctttattgg taccgacaga ccctggggca gggcccagag 1080
tttctgactt acttccagaa tgaagctcaa ctagaaaaat caaggctgct cagtgatcgg 1140
ttctctgcag agaggcctaa gggatctttc tccaccttgg agatccagcg cacagagcag 1200
ggggactcgg ccatgtatct ctgtgccagc agcatcgact ccttcaacga gcagttcttc 1260
gggccgggca ccaggctcac ggtcctcgag gacctgaaaa acgtgttccc acccgaggtc 1320
gctgtgtttg agccatcaga agcagagatc tcccacaccc aaaaggccac actggtgtgc 1380
ctggccacag gcttctaccc cgaccacgtg gagctgagct ggtgggtgaa tgggaaggag 1440
gtgcacagtg ggtctgcac agacccgcag cccctcaagg agcagcccgc cctcaatgac 1500
tccagatact gcctgagcag ccgcctgagg gtgtcggcca ccttctggca gaacccccgc 1560
aaccacttcc gctgtcaagt ccagttctac gggctctcgg agaatgacga gtggacccag 1620
gatagggcca aacctgtcac ccagatcgtc agcgccgagg cctggggtag agcagactgt 1680
ggcttcacct ccgagtctta ccagcaaggg gtcctgtctg ccaccatcct ctatgagatc 1740
ttgctaggga aggccacctt gtatgccgtg ctggtcagtg ccctcgtgct gatggccatg 1800
gtcaagagaa aggattccag aggctag 1827

<210> SEQ ID NO 195
<211> LENGTH: 440
<212> TYPE: PRT
<213> ORGANISM: Artificial Sequence
<220> FEATURE:
<223> OTHER INFORMATION: Ftcr alpha LIR1 HA-1H

<400> SEQUENCE: 195

```
Met Val Lys Ile Arg Gln Phe Leu Leu Ala Ile Leu Trp Leu Gln Leu
1               5                   10                  15

Ser Cys Val Ser Ala Ala Lys Asn Glu Val Glu Gln Ser Pro Gln Asn
            20                  25                  30

Leu Thr Ala Gln Glu Gly Glu Phe Ile Thr Ile Asn Cys Ser Tyr Ser
        35                  40                  45

Val Gly Ile Ser Ala Leu His Trp Leu Gln Gln His Pro Gly Gly Gly
    50                  55                  60

Ile Val Ser Leu Phe Met Leu Ser Ser Gly Lys Lys Lys His Gly Arg
65                  70                  75                  80

Leu Ile Ala Thr Ile Asn Ile Gln Glu Lys His Ser Ser Leu His Ile
                85                  90                  95

Thr Ala Ser His Pro Arg Asp Ser Ala Val Tyr Ile Cys Ala Val Arg
            100                 105                 110

Ser Val Ser Gly Ala Gly Ser Tyr Gln Leu Thr Phe Gly Lys Gly Thr
        115                 120                 125

Lys Leu Ser Val Ile Pro Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Cys Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser Val Val Ile Gly Ile Leu
                245                 250                 255

Val Ala Val Ile Leu Leu Leu Leu Leu Leu Leu Leu Leu Phe Leu Ile
            260                 265                 270

Leu Arg His Arg Arg Gln Gly Lys His Trp Thr Ser Thr Gln Arg Lys
        275                 280                 285

Ala Asp Phe Gln His Pro Ala Gly Ala Val Gly Pro Glu Pro Thr Asp
    290                 295                 300

Arg Gly Leu Gln Trp Arg Ser Ser Pro Ala Ala Asp Ala Gln Glu Glu
305                 310                 315                 320

Asn Leu Tyr Ala Ala Val Lys His Thr Gln Pro Glu Asp Gly Val Glu
                325                 330                 335

Met Asp Thr Arg Ser Pro His Asp Glu Asp Pro Gln Ala Val Thr Tyr
            340                 345                 350

Ala Glu Val Lys His Ser Arg Pro Arg Arg Glu Met Ala Ser Pro Pro
        355                 360                 365

Ser Pro Leu Ser Gly Glu Phe Leu Asp Thr Lys Asp Arg Gln Ala Glu
    370                 375                 380

Glu Asp Arg Gln Met Asp Thr Glu Ala Ala Ala Ser Glu Ala Pro Gln
385                 390                 395                 400

Asp Val Thr Tyr Ala Gln Leu His Ser Leu Thr Leu Arg Arg Glu Ala
```

405 410 415

Thr Glu Pro Pro Pro Ser Gln Glu Gly Pro Ser Pro Ala Val Pro Ser
420 425 430

Ile Tyr Ala Thr Leu Ala Ile His
435 440

<210> SEQ ID NO 196
<211> LENGTH: 1279
<212> TYPE: DNA
<213> ORGANISM: Artificial Sequence
<220> FEATURE:
<223> OTHER INFORMATION: Ftcr alpha LIR1 HA-1H

<400> SEQUENCE: 196
atggtgaaga tccggcaatt tttgttggct attttgtggc ttcagctaag ctgtgtaagt 60
gccgccaaaa atgaagtgga gcagagtcct cagaacctga ctgcccagga aggagaattt 120
atcacaatca actgcagtta ctcggtagga ataagtgcct tacactggct gcaacagcat 180
ccaggaggag gcattgtttc cttgtttatg ctgagctcag ggaagaagaa gcatggaaga 240
ttaattgcca caataaacat acaggaaaag cacagctccc tgcacatcac agcctcccat 300
cccagagact ctgccgtcta catctgtgct gtcagaagcg tgtccggggc cggctcctac 360
cagctcacct ttgggaaggg gaccaaatta tcagtcattc caaatatcca gaaccctgac 420
cctgccgtgt accagctgag agactctaaa tccagtgaca agtctgtctg cctattcacc 480
gattttgatt ctcaaacaaa tgtgtcacaa agtaaggatt ctgatgtgta tatcacagac 540
aaatgtgtgc tagacatgag gtctatggac ttcaagagca acagtgctgt ggcctggagc 600
aacaaatctg actttgcatg tgcaaacgcc ttcaacaaca gcattattcc agaagacacc 660
ttcttcccca gcccagaaag ttcctgtgat gtcaagctgg tcgagaaaag ctttgaaaca 720
gatacgaacc taaactttca aaacctgtca gttgtgatcg gcatcttggt ggccgtcatc 780
ctactgctcc tcctcctcct cctcctcttc ctcatcctcc gacatcgacg tcagggcaaa 840
cactggacat cgacccagag aaaggctgat ttccaacatc ctgcaggggc tgtggggcca 900
gagcccacag acagaggcct gcagtggagg tccagcccag ctgccgatgc ccaggaagaa 960
aacctctatg ctgccgtgaa gcacacacag cctgaggatg gggtggagat ggacactcgg 1020
agcccacacg atgaagaccc ccaggcagtg acgtatgccg aggtgaaaca ctccagacct 1080
aggagagaaa tggcctctcc tccttcccca ctgtctgggg aattcctgga cacaaaggac 1140
agacaggcgg aagaggacag gcagatggac actgaggctg ctgcatctga agccccccag 1200
gatgtgacct acgcccagct gcacagcttg accctcagac gggaggcaac tgagcctcct 1260
ccatcccagg aagggccct 1279

<210> SEQ ID NO 197
<211> LENGTH: 466
<212> TYPE: PRT
<213> ORGANISM: Artificial Sequence
<220> FEATURE:
<223> OTHER INFORMATION: Ftcr beta LIR1 HA-1H

<400> SEQUENCE: 197

Met Gly Thr Ser Leu Leu Cys Trp Met Ala Leu Cys Leu Leu Gly Ala
1 5 10 15

Asp His Ala Asp Thr Gly Val Ser Gln Asn Pro Arg His Lys Ile Thr
20 25 30

Lys Arg Gly Gln Asn Val Thr Phe Arg Cys Asp Pro Ile Ser Glu His

```
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Ile Asp Ser Phe Asn Glu Gln Phe Phe Gly Pro Gly Thr Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Val Val Ile Gly Ile Leu Val Ala Val Ile Leu Leu
        275                 280                 285

Leu Leu Leu Leu Leu Leu Leu Phe Leu Ile Leu Arg His Arg Arg Gln
    290                 295                 300

Gly Lys His Trp Thr Ser Thr Gln Arg Lys Ala Asp Phe Gln His Pro
305                 310                 315                 320

Ala Gly Ala Val Gly Pro Glu Pro Thr Asp Arg Gly Leu Gln Trp Arg
                325                 330                 335

Ser Ser Pro Ala Ala Asp Ala Gln Glu Glu Asn Leu Tyr Ala Ala Val
            340                 345                 350

Lys His Thr Gln Pro Glu Asp Gly Val Glu Met Asp Thr Arg Ser Pro
        355                 360                 365

His Asp Glu Asp Pro Gln Ala Val Thr Tyr Ala Glu Val Lys His Ser
    370                 375                 380

Arg Pro Arg Arg Glu Met Ala Ser Pro Pro Ser Pro Leu Ser Gly Glu
385                 390                 395                 400

Phe Leu Asp Thr Lys Asp Arg Gln Ala Glu Glu Asp Arg Gln Met Asp
                405                 410                 415

Thr Glu Ala Ala Ala Ser Glu Ala Pro Gln Asp Val Thr Tyr Ala Gln
            420                 425                 430

Leu His Ser Leu Thr Leu Arg Arg Glu Ala Thr Glu Pro Pro Pro Ser
        435                 440                 445

Gln Glu Gly Pro Ser Pro Ala Val Pro Ser Ile Tyr Ala Thr Leu Ala
    450                 455                 460
```

Ile His
465

<210> SEQ ID NO 198
<211> LENGTH: 1401
<212> TYPE: DNA
<213> ORGANISM: Artificial Sequence
<220> FEATURE:
<223> OTHER INFORMATION: Ftcr beta LIR1 HA-1H

<400> SEQUENCE: 198
atgggcacca gcctcctctg ctggatggcc ctgtgtctcc tgggggcaga tcacgcagat 60
actggagtct cccagaaccc cagacacaag atcacaaaga ggggacagaa tgtaactttc 120
aggtgtgatc caatttctga acacaaccgc ctttattggt accgacagac cctggggcag 180
ggcccagagt ttctgactta cttccagaat gaagctcaac tagaaaaatc aaggctgctc 240
agtgatcggt tctctgcaga gaggcctaag ggatctttct ccaccttgga gatccagcgc 300
acagagcagg gggactcggc catgtatctc tgtgccagca gcatcgactc cttcaacgag 360
cagttcttcg ggccgggcac caggctcacg gtcctcgagg acctgaaaaa cgtgttccca 420
cccgaggtcg ctgtgtttga gccatcagaa gcagagatct cccacaccca aaaggccaca 480
ctggtgtgcc tggccacagg cttctacccc gaccacgtgg agctgagctg gtgggtgaat 540
gggaaggagg tgcacagtgg ggtctgcaca gacccgcagc ccctcaagga gcagcccgcc 600
ctcaatgact ccagatactg cctgagcagc cgcctgaggg tgtcggccac cttctggcag 660
aacccccgca accacttccg ctgtcaagtc cagttctacg ggctctcgga gaatgacgag 720
tggacccagg atagggccaa acctgtcacc cagatcgtca gcgccgaggc ctggggtaga 780
gcagactgtg gcttcacctc cgagtcttac cagcaagggg tcctgtctgt tgtgatcggc 840
atcttggtgg ccgtcatcct actgctcctc ctcctcctcc tcctcttcct catcctccga 900
catcgacgtc agggcaaaca ctggacatcg acccagagaa aggctgattt ccaacatcct 960
gcaggggctg tggggccaga gcccacagac agaggcctgc agtggaggtc cagcccagct 1020
gccgatgccc aggaagaaaa cctctatgct gccgtgaagc acacacagcc tgaggatggg 1080
gtggagatgg acactcggag cccacacgat gaagaccccc aggcagtgac gtatgccgag 1140
gtgaaacact ccagacctag gagagaaatg gcctctcctc cttccccact gtctggggaa 1200
ttcctggaca caaaggacag acaggcggaa gaggacaggc agatggacac tgaggctgct 1260
gcatctgaag ccccccagga tgtgacctac gcccagctgc acagcttgac cctcagacgg 1320
gaggcaactg agcctcctcc atcccaggaa gggccctctc cagctgtgcc cagcatctac 1380
gccactctgg ccatccacta g 1401

<210> SEQ ID NO 199
<211> LENGTH: 250
<212> TYPE: PRT
<213> ORGANISM: Artificial Sequence
<220> FEATURE:
<223> OTHER INFORMATION: HA-1H TCR alpha

<400> SEQUENCE: 199

Met Val Lys Ile Arg Gln Phe Leu Leu Ala Ile Leu Trp Leu Gln Leu
1 5 10 15

Ser Cys Val Ser Ala Ala Lys Asn Glu Val Glu Gln Ser Pro Gln Asn
20 25 30

Leu Thr Ala Gln Glu Gly Glu Phe Ile Thr Ile Asn Cys Ser Tyr Ser

```
        35                  40                  45

Val Gly Ile Ser Ala Leu His Trp Leu Gln Gln His Pro Gly Gly Gly
    50                  55                  60

Ile Val Ser Leu Phe Met Leu Ser Ser Gly Lys Lys Lys His Gly Arg
65                  70                  75                  80

Leu Ile Ala Thr Ile Asn Ile Gln Glu Lys His Ser Ser Leu His Ile
                85                  90                  95

Thr Ala Ser His Pro Arg Asp Ser Ala Val Tyr Ile Cys Ala Val Arg
            100                 105                 110

Ser Val Ser Gly Ala Gly Ser Tyr Gln Leu Thr Phe Gly Lys Gly Thr
        115                 120                 125

Lys Leu Ser Val Ile Pro Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Cys Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
225                 230                 235                 240

Asp Thr Asn Leu Asn Phe Gln Asn Leu Ser
                245                 250


<210> SEQ ID NO 200
<211> LENGTH: 276
<212> TYPE: PRT
<213> ORGANISM: Artificial Sequence
<220> FEATURE:
<223> OTHER INFORMATION: HA-1H TCR beta

<400> SEQUENCE: 200

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Lys Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Ile Asp Ser Phe Asn Glu Gln Phe Phe Gly Pro Gly Thr Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
```

-continued

```
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Cys Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser
        275
```

<210> SEQ ID NO 201
<211> LENGTH: 750
<212> TYPE: DNA
<213> ORGANISM: Artificial Sequence
<220> FEATURE:
<223> OTHER INFORMATION: HA-1H TCR alpha

<400> SEQUENCE: 201

```
atggtgaaga tccggcaatt tttgttggct attttgtggc ttcagctaag ctgtgtaagt      60

gccgccaaaa atgaagtgga gcagagtcct cagaacctga ctgcccagga aggagaattt     120

atcacaatca actgcagtta ctcggtagga ataagtgcct tacactggct gcaacagcat     180

ccaggaggag gcattgtttc cttgtttatg ctgagctcag ggaagaagaa gcatggaaga     240

ttaattgcca caataaacat acaggaaaag cacagctccc tgcacatcac agcctcccat     300

cccagagact ctgccgtcta catctgtgct gtcagaagcg tgtccggggc cggctcctac     360

cagctcacct ttgggaaggg gaccaaatta tcagtcattc caaatatcca gaaccctgac     420

cctgccgtgt accagctgag agactctaaa tccagtgaca agtctgtctg cctattcacc     480

gattttgatt ctcaaacaaa tgtgtcacaa agtaaggatt ctgatgtgta tatcacagac     540

aaatgtgtgc tagacatgag gtctatggac ttcaagagca acagtgctgt ggcctggagc     600

aacaaatctg actttgcatg tgcaaacgcc ttcaacaaca gcattattcc agaagacacc     660

ttcttcccca gcccagaaag ttcctgtgat gtcaagctgg tcgagaaaag ctttgaaaca     720

gatacgaacc taaactttca aaacctgtca                                      750
```

<210> SEQ ID NO 202
<211> LENGTH: 828
<212> TYPE: DNA
<213> ORGANISM: Artificial Sequence
<220> FEATURE:
<223> OTHER INFORMATION: HA-1H TCR beta

<400> SEQUENCE: 202

```
atgggcacca gcctcctctg ctggatggcc ctgtgtctcc tgggggcaga tcacgcagat      60

actggagtct cccagaaccc cagacacaag atcacaaaga ggggacagaa tgtaactttc     120

aggtgtgatc caatttctga acacaaccgc ctttattggt accgacagac cctggggcag     180

ggcccagagt ttctgactta cttccagaat gaagctcaac tagaaaaatc aaggctgctc     240
```

```
agtgatcggt tctctgcaga gaggcctaag ggatctttct ccaccttgga gatccagcgc    300

acagagcagg gggactcggc catgtatctc tgtgccagca gcatcgactc cttcaacgag    360

cagttcttcg ggccgggcac caggctcacg gtcctcgagg acctgaaaaa cgtgttccca    420

cccgaggtcg ctgtgtttga gccatcagaa gcagagatct cccacaccca aaaggccaca    480

ctggtgtgcc tggccacagg cttctacccc gaccacgtgg agctgagctg gtgggtgaat    540

gggaaggagg tgcacagtgg ggtctgcaca gacccgcagc ccctcaagga gcagcccgcc    600

ctcaatgact ccagatactg cctgagcagc cgcctgaggg tgtcggccac cttctggcag    660

aacccccgca accacttccg ctgtcaagtc cagttctacg ggctctcgga gaatgacgag    720

tggacccagg atagggccaa acctgtcacc cagatcgtca gcgccgaggc ctggggtaga    780

gcagactgtg gcttcacctc cgagtcttac cagcaagggg tcctgtct                 828


<210> SEQ ID NO 203
<211> LENGTH: 13
<212> TYPE: PRT
<213> ORGANISM: Artificial Sequence
<220> FEATURE:
<223> OTHER INFORMATION: NY-ESO CDR

<400> SEQUENCE: 203

Cys Ala Ser Ser Leu Gly Leu Gly Tyr Glu Gln Tyr Phe
1               5                   10


<210> SEQ ID NO 204
<211> LENGTH: 20
<212> TYPE: PRT
<213> ORGANISM: Artificial Sequence
<220> FEATURE:
<223> OTHER INFORMATION: NY-ESO CDR

<400> SEQUENCE: 204

Cys Ala Ser Ser Leu Gly Gly Pro Arg Gly Leu Ala Gly Leu Arg Gly
1               5                   10                  15

Asp Glu Gln Phe
            20


<210> SEQ ID NO 205
<211> LENGTH: 12
<212> TYPE: PRT
<213> ORGANISM: Artificial Sequence
<220> FEATURE:
<223> OTHER INFORMATION: NY-ESO CDR

<400> SEQUENCE: 205

Cys Ala Ser Ser Leu Arg Arg Asp Asn Glu Gln Phe
1               5                   10


<210> SEQ ID NO 206
<211> LENGTH: 19
<212> TYPE: PRT
<213> ORGANISM: Artificial Sequence
<220> FEATURE:
<223> OTHER INFORMATION: MAGE-A3 CDR

<400> SEQUENCE: 206

Cys Ala Ser Ser Leu Glu Val Leu Leu Gly Ala Asp Phe Pro Asp Thr
1               5                   10                  15

Gln Tyr Phe
```

<210> SEQ ID NO 207
<211> LENGTH: 18
<212> TYPE: PRT
<213> ORGANISM: Artificial Sequence
<220> FEATURE:
<223> OTHER INFORMATION: MAGE-A3 CDR

<400> SEQUENCE: 207

Cys Ala Ser Ser Phe Pro Ala Gly His Gly Ala Asp Leu Asp Asn Glu
1               5                   10                  15

Gln Phe

<210> SEQ ID NO 208
<211> LENGTH: 14
<212> TYPE: PRT
<213> ORGANISM: Artificial Sequence
<220> FEATURE:
<223> OTHER INFORMATION: MAGE-A3 CDR

<400> SEQUENCE: 208

Cys Ala Ser Ser Glu Ile Thr Gly Arg Ile Gly Glu Gln Phe
1               5                   10

<210> SEQ ID NO 209
<211> LENGTH: 18
<212> TYPE: PRT
<213> ORGANISM: Artificial Sequence
<220> FEATURE:
<223> OTHER INFORMATION: MAGE-A3 CDR

<400> SEQUENCE: 209

Cys Ala Ser Ser Leu Gly Gly Asp Glu Leu Gly Ala Asp Gly Asn Glu
1               5                   10                  15

Gln Phe

<210> SEQ ID NO 210
<211> LENGTH: 241
<212> TYPE: PRT
<213> ORGANISM: Artificial Sequence
<220> FEATURE:
<223> OTHER INFORMATION: NY-ESO-1 ScFv

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gly Gly Glu Val Gln Leu
        115                 120                 125

Val Glu Ser Gly Gly Gly Leu Val Gln Pro Gly Gly Ser Leu Arg Leu
    130                 135                 140

```
Ser Cys Ala Ala Ser Gly Phe Thr Val Tyr Asp Tyr Met Ser Trp Val
145                 150                 155                 160

Arg Gln Ala Pro Gly Lys Gly Leu Glu Trp Val Ser Val Ile Tyr Ser
                165                 170                 175

Gly Gly Ser Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Tyr Cys Ala Arg Tyr Ser Tyr Tyr
    210                 215                 220

Tyr Tyr Tyr Met Asp Val Trp Gly Lys Gly Thr Thr Val Thr Val Ser
225                 230                 235                 240

Ser


<210> SEQ ID NO 211
<211> LENGTH: 723
<212> TYPE: DNA
<213> ORGANISM: Artificial Sequence
<220> FEATURE:
<223> OTHER INFORMATION: NY-ESO-1 ScFv

<400> SEQUENCE: 211

gacatccaga tgacccagtc tccatcctcc ctgtctgcat ctgtaggaga cagagtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

aggttcagtg gcagtggatc tgggacagat ttcactctca ccatcagcag tctgcaacct    240

gaagattttg caacttacta ctgtcaacag agttacagta cccctctcac tttcggcggc    300

ggaacaaagg tggagatcaa gggcggaggt ggaagcggag ggggaggatc tggcggcgga    360

ggaagcggag gcgaagtgca gctggtggaa agcggcggag gcctggtgca gcctggcggc    420

agcctgagac tgtcttgcgc cgccagcggc ttcaccgtgt acgactacat gagctgggtc    480

cgccaggccc ctggcaaggg actggaatgg gtgtccgtga tctacagcgg cggcagcacc    540

tactacgccg acagcgtgaa gggtcgattc accatcagcc gggacaacag caagaacacc    600

ctgtacctgc agatgaacag cctgcgggcc gaggacaccg ccgtgtatta ctgtgcgagg    660

tactcctact actactacta catggacgtc tggggcaaag ggaccacggt caccgtgtcc    720

tca                                                                  723


<210> SEQ ID NO 212
<211> LENGTH: 244
<212> TYPE: PRT
<213> ORGANISM: Artificial Sequence
<220> FEATURE:
<223> OTHER INFORMATION: MAGE-A3 antigen binding domain

<400> SEQUENCE: 212

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Thr Tyr Tyr Asn Pro Ser Leu
    50                  55                  60

Lys Ser Arg Val Thr Met Ser Val Asp Thr Ser Lys Asn Gln Phe Ser
```

-continued

```
65                  70                  75                  80

Leu Lys Leu Ser Ser Val Thr Ala Val Asp Thr Ala Val Tyr Tyr Cys
                85                  90                  95

Ala Arg Ile Pro Phe Gly Asp Trp Trp Tyr Phe Asp Leu Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ser Tyr Ser Phe Val Leu Thr Phe Gly Gly Gly Thr Lys
225                 230                 235                 240

Val Glu Ile Lys
```

<210> SEQ ID NO 213
<211> LENGTH: 732
<212> TYPE: DNA
<213> ORGANISM: Artificial Sequence
<220> FEATURE:
<223> OTHER INFORMATION: MAGE-A3 antigen binding domain

<400> SEQUENCE: 213

```
caggtgcagc tgcaggaaag cggccctggc ctggtgaaac ccagcgacac cctgagcctg     60

acctgcgccg tgtccggcta cagcatcagc agcagcaatt ggtggggctg gatcagacag    120

ccccctggca agggcctgga atggatcggc tacatctact acagcggcag cacctactac    180

aaccccagcc tgaagtccag agtgaccatg agcgtggaca ccagcaagaa ccagttcagc    240

ctgaagctga gcagcgtgac cgccgtcgat accgctgtgt attactgtgc gagaataccc    300

tttggggatt ggtggtactt cgatctctgg ggccgtggca ccctggtcac tgtgtcctca    360

ggcggaggtg gaagcggagg gggaggatct ggcggcggag gaagcggagg cgacatccag    420

atgacccaga gccccagcag cctgagcgcc agcgtgggcg acagagtgac catcacctgt    480

cgggccagcc agtcgatcag cagctacctg aactggtatc agcagaagcc cggcaaggcc    540

cccaagctgc tgatctacgc cgccagctcc ctgcagagcg gcgtgccaag cagattcagc    600

ggcagcggct ccggcaccga cttcaccctg accatcagca gcctgcagcc cgaggacttc    660

gccacctact actgccagca gagttacagt ttcgttctca ctttcggcgg agggaccaag    720

gtggagatca aa                                                        732
```

<210> SEQ ID NO 214
<211> LENGTH: 248
<212> TYPE: PRT
<213> ORGANISM: Artificial Sequence
<220> FEATURE:
<223> OTHER INFORMATION: MAGE-A3 antigen binding domain

<400> SEQUENCE: 214

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Tyr Ser Ser Ser Trp Tyr Cys Asp Ala Phe Asp Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Gly Ser Gly Gly Asp Ile Gln Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Ser Ile Ser Ser Tyr Leu Asn Trp Tyr
                165                 170                 175

Gln Gln Lys Pro Gly Lys Ala Pro Lys Leu Leu Ile Tyr Ala Ala Ser
            180                 185                 190

Ser Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Ser Trp Ala Ser Thr Pro Leu Thr Phe Gly
225                 230                 235                 240

Gly Gly Thr Lys Val Glu Ile Lys
                245
```

<210> SEQ ID NO 215
<211> LENGTH: 744
<212> TYPE: DNA
<213> ORGANISM: Artificial Sequence
<220> FEATURE:
<223> OTHER INFORMATION: MAGE-A3 antigen binding domain

<400> SEQUENCE: 215

```
caggtgcagc tggtgcagtc tggcgccgaa gtgaagaaac ctggcgcctc cgtgaaggtg     60

tcctgcaagg tgtccggcta caccctgacc gagctgtcga tgcactgggt ccgccaggca    120

cctggcaagg gactggaatg gatgggcggc tttgaccccg aggacggcga gacaatctac    180

gcccagaaat tccagggcag agtgaccatg accgaggaca ccagcaccga caccgcctac    240

atggaactga gcagcctgcg gagcgaggac accgctgtgt attactgtgc aacagatctg    300

tatagcagca gctggtactg tgatgctttt gatatctggg gccaagggac aatggtcacc    360

gtgtcctcag gcggaggtgg aagcggaggg ggaggatctg gcggcggagg aagcggaggc    420

gacatccaga tgacccagag ccccagcagc ctgagcgcca gcgtgggcga cagagtgacc    480

atcacctgtc gggccagcca gtcgatcagc agctacctga actggtatca gcagaagccc    540

ggcaaggccc ccaagctgct gatctacgcc gccagctccc tgcagagcgg cgtgccaagc    600
```

-continued

```
agattcagcg gcagcggctc cggcaccgac ttcaccctga ccatcagcag cctgcagccc    660

gaggacttcg ccacctacta ctgccagcag agttgggcca gcacccctct cactttcggc    720

ggagggacca aggtggagat caaa                                            744


<210> SEQ ID NO 216
<211> LENGTH: 245
<212> TYPE: PRT
<213> ORGANISM: Artificial Sequence
<220> FEATURE:
<223> OTHER INFORMATION: HPV E6 antigen binding domain

<400> SEQUENCE: 216

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Asn Gly Val Val Lys Trp Tyr Phe Asp Leu Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ser Tyr Ser Thr Pro Leu Phe Pro Phe Gly Gly Gly Thr
225                 230                 235                 240

Lys Val Glu Ile Lys
                245


<210> SEQ ID NO 217
<211> LENGTH: 735
<212> TYPE: DNA
<213> ORGANISM: Artificial Sequence
<220> FEATURE:
<223> OTHER INFORMATION: HPV E6 antigen binding domain

<400> SEQUENCE: 217

gaagtgcagc tggtggaaag cggcggaggc ctggtgcagc ctggcggcag cctgagactg     60

tcttgcgccg ccagcggctt caccttcagc agctactgga tgcactgggt ccgccaggcc    120

cctggcaagg gactggtctg ggtgtctcga atcaacagcg acggcagcag caccagctac    180
```

```
gccgacagcg tgaagggccg gttcaccatc agccgggaca acgccaagaa caccctgtac    240

ctgcagatga acagcctgcg ggccgaggac accgccgtgt attactgtgc cagggagaac    300

ggcgtggtga agtggtactt cgacctgtgg ggccgtggca ccctggtcac tgtgtcctca    360

ggcggaggtg gaagcggagg gggaggatct ggcggcggag gaagcggagg cgacatccag    420

atgacccaga gccccagcag cctgagcgcc agcgtgggcg acagagtgac catcacctgt    480

cgggccagcc agtcgatcag cagctacctg aactggtatc agcagaagcc cggcaaggcc    540

cccaagctgc tgatctacgc cgccagctcc ctgcagagcg gcgtgccaag cagattcagc    600

ggcagcggct ccggcaccga cttcaccctg accatcagca gcctgcagcc cgaggacttc    660

gccacctact actgccagca gagttacagt acccctctct ttcccttcgg cggagggacc    720

aaggtggaga tcaaa                                                     735
```

<210> SEQ ID NO 218
<211> LENGTH: 247
<212> TYPE: PRT
<213> ORGANISM: Artificial Sequence
<220> FEATURE:
<223> OTHER INFORMATION: HPV E6 antigen binding domain

<400> SEQUENCE: 218

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gly Arg Gly Ser Pro Phe Tyr Gly Gly Ala Phe Asp Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Gly Ser Gly Gly Asp Ile Gln Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Ser Ile Ser Ser Tyr Leu Asn Trp Tyr
                165                 170                 175

Gln Gln Lys Pro Gly Lys Ala Pro Lys Leu Leu Ile Tyr Ala Ala Ser
            180                 185                 190

Ser Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Ser Tyr Ser Thr Pro Leu Thr Phe Gly Gly
225                 230                 235                 240

Gly Thr Lys Val Glu Ile Lys
                245
```

<210> SEQ ID NO 219
<211> LENGTH: 741
<212> TYPE: DNA
<213> ORGANISM: Artificial Sequence
<220> FEATURE:
<223> OTHER INFORMATION: HPV E6 antigen binding domain

<400> SEQUENCE: 219
gaagtgcagc tggtggaaag cggcggaggc ctggtgcagc ccggtcgaag cctgagactg 60
agctgcgccg ccagcggctt cacctttgac gactacgcca tgcactgggt ccgccaggcc 120
cctggcaagg gactggaatg ggtgtccggc atcagctgga acagcggcag catcggctac 180
gccgacagcg tgaagggccg gttcaccatc agccgggaca acgccaagaa cagcctgtac 240
ctgcagatga acagcctgcg ggccgaggac accgccttgt attactgtgc caaggacggc 300
aggggctccc ccttctacgg cggcgccttc gacatctggg gccaagggac aatggtcacc 360
gtgtcctcag gcggaggtgg aagcggaggg ggaggatctg gcggcggagg aagcggaggc 420
gacatccaga tgacccagtc tccatcctcc ctgtctgcat ctgtaggaga cagagtcacc 480
atcacttgcc gggcaagtca gagcattagc agctatttaa attggtatca gcagaaacca 540
gggaaagccc ctaagctcct gatctatgct gcatccagtt tgcaaagtgg ggtcccatca 600
aggttcagtg gcagtggatc tgggacagat ttcactctca ccatcagcag tctgcaacct 660
gaagattttg caacttacta ctgtcaacag agttacagta cccctctcac tttcggcggc 720
ggaacaaagg tggagatcaa g 741

<210> SEQ ID NO 220
<211> LENGTH: 251
<212> TYPE: PRT
<213> ORGANISM: Artificial Sequence
<220> FEATURE:
<223> OTHER INFORMATION: HPV E7 antigen binding domain

<400> SEQUENCE: 220

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Ser Tyr Asp Tyr Leu Leu Asn Pro Tyr Arg Trp Asn
            100                 105                 110

Trp Phe Asp Pro Trp Gly Gln Gly Thr Leu Val Thr Val Ser Ser Gly
        115                 120                 125

Gly Gly Gly Ser Gly Gly Gly Gly Ser Gly Gly Gly Gly Ser Gly Gly
    130                 135                 140

Asp Ile Gln Met Thr Gln Ser Pro Ser Ser Leu Ser Ala Ser Val Gly
145                 150                 155                 160

Asp Arg Val Thr Ile Thr Cys Arg Ala Ser Gln Ser Ile Ser Ser Tyr
                165                 170                 175

```
Leu Asn Trp Tyr Gln Gln Lys Pro Gly Lys Ala Pro Lys Leu Leu Ile
            180                 185                 190

Tyr Ala Ala Ser Ser Leu Gln Ser Gly Val Pro Ser Arg Phe Ser Gly
        195                 200                 205

Ser Gly Ser Gly Thr Asp Phe Thr Leu Thr Ile Ser Ser Leu Gln Pro
    210                 215                 220

Glu Asp Phe Ala Thr Tyr Tyr Cys Gln Gln Ser Tyr Ser Thr Pro Leu
225                 230                 235                 240

Thr Phe Gly Gly Gly Thr Lys Val Glu Ile Lys
                245                 250


<210> SEQ ID NO 221
<211> LENGTH: 753
<212> TYPE: DNA
<213> ORGANISM: Artificial Sequence
<220> FEATURE:
<223> OTHER INFORMATION: HPV E7 antigen binding domain

<400> SEQUENCE: 221

gaagtgcagc tggtggaaag cggcggaggc ctggtgaaac ctggcggcag cctgagactg      60

agctgcgccg ccagcggctt caccttctcg aacgcctgga tgagctgggt ccgccaggcc     120

cctggcaagg gactggaatg ggtcggacgg atcaagagca agaccgacgg cggcaccacc     180

gactacgctg cccccgtgaa gggccggttc accatcagcc gggacgacag caagaacacc     240

ctgtacctgc agatgaacag cctgaaaacc gaggacaccg ccgtgtatta ctgtaccacc     300

tcctacgatt accttctcaa tccttatcgt tggaactggt tcgacccctg gggccaggga     360

accctggtca ccgtgtcctc aggcggaggt ggaagcggag gggggaggatc tggcggcgga   420

ggaagcggcg gagacatcca gatgacccag tctccatcct ccctgtctgc atctgtagga     480

gacagagtca ccatcacttg ccgggcaagt cagagcatta gcagctattt aaattggtat     540

cagcagaaac cagggaaagc ccctaagctc ctgatctatg ctgcatccag tttgcaaagt     600

ggggtcccat caaggttcag tggcagtgga tctgggacag atttcactct caccatcagc     660

agtctgcaac ctgaagattt tgcaacttac tactgtcaac agagttacag taccccctctc   720

actttcggcg gcggaacaaa ggtggagatc aag                                  753


<210> SEQ ID NO 222
<211> LENGTH: 246
<212> TYPE: PRT
<213> ORGANISM: Artificial Sequence
<220> FEATURE:
<223> OTHER INFORMATION: MAGE-A3 antigen binding domain

<400> SEQUENCE: 222

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

-continued

```
Ala Arg Asp Met Asp Thr Phe Ser Met Val Thr Leu Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Gly Gly Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Ser Ile Ser Ser Tyr Leu Asn Trp Tyr Gln
                165                 170                 175

Gln Lys Pro Gly Lys Ala Pro Lys Leu Leu Ile Tyr Ala Ala Ser Ser
            180                 185                 190

Leu Gln Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Ser Tyr Ser Trp Pro Leu Thr Phe Gly Gly Gly
225                 230                 235                 240

Thr Lys Val Glu Ile Lys
                245


<210> SEQ ID NO 223
<211> LENGTH: 738
<212> TYPE: DNA
<213> ORGANISM: Artificial Sequence
<220> FEATURE:
<223> OTHER INFORMATION: MAGE-A3 antigen binding domain

<400> SEQUENCE: 223

caggtgcagc tggtgcagtc tggcgccgaa gtgaagaaac ccggcagcag cgtgaaggtg      60

tcctgcaagg ccagcggcgg caccttcagc agctacgcca tcagctgggt ccgccaggct     120

cctggacagg gactggaatg gatgggcggc atcatcccca tcttcggcac cgccaactac     180

gcccagaaat tccagggcag agtgaccatc accgccgacg agagcaccag caccgcctac     240

atggaactga gcagccttcg aagcgaggac accgctgtgt attactgtgc cagggacatg     300

gacaccttct ccatggtgac cctgttcgac tactggggcc agggcaccct ggtcaccgtg     360

tcctcaggcg gaggtggaag cggaggggga ggatctggcg gcggaggaag cggaggcgac     420

atccagatga cccagagccc cagcagcctg agcgccagcg tgggcgacag agtgaccatc     480

acctgtcggg ccagccagtc gatcagcagc tacctgaact ggtatcagca gaagcccggc     540

aaggccccca agctgctgat ctacgccgcc agctccctgc agagcggcgt gccaagcaga     600

ttcagcggca gcggctccgg caccgacttc accctgacca tcagcagcct gcagcccgag     660

gacttcgcca cctactactg ccagcagagt tacagttggc ctctcacttt cggcggaggg     720

accaaggtgg agatcaaa                                                   738


<210> SEQ ID NO 224
<211> LENGTH: 245
<212> TYPE: PRT
<213> ORGANISM: Artificial Sequence
<220> FEATURE:
<223> OTHER INFORMATION: KRAS G12V antigen binding domain

<400> SEQUENCE: 224

Gln Val Thr Leu Arg Glu Ser Gly Pro Ala Leu Val Lys Pro Thr Gln
1               5                   10                  15
```

-continued

```
Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Tyr Asp Glu Leu Tyr Tyr Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Ser Ile Trp Thr Ser Tyr Leu Asn Trp Tyr Gln Gln
                165                 170                 175

Lys Pro Gly Lys Ala Pro Lys Leu Leu Ile Tyr Ala Ala Ser Ser Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Ser Tyr Ser Thr Pro Leu Thr Phe Gly Gly Gly Thr
225                 230                 235                 240

Lys Val Glu Ile Lys
                245
```

<210> SEQ ID NO 225
<211> LENGTH: 735
<212> TYPE: DNA
<213> ORGANISM: Artificial Sequence
<220> FEATURE:
<223> OTHER INFORMATION: KRAS G12V antigen binding domain

<400> SEQUENCE: 225

```
caggtcacac tgagagagtc cggccctgcc ctggtgaaac ccacccagac cctgaccctg     60

acatgcacct tcagcggctt cagcctgagc accagcggga tgtgcgtgtc ctggattcga    120

cagccccctg gcaaggccct ggaatggctg gccctgattg actgggacga cgacaagtac    180

tacagcacca gcctgaaaac ccggctgacc atcagcaagg acaccagcaa gaaccaggtg    240

gtgctgacca tgaccaacat ggaccccgtg gacaccgcca cgtattactg tgcacggagt    300

tacgacgagc tctactactt tgactactgg ggccagggaa ccctggtcac cgtgtcctca    360

ggcggaggtg gaagcggagg gggaggatct ggcggcggag gaagcggagg cgacatccag    420

atgacccaga gccccagctc cctctctgca tctgtgggcg acagagtgac catcacctgt    480

cgggccagcc agtcgatctg gaccagctac ctgaactggt atcagcagaa gcccggcaag    540

gcccccaagc tgctgatcta cgccgccagc tccctgcaga gcggcgtgcc aagcagattc    600

agcggcagcg gctccggcac cgacttcacc ctgaccatca gcagcctgca gcccgaggac    660

ttcgccacct actactgcca gcagagttac agtacccctc tcactttcgg cggagggacc    720
```

aaggtggaga tcaaa 735

<210> SEQ ID NO 226
<211> LENGTH: 5
<212> TYPE: PRT
<213> ORGANISM: Artificial Sequence
<220> FEATURE:
<223> OTHER INFORMATION: linker

<400> SEQUENCE: 226

Gly Gly Gly Gly Ser
1 5

<210> SEQ ID NO 227
<211> LENGTH: 10
<212> TYPE: PRT
<213> ORGANISM: Artificial Sequence
<220> FEATURE:
<223> OTHER INFORMATION: linker

<400> SEQUENCE: 227

Gly Gly Gly Gly Ser Gly Gly Gly Gly Ser
1 5 10

<210> SEQ ID NO 228
<211> LENGTH: 15
<212> TYPE: PRT
<213> ORGANISM: Artificial Sequence
<220> FEATURE:
<223> OTHER INFORMATION: linker

<400> SEQUENCE: 228

Gly Gly Gly Gly Ser Gly Gly Gly Gly Ser Gly Gly Gly Gly Ser
1 5 10 15

<210> SEQ ID NO 229
<211> LENGTH: 15
<212> TYPE: PRT
<213> ORGANISM: Artificial Sequence
<220> FEATURE:
<223> OTHER INFORMATION: linker

<400> SEQUENCE: 229

Gly Gly Gly Gly Ser Gly Gly Gly Gly Ser Gly Gly Gly Gly Ser
1 5 10 15

<210> SEQ ID NO 230
<211> LENGTH: 20
<212> TYPE: PRT
<213> ORGANISM: Artificial Sequence
<220> FEATURE:
<223> OTHER INFORMATION: linker

<400> SEQUENCE: 230

Gly Gly Gly Gly Ser Gly Gly Gly Gly Ser Gly Gly Gly Gly Ser Gly
1 5 10 15

Gly Gly Gly Ser
20

<210> SEQ ID NO 231
<211> LENGTH: 4
<212> TYPE: PRT
<213> ORGANISM: Artificial Sequence
<220> FEATURE:
<223> OTHER INFORMATION: linker

<400> SEQUENCE: 231

Gly Gly Gly Ser
1

<210> SEQ ID NO 232
<211> LENGTH: 247
<212> TYPE: PRT
<213> ORGANISM: Artificial Sequence
<220> FEATURE:
<223> OTHER INFORMATION: KRAS ScFv

<400> SEQUENCE: 232

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Ser Trp Ile Arg Gln Ala Pro Gly Lys Gly Leu Glu Trp Val
35 40 45

Ser Tyr Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Phe Thr Arg Asp Tyr Tyr Tyr Tyr Tyr Tyr Met Asp Val
100 105 110

Trp Gly Lys Gly Thr Thr Val Thr Val Ser Ser Gly Gly Gly Gly Ser
115 120 125

Gly Gly Gly Gly Ser Gly Gly Gly Gly Ser Gly Gly Asp Ile Gln Met
130 135 140

Thr Gln Ser Pro Ser Ser Leu Ser Ala Ser Val Gly Asp Arg Val Thr
145 150 155 160

Ile Thr Cys Arg Ala Ser Gln Ser Ile Ser Ser Tyr Leu Asn Trp Tyr
165 170 175

Gln Gln Lys Pro Gly Lys Ala Pro Lys Leu Leu Ile Tyr Ala Ala Ser
180 185 190

Ser Leu Gln Ser Gly Val Pro Ser Arg Phe Ser Gly Ser Gly Ser Gly
195 200 205

Thr Asp Phe Thr Leu Thr Ile Ser Ser Leu Gln Pro Glu Asp Phe Ala
210 215 220

Thr Tyr Tyr Cys Gln Gln Ser Tyr Ser Thr Pro Leu Thr Phe Gly Gly
225 230 235 240

Gly Thr Lys Val Glu Ile Lys
245

<210> SEQ ID NO 233
<211> LENGTH: 741
<212> TYPE: DNA
<213> ORGANISM: Artificial Sequence
<220> FEATURE:
<223> OTHER INFORMATION: KRAS ScFv

<400> SEQUENCE: 233
caggtgcagc tggtggaaag cggcggaggc ctggtgaaac ctggcggcag cctgagactg 60
agctgcgccg ccagcggctt caccttcagc gactactaca tgagctggat cagacaggcc 120
cctggcaagg gactggaatg ggtgtcctac atcagcagca gcggctcgac catctactac 180
gccgacagcg tgaagggccg gttcaccatc agccgggaca acgccaagaa cagcctgtac 240

```
ctgcagatga acagcctgcg ggccgaggac accgccgtgt attactgtgc cagggacttc    300

accagggact actactacta ctactacatg gacgtgtggg gcaaagggac cacggtcacc    360

gtgtcctcag gcggaggtgg aagcggaggg ggaggatctg gcggcggagg aagcggaggc    420

gacatccaga tgacccagtc tccatcctcc ctgtctgcat ctgtaggaga cagagtcacc    480

atcacttgcc gggcaagtca gagcattagc agctatttaa attggtatca gcagaaacca    540

gggaaagccc ctaagctcct gatctatgct gcatccagtt tgcaaagtgg ggtcccatca    600

aggttcagtg gcagtggatc tgggacagat ttcactctca ccatcagcag tctgcaacct    660

gaagattttg caacttacta ctgtcaacag agttacagta cccctctcac tttcggcggc    720

ggaacaaagg tggagatcaa g                                              741
```

```
<210> SEQ ID NO 234
<211> LENGTH: 244
<212> TYPE: PRT
<213> ORGANISM: Artificial Sequence
<220> FEATURE:
<223> OTHER INFORMATION: KRAS ScFv

<400> SEQUENCE: 234

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Tyr Asp Glu Leu Tyr Tyr Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ser Tyr Ser Thr Pro Leu Thr Phe Gly Gly Gly Thr Lys
225                 230                 235                 240

Val Glu Ile Lys

<210> SEQ ID NO 235
<211> LENGTH: 732
```

<212> TYPE: DNA
<213> ORGANISM: Artificial Sequence
<220> FEATURE:
<223> OTHER INFORMATION: KRAS ScFv

<400> SEQUENCE: 235

```
caggtcacac tgagagagtc cggccctgcc ctggtgaaac ccacccagac cctgaccctg     60

acatgcacct tcagcggctt cagcctgagc accagcggga tgtgcgtgtc ctggattcga    120

cagccccctg gcaaggccct ggaatggctg gccctgattg actgggacga cgacaagtac    180

tacagcacca gcctgaaaac ccggctgacc atcagcaagg acaccagcaa gaaccaggtg    240

gtgctgacca tgaccaacat ggaccccgtg gacaccgcca cgtattactg tgcacggagt    300

tacgacgagc tctactactt tgactactgg ggccagggaa ccctggtcac cgtgtcctca    360

ggcggaggtg gaagcggagg gggaggatct ggcggcggag gaagcggagg cgacatccag    420

atgacccagt ctccatcctc cctgtctgca tctgtaggag acagagtcac catcacttgc    480

cgggcaagtc agagcattag cagctattta aattggtatc agcagaaacc agggaaagcc    540

cctaagctcc tgatctatgc tgcatccagt ttgcaaagtg gggtcccatc aaggttcagt    600

ggcagtggat ctgggacaga tttcactctc accatcagca gtctgcaacc tgaagatttt    660

gcaacttact actgtcaaca gagttacagt acccctctca ctttcggcgg cggaacaaag    720

gtggagatca ag                                                        732
```

<210> SEQ ID NO 236
<211> LENGTH: 245
<212> TYPE: PRT
<213> ORGANISM: Artificial Sequence
<220> FEATURE:
<223> OTHER INFORMATION: KRAS ScFv

<400> SEQUENCE: 236

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Tyr Asp Glu Leu Tyr Tyr Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Ser Ile Trp Thr Ser Tyr Leu Asn Trp Tyr Gln Gln
                165                 170                 175

Lys Pro Gly Lys Ala Pro Lys Leu Leu Ile Tyr Ala Ala Ser Ser Leu
            180                 185                 190
```

-continued

```
Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Ser Tyr Ser Thr Pro Leu Thr Phe Gly Gly Gly Thr
225                 230                 235                 240

Lys Val Glu Ile Lys
                245
```

<210> SEQ ID NO 237
<211> LENGTH: 735
<212> TYPE: DNA
<213> ORGANISM: Artificial Sequence
<220> FEATURE:
<223> OTHER INFORMATION: KRAS ScFv

<400> SEQUENCE: 237

```
caggtcacac tgagagagtc cggccctgcc ctggtgaaac ccacccagac cctgaccctg     60

acatgcacct tcagcggctt cagcctgagc accagcggga tgtgcgtgtc ctggattcga    120

cagccccctg gcaaggccct ggaatggctg gccctgattg actgggacga cgacaagtac    180

tacagcacca gcctgaaaac ccggctgacc atcagcaagg acaccagcaa gaaccaggtg    240

gtgctgacca tgaccaacat ggaccccgtg gacaccgcca cgtattactg tgcacggagt    300

tacgacgagc tctactactt tgactactgg ggccagggaa ccctggtcac cgtgtcctca    360

ggcggaggtg gaagcggagg gggaggatct ggcggcggag gaagcggagg cgacatccag    420

atgacccaga gccccagctc cctctctgca tctgtgggcg acagagtgac catcacctgt    480

cgggccagcc agtcgatctg gaccagctac ctgaactggt atcagcagaa gcccggcaag    540

gcccccaagc tgctgatcta cgccgccagc tccctgcaga gcggcgtgcc aagcagattc    600

agcggcagcg gctccggcac cgacttcacc ctgaccatca gcagcctgca gcccgaggac    660

ttcgccacct actactgcca gcagagttac agtacccctc tcactttcgg cggagggacc    720

aaggtggaga tcaaa                                                     735
```

<210> SEQ ID NO 238
<211> LENGTH: 244
<212> TYPE: PRT
<213> ORGANISM: Artificial Sequence
<220> FEATURE:
<223> OTHER INFORMATION: KRAS ScFv

<400> SEQUENCE: 238

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Tyr Asp Glu Leu Tyr Tyr Phe Asp Tyr Trp Gly Gln
            100                 105                 110
```

-continued

Gly Thr Leu Val Thr Val Ser Ser Gly Gly Gly Gly Ser Gly Gly Gly
115 120 125

Gly Ser Gly Gly Gly Gly Ser Gly Gly Asp Ile Gln Met Thr Gln Ser
130 135 140

Pro Ser Ser Leu Ser Ala Ser Val Gly Asp Arg Val Thr Ile Thr Cys
145 150 155 160

Arg Ala Ser Gln Ser Ile Ser Ser Tyr Leu Asn Trp Tyr Gln Gln Lys
165 170 175

Pro Gly Lys Ala Pro Lys Leu Leu Ile Tyr Ala Ala Ser Ser Leu Gln
180 185 190

Ser Gly Val Pro Ser Arg Phe Ser Gly Ser Gly Ser Gly Thr Asp Phe
195 200 205

Thr Leu Thr Ile Ser Ser Leu Gln Pro Glu Asp Phe Ala Thr Tyr Tyr
210 215 220

Cys Gln Gln Ser Tyr Ser Thr Arg Leu Thr Phe Gly Gly Gly Thr Lys
225 230 235 240

Val Glu Ile Lys

<210> SEQ ID NO 239
<211> LENGTH: 732
<212> TYPE: DNA
<213> ORGANISM: Artificial Sequence
<220> FEATURE:
<223> OTHER INFORMATION: KRAS ScFv

<400> SEQUENCE: 239
caggtcacac tgagagagtc cggccctgcc ctggtgaaac ccacccagac cctgaccctg 60
acatgcacct tcagcggctt cagcctgagc accagcggga tgtgcgtgtc ctggattcga 120
cagccccctg gcaaggccct ggaatggctg gccctgattg actgggacga cgacaagtac 180
tacagcacca gcctgaaaac ccggctgacc atcagcaagg acaccagcaa gaaccaggtg 240
gtgctgacca tgaccaacat ggaccccgtg gacaccgcca cgtattactg tgcacggagt 300
tacgacgagc tctactactt tgactactgg ggccagggaa ccctggtcac cgtgtcctca 360
ggcggaggtg gaagcggagg gggaggatct ggcggcggag gaagcggagg cgacatccag 420
atgacccaga gccccagctc cctctctgca tctgtgggcg acagagtgac catcacctgt 480
cgggccagcc agtcgatcag cagctacctg aactggtatc agcagaagcc cggcaaggcc 540
cccaagctgc tgatctacgc cgccagctcc ctgcagagcg gcgtgccaag cagattcagc 600
ggcagcggct ccggcaccga cttcaccctg accatcagca gcctgcagcc cgaggacttc 660
gccacctact actgccagca gagttacagt acccggctca ctttcggcgg agggaccaag 720
gtggagatca aa 732

<210> SEQ ID NO 240
<211> LENGTH: 244
<212> TYPE: PRT
<213> ORGANISM: Artificial Sequence
<220> FEATURE:
<223> OTHER INFORMATION: KRAS TCR alpha

<400> SEQUENCE: 240

Met Gln Arg Asn Leu Gly Ala Val Leu Gly Ile Leu Trp Val Gln Ile
1 5 10 15

Cys Trp Val Arg Gly Asp Gln Val Glu Gln Ser Pro Ser Ala Leu Ser
20 25 30

Leu His Glu Gly Thr Asp Ser Ala Leu Arg Cys Asn Phe Thr Thr Thr

```
        35                  40                  45

Met Arg Ser Val Gln Trp Phe Arg Gln Asn Ser Arg Gly Ser Leu Ile
    50                  55                  60

Ser Leu Phe Tyr Leu Ala Ser Gly Thr Lys Glu Asn Gly Arg Leu Lys
65                  70                  75                  80

Ser Ala Phe Asp Ser Lys Glu Arg Arg Tyr Ser Thr Leu His Ile Arg
                85                  90                  95

Asp Ala Gln Leu Glu Asp Ser Gly Thr Tyr Phe Cys Ala Ala Asp Ser
            100                 105                 110

Ser Asn Thr Gly Tyr Gln Asn Phe Tyr Phe Gly Lys Gly Thr Ser Leu
        115                 120                 125

Thr Val Ile Pro Asn Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Cys Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser
```

```
<210> SEQ ID NO 241
<211> LENGTH: 732
<212> TYPE: DNA
<213> ORGANISM: Artificial Sequence
<220> FEATURE:
<223> OTHER INFORMATION: KRAS TCR alpha

<400> SEQUENCE: 241

atgcagagga acctgggagc tgtgctgggg attctgtggg tgcagatttg ctgggtgaga      60

ggggatcagg tggagcagag tccttcagcc ctgagcctcc acgagggaac cgattctgct     120

ctgagatgca attttacgac caccatgagg agtgtgcagt ggttccgaca gaattccagg     180

ggcagcctca tcagtttgtt ctacttggct tcaggaacaa aggagaatgg gaggctaaag     240

tcagcatttg attctaagga gcggcgctac agcaccctgc acatcaggga tgcccagctg     300

gaggactcag gcacttactt ctgtgctgct gactcttcga acacgggtta ccagaacttc     360

tattttggga aaggaacaag tttgactgtc attccaaaca tccagaaccc agaacctgct     420

gtgtaccagt taaaagatcc tcggtctcag gacagcaccc tctgcctgtt caccgacttt     480

gactcccaaa tcaatgtgcc gaaaaccatg gaatctggaa cgttcatcac tgacaaatgt     540

gtgctggaca tgaaagctat ggattccaag agcaatgggg ccattgcctg gagcaaccag     600

acaagcttca cctgccaaga tatcttcaaa gagaccaacg ccacctaccc cagttcagac     660

gttccctgtg atgccacgtt gaccgagaaa agctttgaaa cagatatgaa cctgaacttt     720

caaaacctgt ct                                                         732

<210> SEQ ID NO 242
<211> LENGTH: 283
```

<212> TYPE: PRT
<213> ORGANISM: Artificial Sequence
<220> FEATURE:
<223> OTHER INFORMATION: KRAS TCR beta

<400> SEQUENCE: 242

```
Met Ser Asn Thr Ala Phe Pro Asp Pro Ala Trp Asn Thr Thr Leu Leu
1               5                   10                  15

Ser Trp Val Ala Leu Phe Leu Leu Gly Thr Ser Ser Ala Asn Ser Gly
            20                  25                  30

Val Val Gln Ser Pro Arg Tyr Ile Ile Lys Gly Lys Gly Glu Arg Ser
        35                  40                  45

Ile Leu Lys Cys Ile Pro Ile Ser Gly His Leu Ser Val Ala Trp Tyr
    50                  55                  60

Gln Gln Thr Gln Gly Gln Glu Leu Lys Phe Phe Ile Gln His Tyr Asp
65                  70                  75                  80

Lys Met Glu Arg Asp Lys Gly Asn Leu Pro Ser Arg Phe Ser Val Gln
                85                  90                  95

Gln Phe Asp Asp Tyr His Ser Glu Met Asn Met Ser Ala Leu Glu Leu
            100                 105                 110

Glu Asp Ser Ala Val Tyr Phe Cys Ala Ser Ser Leu Thr Asp Pro Leu
        115                 120                 125

Asp Ser Asp Tyr Thr Phe Gly Ser Gly Thr Arg Leu Leu Val Ile Glu
    130                 135                 140

Asp Leu Arg Asn Val Thr Pro Pro Lys Val Ser Leu Phe Glu Pro Ser
145                 150                 155                 160

Lys Ala Glu Ile Ala Asn Lys Gln Lys Ala Thr Leu Val Cys Leu Ala
                165                 170                 175

Arg Gly Phe Phe Pro Asp His Val Glu Leu Ser Trp Trp Val Asn Gly
            180                 185                 190

Lys Glu Val His Ser Gly Val Cys Thr Asp Pro Gln Ala Tyr Lys Glu
        195                 200                 205

Ser Asn Tyr Ser Tyr Cys Leu Ser Ser Arg Leu Arg Val Ser Ala Thr
    210                 215                 220

Phe Trp His Asn Pro Arg Asn His Phe Arg Cys Gln Val Gln Phe His
225                 230                 235                 240

Gly Leu Ser Glu Glu Asp Lys Trp Pro Glu Gly Ser Pro Lys Pro Val
                245                 250                 255

Thr Gln Asn Ile Ser Ala Glu Ala Trp Gly Arg Ala Asp Cys Gly Ile
            260                 265                 270

Thr Ser Ala Ser Tyr Gln Gln Gly Val Leu Ser
        275                 280
```

<210> SEQ ID NO 243
<211> LENGTH: 849
<212> TYPE: DNA
<213> ORGANISM: Artificial Sequence
<220> FEATURE:
<223> OTHER INFORMATION: KRAS TCR beta

<400> SEQUENCE: 243

```
atgtctaaca ctgccttccc tgaccccgcc tggaacacca ccctgctatc ttgggttgct      60

ctctttctcc tgggaacaag ttcagcaaat tctggggttg tccagtctcc aagatacata     120

atcaaaggaa agggagaaag gtccattcta aaatgtattc ccatctctgg acatctctct     180

gtggcctggt atcaacagac tcaggggcag gaactaaagt tcttcattca gcattatgat     240
```

```
aaaatggaga gagataaagg aaacctgccc agcagattct cagtccaaca gtttgatgac    300

tatcactctg agatgaacat gagtgccttg gagctagagg actctgccgt gtacttctgt    360

gccagctctc tcacagatcc gctagactcc gactacacct tcggctcagg gaccaggctt    420

ttggtaatag aggatctgag aaatgtgact ccacccaagg tctccttgtt tgagccatca    480

aaagcagaga ttgcaaacaa acaaaaggct accctcgtgt gcttggccag gggcttcttc    540

cctgaccacg tggagctgag ctggtgggtg aatggcaagg aggtccacag tggggtctgc    600

acggaccctc aggcctacaa ggagagcaat tatagctact gcctgagcag ccgcctgagg    660

gtctctgcta ccttctggca caatcctcgc aaccacttcc gctgccaagt gcagttccat    720

gggctttcag aggaggacaa gtggccagag ggctcaccca aacctgtcac acagaacatc    780

agtgcagagg cctggggccg agcagactgt gggattacct cagcatccta tcaacaaggg    840

gtcttgtct                                                            849


<210> SEQ ID NO 244
<211> LENGTH: 283
<212> TYPE: PRT
<213> ORGANISM: Artificial Sequence
<220> FEATURE:
<223> OTHER INFORMATION: KRAS TCR beta

<400> SEQUENCE: 244

Met Ser Asn Thr Ala Phe Pro Asp Pro Ala Trp Asn Thr Thr Leu Leu
1               5                   10                  15

Ser Trp Val Ala Leu Phe Leu Leu Gly Thr Ser Ser Ala Asn Ser Gly
            20                  25                  30

Val Val Gln Ser Pro Arg Tyr Ile Ile Lys Gly Lys Gly Glu Arg Ser
        35                  40                  45

Ile Leu Lys Cys Ile Pro Ile Ser Gly His Leu Ser Val Ala Trp Tyr
    50                  55                  60

Gln Gln Thr Gln Gly Gln Glu Leu Lys Phe Phe Ile Gln His Tyr Asp
65                  70                  75                  80

Lys Met Glu Arg Asp Lys Gly Asn Leu Pro Ser Arg Phe Ser Val Gln
                85                  90                  95

Gln Phe Asp Asp Tyr His Ser Glu Met Asn Met Ser Ala Leu Glu Leu
            100                 105                 110

Glu Asp Ser Ala Val Tyr Phe Cys Ala Ser Ser Leu Thr Asp Pro Leu
        115                 120                 125

Asp Ser Asp Tyr Thr Phe Gly Ser Gly Thr Arg Leu Leu Val Ile Glu
    130                 135                 140

Asp Leu Arg Asn Val Thr Pro Pro Lys Val Ser Leu Phe Glu Pro Ser
145                 150                 155                 160

Lys Ala Glu Ile Ala Asn Lys Gln Lys Ala Thr Leu Val Cys Leu Ala
                165                 170                 175

Arg Gly Phe Phe Pro Asp His Val Glu Leu Ser Trp Trp Val Asn Gly
            180                 185                 190

Lys Glu Val His Ser Gly Val Cys Thr Asp Pro Gln Ala Tyr Lys Glu
        195                 200                 205

Ser Asn Tyr Ser Tyr Cys Leu Ser Ser Arg Leu Arg Val Ser Ala Thr
    210                 215                 220

Phe Trp His Asn Pro Arg Asn His Phe Arg Cys Gln Val Gln Phe His
225                 230                 235                 240

Gly Leu Ser Glu Glu Asp Lys Trp Pro Glu Gly Ser Pro Lys Pro Val
                245                 250                 255
```

```
Thr Gln Asn Ile Ser Ala Glu Ala Trp Gly Arg Ala Asp Cys Gly Ile
            260                 265                 270

Thr Ser Ala Ser Tyr Gln Gln Gly Val Leu Ser
        275                 280


<210> SEQ ID NO 245
<211> LENGTH: 849
<212> TYPE: DNA
<213> ORGANISM: Artificial Sequence
<220> FEATURE:
<223> OTHER INFORMATION: KRAS TCR beta

<400> SEQUENCE: 245

atgtctaaca ctgccttccc tgaccccgcc tggaacacca ccctgctatc ttgggttgct      60

ctctttctcc tgggaacaag ttcagcaaat tctggggttg tccagtctcc aagatacata     120

atcaaaggaa agggagaaag gtccattcta aaatgtattc ccatctctgg acatctctct     180

gtggcctggt atcaacagac tcaggggcag gaactaaagt tcttcattca gcattatgat     240

aaaatggaga gagataaagg aaacctgccc agcagattct cagtccaaca gtttgatgac     300

tatcactctg agatgaacat gagtgccttg gagctagagg actctgccgt gtacttctgt     360

gccagctctc tcacagatcc gctagactcc gactacacct tcggctcagg gaccaggctt     420

ttggtaatag aggatctgag aaatgtgact ccacccaagg tctccttgtt tgagccatca     480

aaagcagaga ttgcaaacaa acaaaaggct accctcgtgt gcttggccag gggcttcttc     540

cctgaccacg tggagctgag ctggtgggtg aatggcaagg aggtccacag tggggtctgc     600

acggaccctc aggcctacaa ggagagcaat tatagctact gcctgagcag ccgcctgagg     660

gtctctgcta ccttctggca caatcctcgc aaccacttcc gctgccaagt gcagttccat     720

gggctttcag aggaggacaa gtggccagag ggctcaccca aacctgtcac acagaacatc     780

agtgcagagg cctggggccg agcagactgt gggattacct cagcatccta tcaacaaggg     840

gtcttgtct                                                             849


<210> SEQ ID NO 246
<211> LENGTH: 248
<212> TYPE: PRT
<213> ORGANISM: Artificial Sequence
<220> FEATURE:
<223> OTHER INFORMATION: KRAS TCRa

<400> SEQUENCE: 246

Met Lys Thr Val Thr Gly Pro Leu Phe Leu Cys Phe Trp Leu Gln Leu
1               5                   10                  15

Asn Cys Val Ser Arg Gly Glu Gln Val Glu Gln Arg Pro Pro His Leu
            20                  25                  30

Ser Val Arg Glu Gly Asp Ser Ala Val Ile Thr Cys Thr Tyr Thr Asp
        35                  40                  45

Pro Asn Ser Tyr Tyr Phe Phe Trp Tyr Lys Gln Glu Pro Gly Ala Ser
    50                  55                  60

Leu Gln Leu Leu Met Lys Val Phe Ser Ser Thr Glu Ile Asn Glu Gly
65                  70                  75                  80

Gln Gly Phe Thr Val Leu Leu Asn Lys Lys Asp Lys Arg Leu Ser Leu
                85                  90                  95

Asn Leu Thr Ala Ala His Pro Gly Asp Ser Ala Ala Tyr Phe Cys Ala
            100                 105                 110

Val Ser Gly Gly Thr Asn Ser Ala Gly Asn Lys Leu Thr Phe Gly Ile
```

-continued

```
        115                 120                 125

Gly Thr Arg Val Leu Val Arg Pro Asp Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Cys Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Ser
                245


<210> SEQ ID NO 247
<211> LENGTH: 744
<212> TYPE: DNA
<213> ORGANISM: Artificial Sequence
<220> FEATURE:
<223> OTHER INFORMATION: KRAS TCRa

<400> SEQUENCE: 247

atgaagacgg tgactggacc tttgttcctg tgcttctggc tgcagctgaa ctgtgtgagc      60

agaggcgagc aggtggagca gcgccctcct cacctgagtg tccgggaggg agacagtgcc     120

gttatcacct gcacctacac agaccctaac agttattact tcttctggta caagcaagag     180

ccgggggcaa gtcttcagtt gcttatgaag gttttctcaa gtacggaaat aaacgaagga     240

caaggattca ctgtcctact gaacaagaaa gacaaacgac tctctctgaa cctcacagct     300

gcccatcctg ggactcagc cgcgtacttc tgcgcagtca gtggagggac taacagtgca      360

gggaacaagc taacttttgg aattggaacc agggtgctgg tcaggccaga catccagaac     420

ccagaacctg ctgtgtacca gttaaaagat cctcggtctc aggacagcac cctctgcctg     480

ttcaccgact ttgactccca aatcaatgtg ccgaaaacca tggaatctgg aacgttcatc     540

actgacaaat gtgtgctgga catgaaagct atggattcca agagcaatgg ggccattgcc     600

tggagcaacc agacaagctt cacctgccaa gatatcttca aagagaccaa cgccacctac     660

cccagttcag acgttccctg tgatgccacg ttgaccgaga aaagctttga aacagatatg     720

aacctgaact ttcaaaacct gtct                                           744


<210> SEQ ID NO 248
<211> LENGTH: 272
<212> TYPE: PRT
<213> ORGANISM: Artificial Sequence
<220> FEATURE:
<223> OTHER INFORMATION: KRAS TCRb

<400> SEQUENCE: 248

Met Gly Cys Arg Leu Leu Ser Cys Val Ala Phe Cys Leu Leu Gly Ile
1               5                   10                  15

Gly Pro Leu Glu Thr Ala Val Phe Gln Thr Pro Asn Tyr His Val Thr
            20                  25                  30

Gln Val Gly Asn Glu Val Ser Phe Asn Cys Lys Gln Thr Leu Gly His
```

```
        35                  40                  45

Asp Thr Met Tyr Trp Tyr Lys Gln Asp Ser Lys Lys Leu Leu Lys Ile
    50                  55                  60

Met Phe Ser Tyr Asn Asn Lys Gln Leu Ile Val Asn Glu Thr Val Pro
65                  70                  75                  80

Arg Arg Phe Ser Pro Gln Ser Ser Asp Lys Ala His Leu Asn Leu Arg
                85                  90                  95

Ile Lys Ser Val Glu Pro Glu Asp Ser Ala Val Tyr Leu Cys Ala Ser
            100                 105                 110

Ser Arg Asp Trp Gly Pro Ala Glu Gln Phe Phe Gly Pro Gly Thr Arg
        115                 120                 125

Leu Thr Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr His Gln Gly Val Leu Ser
            260                 265                 270
```

<210> SEQ ID NO 249
<211> LENGTH: 816
<212> TYPE: DNA
<213> ORGANISM: Artificial Sequence
<220> FEATURE:
<223> OTHER INFORMATION: KRAS TCRb

<400> SEQUENCE: 249

```
atgggctgta ggctcctaag ctgtgtggcc ttctgcctct tgggaatagg ccctttggag     60

acagctgttt tccagactcc aaactatcat gtcacacagg tgggaaatga agtgtctttc    120

aattgtaagc aaactctggg ccacgatact atgtattggt acaagcaaga ctctaagaaa    180

ttgctgaaga ttatgtttag ctacaataat aagcaactca ttgtaaacga aacagttcca    240

aggcgcttct cacctcagtc ttcagataaa gctcatttga atcttcgaat caagtctgta    300

gagccggagg actctgctgt gtatctctgt gccagcagtc gggactgggg gcctgctgag    360

cagttcttcg gaccagggac acgactcacc gtcctagagg atctgagaaa tgtgactcca    420

cccaaggtct ccttgtttga gccatcaaaa gcagagattg caaacaaaca aaaggctacc    480

ctcgtgtgct tggccagggg cttcttccct gaccacgtgg agctgagctg gtgggtgaat    540

ggcaaggagg tccacagtgg ggtctgcacg gaccctcagg cctacaagga gagcaattat    600

agctactgcc tgagcagccg cctgagggtc tctgctacct tctggcacaa tcctcgaaac    660

cacttccgct gccaagtgca gttccatggg ctttcagagg aggacaagtg gccagagggc    720

tcacccaaac ctgtcacaca gaacatcagt gcagaggcct ggggccgagc agactgtgga    780
```

atcacttcag catcctatca tcagggggtt ctgtct 816

<210> SEQ ID NO 250
<211> LENGTH: 272
<212> TYPE: PRT
<213> ORGANISM: Artificial Sequence
<220> FEATURE:
<223> OTHER INFORMATION: KRAS TCRb

<400> SEQUENCE: 250

Met Gly Cys Arg Leu Leu Ser Cys Val Ala Phe Cys Leu Leu Gly Ile
1 5 10 15

Gly Pro Leu Glu Thr Ala Val Phe Gln Thr Pro Asn Tyr His Val Thr
20 25 30

Gln Val Gly Asn Glu Val Ser Phe Asn Cys Lys Gln Thr Leu Gly His
35 40 45

Asp Thr Met Tyr Trp Tyr Lys Gln Asp Ser Lys Lys Leu Leu Lys Ile
50 55 60

Met Phe Ser Tyr Asn Asn Lys Gln Leu Ile Val Asn Glu Thr Val Pro
65 70 75 80

Arg Arg Phe Ser Pro Gln Ser Ser Asp Lys Ala His Leu Asn Leu Arg
85 90 95

Ile Lys Ser Val Glu Pro Glu Asp Ser Ala Val Tyr Leu Cys Ala Ser
100 105 110

Ser Arg Asp Trp Gly Pro Ala Glu Gln Phe Phe Gly Pro Gly Thr Arg
115 120 125

Leu Thr Val Leu Glu Asp Leu Arg Asn Val Thr Pro Pro Lys Val Ser
130 135 140

Leu Phe Glu Pro Ser Lys Ala Glu Ile Ala Asn Lys Gln Lys Ala Thr
145 150 155 160

Leu Val Cys Leu Ala Arg Gly Phe Phe Pro Asp His Val Glu Leu Ser
165 170 175

Trp Trp Val Asn Gly Lys Glu Val His Ser Gly Val Cys Thr Asp Pro
180 185 190

Gln Ala Tyr Lys Glu Ser Asn Tyr Ser Tyr Cys Leu Ser Ser Arg Leu
195 200 205

Arg Val Ser Ala Thr Phe Trp His Asn Pro Arg Asn His Phe Arg Cys
210 215 220

Gln Val Gln Phe His Gly Leu Ser Glu Glu Asp Lys Trp Pro Glu Gly
225 230 235 240

Ser Pro Lys Pro Val Thr Gln Asn Ile Ser Ala Glu Ala Trp Gly Arg
245 250 255

Ala Asp Cys Gly Ile Thr Ser Ala Ser Tyr His Gln Gly Val Leu Ser
260 265 270

<210> SEQ ID NO 251
<211> LENGTH: 816
<212> TYPE: DNA
<213> ORGANISM: Artificial Sequence
<220> FEATURE:
<223> OTHER INFORMATION: KRAS TCRb

<400> SEQUENCE: 251
atgggctgta ggctcctaag ctgtgtggcc ttctgcctct tgggaatagg ccctttggag 60
acagctgttt tccagactcc aaactatcat gtcacacagg tgggaaatga agtgtctttc 120
aattgtaagc aaactctggg ccacgatact atgtattggt acaagcaaga ctctaagaaa 180

-continued

```
ttgctgaaga ttatgtttag ctacaataat aagcaactca ttgtaaacga aacagttcca    240

aggcgcttct cacctcagtc ttcagataaa gctcatttga atcttcgaat caagtctgta    300

gagccggagg actctgctgt gtatctctgt gccagcagtc gggactgggg gcctgctgag    360

cagttcttcg gaccagggac acgactcacc gtcctagagg atctgagaaa tgtgactcca    420

cccaaggtct ccttgtttga gccatcaaaa gcagagattg caaacaaaca aaaggctacc    480

ctcgtgtgct tggccagggg cttcttccct gaccacgtgg agctgagctg gtgggtgaat    540

ggcaaggagg tccacagtgg ggtctgcacg gaccctcagg cctacaagga gagcaattat    600

agctactgcc tgagcagccg cctgagggtc tctgctacct tctggcacaa tcctcgaaac    660

cacttccgct gccaagtgca gttccatggg ctttcagagg aggacaagtg gccagagggc    720

tcacccaaac ctgtcacaca gaacatcagt gcagaggcct ggggccgagc agactgtgga    780

atcacttcag catcctatca tcaggggggtt ctgtct                              816
```

<210> SEQ ID NO 252
<211> LENGTH: 244
<212> TYPE: PRT
<213> ORGANISM: Artificial Sequence
<220> FEATURE:
<223> OTHER INFORMATION: TCRa control

<400> SEQUENCE: 252

```
Met Gln Arg Asn Leu Gly Ala Val Leu Gly Ile Leu Trp Val Gln Ile
1               5                   10                  15

Cys Trp Val Arg Gly Asp Gln Val Glu Gln Ser Pro Ser Ala Leu Ser
            20                  25                  30

Leu His Glu Gly Thr Asp Ser Ala Leu Arg Cys Asn Phe Thr Thr Thr
        35                  40                  45

Met Arg Ser Val Gln Trp Phe Arg Gln Asn Ser Arg Gly Ser Leu Ile
    50                  55                  60

Ser Leu Phe Tyr Leu Ala Ser Gly Thr Lys Glu Asn Gly Arg Leu Lys
65                  70                  75                  80

Ser Ala Phe Asp Ser Lys Glu Arg Arg Tyr Ser Thr Leu His Ile Arg
                85                  90                  95

Asp Ala Gln Leu Glu Asp Ser Gly Thr Tyr Phe Cys Ala Ala Asp Ser
            100                 105                 110

Ser Asn Thr Gly Tyr Gln Asn Phe Tyr Phe Gly Lys Gly Thr Ser Leu
        115                 120                 125

Thr Val Ile Pro Asn Ile Gln Asn Pro Glu Pro Ala Val Tyr Gln Leu
    130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Cys Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
        195                 200                 205

Phe Lys Glu Thr Asn Ala Thr Tyr Pro Ser Ser Asp Val Pro Cys Asp
    210                 215                 220

Ala Thr Leu Thr Glu Lys Ser Phe Glu Thr Asp Met Asn Leu Asn Phe
225                 230                 235                 240

Gln Asn Leu Ser
```

<210> SEQ ID NO 253
<211> LENGTH: 732
<212> TYPE: DNA
<213> ORGANISM: Artificial Sequence
<220> FEATURE:
<223> OTHER INFORMATION: TCRa control

<400> SEQUENCE: 253
atgcagagga acctgggagc tgtgctgggg attctgtggg tgcagatttg ctgggtgaga 60
ggggatcagg tggagcagag tccttcagcc ctgagcctcc acgagggaac cgattctgct 120
ctgagatgca attttacgac caccatgagg agtgtgcagt ggttccgaca gaattccagg 180
ggcagcctca tcagtttgtt ctacttggct tcaggaacaa aggagaatgg gaggctaaag 240
tcagcatttg attctaagga gcggcgctac agcaccctgc acatcaggga tgcccagctg 300
gaggactcag gcacttactt ctgtgctgct gactcttcga acacgggtta ccagaacttc 360
tattttggga aaggaacaag tttgactgtc attccaaaca tccagaaccc agaacctgct 420
gtgtaccagt taaaagatcc tcggtctcag gacagcaccc tctgcctgtt caccgacttt 480
gactcccaaa tcaatgtgcc gaaaaccatg gaatctggaa cgttcatcac tgacaaatgt 540
gtgctggaca tgaaagctat ggattccaag agcaatgggg ccattgcctg gagcaaccag 600
acaagcttca cctgccaaga tatcttcaaa gagaccaacg ccacctaccc cagttcagac 660
gttccctgtg atgccacgtt gaccgagaaa agctttgaaa cagatatgaa cctgaacttt 720
caaaacctgt ct 732

<210> SEQ ID NO 254
<211> LENGTH: 248
<212> TYPE: PRT
<213> ORGANISM: Artificial Sequence
<220> FEATURE:
<223> OTHER INFORMATION: TCRa control

<400> SEQUENCE: 254

Met Lys Thr Val Thr Gly Pro Leu Phe Leu Cys Phe Trp Leu Gln Leu
1 5 10 15

Asn Cys Val Ser Arg Gly Glu Gln Val Glu Gln Arg Pro Pro His Leu
20 25 30

Ser Val Arg Glu Gly Asp Ser Ala Val Ile Thr Cys Thr Tyr Thr Asp
35 40 45

Pro Asn Ser Tyr Tyr Phe Phe Trp Tyr Lys Gln Glu Pro Gly Ala Ser
50 55 60

Leu Gln Leu Leu Met Lys Val Phe Ser Ser Thr Glu Ile Asn Glu Gly
65 70 75 80

Gln Gly Phe Thr Val Leu Leu Asn Lys Lys Asp Lys Arg Leu Ser Leu
85 90 95

Asn Leu Thr Ala Ala His Pro Gly Asp Ser Ala Ala Tyr Phe Cys Ala
100 105 110

Val Ser Gly Gly Thr Asn Ser Ala Gly Asn Lys Leu Thr Phe Gly Ile
115 120 125

Gly Thr Arg Val Leu Val Arg Pro Asp Ile Gln Asn Pro Glu Pro Ala
130 135 140

Val Tyr Gln Leu Lys Asp Pro Arg Ser Gln Asp Ser Thr Leu Cys Leu
145 150 155 160

Phe Thr Asp Phe Asp Ser Gln Ile Asn Val Pro Lys Thr Met Glu Ser
165 170 175

```
Gly Thr Phe Ile Thr Asp Lys Cys Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Ser
                245
```

<210> SEQ ID NO 255
<211> LENGTH: 744
<212> TYPE: DNA
<213> ORGANISM: Artificial Sequence
<220> FEATURE:
<223> OTHER INFORMATION: TCRa control

<400> SEQUENCE: 255

```
atgaagacgg tgactggacc tttgttcctg tgcttctggc tgcagctgaa ctgtgtgagc     60

agaggcgagc aggtggagca gcgccctcct cacctgagtg tccgggaggg agacagtgcc    120

gttatcacct gcacctacac agaccctaac agttattact tcttctggta caagcaagag    180

ccgggggcaa gtcttcagtt gcttatgaag gttttctcaa gtacggaaat aaacgaagga    240

caaggattca ctgtcctact gaacaagaaa gacaaacgac tctctctgaa cctcacagct    300

gcccatcctg ggactcagc cgcgtacttc tgcgcagtca gtggagggac taacagtgca    360

gggaacaagc taacttttgg aattggaacc agggtgctgg tcaggccaga catccagaac    420

ccagaacctg ctgtgtacca gttaaaagat cctcggtctc aggacagcac cctctgcctg    480

ttcaccgact ttgactccca aatcaatgtg ccgaaaacca tggaatctgg aacgttcatc    540

actgacaaat gtgtgctgga catgaaagct atggattcca agagcaatgg ggccattgcc    600

tggagcaacc agacaagctt cacctgccaa gatatcttca aagagaccaa cgccacctac    660

cccagttcag acgttccctg tgatgccacg ttgaccgaga aaagctttga aacagatatg    720

aacctgaact ttcaaaacct gtct                                           744
```

<210> SEQ ID NO 256
<211> LENGTH: 9
<212> TYPE: PRT
<213> ORGANISM: Artificial Sequence
<220> FEATURE:
<223> OTHER INFORMATION: mH-Y-2Db peptide

<400> SEQUENCE: 256

```
Lys Cys Ser Arg Asn Arg Gln Tyr Leu
1               5
```

<210> SEQ ID NO 257
<211> LENGTH: 614
<212> TYPE: PRT
<213> ORGANISM: Artificial Sequence
<220> FEATURE:
<223> OTHER INFORMATION: H-Y TCR alpha and beta

<400> SEQUENCE: 257

```
Met Phe Pro Val Thr Ile Leu Leu Leu Ser Ala Phe Phe Ser Leu Arg
1               5                   10                  15

Gly Asn Ser Ala Gln Ser Val Asp Gln Pro Asp Ala His Val Thr Leu
```

```
            20                  25                  30

Ser Glu Gly Ala Ser Leu Glu Leu Arg Cys Ser Tyr Ser Tyr Ser Ala
        35                  40                  45

Ala Pro Tyr Leu Phe Trp Tyr Val Gln Tyr Pro Gly Gln Ser Leu Gln
    50                  55                  60

Phe Leu Leu Lys Tyr Ile Thr Gly Asp Thr Val Val Lys Gly Thr Lys
65                  70                  75                  80

Gly Phe Glu Ala Glu Phe Arg Lys Ser Asn Ser Ser Phe Asn Leu Lys
                85                  90                  95

Lys Ser Pro Ala His Trp Ser Asp Ser Ala Lys Tyr Phe Cys Ala Leu
            100                 105                 110

Glu Gly Gln Asp Gln Gly Gly Ser Ala Lys Leu Ile Phe Gly Glu Gly
        115                 120                 125

Thr Lys Leu Thr Val Ser Ser Pro Asp Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Thr Val Leu Asp Met Lys Ala Met Asp
            180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Ser Val Met Gly Leu Arg Ile Leu Leu
                245                 250                 255

Leu Lys Val Ala Gly Phe Asn Leu Leu Met Thr Leu Arg Leu Trp Ser
            260                 265                 270

Ser Arg Ala Lys Arg Ser Gly Ser Gly Ala Thr Asn Phe Ser Leu Leu
        275                 280                 285

Lys Gln Ala Gly Asp Val Glu Glu Asn Pro Gly Pro Met Ser Asn Thr
    290                 295                 300

Ala Phe Pro Asp Pro Ala Trp Asn Thr Thr Leu Leu Ser Trp Val Ala
305                 310                 315                 320

Leu Phe Leu Leu Gly Thr Lys His Met Glu Ala Ala Val Thr Gln Ser
                325                 330                 335

Pro Arg Asn Lys Val Ala Val Thr Gly Gly Lys Val Thr Leu Ser Cys
            340                 345                 350

Asn Gln Thr Asn Asn His Asn Asn Met Tyr Trp Tyr Arg Gln Asp Thr
        355                 360                 365

Gly His Gly Leu Arg Leu Ile His Tyr Ser Tyr Gly Ala Gly Ser Thr
    370                 375                 380

Glu Lys Gly Asp Ile Pro Asp Gly Tyr Lys Ala Ser Arg Pro Ser Gln
385                 390                 395                 400

Glu Asn Phe Ser Leu Ile Leu Glu Leu Ala Thr Pro Ser Gln Thr Ser
                405                 410                 415

Val Tyr Phe Cys Ala Ser Gly Asp Asn Ser Ala Glu Thr Leu Tyr Phe
            420                 425                 430

Gly Pro Gly Thr Arg Leu Thr Val Leu Glu Asp Leu Arg Asn Val Thr
        435                 440                 445
```

```
Pro Pro Lys Val Ser Leu Phe Glu Pro Ser Lys Ala Glu Ile Ala Asn
    450                 455                 460

Lys Gln Lys Ala Thr Leu Val Cys Leu Ala Arg Gly Phe Phe Pro Asp
465                 470                 475                 480

His Val Glu Leu Ser Trp Trp Val Asn Gly Lys Glu Val His Ser Gly
                485                 490                 495

Val Ser Thr Asp Pro Gln Ala Tyr Lys Glu Ser Asn Tyr Ser Tyr Cys
            500                 505                 510

Leu Ser Ser Arg Leu Arg Val Ser Ala Thr Phe Trp His Asn Pro Arg
        515                 520                 525

Asn His Phe Arg Cys Gln Val Gln Phe His Gly Leu Ser Glu Glu Asp
    530                 535                 540

Lys Trp Pro Glu Gly Ser Pro Lys Pro Val Thr Gln Asn Ile Ser Ala
545                 550                 555                 560

Glu Ala Trp Gly Arg Ala Asp Cys Gly Ile Thr Ser Ala Ser Tyr His
                565                 570                 575

Gln Gly Val Leu Ser Ala Thr Ile Leu Tyr Glu Ile Leu Leu Gly Lys
            580                 585                 590

Ala Thr Leu Tyr Ala Val Leu Val Ser Gly Leu Val Leu Met Ala Met
        595                 600                 605

Val Lys Lys Lys Asn Ser
    610
```

<210> SEQ ID NO 258
<211> LENGTH: 1845
<212> TYPE: DNA
<213> ORGANISM: Artificial Sequence
<220> FEATURE:
<223> OTHER INFORMATION: H-Y TCR alpha and beta

<400> SEQUENCE: 258

```
atgttccccg ttaccatatt gctcctgagt gctttcttca gtttgcgagg gaactctgcc     60

caatctgtcg atcagccaga tgcacacgtt accctttccg agggtgcgtc acttgaactg    120

aggtgttcct atagctactc agcagcccct tatctgtttt ggtacgtaca atacccaggg    180

cagagtctcc aatttctcct taaatatata accggggaca ctgtagtgaa ggggactaaa    240

ggttttgaag cagagtttag gaagagcaac agctccttca accttaagaa gtcacccgca    300

cactggtcag actccgcgaa atacttctgt gctctggaag ggcaagacca gggtggaagt    360

gccaaattga tatttggtga gggtactaaa ttgactgtta gctcaccaga catccagaac    420

ccagaacctg ctgtgtacca gttaaaagat cctcggtctc aggacagcac cctctgcctg    480

ttcaccgact ttgactccca aatcaatgtg ccgaaaacca tggaatctgg aacgttcatc    540

actgacaaaa ctgtgctgga catgaaagct atggattcca agagcaatgg ggccattgcc    600

tggagcaacc agacaagctt cacctgccaa gatatcttca aagagaccaa cgccacctac    660

cccagttcag acgttccctg tgatgccacg ttgaccgaga aaagctttga aacagatatg    720

aacctaaact ttcaaaacct gtcagttatg ggactccgaa tcctcctgct gaaagtagcg    780

ggatttaacc tgctcatgac gctgaggctg tggtccagtc gggccaagcg gtccggatcc    840

ggagccacca acttcagcct gctgaagcag gccggcgacg tggaggagaa ccccggcccc    900

atgtctaata ctgcatttcc agatccggcc tggaatacta cactccttag ttgggttgcc    960

ctcttcctcc ttggcacgaa gcacatggaa gccgccgtca cccagagtcc gagaaacaaa   1020

gtagcggtca ccggcggtaa ggtaacattg agttgtaacc aaacgaacaa ccataacaat   1080
```

```
atgtactggt atagacaaga cacaggccat ggcttgcgcc tgattcacta cagctatgga   1140

gcggggagta cggagaaggg tgatattccc gatggctata aagcctctcg gcctagccag   1200

gagaatttta gtttgatcct ggagctcgca acccccagtc agactagcgt ctacttttgt   1260

gcctcaggcg acaatagtgc ggaaaccctt tacttcggcc ctgggacaag acttacagtt   1320

ctagaggatc tgagaaatgt gactccaccc aaggtctcct tgtttgagcc atcaaaagca   1380

gagattgcaa acaaacaaaa ggctaccctc gtgtgcttgg ccaggggctt cttccctgac   1440

cacgtggagc tgagctggtg ggtgaatggc aaggaggtcc acagtggggt cagcacggac   1500

cctcaggcct acaaggagag caattatagc tactgcctga gcagccgcct gagggtctct   1560

gctaccttct ggcacaatcc tcgaaaccac ttccgctgcc aagtgcagtt ccatgggctt   1620

tcagaggagg acaagtggcc agagggctca cccaaacctg tcacacagaa catcagtgca   1680

gaggcctggg gccgagcaga ctgtggaatc acttcagcat cctatcatca gggggttctg   1740

tctgcaacca tcctctatga gatcctactg ggaaggccca ccctatatgc tgtgctggtc   1800

agtggcctgg tgctgatggc catggtcaag aaaaaaaatt cctag                   1845
```

```
<210> SEQ ID NO 259
<211> LENGTH: 619
<212> TYPE: PRT
<213> ORGANISM: Artificial Sequence
<220> FEATURE:
<223> OTHER INFORMATION: H-Y TCR alpha and beta

<400> SEQUENCE: 259

Met Phe Pro Val Thr Ile Leu Leu Leu Ser Ala Phe Phe Ser Leu Arg
1               5                   10                  15

Gly Asn Ser Ala Gln Ser Val Asp Gln Pro Asp Ala His Val Thr Leu
            20                  25                  30

Ser Glu Gly Ala Ser Leu Glu Leu Arg Cys Ser Tyr Ser Tyr Ser Ala
        35                  40                  45

Ala Pro Tyr Leu Phe Trp Tyr Val Gln Tyr Pro Gly Gln Ser Leu Gln
    50                  55                  60

Phe Leu Leu Lys Tyr Ile Thr Gly Asp Thr Val Val Lys Gly Thr Lys
65                  70                  75                  80

Gly Phe Glu Ala Glu Phe Arg Lys Ser Asn Ser Ser Phe Asn Leu Lys
                85                  90                  95

Lys Ser Pro Ala His Trp Ser Asp Ser Ala Lys Tyr Phe Cys Ala Leu
            100                 105                 110

Glu Gly Gln Asp Gln Gly Gly Ser Ala Lys Leu Ile Phe Gly Glu Gly
        115                 120                 125

Thr Lys Leu Thr Val Ser Ser Pro Tyr Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Cys Val Leu Asp Met Arg Ser Met Asp
            180                 185                 190

Phe Lys Ser Asn Ser Ala Val Ala Trp Ser Asn Lys Ser Asp Phe Ala
        195                 200                 205

Cys Ala Asn Ala Phe Asn Asn Ser Ile Ile Pro Glu Asp Thr Phe Phe
    210                 215                 220
```

-continued

```
Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser Gly Ser Gly Ala Thr Asn Phe Ser Leu Leu Lys
        275                 280                 285

Gln Ala Gly Asp Val Glu Glu Asn Pro Gly Pro Met Ser Asn Thr Ala
    290                 295                 300

Phe Pro Asp Pro Ala Trp Asn Thr Thr Leu Leu Ser Trp Val Ala Leu
305                 310                 315                 320

Phe Leu Leu Gly Thr Lys His Met Glu Ala Ala Val Thr Gln Ser Pro
                325                 330                 335

Arg Asn Lys Val Ala Val Thr Gly Gly Lys Val Thr Leu Ser Cys Asn
            340                 345                 350

Gln Thr Asn Asn His Asn Asn Met Tyr Trp Tyr Arg Gln Asp Thr Gly
        355                 360                 365

His Gly Leu Arg Leu Ile His Tyr Ser Tyr Gly Ala Gly Ser Thr Glu
    370                 375                 380

Lys Gly Asp Ile Pro Asp Gly Tyr Lys Ala Ser Arg Pro Ser Gln Glu
385                 390                 395                 400

Asn Phe Ser Leu Ile Leu Glu Leu Ala Thr Pro Ser Gln Thr Ser Val
                405                 410                 415

Tyr Phe Cys Ala Ser Gly Asp Asn Ser Ala Glu Thr Leu Tyr Phe Gly
            420                 425                 430

Pro Gly Thr Arg Leu Thr Val Leu Glu Asp Leu Lys Asn Val Phe Pro
        435                 440                 445

Pro Glu Val Ala Val Phe Glu Pro Ser Glu Ala Glu Ile Ser His Thr
    450                 455                 460

Gln Lys Ala Thr Leu Val Cys Leu Ala Thr Gly Phe Tyr Pro Asp His
465                 470                 475                 480

Val Glu Leu Ser Trp Trp Val Asn Gly Lys Glu Val His Ser Gly Val
                485                 490                 495

Cys Thr Asp Pro Gln Pro Leu Lys Glu Gln Pro Ala Leu Asn Asp Ser
            500                 505                 510

Arg Tyr Cys Leu Ser Ser Arg Leu Arg Val Ser Ala Thr Phe Trp Gln
        515                 520                 525

Asn Pro Arg Asn His Phe Arg Cys Gln Val Gln Phe Tyr Gly Leu Ser
    530                 535                 540

Glu Asn Asp Glu Trp Thr Gln Asp Arg Ala Lys Pro Val Thr Gln Ile
545                 550                 555                 560

Val Ser Ala Glu Ala Trp Gly Arg Ala Asp Cys Gly Phe Thr Ser Glu
                565                 570                 575

Ser Tyr Gln Gln Gly Val Leu Ser Ala Thr Ile Leu Tyr Glu Ile Leu
            580                 585                 590

Leu Gly Lys Ala Thr Leu Tyr Ala Val Leu Val Ser Ala Leu Val Leu
        595                 600                 605

Met Ala Met Val Lys Arg Lys Asp Ser Arg Gly
    610                 615
```

<210> SEQ ID NO 260
<211> LENGTH: 1860
<212> TYPE: DNA

<213> ORGANISM: Artificial Sequence
<220> FEATURE:
<223> OTHER INFORMATION: H-Y TCR alpha and beta

<400> SEQUENCE: 260
atgttccccg ttaccatatt gctcctgagt gctttcttca gtttgcgagg gaactctgcc 60
caatctgtcg atcagccaga tgcacacgtt accctttccg agggtgcgtc acttgaactg 120
aggtgttcct atagctactc agcagcccct tatctgtttt ggtacgtaca atacccaggg 180
cagagtctcc aatttctcct taaatatata accggggaca ctgtagtgaa ggggactaaa 240
ggttttgaag cagagtttag gaagagcaac agctccttca accttaagaa gtcacccgca 300
cactggtcag actccgcgaa atacttctgt gctctggaag ggcaagacca gggtggaagt 360
gccaaattga tatttggtga gggtactaaa ttgactgtta gctcaccgta tatccagaac 420
cctgaccctg ccgtgtacca gctgagagac tctaaatcca gtgacaagtc tgtctgccta 480
ttcaccgatt ttgattctca aacaaatgtg tcacaaagta aggattctga tgtgtatatc 540
acagacaaat gtgtgctaga catgaggtct atggacttca agagcaacag tgctgtggcc 600
tggagcaaca aatctgactt tgcatgtgca aacgccttca acaacagcat tattccagaa 660
gacaccttct tccccagccc agaaagttcc tgtgatgtca agctggtcga gaaaagcttt 720
gaaacagata cgaacctaaa ctttcaaaac ctgtcagtga ttgggttccg aatcctcctc 780
ctgaaagtgg ccgggtttaa tctgctcatg acgctgcggc tgtggtccag cggatccgga 840
gccaccaact tcagcctgct gaagcaggcc ggcgacgtgg aggagaaccc cggccccatg 900
tctaatactg catttccaga tccggcctgg aatactacac tccttagttg ggttgccctc 960
ttcctccttg gcacgaagca catggaagcc gccgtcaccc agagtccgag aaacaaagta 1020
gcggtcaccg gcggtaaggt aacattgagt tgtaaccaaa cgaacaacca taacaatatg 1080
tactggtata gacaagacac aggccatggc ttgcgcctga ttcactacag ctatggagcg 1140
gggagtacgg agaagggtga tattcccgat ggctataaag cctctcggcc tagccaggag 1200
aattttagtt tgatcctgga gctcgcaacc cccagtcaga ctagcgtcta cttttgtgcc 1260
tcaggcgaca atagtgcgga aaccctttac ttcggccctg ggacaagact tacagttctg 1320
gaggacctga aaaacgtgtt cccacccgag gtcgctgtgt ttgagccatc agaagcagag 1380
atctcccaca cccaaaaggc cacactggtg tgcctggcca caggcttcta ccccgaccac 1440
gtggagctga gctggtgggt gaatgggaag gaggtgcaca gtggggtctg cacagacccg 1500
cagcccctca aggagcagcc cgccctcaat gactccagat actgcctgag cagccgcctg 1560
agggtgtcgg ccaccttctg gcagaacccc cgcaaccact tccgctgtca agtccagttc 1620
tacgggctct cggagaatga cgagtggacc caggataggg ccaaacctgt cacccagatc 1680
gtcagcgccg aggcctgggg tagagcagac tgtggcttca cctccgagtc ttaccagcaa 1740
ggggtcctgt ctgccaccat cctctatgag atcttgctag ggaaggccac cttgtatgcc 1800
gtgctggtca gtgccctcgt gctgatggcc atggtcaaga gaaaggattc cagaggctag 1860

<210> SEQ ID NO 261
<211> LENGTH: 614
<212> TYPE: PRT
<213> ORGANISM: Artificial Sequence
<220> FEATURE:
<223> OTHER INFORMATION: H-Y TCR alpha and beta

<400> SEQUENCE: 261

Met Phe Pro Val Thr Ile Leu Leu Leu Ser Ala Phe Phe Ser Leu Arg

-continued 1 5 10 15

Gly Asn Ser Ala Gln Ser Val Asp Gln Pro Asp Ala His Val Thr Leu
20 25 30

Ser Glu Gly Ala Ser Leu Glu Leu Arg Cys Ser Tyr Ser Tyr Ser Ala
35 40 45

Ala Pro Tyr Leu Phe Trp Tyr Val Gln Tyr Pro Gly Gln Ser Leu Gln
50 55 60

Phe Leu Leu Lys Tyr Ile Thr Gly Asp Thr Val Val Lys Gly Thr Lys
65 70 75 80

Gly Phe Glu Ala Glu Phe Arg Lys Ser Asn Ser Ser Phe Asn Leu Lys
85 90 95

Lys Ser Pro Ala His Trp Ser Asp Ser Ala Lys Tyr Phe Cys Ala Leu
100 105 110

Glu Gly Gln Asp Gln Gly Gly Ser Ala Lys Leu Ile Phe Gly Glu Gly
115 120 125

Thr Lys Leu Thr Val Ser Ser Pro Asp Ile Gln Asn Pro Glu Pro Ala
130 135 140

Val Tyr Gln Leu Lys Asp Pro Arg Ser Gln Asp Ser Thr Leu Cys Leu
145 150 155 160

Phe Thr Asp Phe Asp Ser Gln Ile Asn Val Pro Lys Thr Met Glu Ser
165 170 175

Gly Thr Phe Ile Thr Asp Lys Thr Val Leu Asp Met Lys Ala Met Asp
180 185 190

Ser Lys Ser Asn Gly Ala Ile Ala Trp Ser Asn Gln Thr Ser Phe Thr
195 200 205

Cys Gln Asp Ile Phe Lys Glu Thr Asn Ala Thr Tyr Pro Ser Ser Asp
210 215 220

Val Pro Cys Asp Ala Thr Leu Thr Glu Lys Ser Phe Glu Thr Asp Met
225 230 235 240

Asn Leu Asn Phe Gln Asn Leu Ser Val Met Gly Leu Arg Ile Leu Leu
245 250 255

Leu Lys Val Ala Gly Phe Asn Leu Leu Met Thr Leu Arg Leu Trp Ser
260 265 270

Ser Arg Ala Lys Arg Ser Gly Ser Gly Ala Thr Asn Phe Ser Leu Leu
275 280 285

Lys Gln Ala Gly Asp Val Glu Glu Asn Pro Gly Pro Met Ser Asn Thr
290 295 300

Ala Phe Pro Asp Pro Ala Trp Asn Thr Thr Leu Leu Ser Trp Val Ala
305 310 315 320

Leu Phe Leu Leu Gly Thr Lys His Met Glu Ala Ala Val Thr Gln Ser
325 330 335

Pro Arg Asn Lys Val Ala Val Thr Gly Gly Lys Val Thr Leu Ser Cys
340 345 350

Asn Gln Thr Asn Asn His Asn Asn Met Tyr Trp Tyr Arg Gln Asp Thr
355 360 365

Gly His Gly Leu Arg Leu Ile His Tyr Ser Tyr Gly Ala Gly Ser Thr
370 375 380

Glu Lys Gly Asp Ile Pro Asp Gly Tyr Lys Ala Ser Arg Pro Ser Gln
385 390 395 400

Glu Asn Phe Ser Leu Ile Leu Glu Leu Ala Thr Pro Ser Gln Thr Ser
405 410 415

Val Tyr Phe Cys Ala Ser Gly Asp Asn Ser Ala Glu Thr Leu Tyr Phe
420 425 430

Gly Pro Gly Thr Arg Leu Leu Val Leu Glu Asp Leu Arg Asn Val Thr
435 440 445

Pro Pro Lys Val Ser Leu Phe Glu Pro Ser Lys Ala Glu Ile Ala Asn
450 455 460

Lys Gln Lys Ala Thr Leu Val Cys Leu Ala Arg Gly Phe Phe Pro Asp
465 470 475 480

His Val Glu Leu Ser Trp Trp Val Asn Gly Lys Glu Val His Ser Gly
485 490 495

Val Ser Thr Asp Pro Gln Ala Tyr Lys Glu Ser Asn Tyr Ser Tyr Cys
500 505 510

Leu Ser Ser Arg Leu Arg Val Ser Ala Thr Phe Trp His Asn Pro Arg
515 520 525

Asn His Phe Arg Cys Gln Val Gln Phe His Gly Leu Ser Glu Glu Asp
530 535 540

Lys Trp Pro Glu Gly Ser Pro Lys Pro Val Thr Gln Asn Ile Ser Ala
545 550 555 560

Glu Ala Trp Gly Arg Ala Asp Cys Gly Ile Thr Ser Ala Ser Tyr His
565 570 575

Gln Gly Val Leu Ser Ala Thr Ile Leu Tyr Glu Ile Leu Leu Gly Lys
580 585 590

Ala Thr Leu Tyr Ala Val Leu Val Ser Gly Leu Val Leu Met Ala Met
595 600 605

Val Lys Lys Lys Asn Ser
610

<210> SEQ ID NO 262
<211> LENGTH: 1845
<212> TYPE: DNA
<213> ORGANISM: Artificial Sequence
<220> FEATURE:
<223> OTHER INFORMATION: H-Y TCR alpha and beta

<400> SEQUENCE: 262
atgttccccg ttaccatatt gctcctgagt gctttcttca gtttgcgagg gaactctgcc 60
caatctgtcg atcagccaga tgcacacgtt accctttccg agggtgcgtc acttgaactg 120
aggtgttcct atagctactc agcagcccct tatctgtttt ggtacgtaca atacccaggg 180
cagagtctcc aatttctcct taaatatata accggggaca ctgtagtgaa ggggactaaa 240
ggttttgaag cagagtttag gaagagcaac agctccttca accttaagaa gtcacccgca 300
cactggtcag actccgcgaa atacttctgt gctctggaag ggcaagacca gggtggaagt 360
gccaaattga tatttggtga gggtactaaa ttgactgtta gctcaccaga catccagaac 420
ccagaacctg ctgtgtacca gttaaaagat cctcggtctc aggacagcac cctctgcctg 480
ttcaccgact ttgactccca aatcaatgtg ccgaaaacca tggaatctgg aacgttcatc 540
actgacaaaa ctgtgctgga catgaaagct atggattcca agagcaatgg ggccattgcc 600
tggagcaacc agacaagctt cacctgccaa gatatcttca aagagaccaa cgccacctac 660
cccagttcag acgttccctg tgatgccacg ttgaccgaga aaagctttga aacagatatg 720
aacctaaact ttcaaaacct gtcagttatg ggactccgaa tcctcctgct gaaagtagcg 780
ggatttaacc tgctcatgac gctgaggctg tggtccagtc gggccaagcg gtccggatcc 840
ggagccacca acttcagcct gctgaagcag gccggcgacg tggaggagaa ccccggcccc 900
atgtctaata ctgcatttcc agatccggcc tggaatacta cactccttag ttgggttgcc 960

-continued

```
ctcttcctcc ttggcacgaa gcacatggaa gccgccgtca cccagagtcc gagaaacaaa   1020

gtagcggtca ccggcggtaa ggtaacattg agttgtaacc aaacgaacaa ccataacaat   1080

atgtactggt atagacaaga cacaggccat ggcttgcgcc tgattcacta cagctatgga   1140

gcggggagta cggagaaggg tgatattccc gatggctata aagcctctcg gcctagccag   1200

gagaatttta gtttgatcct ggagctcgca acccccagtc agactagcgt ctacttttgt   1260

gcctcaggcg acaatagtgc ggaaaccctt tacttcggcc ctgggacaag acttttggtt   1320

ctagaggatc tgagaaatgt gactccaccc aaggtctcct tgtttgagcc atcaaaagca   1380

gagattgcaa acaaacaaaa ggctaccctc gtgtgcttgg ccaggggctt cttccctgac   1440

cacgtggagc tgagctggtg ggtgaatggc aaggaggtcc acagtggggt cagcacggac   1500

cctcaggcct acaaggagag caattatagc tactgcctga gcagccgcct gagggtctct   1560

gctaccttct ggcacaatcc tcgaaaccac ttccgctgcc aagtgcagtt ccatgggctt   1620

tcagaggagg acaagtggcc agagggctca cccaaacctg tcacacagaa catcagtgca   1680

gaggcctggg gccgagcaga ctgtggaatc acttcagcat cctatcatca ggggggttctg   1740

tctgcaacca tcctctatga gatcctactg ggaaggcca ccctatatgc tgtgctggtc   1800

agtggcctgg tgctgatggc catggtcaag aaaaaaaatt cctag                   1845
```

<210> SEQ ID NO 263
<211> LENGTH: 619
<212> TYPE: PRT
<213> ORGANISM: Artificial Sequence
<220> FEATURE:
<223> OTHER INFORMATION: H-Y TCR alpha and beta

<400> SEQUENCE: 263

```
Met Phe Pro Val Thr Ile Leu Leu Leu Ser Ala Phe Phe Ser Leu Arg
1               5                   10                  15

Gly Asn Ser Ala Gln Ser Val Asp Gln Pro Asp Ala His Val Thr Leu
            20                  25                  30

Ser Glu Gly Ala Ser Leu Glu Leu Arg Cys Ser Tyr Ser Tyr Ser Ala
        35                  40                  45

Ala Pro Tyr Leu Phe Trp Tyr Val Gln Tyr Pro Gly Gln Ser Leu Gln
    50                  55                  60

Phe Leu Leu Lys Tyr Ile Thr Gly Asp Thr Val Val Lys Gly Thr Lys
65                  70                  75                  80

Gly Phe Glu Ala Glu Phe Arg Lys Ser Asn Ser Ser Phe Asn Leu Lys
                85                  90                  95

Lys Ser Pro Ala His Trp Ser Asp Ser Ala Lys Tyr Phe Cys Ala Leu
            100                 105                 110

Glu Gly Gln Asp Gln Gly Gly Ser Ala Lys Leu Ile Phe Gly Glu Gly
        115                 120                 125

Thr Lys Leu Thr Val Ser Ser Pro Tyr Ile Gln Asn Pro Asp Pro Ala
    130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Cys Val Leu Asp Met Arg Ser Met Asp
            180                 185                 190

Phe Lys Ser Asn Ser Ala Val Ala Trp Ser Asn Lys Ser Asp Phe Ala
        195                 200                 205
```

```
Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
            260                 265                 270

Arg Leu Trp Ser Ser Gly Ser Gly Ala Thr Asn Phe Ser Leu Leu Lys
        275                 280                 285

Gln Ala Gly Asp Val Glu Glu Asn Pro Gly Pro Met Ser Asn Thr Ala
    290                 295                 300

Phe Pro Asp Pro Ala Trp Asn Thr Thr Leu Leu Ser Trp Val Ala Leu
305                 310                 315                 320

Phe Leu Leu Gly Thr Lys His Met Glu Ala Ala Val Thr Gln Ser Pro
                325                 330                 335

Arg Asn Lys Val Ala Val Thr Gly Gly Lys Val Thr Leu Ser Cys Asn
            340                 345                 350

Gln Thr Asn Asn His Asn Asn Met Tyr Trp Tyr Arg Gln Asp Thr Gly
        355                 360                 365

His Gly Leu Arg Leu Ile His Tyr Ser Tyr Gly Ala Gly Ser Thr Glu
    370                 375                 380

Lys Gly Asp Ile Pro Asp Gly Tyr Lys Ala Ser Arg Pro Ser Gln Glu
385                 390                 395                 400

Asn Phe Ser Leu Ile Leu Glu Leu Ala Thr Pro Ser Gln Thr Ser Val
                405                 410                 415

Tyr Phe Cys Ala Ser Gly Asp Asn Ser Ala Glu Thr Leu Tyr Phe Gly
            420                 425                 430

Pro Gly Thr Arg Leu Leu Val Leu Glu Asp Leu Lys Asn Val Phe Pro
        435                 440                 445

Pro Glu Val Ala Val Phe Glu Pro Ser Glu Ala Glu Ile Ser His Thr
    450                 455                 460

Gln Lys Ala Thr Leu Val Cys Leu Ala Thr Gly Phe Tyr Pro Asp His
465                 470                 475                 480

Val Glu Leu Ser Trp Trp Val Asn Gly Lys Glu Val His Ser Gly Val
                485                 490                 495

Cys Thr Asp Pro Gln Pro Leu Lys Glu Gln Pro Ala Leu Asn Asp Ser
            500                 505                 510

Arg Tyr Cys Leu Ser Ser Arg Leu Arg Val Ser Ala Thr Phe Trp Gln
        515                 520                 525

Asn Pro Arg Asn His Phe Arg Cys Gln Val Gln Phe Tyr Gly Leu Ser
    530                 535                 540

Glu Asn Asp Glu Trp Thr Gln Asp Arg Ala Lys Pro Val Thr Gln Ile
545                 550                 555                 560

Val Ser Ala Glu Ala Trp Gly Arg Ala Asp Cys Gly Phe Thr Ser Glu
                565                 570                 575

Ser Tyr Gln Gln Gly Val Leu Ser Ala Thr Ile Leu Tyr Glu Ile Leu
            580                 585                 590

Leu Gly Lys Ala Thr Leu Tyr Ala Val Leu Val Ser Ala Leu Val Leu
        595                 600                 605

Met Ala Met Val Lys Arg Lys Asp Ser Arg Gly
    610                 615
```

<210> SEQ ID NO 264
<211> LENGTH: 1860
<212> TYPE: DNA
<213> ORGANISM: Artificial Sequence
<220> FEATURE:
<223> OTHER INFORMATION: H-Y TCR alpha and beta

<400> SEQUENCE: 264

```
atgttccccg ttaccatatt gctcctgagt gctttcttca gtttgcgagg gaactctgcc     60
caatctgtcg atcagccaga tgcacacgtt accctttccg agggtgcgtc acttgaactg    120
aggtgttcct atagctactc agcagcccct tatctgtttt ggtacgtaca atacccaggg    180
cagagtctcc aatttctcct taaatatata accggggaca ctgtagtgaa ggggactaaa    240
ggttttgaag cagagtttag gaagagcaac agctccttca accttaagaa gtcacccgca    300
cactggtcag actccgcgaa atacttctgt gctctggaag ggcaagacca gggtggaagt    360
gccaaattga tatttggtga gggtactaaa ttgactgtta gctcaccgta tatccagaac    420
cctgaccctg ccgtgtacca gctgagagac tctaaatcca gtgacaagtc tgtctgccta    480
ttcaccgatt ttgattctca aacaaatgtg tcacaaagta aggattctga tgtgtatatc    540
acagacaaat gtgtgctaga catgaggtct atggacttca agagcaacag tgctgtggcc    600
tggagcaaca aatctgactt tgcatgtgca aacgccttca acaacagcat tattccagaa    660
gacaccttct tccccagccc agaaagttcc tgtgatgtca agctggtcga gaaaagcttt    720
gaaacagata cgaacctaaa ctttcaaaac ctgtcagtga ttgggttccg aatcctcctc    780
ctgaaagtgg ccgggtttaa tctgctcatg acgctgcggc tgtggtccag cggatccgga    840
gccaccaact tcagcctgct gaagcaggcc ggcgacgtgg aggagaaccc cggccccatg    900
tctaatactg catttccaga tccggcctgg aatactacac tccttagttg ggttgccctc    960
ttcctccttg gcacgaagca catggaagcc gccgtcaccc agagtccgag aaacaaagta   1020
gcggtcaccg gcggtaaggt aacattgagt tgtaaccaaa cgaacaacca taacaatatg   1080
tactggtata gacaagacac aggccatggc ttgcgcctga ttcactacag ctatggagcg   1140
gggagtacgg agaagggtga tattcccgat ggctataaag cctctcggcc tagccaggag   1200
aattttagtt tgatcctgga gctcgcaacc cccagtcaga ctagcgtcta cttttgtgcc   1260
tcaggcgaca atagtgcgga aaccctttac ttcggccctg ggacaagact tttggttctg   1320
gaggacctga aaaacgtgtt cccacccgag gtcgctgtgt ttgagccatc agaagcagag   1380
atctcccaca cccaaaaggc cacactggtg tgcctggcca caggcttcta ccccgaccac   1440
gtggagctga gctggtgggt gaatgggaag gaggtgcaca gtggggtctg cacagacccg   1500
cagcccctca aggagcagcc cgccctcaat gactccagat actgcctgag cagccgcctg   1560
agggtgtcgg ccaccttctg gcagaacccc cgcaaccact tccgctgtca agtccagttc   1620
tacgggctct cggagaatga cgagtggacc caggataggg ccaaacctgt cacccagatc   1680
gtcagcgccg aggcctgggg tagagcagac tgtggcttca cctccgagtc ttaccagcaa   1740
ggggtcctgt ctgccaccat cctctatgag atcttgctag ggaaggccac cttgtatgcc   1800
gtgctggtca gtgccctcgt gctgatggcc atggtcaaga gaaaggattc cagaggctag   1860
```

<210> SEQ ID NO 265
<211> LENGTH: 9
<212> TYPE: PRT
<213> ORGANISM: Artificial Sequence
<220> FEATURE:
<223> OTHER INFORMATION: NY-ESO-1

<400> SEQUENCE: 265

Ser Leu Leu Met Trp Ile Thr Gln Val
1               5

<210> SEQ ID NO 266
<211> LENGTH: 9
<212> TYPE: PRT
<213> ORGANISM: Artificial Sequence
<220> FEATURE:
<223> OTHER INFORMATION: HA-1(R) peptide

<400> SEQUENCE: 266

Val Leu Arg Asp Asp Leu Leu Glu Ala
1               5

<210> SEQ ID NO 267
<211> LENGTH: 607
<212> TYPE: PRT
<213> ORGANISM: Artificial Sequence
<220> FEATURE:
<223> OTHER INFORMATION: NY-ESO-1 TCR alpha and beta

<400> SEQUENCE: 267

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Leu Tyr Gly Gly Ser Tyr Ile Pro Thr Phe Gly Arg Gly Thr Ser
        115                 120                 125

Leu Ile Val His Pro Tyr Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Cys Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

```
Ser Ser Gly Ser Gly Ala Thr Asn Phe Ser Leu Leu Lys Gln Ala Gly
        275                 280                 285

Asp Val Glu Glu Asn Pro Gly Pro Met Ser Ile Gly Leu Leu Cys Cys
    290                 295                 300

Ala Ala Leu Ser Leu Leu Trp Ala Gly Pro Val Asn Ala Gly Val Thr
305                 310                 315                 320

Gln Thr Pro Lys Phe Gln Val Leu Lys Thr Gly Gln Ser Met Thr Leu
                325                 330                 335

Gln Cys Ala Gln Asp Met Asn His Glu Tyr Met Ser Trp Tyr Arg Gln
            340                 345                 350

Asp Pro Gly Met Gly Leu Arg Leu Ile His Tyr Ser Val Gly Ala Gly
        355                 360                 365

Ile Thr Asp Gln Gly Glu Val Pro Asn Gly Tyr Asn Val Ser Arg Ser
    370                 375                 380

Thr Thr Glu Asp Phe Pro Leu Arg Leu Leu Ser Ala Ala Pro Ser Gln
385                 390                 395                 400

Thr Ser Val Tyr Phe Cys Ala Ser Ser Tyr Val Gly Asn Thr Gly Glu
                405                 410                 415

Leu Phe Phe Gly Glu Gly Ser Arg Leu Thr Val Leu Glu Asp Leu Lys
            420                 425                 430

Asn Val Phe Pro Pro Glu Val Ala Val Phe Glu Pro Ser Glu Ala Glu
        435                 440                 445

Ile Ser His Thr Gln Lys Ala Thr Leu Val Cys Leu Ala Thr Gly Phe
    450                 455                 460

Tyr Pro Asp His Val Glu Leu Ser Trp Trp Val Asn Gly Lys Glu Val
465                 470                 475                 480

His Ser Gly Val Cys Thr Asp Pro Gln Pro Leu Lys Glu Gln Pro Ala
                485                 490                 495

Leu Asn Asp Ser Arg Tyr Cys Leu Ser Ser Arg Leu Arg Val Ser Ala
            500                 505                 510

Thr Phe Trp Gln Asn Pro Arg Asn His Phe Arg Cys Gln Val Gln Phe
        515                 520                 525

Tyr Gly Leu Ser Glu Asn Asp Glu Trp Thr Gln Asp Arg Ala Lys Pro
    530                 535                 540

Val Thr Gln Ile Val Ser Ala Glu Ala Trp Gly Arg Ala Asp Cys Gly
545                 550                 555                 560

Phe Thr Ser Glu Ser Tyr Gln Gln Gly Val Leu Ser Ala Thr Ile Leu
                565                 570                 575

Tyr Glu Ile Leu Leu Gly Lys Ala Thr Leu Tyr Ala Val Leu Val Ser
            580                 585                 590

Ala Leu Val Leu Met Ala Met Val Lys Arg Lys Asp Ser Arg Gly
        595                 600                 605
```

<210> SEQ ID NO 268
<211> LENGTH: 1824
<212> TYPE: DNA
<213> ORGANISM: Artificial Sequence
<220> FEATURE:
<223> OTHER INFORMATION: NY-ESO-1 TCR alpha and beta

<400> SEQUENCE: 268

```
atggagacac tcttgggcct gcttatcctt tggctgcagc tgcaatgggt gagcagcaaa      60

caggaggtga cgcagattcc tgcagctctg agtgtcccag aaggagaaaa cttggttctg     120

aactgcagtt tcactgatag cgctatttac aacctccagt ggtttaggca ggaccctggg     180
```

-continued

```
aaaggactca catctctgtt gcttattcag tcaagtcaga gagagcaaac aagtggaaga    240
cttaatgcct cgctggataa atcatcagga cgtagtactt tatacattgc agcttctcag    300
cctggtgact cagccaccta cctctgtgct gtgaggcccc tctacggagg aagctacata    360
cctacatttg gaagaggaac cagccttatt gttcatccgt atatccagaa ccctgaccct    420
gccgtgtacc agctgagaga ctctaaatcc agtgacaagt ctgtctgcct attcaccgat    480
tttgattctc aaacaaatgt gtcacaaagt aaggattctg atgtgtatat cacagacaaa    540
tgtgtgctag acatgaggtc tatggacttc aagagcaaca gtgctgtggc ctggagcaac    600
aaatctgact ttgcatgtgc aaacgccttc aacaacagca ttattccaga agacaccttc    660
ttccccagcc cagaaagttc ctgtgatgtc aagctggtcg agaaaagctt tgaaacagat    720
acgaacctaa actttcaaaa cctgtcagtg attgggttcc gaatcctcct cctgaaagtg    780
gccgggttta atctgctcat gacgctgcgg ctgtggtcca gcggatccgg agccaccaac    840
ttcagcctgc tgaagcaggc cggcgacgtg gaggagaacc ccggccccat gagcatcggc    900
ctcctgtgct gtgcagcctt gtctctcctg tgggcaggtc cagtgaatgc tggtgtcact    960
cagaccccaa aattccaggt cctgaagaca ggacagagca tgacactgca gtgtgcccag   1020
gatatgaacc atgaatacat gtcctggtat cgacaagacc caggcatggg gctgaggctg   1080
attcattact cagttggtgc tggtatcact gaccaaggag aagtccccaa tggctacaat   1140
gtctccagat caaccacaga ggatttcccg ctcaggctgc tgtcggctgc tccctcccag   1200
acatctgtgt acttctgtgc cagcagttac gtcgggaaca ccggggagct gtttttttgga   1260
gaaggctcta ggctgaccgt actggaggac ctgaaaaacg tgttcccacc cgaggtcgct   1320
gtgtttgagc catcagaagc agagatctcc cacacccaaa aggccacact ggtgtgcctg   1380
gccacaggct tctaccccga ccacgtggag ctgagctggt gggtgaatgg gaaggaggtg   1440
cacagtgggg tctgcacaga cccgcagccc ctcaaggagc agcccgccct caatgactcc   1500
agatactgcc tgagcagccg cctgagggtg tcggccacct tctggcagaa cccccgcaac   1560
cacttccgct gtcaagtcca gttctacggg ctctcggaga atgacgagtg gacccaggat   1620
agggccaaac ctgtcaccca gatcgtcagc gccgaggcct ggggtagagc agactgtggc   1680
ttcacctccg agtcttacca gcaaggggtc ctgtctgcca ccatcctcta tgagatcttg   1740
ctagggaagg ccaccttgta tgccgtgctg gtcagtgccc tcgtgctgat ggccatggtc   1800
aagagaaagg attccagagg ctag                                          1824
```

<210> SEQ ID NO 269
<211> LENGTH: 612
<212> TYPE: PRT
<213> ORGANISM: Artificial Sequence
<220> FEATURE:
<223> OTHER INFORMATION: KRAS TCR

<400> SEQUENCE: 269

```
Met Gln Arg Asn Leu Gly Ala Val Leu Gly Ile Leu Trp Val Gln Ile
1               5                   10                  15

Cys Trp Val Arg Gly Asp Gln Val Glu Gln Ser Pro Ser Ala Leu Ser
            20                  25                  30

Leu His Glu Gly Thr Asp Ser Ala Leu Arg Cys Asn Phe Thr Thr Thr
        35                  40                  45

Met Arg Ser Val Gln Trp Phe Arg Gln Asn Ser Arg Gly Ser Leu Ile
    50                  55                  60

Ser Leu Phe Tyr Leu Ala Ser Gly Thr Lys Glu Asn Gly Arg Leu Lys
```

-continued 65 70 75 80

Ser Ala Phe Asp Ser Lys Glu Arg Arg Tyr Ser Thr Leu His Ile Arg
85 90 95

Asp Ala Gln Leu Glu Asp Ser Gly Thr Tyr Phe Cys Ala Ala Asp Ser
100 105 110

Ser Asn Thr Gly Tyr Gln Asn Phe Tyr Phe Gly Lys Gly Thr Ser Leu
115 120 125

Thr Val Ile Pro Asn Ile Gln Asn Pro Glu Pro Ala Val Tyr Gln Leu
130 135 140

Lys Asp Pro Arg Ser Gln Asp Ser Thr Leu Cys Leu Phe Thr Asp Phe
145 150 155 160

Asp Ser Gln Ile Asn Val Pro Lys Thr Met Glu Ser Gly Thr Phe Ile
165 170 175

Thr Asp Lys Thr Val Leu Asp Met Lys Ala Met Asp Ser Lys Ser Asn
180 185 190

Gly Ala Ile Ala Trp Ser Asn Gln Thr Ser Phe Thr Cys Gln Asp Ile
195 200 205

Phe Lys Glu Thr Asn Ala Thr Tyr Pro Ser Ser Asp Val Pro Cys Asp
210 215 220

Ala Thr Leu Thr Glu Lys Ser Phe Glu Thr Asp Met Asn Leu Asn Phe
225 230 235 240

Gln Asn Leu Ser Val Met Gly Leu Arg Ile Leu Leu Leu Lys Val Ala
245 250 255

Gly Phe Asn Leu Leu Met Thr Leu Arg Leu Trp Ser Ser Arg Ala Lys
260 265 270

Arg Ser Gly Ser Gly Ala Thr Asn Phe Ser Leu Leu Lys Gln Ala Gly
275 280 285

Asp Val Glu Glu Asn Pro Gly Pro Met Ser Asn Thr Ala Phe Pro Asp
290 295 300

Pro Ala Trp Asn Thr Thr Leu Leu Ser Trp Val Ala Leu Phe Leu Leu
305 310 315 320

Gly Thr Ser Ser Ala Asn Ser Gly Val Val Gln Ser Pro Arg Tyr Ile
325 330 335

Ile Lys Gly Lys Gly Glu Arg Ser Ile Leu Lys Cys Ile Pro Ile Ser
340 345 350

Gly His Leu Ser Val Ala Trp Tyr Gln Gln Thr Gln Gly Gln Glu Leu
355 360 365

Lys Phe Phe Ile Gln His Tyr Asp Lys Met Glu Arg Asp Lys Gly Asn
370 375 380

Leu Pro Ser Arg Phe Ser Val Gln Gln Phe Asp Asp Tyr His Ser Glu
385 390 395 400

Met Asn Met Ser Ala Leu Glu Leu Glu Asp Ser Ala Val Tyr Phe Cys
405 410 415

Ala Ser Ser Leu Thr Asp Pro Leu Asp Ser Asp Tyr Thr Phe Gly Ser
420 425 430

Gly Thr Arg Leu Leu Val Ile Glu Asp Leu Arg Asn Val Thr Pro Pro
435 440 445

Lys Val Ser Leu Phe Glu Pro Ser Lys Ala Glu Ile Ala Asn Lys Gln
450 455 460

Lys Ala Thr Leu Val Cys Leu Ala Arg Gly Phe Phe Pro Asp His Val
465 470 475 480

Glu Leu Ser Trp Trp Val Asn Gly Lys Glu Val His Ser Gly Val Ser
485 490 495

```
Thr Asp Pro Gln Ala Tyr Lys Glu Ser Asn Tyr Ser Tyr Cys Leu Ser
            500                 505                 510

Ser Arg Leu Arg Val Ser Ala Thr Phe Trp His Asn Pro Arg Asn His
        515                 520                 525

Phe Arg Cys Gln Val Gln Phe His Gly Leu Ser Glu Glu Asp Lys Trp
    530                 535                 540

Pro Glu Gly Ser Pro Lys Pro Val Thr Gln Asn Ile Ser Ala Glu Ala
545                 550                 555                 560

Trp Gly Arg Ala Asp Cys Gly Ile Thr Ser Ala Ser Tyr Gln Gln Gly
                565                 570                 575

Val Leu Ser Ala Thr Ile Leu Tyr Glu Ile Leu Leu Gly Lys Ala Thr
            580                 585                 590

Leu Tyr Ala Val Leu Val Ser Thr Leu Val Val Met Ala Met Val Lys
        595                 600                 605

Arg Lys Asn Ser
    610


<210> SEQ ID NO 270
<211> LENGTH: 1839
<212> TYPE: DNA
<213> ORGANISM: Artificial Sequence
<220> FEATURE:
<223> OTHER INFORMATION: KRAS TCR

<400> SEQUENCE: 270

atgcagagga acctgggagc tgtgctgggg attctgtggg tgcagatttg ctgggtgaga      60

ggggatcagg tggagcagag tccttcagcc ctgagcctcc acgagggaac cgattctgct     120

ctgagatgca attttacgac caccatgagg agtgtgcagt ggttccgaca gaattccagg     180

ggcagcctca tcagtttgtt ctacttggct tcaggaacaa aggagaatgg gaggctaaag     240

tcagcatttg attctaagga gcggcgctac agcaccctgc acatcaggga tgcccagctg     300

gaggactcag gcacttactt ctgtgctgct gactcttcga acacgggtta ccagaacttc     360

tattttggga aaggaacaag tttgactgtc attccaaaca tccagaaccc agaacctgct     420

gtgtaccagt taaaagatcc tcggtctcag gacagcaccc tctgcctgtt caccgacttt     480

gactcccaaa tcaatgtgcc gaaaaccatg gaatctggaa cgttcatcac tgacaaaact     540

gtgctggaca tgaaagctat ggattccaag agcaatgggg ccattgcctg gagcaaccag     600

acaagcttca cctgccaaga tatcttcaaa gagaccaacg ccacctaccc cagttcagac     660

gttccctgtg atgccacgtt gaccgagaaa agctttgaaa cagatatgaa cctgaacttt     720

caaaacctgt cagttatggg actccgaatc ctcctgctga aagtagcggg atttaacctg     780

ctcatgacgc tgaggctgtg gtccagtcgg gccaagcggt ccggatccgg agccaccaac     840

ttcagcctgc tgaagcaggc cggcgacgtg gaggagaacc ccggccccat gtctaacact     900

gccttccctg accccgcctg gaacaccacc ctgctatctt gggttgctct ctttctcctg     960

ggaacaagtt cagcaaattc tggggttgtc cagtctccaa gatacataat caaaggaaag    1020

ggagaaaggt ccattctaaa atgtattccc atctctggac atctctctgt ggcctggtat    1080

caacagactc aggggcagga actaaagttc ttcattcagc attatgataa aatggagaga    1140

gataaaggaa acctgcccag cagattctca gtccaacagt ttgatgacta tcactctgag    1200

atgaacatga gtgccttgga gctagaggac tctgccgtgt acttctgtgc cagctctctc    1260

acagatccgc tagactccga ctacaccttc ggctcaggga ccaggctttt ggtaatagag    1320
```

-continued

```
gatctgagaa atgtgactcc acccaaggtc tccttgtttg agccatcaaa agcagagatt    1380

gcaaacaaac aaaaggctac cctcgtgtgc ttggccaggg gcttcttccc tgaccacgtg    1440

gagctgagct ggtgggtgaa tggcaaggag gtccacagtg gggtcagcac ggaccctcag    1500

gcctacaagg agagcaatta tagctactgc ctgagcagcc gcctgagggt ctctgctacc    1560

ttctggcaca atcctcgcaa ccacttccgc tgccaagtgc agttccatgg gctttcagag    1620

gaggacaagt ggccagaggg ctcacccaaa cctgtcacac agaacatcag tgcagaggcc    1680

tggggccgag cagactgtgg gattacctca gcatcctatc aacaaggggt cttgtctgcc    1740

accatcctct atgagatcct gctagggaaa gccaccctgt atgctgtgct tgtcagtaca    1800

ctggtggtga tggctatggt caaaagaaag aattcatag                           1839
```

<210> SEQ ID NO 271
<211> LENGTH: 18
<212> TYPE: PRT
<213> ORGANISM: Artificial Sequence
<220> FEATURE:
<223> OTHER INFORMATION: T2A self cleaving peptide

<400> SEQUENCE: 271

Glu Gly Arg Gly Ser Leu Leu Thr Cys Gly Asp Val Glu Glu Asn Pro
1               5                   10                  15

Gly Pro

<210> SEQ ID NO 272
<211> LENGTH: 20
<212> TYPE: PRT
<213> ORGANISM: Artificial Sequence
<220> FEATURE:
<223> OTHER INFORMATION: E2A self cleaving peptide

<400> SEQUENCE: 272

Gln Cys Thr Asn Tyr Ala Leu Leu Lys Leu Ala Gly Asp Val Glu Ser
1               5                   10                  15

Asn Pro Gly Pro
            20

<210> SEQ ID NO 273
<211> LENGTH: 22
<212> TYPE: PRT
<213> ORGANISM: Artificial Sequence
<220> FEATURE:
<223> OTHER INFORMATION: F2A self cleaving peptide

<400> SEQUENCE: 273

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 274
<211> LENGTH: 6
<212> TYPE: PRT
<213> ORGANISM: Artificial Sequence
<220> FEATURE:
<223> OTHER INFORMATION: ITIM
<220> FEATURE:
<221> NAME/KEY: Z
<222> LOCATION: (1)..(1)
<223> OTHER INFORMATION: Z is S, I V or L
<220> FEATURE:
<221> NAME/KEY: X
<222> LOCATION: (2)..(2)

<223> OTHER INFORMATION: X is any amino acid
<220> FEATURE:
<221> NAME/KEY: X
<222> LOCATION: (4)..(5)
<223> OTHER INFORMATION: X is any amino acid
<220> FEATURE:
<221> NAME/KEY: Z
<222> LOCATION: (6)..(6)
<223> OTHER INFORMATION: Z is I, V or L

<400> SEQUENCE: 274

```
Glx Xaa Tyr Xaa Xaa Glx
1               5
```

<210> SEQ ID NO 275
<211> LENGTH: 242
<212> TYPE: PRT
<213> ORGANISM: Artificial Sequence
<220> FEATURE:
<223> OTHER INFORMATION: CD19 ScFv

<400> SEQUENCE: 275

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser
```

<210> SEQ ID NO 276
<211> LENGTH: 726
<212> TYPE: DNA
<213> ORGANISM: Artificial Sequence
<220> FEATURE:
<223> OTHER INFORMATION: CD19 ScFv

<400> SEQUENCE: 276
gacatccaga tgacacagac tacatcctcc ctgtctgcct ctctgggaga cagagtcacc 60
atcagttgca gggcaagtca ggacattagt aaatatttaa attggtatca gcagaaacca 120
gatggaactg ttaaactcct gatctaccat acatcaagat tacactcagg agtcccatca 180
aggttcagtg gcagtgggtc tggaacagat tattctctca ccattagcaa cctggagcaa 240
gaagatattg ccacttactt ttgccaacag ggtaatacgc ttccgtacac gttcggaggg 300
gggaccaagc tggagatcac aggtggcggt ggctcgggcg gtggtgggtc gggtggcggc 360
ggatctgagg tgaaactgca ggagtcagga cctggcctgg tggcgccctc acagagcctg 420
tccgtcacat gcactgtctc aggggtctca ttacccgact atggtgtaag ctggattcgc 480
cagcctccac gaaagggtct ggagtggctg ggagtaatat ggggtagtga aaccacatac 540
tataattcag ctctcaaatc cagactgacc atcatcaagg acaactccaa gagccaagtt 600
ttcttaaaaa tgaacagtct gcaaactgat gacacagcca tttactactg tgccaaacat 660
tattactacg gtggtagcta tgctatggac tactggggcc aaggaacctc agtcaccgtg 720
tcctca 726

<210> SEQ ID NO 277
<211> LENGTH: 244
<212> TYPE: PRT
<213> ORGANISM: Artificial Sequence
<220> FEATURE:
<223> OTHER INFORMATION: CD19 ScFv

<400> SEQUENCE: 277

Asp Ile Gln Met Thr Gln Thr Thr Ser Ser Leu Ser Ala Ser Leu Gly
1 5 10 15

Asp Arg Val Thr Ile Ser Cys Arg Ala Ser Gln Asp Ile Ser Lys Tyr
20 25 30

Leu Asn Trp Tyr Gln Gln Lys Pro Asp Gly Thr Val Lys Leu Leu Ile
35 40 45

Tyr His Thr Ser Arg Leu His Ser Gly Val Pro Ser Arg Phe Ser Gly
50 55 60

Ser Gly Ser Gly Thr Asp Tyr Ser Leu Thr Ile Ser Asn Leu Glu Gln
65 70 75 80

Glu Asp Ile Ala Thr Tyr Phe Cys Gln Gln Gly Asn Thr Leu Pro Tyr
85 90 95

Thr Phe Gly Gly Gly Thr Lys Leu Glu Ile Thr Gly Gly Gly Gly Ser
100 105 110

Gly Gly Gly Gly Ser Gly Gly Gly Gly Ser Gly Gly Glu Val Lys Leu
115 120 125

Gln Glu Ser Gly Pro Gly Leu Val Ala Pro Ser Gln Ser Leu Ser Val
130 135 140

Thr Cys Thr Val Ser Gly Val Ser Leu Pro Asp Tyr Gly Val Ser Trp
145 150 155 160

Ile Arg Gln Pro Pro Arg Lys Gly Leu Glu Trp Leu Gly Val Ile Trp
165 170 175

Gly Ser Glu Thr Thr Tyr Tyr Asn Ser Ala Leu Lys Ser Arg Leu Thr
180 185 190

Ile Ile Lys Asp Asn Ser Lys Ser Gln Val Phe Leu Lys Met Asn Ser
195 200 205

Leu Gln Thr Asp Asp Thr Ala Ile Tyr Tyr Cys Ala Lys His Tyr Tyr

-continued

```
    210                 215                 220

Tyr Gly Gly Ser Tyr Ala Met Asp Tyr Trp Gly Gln Gly Thr Ser Val
225                 230                 235                 240

Thr Val Ser Ser


<210> SEQ ID NO 278
<211> LENGTH: 732
<212> TYPE: DNA
<213> ORGANISM: Artificial Sequence
<220> FEATURE:
<223> OTHER INFORMATION: CD19 ScFv

<400> SEQUENCE: 278

gacatccaga tgacacagac tacatcctcc ctgtctgcct ctctgggaga cagagtcacc      60

atcagttgca gggcaagtca ggacattagt aaatatttaa attggtatca gcagaaacca     120

gatggaactg ttaaactcct gatctaccat acatcaagat tacactcagg agtcccatca     180

aggttcagtg gcagtgggtc tggaacagat tattctctca ccattagcaa cctggagcaa     240

gaagatattg ccacttactt ttgccaacag ggtaatacgc ttccgtacac gttcggaggg     300

gggaccaagc tggagatcac aggcggaggt ggaagcggag ggggaggatc tggcggcgga     360

ggaagcggag gcgaggtgaa actgcaggag tcaggacctg gcctggtggc gccctcacag     420

agcctgtccg tcacatgcac tgtctcaggg gtctcattac ccgactatgg tgtaagctgg     480

attcgccagc ctccacgaaa gggtctggag tggctgggag taatatgggg tagtgaaacc     540

acatactata attcagctct caaatccaga ctgaccatca tcaaggacaa ctccaagagc     600

caagttttct taaaaatgaa cagtctgcaa actgatgaca cagccattta ctactgtgcc     660

aaacattatt actacggtgg tagctatgct atggactact ggggccaagg aacctcagtc     720

accgtgtcct ca                                                         732


<210> SEQ ID NO 279
<211> LENGTH: 509
<212> TYPE: PRT
<213> ORGANISM: Artificial Sequence
<220> FEATURE:
<223> OTHER INFORMATION: CD19 CAR

<400> SEQUENCE: 279

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140
```

Thr Val Ser Gly Val Ser Leu Pro Asp Tyr Gly Val Ser Trp Ile Arg
145 150 155 160

Gln Pro Pro Arg Lys Gly Leu Glu Trp Leu Gly Val Ile Trp Gly Ser
165 170 175

Glu Thr Thr Tyr Tyr Asn Ser Ala Leu Lys Ser Arg Leu Thr Ile Ile
180 185 190

Lys Asp Asn Ser Lys Ser Gln Val Phe Leu Lys Met Asn Ser Leu Gln
195 200 205

Thr Asp Asp Thr Ala Ile Tyr Tyr Cys Ala Lys His Tyr Tyr Tyr Gly
210 215 220

Gly Ser Tyr Ala Met Asp Tyr Trp Gly Gln Gly Thr Ser Val Thr Val
225 230 235 240

Ser Ser Thr Thr Thr Pro Ala Pro Arg Pro Pro Thr Pro Ala Pro Thr
245 250 255

Ile Ala Ser Gln Pro Leu Ser Leu Arg Pro Glu Ala Cys Arg Pro Ala
260 265 270

Ala Gly Gly Ala Val His Thr Arg Gly Leu Asp Phe Ala Cys Asp Phe
275 280 285

Trp Val Leu Val Val Val Gly Gly Val Leu Ala Cys Tyr Ser Leu Leu
290 295 300

Val Thr Val Ala Phe Ile Ile Phe Trp Val Arg Ser Lys Arg Ser Arg
305 310 315 320

Leu Leu His Ser Asp Tyr Met Asn Met Thr Pro Arg Arg Pro Gly Pro
325 330 335

Thr Arg Lys His Tyr Gln Pro Tyr Ala Pro Pro Arg Asp Phe Ala Ala
340 345 350

Tyr Arg Ser Lys Arg Gly Arg Lys Lys Leu Leu Tyr Ile Phe Lys Gln
355 360 365

Pro Phe Met Arg Pro Val Gln Thr Thr Gln Glu Glu Asp Gly Cys Ser
370 375 380

Cys Arg Phe Pro Glu Glu Glu Glu Gly Gly Cys Glu Leu Arg Val Lys
385 390 395 400

Phe Ser Arg Ser Ala Asp Ala Pro Ala Tyr Lys Gln Gly Gln Asn Gln
405 410 415

Leu Tyr Asn Glu Leu Asn Leu Gly Arg Arg Glu Glu Tyr Asp Val Leu
420 425 430

Asp Lys Arg Arg Gly Arg Asp Pro Glu Met Gly Gly Lys Pro Arg Arg
435 440 445

Lys Asn Pro Gln Glu Gly Leu Tyr Asn Glu Leu Gln Lys Asp Lys Met
450 455 460

Ala Glu Ala Tyr Ser Glu Ile Gly Met Lys Gly Glu Arg Arg Arg Gly
465 470 475 480

Lys Gly His Asp Gly Leu Tyr Gln Gly Leu Ser Thr Ala Thr Lys Asp
485 490 495

Thr Tyr Asp Ala Leu His Met Gln Ala Leu Pro Pro Arg
500 505

<210> SEQ ID NO 280
<211> LENGTH: 1527
<212> TYPE: DNA
<213> ORGANISM: Artificial Sequence
<220> FEATURE:
<223> OTHER INFORMATION: CD19 CAR

<400> SEQUENCE: 280

```
gacatccaga tgacacagac tacatcctcc ctgtctgcct ctctgggaga cagagtcacc     60

atcagttgca gggcaagtca ggacattagt aaatatttaa attggtatca gcagaaacca    120

gatggaactg ttaaactcct gatctaccat acatcaagat tacactcagg agtcccatca    180

aggttcagtg gcagtgggtc tggaacagat tattctctca ccattagcaa cctggagcaa    240

gaagatattg ccacttactt ttgccaacag ggtaatacgc ttccgtacac gttcggaggg    300

gggaccaagc tggagatcac aggtggcggt ggctcgggcg gtggtgggtc gggtggcggc    360

ggatctgagg tgaaactgca ggagtcagga cctggcctgg tggcgccctc acagagcctg    420

tccgtcacat gcactgtctc aggggtctca ttacccgact atggtgtaag ctggattcgc    480

cagcctccac gaaagggtct ggagtggctg ggagtaatat ggggtagtga aaccacatac    540

tataattcag ctctcaaatc cagactgacc atcatcaagg acaactccaa gagccaagtt    600

ttcttaaaaa tgaacagtct gcaaactgat gacacagcca tttactactg tgccaaacat    660

tattactacg gtggtagcta tgctatggac tactggggcc aaggaacctc agtcaccgtg    720

tcctcaacca cgacgccagc gccgcgacca ccaacaccgg cgcccaccat cgcgtcgcag    780

cccctgtccc tgcgcccaga ggcgtgccgg ccagcggcgg ggggcgcagt gcacacgagg    840

gggctggact tcgcctgtga tttctgggtg ctggtcgttg tgggcggcgt gctggcctgc    900

tacagcctgc tggtgacagt ggccttcatc atcttttggg tgaggagcaa gcggagcaga    960

ctgctgcaca gcgactacat gaacatgacc ccccggaggc ctggccccac ccggaagcac   1020

taccagccct acgcccctcc cagggatttc gccgcctacc ggagcaaacg gggcagaaag   1080

aaactcctgt atatattcaa acaaccattt atgaggccag tacaaactac tcaagaggaa   1140

gatggctgta gctgccgatt tccagaagaa gaagaaggag gatgtgaact gagagtgaag   1200

ttcagcagga gcgcagacgc ccccgcgtac aagcagggcc agaaccagct ctataacgag   1260

ctcaatctag gacgaagaga ggagtacgat gttttggaca agcgtagagg ccgggaccct   1320

gagatggggg gaaagccgag aaggaagaac cctcaggaag gcctgtacaa tgaactgcag   1380

aaagataaga tggcggaggc ctacagtgag attgggatga aaggcgagcg ccggaggggc   1440

aaggggcacg atggccttta ccagggactc agtacagcca ccaaggacac ctacgacgcc   1500

cttcacatgc aggccctgcc ccctcgc                                       1527
```

```
<210> SEQ ID NO 281
<211> LENGTH: 509
<212> TYPE: PRT
<213> ORGANISM: Artificial Sequence
<220> FEATURE:
<223> OTHER INFORMATION: CD19 CAR

<400> SEQUENCE: 281

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
```

-continued

```
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser Thr Thr Thr Pro Ala Pro Arg Pro Pro Thr Pro Ala Pro Thr
                245                 250                 255

Ile Ala Ser Gln Pro Leu Ser Leu Arg Pro Glu Ala Cys Arg Pro Ala
            260                 265                 270

Ala Gly Gly Ala Val His Thr Arg Gly Leu Asp Phe Ala Cys Asp Phe
        275                 280                 285

Trp Val Leu Val Val Val Gly Gly Val Leu Ala Cys Tyr Ser Leu Leu
    290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350

Tyr Arg Ser Lys Arg Gly Arg Lys Lys Leu Leu Tyr Ile Phe Lys Gln
        355                 360                 365

Pro Phe Met Arg Pro Val Gln Thr Thr Gln Glu Glu Asp Gly Cys Ser
    370                 375                 380

Cys Arg Phe Pro Glu Glu Glu Glu Gly Gly Cys Glu Leu Arg Val Lys
385                 390                 395                 400

Phe Ser Arg Ser Ala Asp Ala Pro Ala Tyr Lys Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505
```

<210> SEQ ID NO 282
<211> LENGTH: 246
<212> TYPE: PRT
<213> ORGANISM: Artificial Sequence
<220> FEATURE:
<223> OTHER INFORMATION: CEA ScFv

<400> SEQUENCE: 282

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Gly Gly Gly Gly Ser Gly Gly
        115                 120                 125

Gly Gly Ser Gly Gly Gly Gly Ser Gly Gly Asp Ile Gln Met Thr Gln
    130                 135                 140

Ser Pro Ser Ser Leu Ser Ala Ser Val Gly Asp Arg Val Thr Ile Thr
145                 150                 155                 160

Cys Lys Ala Ser Gln Asn Val Gly Thr Asn Val Ala Trp Tyr Gln Gln
                165                 170                 175

Lys Pro Gly Lys Ala Pro Lys Leu Leu Ile Tyr Ser Ala Ser Tyr Arg
            180                 185                 190

Tyr Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys His Gln Tyr Tyr Thr Tyr Pro Leu Phe Thr Phe Gly Gln Gly
225                 230                 235                 240

Thr Lys Leu Glu Ile Lys
                245

<210> SEQ ID NO 283
<211> LENGTH: 1542
<212> TYPE: DNA
<213> ORGANISM: Artificial Sequence
<220> FEATURE:
<223> OTHER INFORMATION: CEA ScFv

<400> SEQUENCE: 283
caggtgcagc tggtgcaatc tgggtctgag ttgaagaagc ctggggcctc agtgaaggtt 60
tcctgcaagg cttctggata caccttcact gagtttggaa tgaactgggt gcgacaggcc 120
cctggacaag ggcttgagtg gatgggatgg ataaacacca aaactggaga ggcaacatat 180
gttgaagagt ttaagggacg gtttgtcttc tccttggaca cctctgtcag cacggcatat 240
ctgcagatca gcagcctaaa ggctgaagac actgccgtgt attactgtgc gagatgggac 300

```
ttcgcttatt acgtggaggc tatggactac tggggccaag ggaccacggt caccgtctcc    360
tcaggcggag gtggaagcgg agggggagga tctggcggcg gaggaagcgg aggcgatatc    420
cagatgaccc agtctccatc ctccctgtct gcatctgtgg gagacagagt caccatcact    480
tgcaaggcca gtcagaatgt gggtactaat gttgcctggt atcagcagaa accagggaaa    540
gcacctaagc tcctgatcta ttcggcatcc taccgctaca gtggagtccc atcaaggttc    600
agtggcagtg gatctgggac agatttcact ctcaccatca gcagtctgca acctgaagat    660
ttcgcaactt actactgtca ccaatattac acctatcctc tattcacgtt tggccagggc    720
accaagctcg agatcaagat ggacatgagg gtccccgctc agctcctggg gctcctgcta    780
ctctggctcc gaggtgccag atgtcaggtg cagctggtgc aatctgggtc tgagttgaag    840
aagcctgggg cctcagtgaa ggtttcctgc aaggcttctg gatacacctt cactgagttt    900
ggaatgaact gggtgcgaca ggcccctgga caagggcttg agtggatggg atggataaac    960
accaaaactg gagaggcaac atatgttgaa gagtttaagg gacggtttgt cttctccttg   1020
gacacctctg tcagcacggc atatctgcag atcagcagcc taaaggctga agacactgcc   1080
gtgtattact gtgcgagatg ggacttcgct tattacgtgg aggctatgga ctactggggc   1140
caagggacca cggtcaccgt ctcctcaggc ggaggtggaa gcggaggggg aggatctggc   1200
ggcggaggaa gcggaggcga tatccagatg acccagtctc catcctccct gtctgcatct   1260
gtgggagaca gagtcaccat cacttgcaag gccagtcaga atgtgggtac taatgttgcc   1320
tggtatcagc agaaaccagg gaaagcacct aagctcctga tctattcggc atcctaccgc   1380
tacagtggag tcccatcaag gttcagtggc agtggatctg ggacagattt cactctcacc   1440
atcagcagtc tgcaacctga agatttcgca acttactact gtcaccaata ttacacctat   1500
cctctattca cgtttggcca gggcaccaag ctcgagatca ag                      1542
```

<210> SEQ ID NO 284
<211> LENGTH: 246
<212> TYPE: PRT
<213> ORGANISM: Artificial Sequence
<220> FEATURE:
<223> OTHER INFORMATION: CEA ScFv

<400> SEQUENCE: 284

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Trp Asp Phe Ala Tyr Tyr Val Glu Ala Met Asp Tyr Trp Gly
            100                 105                 110

Gln Gly Thr Thr Val Thr Val Ser Ser Gly Gly Gly Gly Ser Gly Gly
        115                 120                 125

Gly Gly Ser Gly Gly Gly Gly Ser Gly Gly Asp Ile Gln Met Thr Gln
    130                 135                 140
```

-continued

```
Ser Pro Ser Ser Leu Ser Ala Ser Val Gly Asp Arg Val Thr Ile Thr
145                 150                 155                 160

Cys Lys Ala Ser Ala Ala Val Gly Thr Tyr Val Ala Trp Tyr Gln Gln
                165                 170                 175

Lys Pro Gly Lys Ala Pro Lys Leu Leu Ile Tyr Ser Ala Ser Tyr Arg
            180                 185                 190

Lys Arg Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys His Gln Tyr Tyr Thr Tyr Pro Leu Phe Thr Phe Gly Gln Gly
225                 230                 235                 240

Thr Lys Leu Glu Ile Lys
                245


<210> SEQ ID NO 285
<211> LENGTH: 738
<212> TYPE: DNA
<213> ORGANISM: Artificial Sequence
<220> FEATURE:
<223> OTHER INFORMATION: CEA ScFv

<400> SEQUENCE: 285

caggtgcagc tggtgcagtc tggcgccgaa gtgaagaaac ctggagctag tgtgaaggtg      60

tcctgcaagg ccagcggcta caccttcacc gagttcggca tgaactgggt ccgacaggct     120

ccaggccagg gcctcgaatg gatgggctgg atcaacacca agaccggcga ggccacctac     180

gtggaagagt tcaagggcag agtgaccttc accacggaca ccagcaccag caccgcctac     240

atggaactgc ggagcctgag aagcgacgac accgccgtgt actactgcgc cagatgggac     300

ttcgcttatt acgtggaagc catggactac tggggccagg gcaccaccgt gaccgtgtct     360

agcggcggag gtggaagcgg agggggagga tctggcggcg gaggaagcgg aggcgatatc     420

cagatgaccc agtctccatc ctccctgtct gcatctgtgg gagacagagt caccatcact     480

tgcaaggcca gtgcggctgt gggtacgtat gttgcgtggt atcagcagaa accagggaaa     540

gcacctaagc tcctgatcta ttcggcatcc taccgcaaaa ggggagtccc atcaaggttc     600

agtggcagtg gatctgggac agatttcact ctcaccatca gcagtctgca acctgaagat     660

ttcgcaactt actactgtca ccaatattac acctatcctc tattcacgtt tggccagggc     720

accaagctcg agatcaag                                                   738


<210> SEQ ID NO 286
<211> LENGTH: 246
<212> TYPE: PRT
<213> ORGANISM: Artificial Sequence
<220> FEATURE:
<223> OTHER INFORMATION: CEA ScFv

<400> SEQUENCE: 286

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Glu Phe
            20                  25                  30

Gly Met Asn Trp Val Arg Gln Ala Pro Gly Gln Gly Leu Glu Trp Met
        35                  40                  45

Gly Trp Ile Asn Thr Lys Thr Gly Glu Ala Thr Tyr Val Glu Glu Phe
    50                  55                  60
```

-continued

Lys Gly Arg Phe Val Phe Ser Leu Asp Thr Ser Val Ser Thr Ala Tyr
65 70 75 80

Leu Gln Ile Ser Ser Leu Lys Ala Glu Asp Thr Ala Val Tyr Tyr Cys
85 90 95

Ala Arg Trp Asp Phe Ala His Tyr Phe Gln Thr Met Asp Tyr Trp Gly
100 105 110

Gln Gly Thr Thr Val Thr Val Ser Ser Gly Gly Gly Gly Ser Gly Gly
115 120 125

Gly Gly Ser Gly Gly Gly Gly Ser Gly Gly Asp Ile Gln Met Thr Gln
130 135 140

Ser Pro Ser Ser Leu Ser Ala Ser Val Gly Asp Arg Val Thr Ile Thr
145 150 155 160

Cys Lys Ala Ser Ala Ala Val Gly Thr Tyr Val Ala Trp Tyr Gln Gln
165 170 175

Lys Pro Gly Lys Ala Pro Lys Leu Leu Ile Tyr Ser Ala Ser Tyr Arg
180 185 190

Lys Arg Gly Val Pro Ser Arg Phe Ser Gly Ser Gly Ser Gly Thr Asp
195 200 205

Phe Thr Leu Thr Ile Ser Ser Leu Gln Pro Glu Asp Phe Ala Thr Tyr
210 215 220

Tyr Cys His Gln Tyr Tyr Thr Tyr Pro Leu Phe Thr Phe Gly Gln Gly
225 230 235 240

Thr Lys Leu Glu Ile Lys
245

<210> SEQ ID NO 287
<211> LENGTH: 738
<212> TYPE: DNA
<213> ORGANISM: Artificial Sequence
<220> FEATURE:
<223> OTHER INFORMATION: CEA ScFv

<400> SEQUENCE: 287
caggtgcagc tggtgcaatc tggtctgag ttgaagaagc ctggggcctc agtgaaggtt 60
tcctgcaagg cttctggata caccttcact gagtttggaa tgaactgggt gcgacaggcc 120
cctggacaag ggcttgagtg gatgggatgg ataaacacca aaactggaga ggcaacatat 180
gttgaagagt ttaagggacg gtttgtcttc tccttggaca cctctgtcag cacggcatat 240
ctgcagatca gcagcctaaa ggctgaagac actgccgtgt attactgtgc gagatgggac 300
tttgctcatt actttcagac tatggactac tggggccaag ggaccacggt caccgtctcc 360
tcaggcggag gtggaagcgg agggggagga tctggcggcg gaggaagcgg aggcgatatc 420
cagatgaccc agtctccatc ctccctgtct gcatctgtgg gagacagagt caccatcact 480
tgcaaggcca gtgcggctgt gggtacgtat gttgcgtggt atcagcagaa accagggaaa 540
gcacctaagc tcctgatcta ttcggcatcc taccgcaaaa ggggagtccc atcaaggttc 600
agtggcagtg gatctgggac agatttcact ctcaccatca gcagtctgca acctgaagat 660
ttcgcaactt actactgtca ccaatattac acctatcctc tattcacgtt tggccagggc 720
accaagctcg agatcaag 738

<210> SEQ ID NO 288
<211> LENGTH: 535
<212> TYPE: PRT
<213> ORGANISM: Artificial Sequence
<220> FEATURE:
<223> OTHER INFORMATION: CEA CAR

<400> SEQUENCE: 288

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ser Glu
            20                  25                  30

Leu Lys Lys Pro Gly Ala Ser Val Lys Val Ser Cys Lys Ala Ser Gly
        35                  40                  45

Tyr Thr Phe Thr Glu Phe Gly Met Asn Trp Val Arg Gln Ala Pro Gly
    50                  55                  60

Gln Gly Leu Glu Trp Met Gly Trp Ile Asn Thr Lys Thr Gly Glu Ala
65                  70                  75                  80

Thr Tyr Val Glu Glu Phe Lys Gly Arg Phe Val Phe Ser Leu Asp Thr
                85                  90                  95

Ser Val Ser Thr Ala Tyr Leu Gln Ile Ser Ser Leu Lys Ala Glu Asp
            100                 105                 110

Thr Ala Val Tyr Tyr Cys Ala Arg Trp Asp Phe Ala Tyr Tyr Val Glu
        115                 120                 125

Ala Met Asp Tyr Trp Gly Gln Gly Thr Thr Val Thr Val Ser Ser Gly
    130                 135                 140

Gly Gly Gly Ser Gly Gly Gly Gly Ser Gly Gly Gly Gly Ser Gly Gly
145                 150                 155                 160

Asp Ile Gln Met Thr Gln Ser Pro Ser Ser Leu Ser Ala Ser Val Gly
                165                 170                 175

Asp Arg Val Thr Ile Thr Cys Lys Ala Ser Gln Asn Val Gly Thr Asn
            180                 185                 190

Val Ala Trp Tyr Gln Gln Lys Pro Gly Lys Ala Pro Lys Leu Leu Ile
        195                 200                 205

Tyr Ser Ala Ser Tyr Arg Tyr Ser Gly Val Pro Ser Arg Phe Ser Gly
    210                 215                 220

Ser Gly Ser Gly Thr Asp Phe Thr Leu Thr Ile Ser Ser Leu Gln Pro
225                 230                 235                 240

Glu Asp Phe Ala Thr Tyr Tyr Cys His Gln Tyr Tyr Thr Tyr Pro Leu
                245                 250                 255

Phe Thr Phe Gly Gln Gly Thr Lys Leu Glu Ile Lys Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Phe Trp Val Leu Val Val Val
305                 310                 315                 320

Gly Gly Val Leu Ala Cys Tyr Ser Leu Leu Val Thr Val Ala Phe Ile
                325                 330                 335

Ile Phe Trp Val Arg Ser Lys Arg Ser Arg Leu Leu His Ser Asp Tyr
            340                 345                 350

Met Asn Met Thr Pro Arg Arg Pro Gly Pro Thr Arg Lys His Tyr Gln
        355                 360                 365

Pro Tyr Ala Pro Pro Arg Asp Phe Ala Ala Tyr Arg Ser Lys Arg Gly
    370                 375                 380

Arg Lys Lys Leu Leu Tyr Ile Phe Lys Gln Pro Phe Met Arg Pro Val
385                 390                 395                 400

Gln Thr Thr Gln Glu Glu Asp Gly Cys Ser Cys Arg Phe Pro Glu Glu

-continued

```
                405                 410                 415

Glu Glu Gly Gly Cys Glu Leu Arg Val Lys Phe Ser Arg Ser Ala Asp
            420                 425                 430

Ala Pro Ala Tyr Lys Gln Gly Gln Asn Gln Leu Tyr Asn Glu Leu Asn
        435                 440                 445

Leu Gly Arg Arg Glu Glu Tyr Asp Val Leu Asp Lys Arg Arg Gly Arg
    450                 455                 460

Asp Pro Glu Met Gly Gly Lys Pro Arg Arg Lys Asn Pro Gln Glu Gly
465                 470                 475                 480

Leu Tyr Asn Glu Leu Gln Lys Asp Lys Met Ala Glu Ala Tyr Ser Glu
            485                 490                 495

Ile Gly Met Lys Gly Glu Arg Arg Arg Gly Lys Gly His Asp Gly Leu
            500                 505                 510

Tyr Gln Gly Leu Ser Thr Ala Thr Lys Asp Thr Tyr Asp Ala Leu His
        515                 520                 525

Met Gln Ala Leu Pro Pro Arg
    530                 535


<210> SEQ ID NO 289
<211> LENGTH: 1608
<212> TYPE: DNA
<213> ORGANISM: Artificial Sequence
<220> FEATURE:
<223> OTHER INFORMATION: CEA CAR

<400> SEQUENCE: 289

atggacatga gggtccccgc tcagctcctg gggctcctgc tactctggct ccgaggtgcc     60

agatgtcagg tgcagctggt gcaatctggg tctgagttga agaagcctgg ggcctcagtg    120

aaggtttcct gcaaggcttc tggatacacc ttcactgagt ttggaatgaa ctgggtgcga    180

caggcccctg gacaagggct tgagtggatg ggatggataa acaccaaaac tggagaggca    240

acatatgttg aagagtttaa gggacggttt gtcttctcct tggacacctc tgtcagcacg    300

gcatatctgc agatcagcag cctaaaggct gaagacactg ccgtgtatta ctgtgcgaga    360

tgggacttcg cttattacgt ggaggctatg gactactggg gccaagggac cacggtcacc    420

gtctcctcag gcggaggtgg aagcggaggg ggaggatctg gcggcggagg aagcggaggc    480

gatatccaga tgacccagtc tccatcctcc ctgtctgcat ctgtgggaga cagagtcacc    540

atcacttgca aggccagtca gaatgtgggt actaatgttg cctggtatca gcagaaacca    600

gggaaagcac ctaagctcct gatctattcg gcatcctacc gctacagtgg agtcccatca    660

aggttcagtg gcagtggatc tgggacagat ttcactctca ccatcagcag tctgcaacct    720

gaagatttcg caacttacta ctgtcaccaa tattacacct atcctctatt cacgtttggc    780

cagggcacca agctcgagat caagacaacg acgccagctc cccgcccgcc aacccctgca    840

cctacgattg catcacaacc gctgtccctg cggcctgaag cttgtcgccc agccgcaggt    900

ggcgccgtac atacacgggg gctggatttt gcctgtgatt tctgggtgct ggtcgttgtg    960

ggcggcgtgc tggcctgcta cagcctgctg gtgacagtgg ccttcatcat cttttgggtg   1020

aggagcaagc ggagtcgact gctgcacagc gactacatga acatgacccc ccggaggcct   1080

ggccccaccc ggaagcacta ccagccctac gcccctccca gggatttcgc cgcctaccgg   1140

agcaaacggg gcagaaagaa actcctgtat atattcaaac aaccatttat gaggccagta   1200

caaactactc aagaggaaga tggctgtagc tgccgatttc cagaagaaga agaaggagga   1260

tgtgaactga gagtgaagtt cagcaggagc gcagacgccc ccgcgtacaa gcagggccag   1320
```

```
aaccagctct ataacgagct caatctagga cgaagagagg agtacgatgt tttggacaag   1380

cgtagaggcc gggaccctga gatgggggga aagccgagaa ggaagaaccc tcaggaaggc   1440

ctgtacaatg aactgcagaa agataagatg gcggaggcct acagtgagat tgggatgaaa   1500

ggcgagcgcc ggaggggcaa ggggcacgat ggcctttacc agggactcag tacagccacc   1560

aaggacacct acgacgccct tcacatgcag gccctgcccc ctcgctag                1608
```

```
<210> SEQ ID NO 290
<211> LENGTH: 537
<212> TYPE: PRT
<213> ORGANISM: Artificial Sequence
<220> FEATURE:
<223> OTHER INFORMATION: CEA CAR

<400> SEQUENCE: 290

Met Asp Met Arg Val Pro Ala Gln Leu Leu Gly Leu Leu Leu Leu Trp
1               5                   10                  15

Leu Arg Gly Ala Arg Cys Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr Glu Phe Gly Met Asn Trp Val Arg Gln Ala Pro Gly
    50                  55                  60

Gln Gly Leu Glu Trp Met Gly Trp Ile Asn Thr Lys Thr Gly Glu Ala
65                  70                  75                  80

Thr Tyr Val Glu Glu Phe Lys Gly Arg Val Thr Phe Thr Thr Asp Thr
                85                  90                  95

Ser Thr Ser Thr Ala Tyr Met Glu Leu Arg Ser Leu Arg Ser Asp Asp
            100                 105                 110

Thr Ala Val Tyr Tyr Cys Ala Arg Trp Asp Phe Ala Tyr Tyr Val Glu
        115                 120                 125

Ala Met Asp Tyr Trp Gly Gln Gly Thr Thr Val Thr Val Ser Ser Gly
    130                 135                 140

Gly Gly Gly Ser Gly Gly Gly Gly Ser Gly Gly Gly Gly Ser Gly Gly
145                 150                 155                 160

Asp Ile Gln Met Thr Gln Ser Pro Ser Ser Leu Ser Ala Ser Val Gly
                165                 170                 175

Asp Arg Val Thr Ile Thr Cys Lys Ala Ser Ala Ala Val Gly Thr Tyr
            180                 185                 190

Val Ala Trp Tyr Gln Gln Lys Pro Gly Lys Ala Pro Lys Leu Leu Ile
        195                 200                 205

Tyr Ser Ala Ser Tyr Arg Lys Arg Gly Val Pro Ser Arg Phe Ser Gly
    210                 215                 220

Ser Gly Ser Gly Thr Asp Phe Thr Leu Thr Ile Ser Ser Leu Gln Pro
225                 230                 235                 240

Glu Asp Phe Ala Thr Tyr Tyr Cys His Gln Tyr Tyr Thr Tyr Pro Leu
                245                 250                 255

Phe Thr Phe Gly Gln Gly Thr Lys Leu Glu Ile Lys Arg Thr Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Phe Trp Val Leu Val
```

```
305                 310                 315                 320

Val Val Gly Gly Val Leu Ala Cys Tyr Ser Leu Leu Val Thr Val Ala
                325                 330                 335

Phe Ile Ile Phe Trp Val Arg Ser Lys Arg Ser Arg Leu Leu His Ser
            340                 345                 350

Asp Tyr Met Asn Met Thr Pro Arg Arg Pro Gly Pro Thr Arg Lys His
        355                 360                 365

Tyr Gln Pro Tyr Ala Pro Pro Arg Asp Phe Ala Ala Tyr Arg Ser Lys
    370                 375                 380

Arg Gly Arg Lys Lys Leu Leu Tyr Ile Phe Lys Gln Pro Phe Met Arg
385                 390                 395                 400

Pro Val Gln Thr Thr Gln Glu Glu Asp Gly Cys Ser Cys Arg Phe Pro
                405                 410                 415

Glu Glu Glu Glu Gly Gly Cys Glu Leu Arg Val Lys Phe Ser Arg Ser
            420                 425                 430

Ala Asp Ala Pro Ala Tyr Lys Gln Gly Gln Asn Gln Leu Tyr Asn Glu
        435                 440                 445

Leu Asn Leu Gly Arg Arg Glu Glu Tyr Asp Val Leu Asp Lys Arg Arg
    450                 455                 460

Gly Arg Asp Pro Glu Met Gly Gly Lys Pro Arg Arg Lys Asn Pro Gln
465                 470                 475                 480

Glu Gly Leu Tyr Asn Glu Leu Gln Lys Asp Lys Met Ala Glu Ala Tyr
                485                 490                 495

Ser Glu Ile Gly Met Lys Gly Glu Arg Arg Arg Gly Lys Gly His Asp
            500                 505                 510

Gly Leu Tyr Gln Gly Leu Ser Thr Ala Thr Lys Asp Thr Tyr Asp Ala
        515                 520                 525

Leu His Met Gln Ala Leu Pro Pro Arg
    530                 535
```

<210> SEQ ID NO 291
<211> LENGTH: 1614
<212> TYPE: DNA
<213> ORGANISM: Artificial Sequence
<220> FEATURE:
<223> OTHER INFORMATION: CEA CAR

<400> SEQUENCE: 291

```
atggacatga gggtccccgc tcagctcctg gggctcctgc tactctggct ccgaggtgcc     60

agatgtcagg tgcagctggt gcagtctggc gccgaagtga agaaacctgg agctagtgtg    120

aaggtgtcct gcaaggccag cggctacacc ttcaccgagt tcggcatgaa ctgggtccga    180

caggctccag gccagggcct cgaatggatg ggctggatca acaccaagac cggcgaggcc    240

acctacgtgg aagagttcaa gggcagagtg accttcacca cggacaccag caccagcacc    300

gcctacatgg aactgcggag cctgagaagc gacgacaccg ccgtgtacta ctgcgccaga    360

tgggacttcg cttattacgt ggaagccatg gactactggg gccagggcac caccgtgacc    420

gtgtctagcg gcggaggtgg aagcggaggg ggaggatctg gcggcggagg aagcggaggc    480

gatatccaga tgacccagtc tccatcctcc ctgtctgcat ctgtgggaga cagagtcacc    540

atcacttgca aggccagtgc ggctgtgggt acgtatgttg cgtggtatca gcagaaacca    600

gggaaagcac ctaagctcct gatctattcg gcatcctacc gcaaaagggg agtcccatca    660

aggttcagtg gcagtggatc tgggacagat ttcactctca ccatcagcag tctgcaacct    720

gaagatttcg caacttacta ctgtcaccaa tattacacct atcctctatt cacgtttggc    780
```

cagggcacca agctcgagat caagcgtacg acaacgacgc cagctccccg cccgccaacc 840
cctgcaccta cgattgcatc acaaccgctg tccctgcggc ctgaagcttg tcgcccagcc 900
gcaggtggcg ccgtacatac acgggggctg gattttgcct gtgatttctg ggtgctggtc 960
gttgtgggcg gcgtgctggc ctgctacagc ctgctggtga cagtggcctt catcatcttt 1020
tgggtgagga gcaagcggag tcgactgctg cacagcgact acatgaacat gaccccccgg 1080
aggcctggcc ccacccggaa gcactaccag ccctacgccc ctcccaggga tttcgccgcc 1140
taccggagca aacggggcag aaagaaactc ctgtatatat tcaaacaacc atttatgagg 1200
ccagtacaaa ctactcaaga ggaagatggc tgtagctgcc gatttccaga agaagaagaa 1260
ggaggatgtg aactgagagt gaagttcagc aggagcgcag acgcccccgc gtacaagcag 1320
ggccagaacc agctctataa cgagctcaat ctaggacgaa gagaggagta cgatgttttg 1380
gacaagcgta gaggccggga ccctgagatg gggggaaagc cgagaaggaa gaaccctcag 1440
gaaggcctgt acaatgaact gcagaaagat aagatggcgg aggcctacag tgagattggg 1500
atgaaaggcg agcgccggag gggcaagggg cacgatggcc tttaccaggg actcagtaca 1560
gccaccaagg acacctacga cgcccttcac atgcaggccc tgccccctcg ctag 1614

<210> SEQ ID NO 292
<211> LENGTH: 536
<212> TYPE: PRT
<213> ORGANISM: Artificial Sequence
<220> FEATURE:
<223> OTHER INFORMATION: CEA CAR

<400> SEQUENCE: 292

Met Asp Met Arg Val Pro Ala Gln Leu Leu Gly Leu Leu Leu Leu Trp
1 5 10 15

Leu Arg Gly Ala Arg Cys Gln Val Gln Leu Val Gln Ser Gly Ser Glu
20 25 30

Leu Lys Lys Pro Gly Ala Ser Val Lys Val Ser Cys Lys Ala Ser Gly
35 40 45

Tyr Thr Phe Thr Glu Phe Gly Met Asn Trp Val Arg Gln Ala Pro Gly
50 55 60

Gln Gly Leu Glu Trp Met Gly Trp Ile Asn Thr Lys Thr Gly Glu Ala
65 70 75 80

Thr Tyr Val Glu Glu Phe Lys Gly Arg Phe Val Phe Ser Leu Asp Thr
85 90 95

Ser Val Ser Thr Ala Tyr Leu Gln Ile Ser Ser Leu Lys Ala Glu Asp
100 105 110

Thr Ala Val Tyr Tyr Cys Ala Arg Trp Asp Phe Ala His Tyr Phe Gln
115 120 125

Thr Met Asp Tyr Trp Gly Gln Gly Thr Thr Val Thr Val Ser Ser Gly
130 135 140

Gly Gly Gly Ser Gly Gly Gly Gly Ser Gly Gly Gly Gly Ser Gly Gly
145 150 155 160

Asp Ile Gln Met Thr Gln Ser Pro Ser Ser Leu Ser Ala Ser Val Gly
165 170 175

Asp Arg Val Thr Ile Thr Cys Lys Ala Ser Ala Ala Val Gly Thr Tyr
180 185 190

Val Ala Trp Tyr Gln Gln Lys Pro Gly Lys Ala Pro Lys Leu Leu Ile
195 200 205

Tyr Ser Ala Ser Tyr Arg Lys Arg Gly Val Pro Ser Arg Phe Ser Gly

```
    210                 215                 220

Ser Gly Ser Gly Thr Asp Phe Thr Leu Thr Ile Ser Ser Leu Gln Pro
225                 230                 235                 240

Glu Asp Phe Ala Thr Tyr Tyr Cys His Gln Tyr Tyr Thr Tyr Pro Leu
                245                 250                 255

Phe Thr Phe Gly Gln Gly Thr Lys Leu Glu Ile Lys Arg Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Phe Trp Val Leu Val Val
305                 310                 315                 320

Val Gly Gly Val Leu Ala Cys Tyr Ser Leu Leu Val Thr Val Ala Phe
                325                 330                 335

Ile Ile Phe Trp Val Arg Ser Lys Arg Ser Arg Leu Leu His Ser Asp
            340                 345                 350

Tyr Met Asn Met Thr Pro Arg Arg Pro Gly Pro Thr Arg Lys His Tyr
        355                 360                 365

Gln Pro Tyr Ala Pro Pro Arg Asp Phe Ala Ala Tyr Arg Ser Lys Arg
    370                 375                 380

Gly Arg Lys Lys Leu Leu Tyr Ile Phe Lys Gln Pro Phe Met Arg Pro
385                 390                 395                 400

Val Gln Thr Thr Gln Glu Glu Asp Gly Cys Ser Cys Arg Phe Pro Glu
                405                 410                 415

Glu Glu Glu Gly Gly Cys Glu Leu Arg Val Lys Phe Ser Arg Ser Ala
            420                 425                 430

Asp Ala Pro Ala Tyr Lys Gln Gly Gln Asn Gln Leu Tyr Asn Glu Leu
        435                 440                 445

Asn Leu Gly Arg Arg Glu Glu Tyr Asp Val Leu Asp Lys Arg Arg Gly
    450                 455                 460

Arg Asp Pro Glu Met Gly Gly Lys Pro Arg Arg Lys Asn Pro Gln Glu
465                 470                 475                 480

Gly Leu Tyr Asn Glu Leu Gln Lys Asp Lys Met Ala Glu Ala Tyr Ser
                485                 490                 495

Glu Ile Gly Met Lys Gly Glu Arg Arg Arg Gly Lys Gly His Asp Gly
            500                 505                 510

Leu Tyr Gln Gly Leu Ser Thr Ala Thr Lys Asp Thr Tyr Asp Ala Leu
        515                 520                 525

His Met Gln Ala Leu Pro Pro Arg
    530                 535
```

<210> SEQ ID NO 293
<211> LENGTH: 1611
<212> TYPE: DNA
<213> ORGANISM: Artificial Sequence
<220> FEATURE:
<223> OTHER INFORMATION: CEA CAR

<400> SEQUENCE: 293

```
atggacatga gggtccccgc tcagctcctg gggctcctgc tactctggct ccgaggtgcc      60

agatgtcagg tgcagctggt gcaatctggg tctgagttga agaagcctgg ggcctcagtg     120

aaggtttcct gcaaggcttc tggatacacc ttcactgagt ttggaatgaa ctgggtgcga     180

caggcccctg gacaagggct tgagtggatg ggatggataa acaccaaaac tggagaggca     240
```

```
acatatgttg aagagtttaa gggacggttt gtcttctcct tggacacctc tgtcagcacg    300

gcatatctgc agatcagcag cctaaaggct gaagacactg ccgtgtatta ctgtgcgaga    360

tgggactttg ctcattactt tcagactatg gactactggg gccaagggac cacggtcacc    420

gtctcctcag gcggaggtgg aagcggaggg ggaggatctg gcggcggagg aagcggaggc    480

gatatccaga tgacccagtc tccatcctcc ctgtctgcat ctgtgggaga cagagtcacc    540

atcacttgca aggccagtgc ggctgtgggt acgtatgttg cgtggtatca gcagaaacca    600

gggaaagcac ctaagctcct gatctattcg gcatcctacc gcaaaagggg agtcccatca    660

aggttcagtg gcagtggatc tgggacagat ttcactctca ccatcagcag tctgcaacct    720

gaagatttcg caacttacta ctgtcaccaa tattacacct atcctctatt cacgtttggc    780

cagggcacca agctcgagat caagcgtaca acgacgccag ctccccgccc gccaacccct    840

gcacctacga ttgcatcaca accgctgtcc ctgcggcctg aagcttgtcg cccagccgca    900

ggtggcgccg tacatacacg gggctggat tttgcctgtg atttctgggt gctggtcgtt    960

gtgggcggcg tgctggcctg ctacagcctg ctggtgacag tggccttcat catcttttgg   1020

gtgaggagca agcggagtcg actgctgcac agcgactaca tgaacatgac cccccggagg   1080

cctggcccca cccggaagca ctaccagccc tacgcccctc ccagggattt cgccgcctac   1140

cggagcaaac ggggcagaaa gaaactcctg tatatattca aacaaccatt tatgaggcca   1200

gtacaaacta ctcaagagga agatggctgt agctgccgat ttccagaaga agaagaagga   1260

ggatgtgaac tgagagtgaa gttcagcagg agcgcagacg cccccgcgta caagcagggc   1320

cagaaccagc tctataacga gctcaatcta ggacgaagag aggagtacga tgttttggac   1380

aagcgtagag gccgggaccc tgagatgggg ggaaagccga gaaggaagaa ccctcaggaa   1440

ggcctgtaca atgaactgca gaaagataag atggcggagg cctacagtga gattgggatg   1500

aaaggcgagc gccggagggg caaggggcac gatggccttt accagggact cagtacagcc   1560

accaaggaca cctacgacgc ccttcacatg caggccctgc cccctcgcta g            1611
```

<210> SEQ ID NO 294
<211> LENGTH: 5
<212> TYPE: PRT
<213> ORGANISM: Artificial Sequence
<220> FEATURE:
<223> OTHER INFORMATION: CEA CDR-H1

<400> SEQUENCE: 294

```
Glu Phe Gly Met Asn
1               5
```

<210> SEQ ID NO 295
<211> LENGTH: 17
<212> TYPE: PRT
<213> ORGANISM: Artificial Sequence
<220> FEATURE:
<223> OTHER INFORMATION: CEA CDR-H2

<400> SEQUENCE: 295

```
Trp Ile Asn Thr Lys Thr Gly Glu Ala Thr Tyr Val Glu Glu Phe Lys
1               5                   10                  15

Gly
```

<210> SEQ ID NO 296
<211> LENGTH: 12
<212> TYPE: PRT

<213> ORGANISM: Artificial Sequence
<220> FEATURE:
<223> OTHER INFORMATION: CEA CDR-H3

<400> SEQUENCE: 296

Trp Asp Phe Ala Tyr Tyr Val Glu Ala Met Asp Tyr
1 5 10

<210> SEQ ID NO 297
<211> LENGTH: 12
<212> TYPE: PRT
<213> ORGANISM: Artificial Sequence
<220> FEATURE:
<223> OTHER INFORMATION: CEA CDR-H3

<400> SEQUENCE: 297

Trp Asp Phe Ala His Tyr Phe Gln Thr Met Asp Tyr
1 5 10

<210> SEQ ID NO 298
<211> LENGTH: 11
<212> TYPE: PRT
<213> ORGANISM: Artificial Sequence
<220> FEATURE:
<223> OTHER INFORMATION: CEA CDR-L1

<400> SEQUENCE: 298

Lys Ala Ser Gln Asn Val Gly Thr Asn Val Ala
1 5 10

<210> SEQ ID NO 299
<211> LENGTH: 11
<212> TYPE: PRT
<213> ORGANISM: Artificial Sequence
<220> FEATURE:
<223> OTHER INFORMATION: CEA CDR-L1

<400> SEQUENCE: 299

Lys Ala Ser Ala Ala Val Gly Thr Tyr Val Ala
1 5 10

<210> SEQ ID NO 300
<211> LENGTH: 7
<212> TYPE: PRT
<213> ORGANISM: Artificial Sequence
<220> FEATURE:
<223> OTHER INFORMATION: CEA CDR-L2

<400> SEQUENCE: 300

Ser Ala Ser Tyr Arg Tyr Ser
1 5

<210> SEQ ID NO 301
<211> LENGTH: 7
<212> TYPE: PRT
<213> ORGANISM: Artificial Sequence
<220> FEATURE:
<223> OTHER INFORMATION: CEA CDR-L2

<400> SEQUENCE: 301

Ser Ala Ser Tyr Arg Lys Arg
1 5

<210> SEQ ID NO 302
<211> LENGTH: 10
<212> TYPE: PRT
<213> ORGANISM: Artificial Sequence -continued

<220> FEATURE:
<223> OTHER INFORMATION: CEA CDR-L3

<400> SEQUENCE: 302

His Gln Tyr Tyr Thr Tyr Pro Leu Phe Thr
1 5 10

<210> SEQ ID NO 303
<211> LENGTH: 10
<212> TYPE: PRT
<213> ORGANISM: Artificial Sequence
<220> FEATURE:
<223> OTHER INFORMATION: LB-CYBA-1Y peptide
<220> FEATURE:
<221> NAME/KEY: X
<222> LOCATION: (10)..(10)
<223> OTHER INFORMATION: X is Y or H

<400> SEQUENCE: 303

Ser Thr Met Glu Arg Trp Gly Gln Lys Xaa
1 5 10

<210> SEQ ID NO 304
<211> LENGTH: 11
<212> TYPE: PRT
<213> ORGANISM: Artificial Sequence
<220> FEATURE:
<223> OTHER INFORMATION: LB-OAS1-1R
<220> FEATURE:
<221> NAME/KEY: X
<222> LOCATION: (7)..(7)
<223> OTHER INFORMATION: X is R or T

<400> SEQUENCE: 304

Glu Thr Asp Asp Pro Arg Xaa Tyr Gln Lys Tyr
1 5 10

<210> SEQ ID NO 305
<211> LENGTH: 9
<212> TYPE: PRT
<213> ORGANISM: Artificial Sequence
<220> FEATURE:
<223> OTHER INFORMATION: HA-2 peptide
<220> FEATURE:
<221> NAME/KEY: X
<222> LOCATION: (9)..(9)
<223> OTHER INFORMATION: X is V or M

<400> SEQUENCE: 305

Tyr Ile Gly Glu Val Leu Val Ser Xaa
1 5

<210> SEQ ID NO 306
<211> LENGTH: 9
<212> TYPE: PRT
<213> ORGANISM: Artificial Sequence
<220> FEATURE:
<223> OTHER INFORMATION: HA-8 peptide
<220> FEATURE:
<221> NAME/KEY: X
<222> LOCATION: (1)..(1)
<223> OTHER INFORMATION: X is R or P

<400> SEQUENCE: 306

Xaa Thr Leu Asp Lys Val Leu Glu Val
1 5

<210> SEQ ID NO 307
<211> LENGTH: 9

<212> TYPE: PRT
<213> ORGANISM: Artificial Sequence
<220> FEATURE:
<223> OTHER INFORMATION: HA-3 peptide
<220> FEATURE:
<221> NAME/KEY: X
<222> LOCATION: (2)..(2)
<223> OTHER INFORMATION: X is T or M

<400> SEQUENCE: 307

Val Xaa Glu Pro Gly Thr Ala Gln Tyr
1               5

<210> SEQ ID NO 308
<211> LENGTH: 11
<212> TYPE: PRT
<213> ORGANISM: Artificial Sequence
<220> FEATURE:
<223> OTHER INFORMATION: HwA11-S peptide
<220> FEATURE:
<221> NAME/KEY: X
<222> LOCATION: (6)..(6)
<223> OTHER INFORMATION: X is S or T

<400> SEQUENCE: 308

Cys Ile Pro Pro Asp Xaa Leu Leu Phe Pro Ala
1               5                   10

<210> SEQ ID NO 309
<211> LENGTH: 11
<212> TYPE: PRT
<213> ORGANISM: Artificial Sequence
<220> FEATURE:
<223> OTHER INFORMATION: LB-ADIR-1F peptide
<220> FEATURE:
<221> NAME/KEY: X
<222> LOCATION: (9)..(9)
<223> OTHER INFORMATION: X is F or S

<400> SEQUENCE: 309

Ser Val Ala Pro Ala Leu Ala Leu Xaa Pro Ala
1               5                   10

<210> SEQ ID NO 310
<211> LENGTH: 9
<212> TYPE: PRT
<213> ORGANISM: Artificial Sequence
<220> FEATURE:
<223> OTHER INFORMATION: LB-HIVEP1-1S peptide
<220> FEATURE:
<221> NAME/KEY: X
<222> LOCATION: (6)..(6)
<223> OTHER INFORMATION: X is S or N

<400> SEQUENCE: 310

Ser Leu Pro Lys His Xaa Val Thr Ile
1               5

<210> SEQ ID NO 311
<211> LENGTH: 9
<212> TYPE: PRT
<213> ORGANISM: Artificial Sequence
<220> FEATURE:
<223> OTHER INFORMATION: LB-NISCH-1A peptide
<220> FEATURE:
<221> NAME/KEY: X
<222> LOCATION: (7)..(7)
<223> OTHER INFORMATION: X is A or V

<400> SEQUENCE: 311

Ala Leu Ala Pro Ala Pro Xaa Glu Val
1 5

<210> SEQ ID NO 312
<211> LENGTH: 9
<212> TYPE: PRT
<213> ORGANISM: Artificial Sequence
<220> FEATURE:
<223> OTHER INFORMATION: LB-SSR1-1S peptide
<220> FEATURE:
<221> NAME/KEY: X
<222> LOCATION: (1)..(1)
<223> OTHER INFORMATION: X is S or L

<400> SEQUENCE: 312

Xaa Leu Ala Val Ala Gln Asp Leu Thr
1 5

<210> SEQ ID NO 313
<211> LENGTH: 10
<212> TYPE: PRT
<213> ORGANISM: Artificial Sequence
<220> FEATURE:
<223> OTHER INFORMATION: LB-WNK1-1I peptide
<220> FEATURE:
<221> NAME/KEY: X
<222> LOCATION: (7)..(7)
<223> OTHER INFORMATION: X is I or M

<400> SEQUENCE: 313

Arg Thr Leu Ser Pro Glu Xaa Ile Thr Val
1 5 10

<210> SEQ ID NO 314
<211> LENGTH: 10
<212> TYPE: PRT
<213> ORGANISM: Artificial Sequence
<220> FEATURE:
<223> OTHER INFORMATION: T4A peptide
<220> FEATURE:
<221> NAME/KEY: X
<222> LOCATION: (10)..(10)
<223> OTHER INFORMATION: X is A or E

<400> SEQUENCE: 314

Gly Leu Tyr Thr Tyr Trp Ser Ala Gly Xaa
1 5 10

<210> SEQ ID NO 315
<211> LENGTH: 9
<212> TYPE: PRT
<213> ORGANISM: Artificial Sequence
<220> FEATURE:
<223> OTHER INFORMATION: UTA2-1 peptide
<220> FEATURE:
<221> NAME/KEY: X
<222> LOCATION: (3)..(3)
<223> OTHER INFORMATION: X is L or P

<400> SEQUENCE: 315

Gln Leu Xaa Asn Ser Val Leu Thr Leu
1 5

<210> SEQ ID NO 316
<211> LENGTH: 9
<212> TYPE: PRT
<213> ORGANISM: Artificial Sequence
<220> FEATURE:
<223> OTHER INFORMATION: LB-CLYBL-1Y peptide
<220> FEATURE:

<221> NAME/KEY: X
<222> LOCATION: (5)..(5)
<223> OTHER INFORMATION: X is Y or D

<400> SEQUENCE: 316

Ser Leu Ala Ala Xaa Ile Pro Arg Leu
1 5

<210> SEQ ID NO 317
<211> LENGTH: 10
<212> TYPE: PRT
<213> ORGANISM: Artificial Sequence
<220> FEATURE:
<223> OTHER INFORMATION: TRIM22 peptide
<220> FEATURE:
<221> NAME/KEY: X
<222> LOCATION: (7)..(7)
<223> OTHER INFORMATION: X is C or R

<400> SEQUENCE: 317

Met Ala Val Pro Pro Cys Xaa Ile Gly Val
1 5 10

<210> SEQ ID NO 318
<211> LENGTH: 11
<212> TYPE: PRT
<213> ORGANISM: Artificial Sequence
<220> FEATURE:
<223> OTHER INFORMATION: PARP10-1L peptide
<220> FEATURE:
<221> NAME/KEY: X
<222> LOCATION: (3)..(3)
<223> OTHER INFORMATION: X is L or P

<400> SEQUENCE: 318

Gly Leu Xaa Gly Gln Glu Gly Leu Val Glu Ile
1 5 10

<210> SEQ ID NO 319
<211> LENGTH: 9
<212> TYPE: PRT
<213> ORGANISM: Artificial Sequence
<220> FEATURE:
<223> OTHER INFORMATION: FAM119A-1T peptide
<220> FEATURE:
<221> NAME/KEY: X
<222> LOCATION: (8)..(8)
<223> OTHER INFORMATION: X is T or I

<400> SEQUENCE: 319

Ala Met Leu Glu Arg Gln Phe Xaa Val
1 5

<210> SEQ ID NO 320
<211> LENGTH: 9
<212> TYPE: PRT
<213> ORGANISM: Artificial Sequence
<220> FEATURE:
<223> OTHER INFORMATION: GLRX3-1S peptide
<220> FEATURE:
<221> NAME/KEY: X
<222> LOCATION: (3)..(3)
<223> OTHER INFORMATION: X is S or P

<400> SEQUENCE: 320

Phe Leu Xaa Ser Ala Asn Glu His Leu
1 5

<210> SEQ ID NO 321

<211> LENGTH: 9
<212> TYPE: PRT
<213> ORGANISM: Artificial Sequence
<220> FEATURE:
<223> OTHER INFORMATION: HNF4G-1M peptide
<220> FEATURE:
<221> NAME/KEY: X
<222> LOCATION: (2)..(2)
<223> OTHER INFORMATION: X is M or I

<400> SEQUENCE: 321

Met Xaa Tyr Lys Asp Ile Leu Leu Leu
1 5

<210> SEQ ID NO 322
<211> LENGTH: 9
<212> TYPE: PRT
<213> ORGANISM: Artificial Sequence
<220> FEATURE:
<223> OTHER INFORMATION: HMMR-1V peptide
<220> FEATURE:
<221> NAME/KEY: X
<222> LOCATION: (6)..(6)
<223> OTHER INFORMATION: X is V or A

<400> SEQUENCE: 322

Ser Leu Gln Glu Lys Xaa Ala Lys Ala
1 5

<210> SEQ ID NO 323
<211> LENGTH: 9
<212> TYPE: PRT
<213> ORGANISM: Artificial Sequence
<220> FEATURE:
<223> OTHER INFORMATION: BCL2A1 peptide
<220> FEATURE:
<221> NAME/KEY: X
<222> LOCATION: (4)..(4)
<223> OTHER INFORMATION: X is N or K

<400> SEQUENCE: 323

Val Leu Gln Xaa Val Ala Phe Ser Val
1 5

<210> SEQ ID NO 324
<211> LENGTH: 10
<212> TYPE: PRT
<213> ORGANISM: Artificial Sequence
<220> FEATURE:
<223> OTHER INFORMATION: CDC26-1F peptide
<220> FEATURE:
<221> NAME/KEY: X
<222> LOCATION: (1)..(1)
<223> OTHER INFORMATION: X is F or S

<400> SEQUENCE: 324

Xaa Val Ala Gly Thr Gln Glu Val Phe Val
1 5 10

<210> SEQ ID NO 325
<211> LENGTH: 10
<212> TYPE: PRT
<213> ORGANISM: Artificial Sequence
<220> FEATURE:
<223> OTHER INFORMATION: APOBEC3F-1S/A peptide
<220> FEATURE:
<221> NAME/KEY: X
<222> LOCATION: (3)..(3)
<223> OTHER INFORMATION: X is S or A

<400> SEQUENCE: 325

Phe Leu Xaa Glu His Pro Asn Val Thr Leu
1 5 10

<210> SEQ ID NO 326
<211> LENGTH: 9
<212> TYPE: PRT
<213> ORGANISM: Artificial Sequence
<220> FEATURE:
<223> OTHER INFORMATION: LB-PRCP-1D peptide
<220> FEATURE:
<221> NAME/KEY: X
<222> LOCATION: (8)..(8)
<223> OTHER INFORMATION: X is D or E

<400> SEQUENCE: 326

Phe Met Trp Asp Val Ala Glu Xaa Leu
1 5

<210> SEQ ID NO 327
<211> LENGTH: 11
<212> TYPE: PRT
<213> ORGANISM: Artificial Sequence
<220> FEATURE:
<223> OTHER INFORMATION: LB-PRCP-1D peptide
<220> FEATURE:
<221> NAME/KEY: X
<222> LOCATION: (8)..(8)
<223> OTHER INFORMATION: X is D or E

<400> SEQUENCE: 327

Phe Met Trp Asp Val Ala Glu Xaa Leu Lys Ala
1 5 10

<210> SEQ ID NO 328
<211> LENGTH: 9
<212> TYPE: PRT
<213> ORGANISM: Artificial Sequence
<220> FEATURE:
<223> OTHER INFORMATION: LB-CCL4-1T peptide
<220> FEATURE:
<221> NAME/KEY: X
<222> LOCATION: (7)..(7)
<223> OTHER INFORMATION: X is T or S

<400> SEQUENCE: 328

Cys Ala Asp Pro Ser Glu Xaa Trp Val
1 5

<210> SEQ ID NO 329
<211> LENGTH: 9
<212> TYPE: PRT
<213> ORGANISM: Artificial Sequence
<220> FEATURE:
<223> OTHER INFORMATION: LB-NCAPD3-1Q peptide
<220> FEATURE:
<221> NAME/KEY: X
<222> LOCATION: (3)..(3)
<223> OTHER INFORMATION: X is Q or R

<400> SEQUENCE: 329

Trp Leu Xaa Gly Val Val Pro Val Val
1 5

<210> SEQ ID NO 330
<211> LENGTH: 9
<212> TYPE: PRT
<213> ORGANISM: Artificial Sequence
<220> FEATURE:
<223> OTHER INFORMATION: LB-NDC80-1P peptide
<220> FEATURE:
<221> NAME/KEY: X
<222> LOCATION: (7)..(7)
<223> OTHER INFORMATION: X is P or A

<400> SEQUENCE: 330

His Leu Glu Glu Gln Ile Xaa Lys Val
1 5

<210> SEQ ID NO 331
<211> LENGTH: 9
<212> TYPE: PRT
<213> ORGANISM: Artificial Sequence
<220> FEATURE:
<223> OTHER INFORMATION: LB-TTK-1D peptide
<220> FEATURE:
<221> NAME/KEY: X
<222> LOCATION: (4)..(4)
<223> OTHER INFORMATION: X is D or E

<400> SEQUENCE: 331

Arg Leu His Xaa Gly Arg Val Phe Val
1 5

<210> SEQ ID NO 332
<211> LENGTH: 9
<212> TYPE: PRT
<213> ORGANISM: Artificial Sequence
<220> FEATURE:
<223> OTHER INFORMATION: WDR27-1L peptide
<220> FEATURE:
<221> NAME/KEY: X
<222> LOCATION: (2)..(2)
<223> OTHER INFORMATION: X is L or P

<400> SEQUENCE: 332

Ser Xaa Asp Asp His Val Val Ala Val
1 5

<210> SEQ ID NO 333
<211> LENGTH: 11
<212> TYPE: PRT
<213> ORGANISM: Artificial Sequence
<220> FEATURE:
<223> OTHER INFORMATION: MIIP peptide
<220> FEATURE:
<221> NAME/KEY: X
<222> LOCATION: (8)..(8)
<223> OTHER INFORMATION: X is K or E

<400> SEQUENCE: 333

Ser Glu Glu Ser Ala Val Pro Xaa Arg Ser Trp
1 5 10

<210> SEQ ID NO 334
<211> LENGTH: 10
<212> TYPE: PRT
<213> ORGANISM: Artificial Sequence
<220> FEATURE:
<223> OTHER INFORMATION: MIIP peptide
<220> FEATURE:
<221> NAME/KEY: X
<222> LOCATION: (7)..(7)
<223> OTHER INFORMATION: X is K or E

<400> SEQUENCE: 334

Glu Glu Ser Ala Val Pro Xaa Arg Ser Trp
1 5 10

<210> SEQ ID NO 335
<211> LENGTH: 9
<212> TYPE: PRT
<213> ORGANISM: Artificial Sequence
<220> FEATURE:
<223> OTHER INFORMATION: LB-DHX33-1C peptide
<220> FEATURE:
<221> NAME/KEY: X
<222> LOCATION: (9)..(9)
<223> OTHER INFORMATION: X is C or R

<400> SEQUENCE: 335

Tyr Leu Tyr Glu Gly Gly Ile Ser Xaa
1               5

<210> SEQ ID NO 336
<211> LENGTH: 10
<212> TYPE: PRT
<213> ORGANISM: Artificial Sequence
<220> FEATURE:
<223> OTHER INFORMATION: PANE1 peptide

<400> SEQUENCE: 336

Arg Val Trp Asp Leu Pro Gly Val Leu Lys
1               5                   10

<210> SEQ ID NO 337
<211> LENGTH: 10
<212> TYPE: PRT
<213> ORGANISM: Artificial Sequence
<220> FEATURE:
<223> OTHER INFORMATION: SP110 peptide
<220> FEATURE:
<221> NAME/KEY: X
<222> LOCATION: (4)..(4)
<223> OTHER INFORMATION: X is R or G

<400> SEQUENCE: 337

Ser Leu Pro Xaa Gly Thr Ser Thr Pro Lys
1               5                   10

<210> SEQ ID NO 338
<211> LENGTH: 9
<212> TYPE: PRT
<213> ORGANISM: Artificial Sequence
<220> FEATURE:
<223> OTHER INFORMATION: ACC-1C/Y
<220> FEATURE:
<221> NAME/KEY: X
<222> LOCATION: (5)..(5)
<223> OTHER INFORMATION: X is Y or C

<400> SEQUENCE: 338

Asp Tyr Leu Gln Xaa Val Leu Gln Ile
1               5

<210> SEQ ID NO 339
<211> LENGTH: 9
<212> TYPE: PRT
<213> ORGANISM: Artificial Sequence
<220> FEATURE:
<223> OTHER INFORMATION: P2RX7 peptide
<220> FEATURE:
<221> NAME/KEY: X
<222> LOCATION: (6)..(6)
<223> OTHER INFORMATION: X is H or R

<400> SEQUENCE: 339

Trp Phe His His Cys Xaa Pro Lys Tyr
1               5

<210> SEQ ID NO 340
<211> LENGTH: 9
<212> TYPE: PRT
<213> ORGANISM: Artificial Sequence
<220> FEATURE:
<223> OTHER INFORMATION: ACC-4 peptide
<220> FEATURE:
<221> NAME/KEY: X
<222> LOCATION: (9)..(9)
<223> OTHER INFORMATION: X is R or G

<400> SEQUENCE: 340

Ala Thr Leu Pro Leu Leu Cys Ala Xaa
1               5

<210> SEQ ID NO 341
<211> LENGTH: 10
<212> TYPE: PRT
<213> ORGANISM: Artificial Sequence
<220> FEATURE:
<223> OTHER INFORMATION: ACC-5
<220> FEATURE:
<221> NAME/KEY: X
<222> LOCATION: (10)..(10)
<223> OTHER INFORMATION: X is R or G

<400> SEQUENCE: 341

Trp Ala Thr Leu Pro Leu Leu Cys Ala Xaa
1               5                   10

<210> SEQ ID NO 342
<211> LENGTH: 9
<212> TYPE: PRT
<213> ORGANISM: Artificial Sequence
<220> FEATURE:
<223> OTHER INFORMATION: AKAP13 peptide
<220> FEATURE:
<221> NAME/KEY: X
<222> LOCATION: (9)..(9)
<223> OTHER INFORMATION: X is M or T

<400> SEQUENCE: 342

Ala Pro Ala Gly Val Arg Glu Val Xaa
1               5

<210> SEQ ID NO 343
<211> LENGTH: 10
<212> TYPE: PRT
<213> ORGANISM: Artificial Sequence
<220> FEATURE:
<223> OTHER INFORMATION: LB-APOBEC3B-1K peptide
<220> FEATURE:
<221> NAME/KEY: X
<222> LOCATION: (1)..(1)
<223> OTHER INFORMATION: X is K or E

<400> SEQUENCE: 343

Xaa Pro Gln Tyr His Ala Glu Met Cys Phe
1               5                   10

<210> SEQ ID NO 344
<211> LENGTH: 9
<212> TYPE: PRT
<213> ORGANISM: Artificial Sequence
<220> FEATURE:
<223> OTHER INFORMATION: APOBEC3H peptide
<220> FEATURE:
<221> NAME/KEY: X
<222> LOCATION: (5)..(5)

<223> OTHER INFORMATION: X is K or E

<400> SEQUENCE: 344

Lys Pro Gln Gln Xaa Gly Leu Arg Leu
1 5

<210> SEQ ID NO 345
<211> LENGTH: 8
<212> TYPE: PRT
<213> ORGANISM: Artificial Sequence
<220> FEATURE:
<223> OTHER INFORMATION: LB-ARHGDIB-1R peptide
<220> FEATURE:
<221> NAME/KEY: X
<222> LOCATION: (6)..(6)
<223> OTHER INFORMATION: X is R or P

<400> SEQUENCE: 345

Pro Arg Ala Cys Trp Xaa Glu Ala
1 5

<210> SEQ ID NO 346
<211> LENGTH: 10
<212> TYPE: PRT
<213> ORGANISM: Artificial Sequence
<220> FEATURE:
<223> OTHER INFORMATION: LB-BCAT2-1R peptide
<220> FEATURE:
<221> NAME/KEY: X
<222> LOCATION: (3)..(3)
<223> OTHER INFORMATION: X is R or T

<400> SEQUENCE: 346

Gln Pro Xaa Arg Ala Leu Leu Phe Val Ile
1 5 10

<210> SEQ ID NO 347
<211> LENGTH: 11
<212> TYPE: PRT
<213> ORGANISM: Artificial Sequence
<220> FEATURE:
<223> OTHER INFORMATION: BFAR peptide
<220> FEATURE:
<221> NAME/KEY: X
<222> LOCATION: (11)..(11)
<223> OTHER INFORMATION: X is M or R

<400> SEQUENCE: 347

Ala Pro Asn Thr Gly Arg Ala Asn Gln Gln Xaa
1 5 10

<210> SEQ ID NO 348
<211> LENGTH: 11
<212> TYPE: PRT
<213> ORGANISM: Artificial Sequence
<220> FEATURE:
<223> OTHER INFORMATION: C14orf169 peptide
<220> FEATURE:
<221> NAME/KEY: X
<222> LOCATION: (4)..(4)
<223> OTHER INFORMATION: X is A or V

<400> SEQUENCE: 348

Arg Pro Arg Xaa Pro Thr Glu Glu Leu Ala Leu
1 5 10

<210> SEQ ID NO 349
<211> LENGTH: 11
<212> TYPE: PRT

<213> ORGANISM: Artificial Sequence
<220> FEATURE:
<223> OTHER INFORMATION: LB-C16ORF-1R peptide
<220> FEATURE:
<221> NAME/KEY: X
<222> LOCATION: (1)..(1)
<223> OTHER INFORMATION: X is R or W

<400> SEQUENCE: 349

Xaa Pro Cys Pro Ser Val Gly Leu Ser Phe Leu
1 5 10

<210> SEQ ID NO 350
<211> LENGTH: 9
<212> TYPE: PRT
<213> ORGANISM: Artificial Sequence
<220> FEATURE:
<223> OTHER INFORMATION: C18orf21 peptide
<220> FEATURE:
<221> NAME/KEY: X
<222> LOCATION: (6)..(6)
<223> OTHER INFORMATION: X is A or T

<400> SEQUENCE: 350

Asn Pro Ala Thr Pro Xaa Ser Lys Leu
1 5

<210> SEQ ID NO 351
<211> LENGTH: 10
<212> TYPE: PRT
<213> ORGANISM: Artificial Sequence
<220> FEATURE:
<223> OTHER INFORMATION: LB-EBI3-1I peptide
<220> FEATURE:
<221> NAME/KEY: X
<222> LOCATION: (8)..(8)
<223> OTHER INFORMATION: X is I or V

<400> SEQUENCE: 351

Arg Pro Arg Ala Arg Tyr Tyr Xaa Gln Val
1 5 10

<210> SEQ ID NO 352
<211> LENGTH: 9
<212> TYPE: PRT
<213> ORGANISM: Artificial Sequence
<220> FEATURE:
<223> OTHER INFORMATION: POP1 peptide
<220> FEATURE:
<221> NAME/KEY: X
<222> LOCATION: (7)..(7)
<223> OTHER INFORMATION: X is N or K

<400> SEQUENCE: 352

Leu Pro Gln Lys Lys Ser Xaa Ala Leu
1 5

<210> SEQ ID NO 353
<211> LENGTH: 9
<212> TYPE: PRT
<213> ORGANISM: Artificial Sequence
<220> FEATURE:
<223> OTHER INFORMATION: SCRIB peptide
<220> FEATURE:
<221> NAME/KEY: X
<222> LOCATION: (7)..(7)
<223> OTHER INFORMATION: X is L or P

<400> SEQUENCE: 353

Leu Pro Gln Gln Pro Pro Xaa Ser Leu 1 5

<210> SEQ ID NO 354
<211> LENGTH: 9
<212> TYPE: PRT
<213> ORGANISM: Artificial Sequence
<220> FEATURE:
<223> OTHER INFORMATION: MTRR peptide
<220> FEATURE:
<221> NAME/KEY: X
<222> LOCATION: (5)..(5)
<223> OTHER INFORMATION: X is S or L

<400> SEQUENCE: 354

Ser Pro Ala Ser Xaa Arg Thr Asp Leu
1 5

<210> SEQ ID NO 355
<211> LENGTH: 9
<212> TYPE: PRT
<213> ORGANISM: Artificial Sequence
<220> FEATURE:
<223> OTHER INFORMATION: LLGL2
<220> FEATURE:
<221> NAME/KEY: X
<222> LOCATION: (5)..(5)
<223> OTHER INFORMATION: X is R or H

<400> SEQUENCE: 355

Ser Pro Ser Leu Xaa Ile Leu Ala Ile
1 5

<210> SEQ ID NO 356
<211> LENGTH: 11
<212> TYPE: PRT
<213> ORGANISM: Artificial Sequence
<220> FEATURE:
<223> OTHER INFORMATION: LB-ECGF-1H peptide
<220> FEATURE:
<221> NAME/KEY: X
<222> LOCATION: (3)..(3)
<223> OTHER INFORMATION: X is H or R

<400> SEQUENCE: 356

Arg Pro Xaa Ala Ile Arg Arg Pro Leu Ala Leu
1 5 10

<210> SEQ ID NO 357
<211> LENGTH: 11
<212> TYPE: PRT
<213> ORGANISM: Artificial Sequence
<220> FEATURE:
<223> OTHER INFORMATION: LB-ERAP1-1R peptide
<220> FEATURE:
<221> NAME/KEY: X
<222> LOCATION: (3)..(3)
<223> OTHER INFORMATION: X is R or P

<400> SEQUENCE: 357

His Pro Xaa Gln Glu Gln Ile Ala Leu Leu Ala
1 5 10

<210> SEQ ID NO 358
<211> LENGTH: 9
<212> TYPE: PRT
<213> ORGANISM: Artificial Sequence
<220> FEATURE:
<223> OTHER INFORMATION: LB-ERAP1-1R peptide
<220> FEATURE:
<221> NAME/KEY: X
<222> LOCATION: (3)..(3)
<223> OTHER INFORMATION: X is R or P

<400> SEQUENCE: 358

His Pro Xaa Gln Glu Gln Ile Ala Leu
1 5

<210> SEQ ID NO 359
<211> LENGTH: 9
<212> TYPE: PRT
<213> ORGANISM: Artificial Sequence
<220> FEATURE:
<223> OTHER INFORMATION: LB-FUCA2-1V peptide
<220> FEATURE:
<221> NAME/KEY: X
<222> LOCATION: (5)..(5)
<223> OTHER INFORMATION: X is V or M

<400> SEQUENCE: 359

Arg Leu Arg Gln Xaa Gly Ser Trp Leu
1 5

<210> SEQ ID NO 360
<211> LENGTH: 9
<212> TYPE: PRT
<213> ORGANISM: Artificial Sequence
<220> FEATURE:
<223> OTHER INFORMATION: LB-GEMIN4-1V peptide
<220> FEATURE:
<221> NAME/KEY: X
<222> LOCATION: (9)..(9)
<223> OTHER INFORMATION: X is V or E

<400> SEQUENCE: 360

Phe Pro Ala Leu Arg Phe Val Glu Xaa
1 5

<210> SEQ ID NO 361
<211> LENGTH: 11
<212> TYPE: PRT
<213> ORGANISM: Artificial Sequence
<220> FEATURE:
<223> OTHER INFORMATION: HDGF peptide
<220> FEATURE:
<221> NAME/KEY: X
<222> LOCATION: (11)..(11)
<223> OTHER INFORMATION: X is L or P

<400> SEQUENCE: 361

Leu Pro Met Glu Val Glu Lys Asn Ser Thr Xaa
1 5 10

<210> SEQ ID NO 362
<211> LENGTH: 11
<212> TYPE: PRT
<213> ORGANISM: Artificial Sequence
<220> FEATURE:
<223> OTHER INFORMATION: LB-PDCD11-1F peptide
<220> FEATURE:
<221> NAME/KEY: X
<222> LOCATION: (8)..(8)
<223> OTHER INFORMATION: X is F or L

<400> SEQUENCE: 362

Gly Pro Asp Ser Ser Lys Thr Xaa Leu Cys Leu
1 5 10

<210> SEQ ID NO 363
<211> LENGTH: 9

<212> TYPE: PRT
<213> ORGANISM: Artificial Sequence
<220> FEATURE:
<223> OTHER INFORMATION: LB-PFAS-1P peptide
<220> FEATURE:
<221> NAME/KEY: X
<222> LOCATION: (2)..(2)
<223> OTHER INFORMATION: X is P or S

<400> SEQUENCE: 363

Ala Xaa Gly His Thr Arg Arg Lys Leu
1 5

<210> SEQ ID NO 364
<211> LENGTH: 10
<212> TYPE: PRT
<213> ORGANISM: Artificial Sequence
<220> FEATURE:
<223> OTHER INFORMATION: LB-TEP1-1S peptide
<220> FEATURE:
<221> NAME/KEY: X
<222> LOCATION: (9)..(9)
<223> OTHER INFORMATION: X is S or P

<400> SEQUENCE: 364

Ala Pro Asp Gly Ala Lys Val Ala Xaa Leu
1 5 10

<210> SEQ ID NO 365
<211> LENGTH: 11
<212> TYPE: PRT
<213> ORGANISM: Artificial Sequence
<220> FEATURE:
<223> OTHER INFORMATION: LB-TMEM8A-1I peptide
<220> FEATURE:
<221> NAME/KEY: X
<222> LOCATION: (7)..(7)
<223> OTHER INFORMATION: X is I or V

<400> SEQUENCE: 365

Arg Pro Arg Ser Val Thr Xaa Gln Pro Leu Leu
1 5 10

<210> SEQ ID NO 366
<211> LENGTH: 10
<212> TYPE: PRT
<213> ORGANISM: Artificial Sequence
<220> FEATURE:
<223> OTHER INFORMATION: LB-USP15-1I peptide
<220> FEATURE:
<221> NAME/KEY: X
<222> LOCATION: (8)..(8)
<223> OTHER INFORMATION: X is I or T

<400> SEQUENCE: 366

Met Pro Ser His Leu Arg Asn Xaa Leu Leu
1 5 10

<210> SEQ ID NO 367
<211> LENGTH: 9
<212> TYPE: PRT
<213> ORGANISM: Artificial Sequence
<220> FEATURE:
<223> OTHER INFORMATION: LRH-1 peptide

<400> SEQUENCE: 367

Thr Pro Asn Gln Arg Gln Asn Val Cys
1 5

<210> SEQ ID NO 368
<211> LENGTH: 9
<212> TYPE: PRT
<213> ORGANISM: Artificial Sequence
<220> FEATURE:
<223> OTHER INFORMATION: LB-MOB3A-1C peptide
<220> FEATURE:
<221> NAME/KEY: X
<222> LOCATION: (1)..(1)
<223> OTHER INFORMATION: X is C or S

<400> SEQUENCE: 368

Xaa Pro Arg Pro Gly Thr Trp Thr Cys
1 5

<210> SEQ ID NO 369
<211> LENGTH: 11
<212> TYPE: PRT
<213> ORGANISM: Artificial Sequence
<220> FEATURE:
<223> OTHER INFORMATION: LB-ZDHHC6-1Y peptide
<220> FEATURE:
<221> NAME/KEY: X
<222> LOCATION: (4)..(4)
<223> OTHER INFORMATION: X is Y or H

<400> SEQUENCE: 369

Arg Pro Arg Xaa Trp Ile Leu Leu Val Lys Ile
1 5 10

<210> SEQ ID NO 370
<211> LENGTH: 10
<212> TYPE: PRT
<213> ORGANISM: Artificial Sequence
<220> FEATURE:
<223> OTHER INFORMATION: ZAPHIR peptide

<400> SEQUENCE: 370

Ile Pro Arg Asp Ser Trp Trp Val Glu Leu
1 5 10

<210> SEQ ID NO 371
<211> LENGTH: 9
<212> TYPE: PRT
<213> ORGANISM: Artificial Sequence
<220> FEATURE:
<223> OTHER INFORMATION: HEATR1 peptide
<220> FEATURE:
<221> NAME/KEY: X
<222> LOCATION: (7)..(7)
<223> OTHER INFORMATION: X is E or G

<400> SEQUENCE: 371

Ile Ser Lys Glu Arg Ala Xaa Ala Leu
1 5

<210> SEQ ID NO 372
<211> LENGTH: 9
<212> TYPE: PRT
<213> ORGANISM: Artificial Sequence
<220> FEATURE:
<223> OTHER INFORMATION: LB-GSTP1-1V peptide
<220> FEATURE:
<221> NAME/KEY: X
<222> LOCATION: (7)..(7)
<223> OTHER INFORMATION: X is V or I

<400> SEQUENCE: 372

Asp Leu Arg Cys Lys Tyr Xaa Ser Leu
1 5

<210> SEQ ID NO 373
<211> LENGTH: 9
<212> TYPE: PRT
<213> ORGANISM: Artificial Sequence
<220> FEATURE:
<223> OTHER INFORMATION: HA-1/B60 peptide
<220> FEATURE:
<221> NAME/KEY: X
<222> LOCATION: (6)..(6)
<223> OTHER INFORMATION: X is H or R

<400> SEQUENCE: 373

Lys Glu Cys Val Leu Xaa Asp Asp Leu
1 5

<210> SEQ ID NO 374
<211> LENGTH: 9
<212> TYPE: PRT
<213> ORGANISM: Artificial Sequence
<220> FEATURE:
<223> OTHER INFORMATION: LB-SON-1R peptide
<220> FEATURE:
<221> NAME/KEY: X
<222> LOCATION: (6)..(6)
<223> OTHER INFORMATION: X is R or C

<400> SEQUENCE: 374

Ser Glu Thr Lys Gln Xaa Thr Val Leu
1 5

<210> SEQ ID NO 375
<211> LENGTH: 9
<212> TYPE: PRT
<213> ORGANISM: Artificial Sequence
<220> FEATURE:
<223> OTHER INFORMATION: LB-SWAP70-1Q peptide
<220> FEATURE:
<221> NAME/KEY: X
<222> LOCATION: (6)..(6)
<223> OTHER INFORMATION: X is Q or E

<400> SEQUENCE: 375

Met Glu Gln Leu Glu Xaa Leu Glu Leu
1 5

<210> SEQ ID NO 376
<211> LENGTH: 9
<212> TYPE: PRT
<213> ORGANISM: Artificial Sequence
<220> FEATURE:
<223> OTHER INFORMATION: LB-TRIP10-1EPC peptide
<220> FEATURE:
<221> NAME/KEY: X
<222> LOCATION: (2)..(2)
<223> OTHER INFORMATION: X is E or G
<220> FEATURE:
<221> NAME/KEY: X
<222> LOCATION: (3)..(3)
<223> OTHER INFORMATION: X is P or S
<220> FEATURE:
<221> NAME/KEY: X
<222> LOCATION: (7)..(7)
<223> OTHER INFORMATION: X is C or G

<400> SEQUENCE: 376

Gly Xaa Xaa Gln Asp Leu Xaa Thr Leu
1 5

<210> SEQ ID NO 377

<211> LENGTH: 9
<212> TYPE: PRT
<213> ORGANISM: Artificial Sequence
<220> FEATURE:
<223> OTHER INFORMATION: LB-NUP133-1R peptide
<220> FEATURE:
<221> NAME/KEY: X
<222> LOCATION: (8)..(8)
<223> OTHER INFORMATION: X is R or Q

<400> SEQUENCE: 377

Ser Glu Asp Leu Ile Leu Cys Xaa Leu
1               5

<210> SEQ ID NO 378
<211> LENGTH: 11
<212> TYPE: PRT
<213> ORGANISM: Artificial Sequence
<220> FEATURE:
<223> OTHER INFORMATION: LB-ZNFX1-1Q peptide
<220> FEATURE:
<221> NAME/KEY: X
<222> LOCATION: (8)..(8)
<223> OTHER INFORMATION: X is Q or H

<400> SEQUENCE: 378

Asn Glu Ile Glu Asp Val Trp Xaa Leu Asp Leu
1               5                   10

<210> SEQ ID NO 379
<211> LENGTH: 11
<212> TYPE: PRT
<213> ORGANISM: Artificial Sequence
<220> FEATURE:
<223> OTHER INFORMATION: SLC1A5 peptide
<220> FEATURE:
<221> NAME/KEY: X
<222> LOCATION: (3)..(3)
<223> OTHER INFORMATION: X is A or P

<400> SEQUENCE: 379

Ala Glu Xaa Thr Ala Asn Gly Gly Leu Ala Leu
1               5                   10

<210> SEQ ID NO 380
<211> LENGTH: 10
<212> TYPE: PRT
<213> ORGANISM: Artificial Sequence
<220> FEATURE:
<223> OTHER INFORMATION: ACC-2 peptide
<220> FEATURE:
<221> NAME/KEY: X
<222> LOCATION: (6)..(6)
<223> OTHER INFORMATION: X is D or G

<400> SEQUENCE: 380

Lys Glu Phe Glu Asp Xaa Ile Ile Asn Trp
1               5                   10

<210> SEQ ID NO 381
<211> LENGTH: 11
<212> TYPE: PRT
<213> ORGANISM: Artificial Sequence
<220> FEATURE:
<223> OTHER INFORMATION: ACC-6 peptide

<400> SEQUENCE: 381

Met Glu Ile Phe Ile Glu Val Phe Ser His Phe
1               5                   10

<210> SEQ ID NO 382
<211> LENGTH: 10
<212> TYPE: PRT
<213> ORGANISM: Artificial Sequence
<220> FEATURE:
<223> OTHER INFORMATION: HB-1H/Y peptide
<220> FEATURE:
<221> NAME/KEY: X
<222> LOCATION: (8)..(8)
<223> OTHER INFORMATION: X is H or Y

<400> SEQUENCE: 382

Glu Glu Lys Arg Gly Ser Leu Xaa Val Trp
1 5 10

<210> SEQ ID NO 383
<211> LENGTH: 9
<212> TYPE: PRT
<213> ORGANISM: Artificial Sequence
<220> FEATURE:
<223> OTHER INFORMATION: DPH1 peptide
<220> FEATURE:
<221> NAME/KEY: X
<222> LOCATION: (2)..(2)
<223> OTHER INFORMATION: X is V or L

<400> SEQUENCE: 383

Ser Xaa Leu Pro Glu Val Asp Val Trp
1 5

<210> SEQ ID NO 384
<211> LENGTH: 9
<212> TYPE: PRT
<213> ORGANISM: Artificial Sequence
<220> FEATURE:
<223> OTHER INFORMATION: UGT2B17/A02 peptide

<400> SEQUENCE: 384

Cys Val Ala Thr Met Ile Phe Met Ile
1 5

<210> SEQ ID NO 385
<211> LENGTH: 10
<212> TYPE: PRT
<213> ORGANISM: Artificial Sequence
<220> FEATURE:
<223> OTHER INFORMATION: UGT2B17/A29

<400> SEQUENCE: 385

Ala Glu Leu Leu Asn Ile Pro Phe Leu Tyr
1 5 10

<210> SEQ ID NO 386
<211> LENGTH: 10
<212> TYPE: PRT
<213> ORGANISM: Artificial Sequence
<220> FEATURE:
<223> OTHER INFORMATION: UGT2B17/B44 peptide

<400> SEQUENCE: 386

Ala Glu Leu Leu Asn Ile Pro Phe Leu Tyr
1 5 10

<210> SEQ ID NO 387
<211> LENGTH: 9
<212> TYPE: PRT
<213> ORGANISM: Artificial Sequence
<220> FEATURE:

<223> OTHER INFORMATION: DFFRY peptide
<220> FEATURE:
<221> NAME/KEY: X
<222> LOCATION: (4)..(4)
<223> OTHER INFORMATION: X is C or S

<400> SEQUENCE: 387

Ile Val Asp Xaa Leu Thr Glu Met Tyr
1               5

<210> SEQ ID NO 388
<211> LENGTH: 9
<212> TYPE: PRT
<213> ORGANISM: Artificial Sequence
<220> FEATURE:
<223> OTHER INFORMATION: SMCY peptide

<400> SEQUENCE: 388

Phe Ile Asp Ser Tyr Ile Cys Gln Val
1               5

<210> SEQ ID NO 389
<211> LENGTH: 11
<212> TYPE: PRT
<213> ORGANISM: Artificial Sequence
<220> FEATURE:
<223> OTHER INFORMATION: TMSB4Y peptide

<400> SEQUENCE: 389

Glu Val Leu Leu Arg Pro Gly Leu His Phe Arg
1               5                   10

<210> SEQ ID NO 390
<211> LENGTH: 1533
<212> TYPE: DNA
<213> ORGANISM: Artificial Sequence
<220> FEATURE:
<223> OTHER INFORMATION: CD19 CAR

<400> SEQUENCE: 390
gacatccaga tgacacagac tacatcctcc ctgtctgcct ctctgggaga cagagtcacc 60
atcagttgca gggcaagtca ggacattagt aaatatttaa attggtatca gcagaaacca 120
gatggaactg ttaaactcct gatctaccat acatcaagat tacactcagg agtcccatca 180
aggttcagtg gcagtgggtc tggaacagat tattctctca ccattagcaa cctggagcaa 240
gaagatattg ccacttactt ttgccaacag ggtaatacgc ttccgtacac gttcggaggg 300
gggaccaagc tggagatcac aggcggaggt ggaagcggag gggggaggatc tggcggcgga 360 ggaagcggag gcgaggtgaa actgcaggag tcaggacctg gcctggtggc gccctcacag 420
agcctgtccg tcacatgcac tgtctcaggg gtctcattac ccgactatgg tgtaagctgg 480
attcgccagc ctccacgaaa gggtctggag tggctgggag taatatgggg tagtgaaacc 540
acatactata attcagctct caaatccaga ctgaccatca tcaaggacaa ctccaagagc 600
caagttttct taaaaatgaa cagtctgcaa actgatgaca cagccattta ctactgtgcc 660
aaacattatt actacggtgg tagctatgct atggactact ggggccaagg aacctcagtc 720
accgtgtcct caaccacgac gccagcgccg cgaccaccaa caccggcgcc caccatcgcg 780
tcgcagcccc tgtccctgcg cccagaggcg tgccggccag cggcgggggg cgcagtgcac 840
acgagggggc tggacttcgc ctgtgatttc tgggtgctgg tcgttgtggg cggcgtgctg 900
gcctgctaca gcctgctggt gacagtggcc ttcatcatct tttgggtgag gagcaagcgg 960

```
agcagactgc tgcacagcga ctacatgaac atgacccccc ggaggcctgg ccccacccgg   1020

aagcactacc agccctacgc ccctcccagg gatttcgccg cctaccggag caaacggggc   1080

agaaagaaac tcctgtatat attcaaacaa ccatttatga ggccagtaca aactactcaa   1140

gaggaagatg gctgtagctg ccgatttcca gaagaagaag aaggaggatg tgaactgaga   1200

gtgaagttca gcaggagcgc agacgccccc gcgtacaagc agggccagaa ccagctctat   1260

aacgagctca atctaggacg aagagaggag tacgatgttt tggacaagcg tagaggccgg   1320

gaccctgaga tgggggggaaa gccgagaagg aagaaccctc aggaaggcct gtacaatgaa   1380

ctgcagaaag ataagatggc ggaggcctac agtgagattg ggatgaaagg cgagcgccgg   1440

aggggcaagg ggcacgatgg cctttaccag ggactcagta cagccaccaa ggacacctac   1500

gacgcccttc acatgcaggc cctgccccct cgc                                 1533
```

<210> SEQ ID NO 391
<211> LENGTH: 245
<212> TYPE: PRT
<213> ORGANISM: Artificial Sequence
<220> FEATURE:
<223> OTHER INFORMATION: EGFR ScFv

<400> SEQUENCE: 391

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asp Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Val Asn Ser Val Thr Ala Ala Asp Thr Ala Val Tyr Tyr
                85                  90                  95

Cys Ala Arg Val Ser Ile Phe Gly Val Gly Thr Phe Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Glu Ile Val Met Thr Gln
    130                 135                 140

Ser Pro Ala Thr Leu Ser Leu Ser Pro Gly Glu Arg Ala Thr Leu Ser
145                 150                 155                 160

Cys Arg Ala Ser Gln Ser Val Ser Ser Tyr Leu Ala Trp Tyr Gln Gln
                165                 170                 175

Lys Pro Gly Gln Ala Pro Arg Leu Leu Ile Tyr Asp Ala Ser Asn Arg
            180                 185                 190

Ala Thr Gly Ile Pro Ala Arg Phe Ser Gly Ser Gly Ser Gly Thr Asp
        195                 200                 205

Phe Thr Leu Thr Ile Ser Ser Leu Glu Pro Glu Asp Phe Ala Val Tyr
    210                 215                 220

Tyr Cys His Gln Tyr Gly Ser Thr Pro Leu Thr Phe Gly Gly Gly Thr
225                 230                 235                 240

Lys Ala Glu Ile Lys
                245
```

ENGINEERED IMMUNE CELLS WITH RECEPTOR CROSS-TALK

TECHNICAL FIELD

The present disclosure relates to engineered immune cells that have an enhanced safety profile and large therapeutic window.

SEQUENCE LISTING

The present application is being filed with a Sequence Listing in electronic format. The Sequence Listing is provided as a file entitled A2TH-003-01US-Sequence-Listing.txt, created on Nov. 24, 2021 and is 404 kilobytes in size. The information in electronic format of the Sequence Listing is incorporated by reference in its entirety.

BACKGROUND

Approximately 1.8 million people per year are diagnosed with a form of cancer in the United States. Similarly, it is estimated that 23.5 million Americans suffer from an autoimmune disease, almost all of which decrease life expectancy. Despite continual advances in treatment, education, and detection, there are over 600,000 deaths per year attributed to cancer in the U.S., while autoimmune diseases remain a leading cause of death among patients under the age 65.

Engineered immune cells have been touted as potentially effective treatments for a variety of severe conditions like cancer, viral infections, auto-immune ailments, and organ transplant rejection. These immune cells, whether chimeric antigen receptor (CAR)-engineered cells or T cell receptor (TCR)-engineered cells, often show efficacious results in vitro. However, in vivo, these results are rarely duplicated. Often, these treatments show a lack of efficacy in vivo and/or produce such severe side effects, that they cannot be used as therapeutics. Thus, despite decades of consistent research, only two CAR T cell therapies have received FDA approval—Kymriah™ for acute lymphoblastic leukemia and Yescarta™ for diffuse large B-cell lymphoma.

SUMMARY OF THE INVENTION

The present disclosure provides engineered immune cells that comprise two types of modular, engineered ligand binding receptors caused to be expressed on the surface of the cells. The first of these receptors is an activating receptor, which is designed to activate when bound to a cognate ligand on the surface of another cell, causing it to trigger an activating signal. The immune cells are engineered such that when the strength of the activating signal crosses a threshold, it causes a cytotoxic response by the immune cell, killing the cell expressing the cognate ligand. The second of these receptors is a blocking receptor, which when bound to a cognate blocking ligand on the surface of a non-target cell, is designed to activate and trigger a blocking signal. The blocking signal blocks the activating signal, which prevents the cytotoxic response against the non-target cell.

Generally, the activating receptors are designed to bind to cognate activating ligands that are expressed on both target cells, such as tumor cells, and non-target cells. The blocking ligands may be expressed only by non-target cells, or expressed at lower levels by target cells compared to non-target cells. In this way, when the engineered immune cells contact target cells, the activating receptors bind to the activating ligands, which leads to the cytotoxic response. In contrast, when the engineered immune cells contact non-target cells, the blocking receptors bind to the blocking ligands, blocking the cytotoxic response. This designed scheme provides the general means by which the engineered immune cells safely kill target cells, while limiting effects on non-target cells. However, the immune cells of the present disclosure have been engineered to provide several other advantageous features that expand their therapeutic window and efficacy, while limiting deleterious effects.

One of these advantageous features is that, when activated, the blocking receptors have been designed to reduce cell surface expression of the activating receptors. Thus, as the immune cells circulate to areas of a patient's body lacking target cells, the levels of activating receptors expressed on the surface of the cell are reduced. The receptors can be configured such that this reduction is reversible upon the activating receptors binding to their cognate ligands in the absence of the blocking ligands. This intentionally lowers the likelihood that a cytotoxic response will be triggered in the absence of an appropriate target, which enhances the safety profile of the immune cells.

Further, by engineering the immune cells to reduce the expression of activating receptors in the absence of an appropriate target cell, the immune cells are less likely to exhibit chronic activation and/or ligand-independent tonic signaling. As a result, the immune cells of the present disclosure are designed to limit immune cell exhaustion, differentiation, and activation-induced immune cell death, while concurrently exhibiting high generation and persistence.

A further advantage of the engineered immune cells of the present disclosure is that, when they contact target and/or non-target cells, the activating and blocking receptors are designed to diffuse into regions on the immune cell surface proximate to the target and/or non-target cells. The receptors form micro-clusters in these regions. In micro-clusters proximate to non-target cells, the blocking receptors bind to cognate ligands on the proximate non-target cells. The receptors can be configured such that cross-talk between the receptors causes a localized reduction in surface expression of the activating receptors, recruits more blocking receptors to the micro-cluster, and prevents breakup of the micro-cluster. This leads to a localized signal that blocks cytotoxic effects on the non-target cell.

In contrast, when the engineered immune cells contact target cells, activating receptors in micro-clusters proximate to the target cells are activated. This leads to a localized signal that, when it passes a threshold, triggers a cytotoxic response by the immune cell that kills the proximate target cells. The immune cells and receptors can be configured such that binding of the activating receptors to their cognate ligands may also locally reverse any reduced surface expression of the activating receptor. This ensures a sufficiently strong activating signal to trigger the cytotoxic response on the proximate target cell.

The immune cells of the present disclosure can form these aforementioned micro-clusters when simultaneously contacting both target and non-target cells. This ensures an appropriate, localized response that kills target cells, while minimizing deleterious effects on non-target cells.

The immune cells of the present disclosure also feature blocking receptors that are engineered to produce a ligand-dependent signal that dominates and blocks the activating signal from the activating receptors. This ensures that the immune cells can be configured to possess a strong safety profile with a wide therapeutic window.

Moreover, in some methods and systems of the disclosure, the engineered immune cells can be produced based on the levels of blocking and activating ligands expressed by non-target cells. Because the blocking receptors can be tuned to have a signal that dominates initial contact with a non-target cells, a sufficiently safe immune cell can be produced, without relying on a large surplus of blocking receptors expressed as compared to activating receptors. Further, the ability of the blocking receptors to reduce the surface expression of the activating receptors ensures that this level of safety increases in the presence of non-target cells.

Another advantage conferred by the immune cells of the present disclosure is that receptors can be produced using modular receptor components. Thus, the immune cells can be readily engineered to have receptor pairs that target desired ligands expressed on target and non-target cells. Moreover, the modular receptor components can be used and interchanged to tune or adjust the relative signal strengths of each receptor type. This ensures that an engineered immune cell's receptors provide a sufficiently strong activation signal, which can be adequately blocked to prevent non-target effects. A surprising discovery is that this modular nature extends to both chimeric antigen receptors (CAR) and T cell receptors (TCR). Not only are CARs and TCRs of the present disclosure able to interact with each other, but parts of CARs and TCRs can be interchanged to produce customized receptors and cells.

The relative signal strength and activity of each receptor type can also be modulated based on cross-talk between receptors. A surprising feature of the present disclosure is, not only that cross-talk can impact signal strength and activity, but that the impact of this cross-talk can change depending on the distance between pairs of blocking and activating receptors. As the distance between a blocking receptor and activating receptor decreases, the impact of this cross-talk increases. Thus, the present disclosure provides engineered immune cells configured to express receptors such that they are proximate to one another to ensure optimal interaction and strong cross-talk.

The receptors may be designed, for example, with physiochemical properties that ensure the receptors have a desired spacing. This spacing may ensure a maximum level of cross-talk between receptors and/or ensure that the receptors do not diffuse close enough to, for instance, invert the blocking receptor signal. The receptors can be engineered, for example, to have opposing charges or steric hindrances to prevent them from moving too close to one another. Alternatively, or in addition, the immune cells may be engineered to have receptors that are covalently linked to achieve a desired spacing. For example, a rigid covalent linker between the receptors can hold the receptors at a desired spacing from one another. The rigid linker concurrently keeps the receptors close enough to ensure cross-talk while maintain adequate spacing to prevent the blocking receptor from, for instance, inverting or becoming ligand-independent.

Another feature of the present disclosure is that the blocking receptor can be designed using interchangeable hinges that connect an extracellular ligand binding domain to a transmembrane domain and/or an intracellular domain. The hinges can be designed to have different lengths and flexibilities. The length and flexibility of a hinge can be used to tune the strength of the blocking signal. Longer and/or more flexible hinges can be used to increase the strength of the blocking receptor's signal or surface expression. In contrast, the blocking receptor can be engineered with shorter and/or more rigid hinges to decrease the strength of the blocking receptor's signal or surface expression. The blocking receptor can be configured to use a hinge selected from a group of hinges that have a known impact on the half maximal concentration ($EC_{50}$) of the activating ligand for the activating receptor to cause the immune cell to trigger a cytotoxic response. This allows pairs of blocking and activating receptors to be chosen or engineered to exhibit a desired level of activation/inhibition.

Thus, the present disclosure provides engineered immune cells, and methods for reliably producing them, with a large therapeutic window, i.e., cells with a large range between their minimum effective dose and maximum tolerated dose. The cells possess target-sensitive receptors that produce an activation signal sufficient to trigger cytotoxic effects when encountering target cells, while concurrently producing minimal non-target effects. The engineered immune cells of the present disclosure also exhibit low exhaustion, differentiation, tonic signaling, and activation-induced immune cell death, and other features consistent with effective in vitro and in vivo function.

In one aspect, the present disclosure provides an engineered immune cell that includes an activating receptor expressed on a surface of the engineered immune cell. Binding of the activating receptor to an activating ligand on a target cell promotes a cytotoxic response by the engineered immune cell. The immune cell also includes a blocking receptor expressed on the surface of the engineered immune cell. Binding of the blocking receptor to a blocking ligand on a target cell causes the engineered immune cell to exhibit reduced surface expression of the activating receptor. High exogenous IL-2 may overcome this level of regulation, though the activation/blockade is still enforced by other features of intracellular signaling of the activator and blocker receptors.

Binding of the blocking receptor to the blocking ligand on the target cell may also cause the blocking receptor to trigger an inhibitory signal that blocks the activating signal, thereby preventing the cytotoxic response by the immune cell. The engineered immune may have an inhibitory signal dominates and blocks the activating signal.

The reduced surface expression of the activating receptor of the cells of the present disclosure may be reversible. The reduced surface expression of the activating receptor may reverse upon the engineered immune cell binding to the activating ligand on a target cell in the absence of the blocking ligand. The reduced surface expression of the activating receptor may be localized to a region of the engineered immune cell surface proximal to the blocking receptor. When a plurality of the blocking receptor binds to a plurality of the blocking ligand, the reduced surface expression may be localized to regions of the engineered immune cell surface proximal to blocking receptors.

When the immune cell encounters a target cell having both the blocking and activating ligands, a plurality of activating and blocking receptors diffuse into a region on the of the immune cell surface proximal to the target cell and form a micro-cluster. In the micro-cluster, binding of blocking receptors to the blocking ligands causes the engineered immune cell to exhibit reduced surface expression of the activating receptor in the micro-cluster.

In certain immune cells of the disclosure, the blocking receptor cannot bind to the blocking ligand until the activating receptor binds to the activating ligand.

The present disclosure also provides method for treating a cancer using the immune cells of the disclosure. In certain methods of the disclosure, the method includes providing an engineered immune cell to a patient, wherein the engineered immune cell comprises an activating receptor and a blocking receptor, each expressed on a surface of the engineered immune cell. In certain methods, when the engineered immune cell encounters a tumor cell of the patient, the activating receptor binds to an activating ligand on the tumor cell while the blocking receptor remains unbound. This promotes a cytotoxic response by the engineered immune cell that results in a cytotoxic effect on the tumor cell. When the engineered immune cell encounters a normal cell of the patient, the blocking receptor binds to a blocking ligand on the normal cell and causes the engineered immune cell to exhibit reduced surface expression of the activating receptor. This causes a signal from the blocking receptor to dominate a signal from the activating receptor, which prevents the cytotoxic response by the engineered immune cell.

In certain methods, the reduced surface expression of the activating receptor is temporary. The reduced surface expression may be reversible. The reduced surface expression may be reversed upon the engineered immune cell binding to the first ligand on a tumor cell.

In certain methods of the disclosure, the reduced surface expression of the activating receptor may be localized to a region of the engineered immune cell surface proximal to the blocking receptor bound to the blocking ligand on the normal cell. A plurality of the blocking receptor may bind to a plurality of the blocking ligand on the normal cell, and the reduced surface expression may be localized to the region of the engineered immune cell surface proximal to the plurality of the blocking receptor.

A further aspect of the disclosure are methods of producing an engineered immune cell with activating and blocking receptors. The methods of the disclosure may include, producing an engineered immune cell that expresses activating receptors and blocking receptors based on a ratio of a quantity of an activating ligand to a quantity of a blocking ligand that are expressed in non-tumor cells of a patient.

In certain methods, a tumor cell of a patient expresses the activating ligand and does not express the blocking ligand.

In certain methods of the disclosure, binding of the activating receptors to the activating ligands triggers an activating signal that promotes a cytotoxic response by the engineered immune cell. Additionally, binding of the blocking receptors to blocking ligands on a non-tumor cell may cause the blocking receptors to trigger an inhibitory signal that blocks the activating signal.

In certain methods of the disclosure, the engineered immune cell expresses the blocking and activating receptors at a ratio based on the ratio of the quantity of the activating ligand to the quantity of the blocking ligand that are expressed in the non-tumor cells of the patient.

In some methods, the inhibitory signal of one of the blocking receptors dominates and blocks the activating signal of one of the activating receptors.

In certain methods, the ratio of the blocking receptors to the activating receptors is less than 1. The ratio of the blocking receptors to the activating receptors, needed to achieve a blocking signal to provide a certain level of blocking for the activating signal, may be inversely proportional to the quantity of the activating ligand expressed on non-tumor cells of the patient. In certain methods, when the immune cell contacts a non-tumor cell of the patient the blocking receptors bind to blocking ligands on the non-tumor cell and reversibly increase the ratio of blocking receptors to activating receptors expressed by the immune cell.

In certain methods of the disclosure, each blocking receptor comprises a ligand binding domain (LBD), a hinge, transmembrane domain, and intracellular domain (ICD), and the LBD, hinge, and ICD have a known effect on the strength of the inhibitory signal. Each activating receptor may comprise a ligand binding domain (LBD), a hinge, transmembrane domain, and the LBD has a known effect on the activation signal.

The present disclosure also provides a method of producing an engineered immune cell that includes obtaining a sample from a patient comprising target and non-target cells; performing an assay to determine a ratio of a quantity of an activating ligand to a quantity of a blocking ligand expressed on the non-target cells; and producing an engineered immune cell that expresses activating receptors and blocking receptors based on the determined ratio.

In certain methods, the target cells express the activating ligand and do not express the blocking ligand.

In some methods, binding of the activating receptors to the activating ligands triggers an activating signal that promotes a cytotoxic response by the engineered immune cell; and binding of the blocking receptors to blocking ligands on a non-target cell causes the blocking receptors to trigger an inhibitory signal that blocks the activating signal.

In some methods, the engineered immune cell expresses the blocking and activating receptors at a ratio based on the ratio of the quantity of the activating ligand to the quantity of the blocking ligand that are expressed in the non-target cells of the patient.

In certain methods, the inhibitory signal of one of the blocking receptors dominates and blocks the activating signal of one of the activating receptors. The ratio of the blocking receptors to the activating receptors is less than 1 in certain methods. The ratio of the blocking receptors to the activating receptors may be inversely proportional to the quantity of the activating ligand expressed on non-target cells of the patient. In some methods, when the immune cell contacts a non-target cell of the patient the blocking receptors bind to blocking ligands on the non-target cell and reversibly increases the ratio of blocking receptors to activating receptors expressed by the immune cell.

In certain methods of the disclosure, each blocking receptor comprises a ligand binding domain (LBD), a hinge, transmembrane domain, and intracellular domain (ICD), and the LBD, hinge, and ICD have a known effect on the strength of the inhibitory signal. Each activating receptor may comprise a ligand binding domain (LBD), a hinge, transmembrane domain, and the LBD has a known effect on the activation signal.

In a further aspect, the present disclosure provides engineered immune cells with activating and blocking receptors that exhibit cross-talk between receptors. Thus, the present disclosure provides an engineered immune cell with an activating receptor that triggers a cytotoxic signal that promotes a cytotoxic response of the engineered immune cell when the activating receptor binds a first ligand of a target cell; a blocking receptor that sends an interfering signal that inhibits the cytotoxic response of the engineered immune cell when the blocking receptor binds a second ligand of the target cell, wherein cross-talk between the activating receptor and the blocking receptor affects an activation threshold for the cytotoxic response.

In certain immune cells, in the absence of the first and second ligands, the effect of the cross-talk on the activation threshold is minimized and/or reduced. The effect of the cross-talk on the activation threshold may increase with proximity of the activating receptor to the blocking receptor.

In certain immune cells of the disclosure, the activating receptor and blocking receptor are covalently linked together, or have physicochemical properties favoring interaction with one another such that the receptors are proximal to one another.

In some immune cells of the disclosure, when the blocking receptor binds to the second ligand, the cross-talk between the blocking and activating receptors causes the immune cell to exhibit reduced surface expression of the activating receptor.

An immune cell of the disclosure may include a plurality of the activating and blocking receptors, and when the immune cell contacts a target cell the plurality of the activating and blocking receptors diffuses into a region on the surface of the immune cell proximal to the target cell and forms a micro-cluster in which the effect of the cross-talk on the activation threshold is localized.

In some immune cells of the disclosure, cross-talk between the activating receptor and the blocking receptor prevents the blocking receptor from binding to the second ligand until the activating receptor binds to the first ligand.

The present disclosure also provides methods for treating cancer using the immune cells of the present disclosure. Certain methods may include providing an engineered immune cell to a patient, wherein the engineered immune cell comprises an activating receptor and a blocking receptor, each expressed on a surface of the engineered immune cell. The activating receptor may trigger a cytotoxic signal that promotes a cytotoxic response of the engineered immune cell when the activating receptor binds a first ligand of a target cell; and the blocking receptor may send an interfering signal that inhibits the cytotoxic response of the engineered immune cell when the blocking receptor binds a second ligand of the target cell, wherein cross-talk between the activating receptor and the blocking receptor affects an activation threshold for the cytotoxic response.

In certain methods, the absence of the second ligand, the effect of the cross-talk on the activation threshold is minimized and/or reduced. The effect of the cross-talk on the activation threshold may increase with proximity of the activating receptor to the blocking receptor.

In certain methods, the activating receptor and blocking receptor are linked together or have physicochemical properties favoring interaction with one another, such that the receptors are proximal to one another.

In certain methods, when the blocking receptor binds to the second ligand, the cross-talk between the blocking and activating receptors causes the immune cell to exhibit reduced surface expression of the activating receptor. The immune cell may include a plurality of the activating and blocking receptors, and when the immune cell contacts a target cell the plurality of the activating and blocking receptors diffuses into a region on the surface of the immune cell proximal to the target cell and forms a micro-cluster in which the effect of the cross-talk on the activation threshold is localized.

In methods of the disclosure, the cross-talk between the activating receptor and the blocking receptor may prevent the blocking receptor from binding to the second ligand until the activating receptor binds to the first ligand.

The present disclosure also provides methods of producing engineered immune cells as disclosed herein. Certain methods include, determining an amount of cross-talk between an activating receptor and a blocking receptor for an engineered immune cell, wherein the amount of cross-talk between the activating receptor and the blocking receptor affects an activation threshold for the cytotoxic response; and producing an engineered immune cell that expresses different concentrations of activating receptors and blocking receptors based on the determined amount of cross-talk between the activating receptor and the blocking receptor.

In some methods for producing immune cells, in the absence of cognate ligands for the activating and blocking receptors, the amount of the cross-talk is minimized and/or reduced. The methods may include producing an engineered immune cell that expresses different concentrations of activating receptors and blocking receptors is further based on a ratio of a quantity of an activating ligand to a quantity of a blocking ligand that are expressed in non-tumor cells of a sample.

The cross-talk between the activating receptor and the blocking receptor may prevent the blocking receptor from binding to the blocking ligand until the activating receptor binds to the activating ligand. In certain methods, an amount of the cross-talk between the activating receptor and blocking receptor increases with proximity of the activating receptor to the blocking receptor.

Methods include producing immune cells where the activating receptor and blocking receptor may be covalently linked, or have physicochemical properties favoring interaction with one another such that the receptors are proximal to one another.

In a further aspect, the present disclosure provides engineered immune cells with activating and blocking receptors in which the blocking receptor provides an inhibitory signal that dominates the activation signal from the activating receptor.

Thus, the present disclosure includes an engineered immune cell with an activating receptor on the surface of the engineered immune cell, wherein binding of the activating receptor to a first ligand on a target cell causes the activating receptor to trigger an activating signal that promotes a cytotoxic response by the engineered immune cell; and a blocking receptor on the surface of the immune cell, wherein binding of the blocking receptor to a second ligand on a target cell causes the blocking receptor to trigger an inhibitory signal stronger than the activating signal such that the inhibitory signal dominates and blocks the activating signal from the activating receptor, thereby preventing a localized cytotoxic response by the engineered immune cell.

In certain immune cells of the disclosure, binding of the blocking receptor to the second ligand may cause the engineered immune cell to exhibit reduced surface expression of the activating receptor. The reduced surface expression may be reversible.

The immune cells may include a plurality of activating and blocking receptors and the ratio of the blocking receptors to the activating receptors expressed by the immune cells is less than or equal to 1.

In certain immune cells of the disclosure, the blocking receptor does not bind to the second ligand until the activating receptor binds to the activating ligand.

In certain cells, the inhibitory signal may be localized to a region of the engineered immune cell surface adjacent to the blocking receptor. Similarly, the activation signal may be localized to a region of the engineered immune cell surface adjacent to the activating receptor.

When the immune cells of the disclosure encounter a target cell having both the first and second ligands, a plurality of activating and blocking receptors may diffuse into a region on the of the immune cell surface proximal to the target cell and form a micro-cluster in which the blocking receptors prevent the localized cytotoxic response by the engineered immune cells. Binding of the blocking receptors in the micro-cluster to the second target antigen may prevent breakup of the micro-cluster. When the immune cells simultaneously contact a second target cell having the first ligand and lacking the second ligand, a second plurality of the activating receptors may diffuse into a second region on the surface of the immune cells proximal to the second target cell and form a second micro-cluster that promotes the localized cytotoxic response by the engineered immune cells that results in a cytotoxic effect on the second target cell.

The present disclosure also provides methods for treating cancer using the immune cells of the present disclosure. The methods include a method in which an engineered immune cell is provided to a patient, wherein the engineered immune cell comprises an activating receptor and a blocking receptor, each expressed on a surface of the engineered immune cell, wherein: when the engineered immune cell encounters a tumor cell, the activating receptor binds to a first ligand on the tumor cell and the activating receptor triggers an activating signal in the engineered immune cell that promotes a cytotoxic response by the engineered immune cell that results in a cytotoxic effect on the tumor cell; and when the engineered immune cell encounters a normal cell, the activating receptor binds to the first ligand on the normal cell and the blocking receptor binds to a second ligand on the normal cell, wherein the activating receptor triggers an activating signal in the engineered immune cell and the blocking receptor triggers an inhibitory signal in the engineered immune cell that is stronger than the activating signal such that the inhibitory signal dominates and blocks the activating signal from the activating receptor, thereby preventing a localized cytotoxic response by the engineered immune cell.

In some methods, binding of the blocking receptor to the second ligand causes the engineered immune cell to exhibit reduced surface expression of the activating receptor. The reduced surface expression may be reversible.

In methods of the disclosure, the immune cell may express different concentrations of the activating and blocking receptors based on a ratio of a quantity of the first ligand to a quantity of a second ligand expressed in a normal cell of the patient. The ratio of the concentration of blocking receptors expressed to activating receptors expressed may be less than or equal to 1.

In certain methods, when the immune cell encounters at least one tumor cell, a first plurality of the activating receptors diffuses into a first region on the surface of the immune cell proximal to the tumor cell and forms a first micro-cluster that promotes the localized cytotoxic response by the immune cell that results in a cytotoxic effect on the tumor cell. When the immune cell simultaneously encounters a normal cell, a plurality of the activating and blocking receptors may diffuse into a second region on the surface of the immune cell proximal to the normal cell and form a second micro-cluster causing the inhibitory signal from the blocking receptors to dominate the activating signal from the activating receptors in the second micro-cluster preventing the localized cytotoxic response by the engineered immune cell on the normal cell. Binding of the blocking receptors in the second micro-cluster to the second ligand may prevent breakup of the second micro-cluster.

In some methods of the disclosure, the blocking receptor does not bind to the second ligand until the activating receptor binds to the activating ligand.

Some methods include cross-talk between the activating receptor and the blocking receptor that affects an activation threshold for the localize cytotoxic response.

In a further aspect, the present disclosure provides engineered immune cells with activating and blocking receptors that have multiplex and localized activity. An immune cell of the disclosure may include activating and blocking receptors on a surface of the cell. When the engineered immune cell encounters a tumor cell and a healthy cell a first region of the activating and blocking receptors forms proximal to the healthy cell and blocking receptors in the first region inhibit cytotoxic effects on the healthy cell, while, simultaneously, a second region of the activating and blocking receptors forms proximal to the tumor cell and promotes a cytotoxic response by the engineered immune cell that exhibits cytotoxic effects on the tumor cell.

The activating and blocking receptors in the first region may bind to cognate activating and blocking ligands on the healthy cell, and the activating receptors in the second region may bind to cognate activating ligands on the tumor cell. The activating and blocking receptors may form a first micro-cluster in the first region, and the activating and blocking receptors may form a second micro-cluster in the second region.

Binding of the blocking receptors in the first micro-cluster to the cognate blocking ligands on the healthy cell may cause the engineered immune cell to exhibit reduced surface expression of the activating receptor in the first micro-cluster. Binding of the blocking receptors in the first micro-cluster to the cognate blocking ligands on the healthy cell may prevent breakup of the first micro-cluster.

The immune cell may express different concentrations of the activating and blocking receptors based on a ratio of a quantity of the activating ligand to a quantity of the blocking ligand expressed in a healthy cell. The ratio of the concentration of blocking receptors to activating receptors expressed by the immune cell may be less than or equal to 1.

In certain immune cells of the disclosure, the blocking receptors do not bind to the cognate blocking ligands until the activating receptors bind to cognate activating ligands.

In some immune cells of the disclosure, the cytotoxic response by the engineered immune cell that exhibits cytotoxic effects on the tumor cell is localized to the second region. The localized cytotoxic response does not exhibit cytotoxic effects on the healthy cell.

The present disclosure also provides methods for treating cancer using the immune cells of the disclosure. A method for treating cancer may include providing an engineered immune cell to a patient, the engineered immune cell comprising activating and blocking cell-surface receptors. When the engineered immune cell encounters a tumor cell and a healthy cell of the patient, a first set of the activating and blocking receptors collect into a first cell-surface region of the engineered immune cell proximal to the healthy cell in which the blocking receptors inhibit cytotoxic effects of the engineered immune cell on the healthy cell. Simultaneously, a second set of the activating and blocking receptors collect into a second cell-surface region of the engineered immune cell proximal to the tumor cell in which the activating receptors promote a cytotoxic response by the engineered immune cell that kills the tumor cell.

The activating and blocking receptors in the first cell-surface region may bind to cognate activating and blocking ligands on the healthy cell, and the activating receptors in the second cell-surface region may bind to cognate activating ligands on the tumor cell.

The activating and blocking receptors may form a first micro-cluster on the first cell-surface region, and the activating and blocking receptors may form a second micro-cluster on the second cell-surface region.

Binding of the blocking receptors in the first micro-cluster to the cognate blocking ligands on the healthy cell may cause the engineered immune cell to exhibit reduced surface expression of the activating receptor in the first micro-cluster. Binding of the blocking receptors in the first micro-cluster to the cognate blocking ligands on the healthy cell may prevent breakup of the first micro-cluster.

In some methods of the disclosure, the immune cell expresses different concentrations of the activating and blocking receptors based on a ratio of a quantity of the activating ligand to a quantity of a blocking ligand expressed in a healthy cell. The ratio of the concentration of blocking receptors to activating receptors expressed by the immune cell may be less than or equal to 1.

In certain methods, blocking receptors do not bind to the cognate blocking ligands until the activating receptors bind to the cognate activating ligands.

In certain methods of the disclosure, the cytotoxic response is localized to the second cell-surface region. The localized cytotoxic response does not exhibit cytotoxic effects on the healthy cell.

In a further aspect, the present disclosure provides immune cells that have activating and blocking receptors that form micro-clusters on the surface of the immune cells.

An engineered immune cell of the disclosure may include activating and blocking receptors on a surface of the engineered immune cell, wherein: when the engineered immune cell encounters a tumor cell, a first plurality of the activating receptors diffuse into a first region on the surface of the engineered immune cell and form a first micro-cluster proximal to the tumor cell that promotes a cytotoxic response by the engineered immune cell that results in cytotoxic effects on the tumor cell; and when the engineered immune cell encounters a normal cell, a second plurality of the activating and blocking receptors diffuse into a second region on the surface of the engineered immune cell and form a second micro-cluster proximal to the normal cell, wherein the blocking receptors in the second micro-cluster inhibit cytotoxic effects on the normal cell.

The activating receptors in the first micro-cluster may bind to cognate activating ligands on the tumor cell, and the activating and blocking receptors in the second micro-cluster may bind to cognate activating and blocking ligands on the normal cell. When the immune cell encounters a normal cell, the second micro-cluster may mediate formation of a complementary cluster of ligands on the normal cell. Binding of the blocking receptors in the second micro-cluster to the cognate blocking ligands on the normal cell may cause the engineered immune cell to exhibit reduced surface expression of the activating receptor in the second micro-cluster. Binding of the blocking receptors in the second micro-cluster to the cognate blocking ligands on the normal cell may prevent breakup of the second micro-cluster.

In some immune cells of the disclosure, when the immune cell simultaneously contacts a normal cell and a tumor cell, the first plurality of the activating receptors diffuse into the first region and form the first micro-cluster proximal to the tumor cell that promotes the cytotoxic response by the engineered immune cell that results in cytotoxic effects on the tumor cell; and the second plurality of the activating and blocking receptors diffuse into the second region and form the second micro-cluster proximal to the normal cell in which the blocking receptors inhibit cytotoxic effects on the normal cell. Expression of the activating receptor in the second micro-cluster may be reduced after the second micro-cluster forms.

The immune cell may express different concentrations of the activating and blocking receptors based on a ratio of a quantity of the activating ligand to a quantity of a blocking ligand expressed in a normal cell of a patient. The ratio of the concentration of blocking receptors expressed to activating receptors expressed is less than or equal to 1.

In some immune cells of the disclosure, the blocking receptors do not bind to the cognate blocking ligands until the activating receptors bind to the cognate activating ligands.

The present disclosure provides methods for treating cancer using the immune cells disclosed herein. A method for treating cancer may include providing an engineered immune cell to a patient, the engineered immune cell comprising activating and blocking cell-surface receptors.

When the engineered immune cell encounters a normal cell, a first plurality of the activating and blocking receptors collect into a micro-cluster within a region of the cell-surface of the engineered immune cell proximal to the normal cell, wherein binding of one of the blocking receptors in the micro-cluster to a blocking ligand on the normal cell inhibits breakup of the micro-cluster, and wherein the engineered immune cell kills tumor cells that exhibit an activating ligand bound by the activating receptor and do not exhibit the blocking ligand such that the blocking receptor remains unbound.

When the immune cell simultaneously contacts a normal cell and a tumor cell, a first plurality of the activating receptors may diffuse into the first region and form the first micro-cluster proximal to the tumor cell that promotes the cytotoxic response by the engineered immune cell that results in cytotoxic effects on the tumor cell, and a second plurality of the activating and blocking receptors may diffuse into the second region and form the second micro-cluster proximal to the normal cell, wherein binding of one of the blocking receptors in the second micro-cluster to a first ligand on the normal cell inhibits breakup of the micro-cluster.

Binding of the blocking receptors in the second micro-cluster to the first ligands on the normal cell inhibits the cytotoxic effects on the normal cell. The cytotoxic effects on the tumor cell may be localized proximal to the first micro-cluster.

Binding of the blocking receptor to the first ligand on the normal cell may cause a plurality of the first ligand on the normal cell to diffuse into a region proximal to the immune cell and form a complementary micro-cluster. Binding of the blocking receptors in the micro-cluster to the first ligand on the normal cell may cause the engineered immune cell to exhibit reduced surface expression of the activating receptor in the micro-cluster. The reduced surface expression may be reversible.

The immune cell may express different concentrations of the activating and blocking receptors based on a ratio of a quantity of the first ligand to a quantity of the second ligand expressed on a normal cell. The ratio of the concentration of blocking receptors to activating receptors expressed by the immune cell may be less than or equal to 1.

In certain methods of the disclosure, the blocking receptors in the micro-cluster do not bind to the first ligands until the activating receptors bind to the second ligands on the normal cell.

In a further aspect, the present disclosure provides engineered immune cells and methods of making and using them wherein the immune cells comprise a hinge that modulates an effect of the blocking signal and/or receptors.

Thus, the present disclosure provides a method of producing an engineered immune cell, the method including, causing an immune cell to express cell surface activating receptors and blocking receptors, wherein the blocking receptors comprise a selected hinge. Binding of the activating receptors to activating ligands on a target cell triggers an activating signal that promotes a cytotoxic response by the immune cell. Binding of the blocking receptors to blocking ligands on a non-target cell causes the blocking receptors to trigger a blocking signal that inhibits the activating signal. The selected hinge is selected to modulate an effect of the blocking signal on the activating signal.

In certain methods, the selected hinge comprises a peptide having a certain length, and the length of the peptide modulates the effect of the blocking signal on the activating signal. The effect of the blocking signal on the activating signal may be an increased inhibition of the activating signal. The increased inhibition of the activating signal may increase a half maximal effective concentration ($EC_{50}$) of the activating ligand for the activating receptors to promote the cytotoxic response.

In certain methods and immune cells of the disclosure, cross-talk and/or structure function interactions between the hinge of the blocking receptor and the activating receptor further impart different signal strengths for the blocking receptor.

The effect of the blocking signal on the activating signal may be a decreased inhibition of the activating signal, and the length of the peptide is less than about 24 amino acids.

In certain aspects of the disclosure, the engineered immune cell is caused to express the blocking and activating receptors at a ratio, and the ratio blocking receptors to activating receptors expressed is decreased as the length of the peptide of the selected hinge is increased. The peptide may further have a degree of flexibility, and the peptide's length and degree of flexibility modulate the effect of the blocking signal on the activating signal.

The selected hinge may be selected from hinges that each have a known effect on the $EC_{50}$ of the activating ligand for the activating receptors to promote the cytotoxic response. The length of the peptide of each hinge that may have a known effect on the $EC_{50}$ of the activating ligand is between 10 and 64 amino acids in length. The peptide of the selected hinge may be at least 24 amino acids in length. The peptide of the selected hinge may be at least 64 amino acids in length. In certain aspects, the hinge having a peptide of 64 amino acids in length causes at least a fifty-fold increase in the $EC_{50}$ relative to a hinge having a peptide of 10 amino acid in length. In certain aspects, the hinges that each have a known effect on the EC50 comprise hinges 2B1, 2B1 truncated, PD-1, CTLA4, BTLA, SEQ ID NO: 392, SEQ ID NO: 393, SEQ ID NO: 394, SEQ ID NO: 395, SEQ ID NO: 396 and SEQ ID NO: 397.

In certain aspects of the disclosure, the length of the peptide increases surface expression of the blocking receptor.

In certain aspects, the hinge peptide is derived from leukocyte immunoglobulin-like receptor subfamily B member 1 (LILRB1).

In certain aspects of the disclosure, the hinge comprises a peptide having a degree of flexibility, and the peptide's degree of flexibility modulates the effect of the blocking signal on the activating signal. The peptide may be a flexible peptide and the effect of the blocking signal on the activating signal is an increased inhibition of the activating signal. The flexible peptide may comprise glycine-glutamine repeats and/or glycine-serine repeats.

In certain aspects, the hinge comprises a rigid peptide, and the peptide and the effect of the blocking signal on the activating signal is reduced inhibition of the activating signal. The rigid peptide may include, for example, an alpha-helix, repeats of (XP) where X is any amino acid, and/or repeats consisting of alanine, glutamic acid, and lysine.

In certain aspects, the present disclosure provides engineered immune cells, and methods of making and using the same, wherein activating and blocking receptors are spaced apart by at least an average minimum distance on the immune cell surface.

Thus, in certain aspects, the disclosure provides a method of producing an engineered immune cell, the method including, causing an immune cell to express cell surface activating and blocking receptors. Binding of the activating receptor to an activating ligand on a target cell triggers an activating signal that promotes a cytotoxic response by the engineered immune cell. Binding of the blocking receptor to a blocking ligand on a non-target cell causes the blocking receptor to trigger a blocking signal that inhibits the activating signal. Wherein the receptors remain spaced apart by at least an average minimum distance on the immune cell surface.

The blocking signal of a blocking receptor may invert to an activating signal when a blocking receptor is spaced at a distance less than the average minimum distance from the activating receptor.

In certain aspects, the method also includes determining the distance less than the average minimum distance at which the blocking signal inverts.

In certain methods, the average minimum distance is about 100-1000 angstroms. In certain methods, the average minimum distance is about between about 100 to 200, 200 to 300, 300 to 400, 400 to 500, 500 to 600, 600 to 700, 700 to 800, 800 to 900, or 900 to 1000 angstroms. In certain methods, the average minimum distance is greater or equal to 200 angstroms. In certain methods, the average minimum distance is about 200 angstroms.

In certain methods, each receptor has a ligand binding domain (LBD), a hinge, a transmembrane domain, and an intracellular domain (ICD).

Certain methods further include covalently or non-covalently linking the receptors via a spacer such that the receptors are separated by a known spacing. The spacer may comprise a C- or N-terminal fusion. The receptors may be linked to the spacer via the LBD or ICD of each receptor. The receptors may be linked to the spacer at their respective hinge. The spacer may comprise one or more moieties that allow non-covalent binding of the receptors at their respective hinge. The spacer may comprise, for example, two moieties, that are independently fused to the LBD, ICD, or hinge of each receptor. The receptors may be linked via a spacer that comprises a non-covalent interacting motif that mediates protein-protein interaction, such as leucine zipper. The receptors may be covalently attached via the spacer, and the spacer may comprise a cleavable linker such as a disulfide linker.

In certain aspects, the receptors are linked via a spacer that comprises a rigid peptide linker. The rigid peptide may include, for example, an alpha-helix, repeats of XP where X is any amino acid, and/or repeats consisting of alanine, glutamic acid, and lysine.

In certain aspects, the receptors have physiochemical properties that prevent the receptors from being spaced at a distance less than the average minimum distance. The physiochemical properties may include, for example, opposite charges engineered by design on the receptor sequences, leading to attraction, compared to neutral or similar charges. The physiochemical properties may also or alternatively include, for example, steric effects, non-covalent interactions, and/or van der Waals interactions.

In certain aspects, the present disclosure includes an engineered immune cell comprising a cell surface activating receptor and a cell surface blocking receptor, wherein each of the cell surface activating receptor and the cell surface blocking receptor comprise physiochemical properties that prevent the cell surface activating receptor and the cell surface blocking receptor from being spaced at a distance less than an average minimum distance.

In certain aspects, the average minimum distance is about 100-1000 angstroms. In certain methods, the average minimum distance is about 1000, 900, 800, 700, 600, 500, 400, 300, 200, or 100 angstroms. In certain methods, the average minimum distance is greater or equal to 200 angstroms. In certain methods, the average minimum distance is about 200 angstroms.

In certain aspects, the receptors have physiochemical properties that prevent the receptors from being spaced at a distance less than the average minimum distance. The physiochemical properties may include, for example, opposite charges engineered by design on the receptor sequences, leading to attraction, compared to neutral or similar charges. The physiochemical properties may also or alternatively include, for example, steric effects, non-covalent interactions, and/or van der Waals interactions.

In a further aspect, the present disclosure provides an engineered immune cell comprising a cell surface activating receptor, a cell surface blocking receptor, and a spacer operably associated with the cell surface activating receptor and the cell surface blocking receptor, wherein the spacer is configured to maintain the cell surface activating receptor and the cell surface blocking receptor spaced apart by at least an average minimum distance on the immune cell surface.

In certain aspects, the average minimum distance is about 100-1000 angstroms. In certain methods, the average minimum distance is about 1000, 900, 800, 700, 600, 500, 400, 300, 200, or 100 angstroms. In certain methods, the average minimum distance is greater or equal to 200 angstroms. In certain methods, the average minimum distance is about 200 angstroms.

In certain aspects, each receptor of the engineered immune cell has a ligand binding domain (LBD), a hinge, a transmembrane domain, and an intracellular domain (ICD).

The spacer may covalently or non-covalently link the receptors such that the receptors are separated by a known spacing. The spacer may comprise a C- or N-terminal fusion. The receptors may be linked to the spacer via the LBD or ICD of each receptor. The receptors may be linked to the spacer at their respective hinge. The spacer may comprise one or more moieties that allow non-covalent binding of the receptors at their respective hinge. The spacer may comprise, for example, two moieties that are independently fused to the LBD, ICD, or hinge of each receptor. The receptors may be linked via a spacer that comprises a non-covalent interacting motif that mediates protein-protein interaction, such as leucine zipper. The receptors may be covalently attached via the spacer, and the spacer may comprise a cleavable linker such as a disulfide linker.

In certain aspects, the receptors are linked via a spacer that comprises a rigid peptide linker. The rigid peptide may include, for example, an alpha-helix, repeats of XP where X is any amino acid, and/or repeats consisting of alanine, glutamic acid, and lysine.

In a further aspect, the disclosure provides a method for treating cancer that includes providing an engineered immune cell to a patient, wherein the engineered immune cell comprises an activating receptor and a blocking receptor, each expressed on a surface of the engineered immune cell. The activating receptor triggers a cytotoxic signal that promotes a cytotoxic response of the engineered immune cell when the activating receptor binds a first ligand of a target cell. The blocking receptor sends an interfering signal that inhibits the cytotoxic response of the engineered immune cell when the blocking receptor binds a second ligand of the target cell. The receptors remain spaced apart by at least an average minimum distance on the immune cell surface.

In certain methods, the average minimum distance is about 100-1000 angstroms. In certain methods, the average minimum distance is about 1000, 900, 800, 700, 600, 500, 400, 300, 200, or 100 angstroms. In certain methods, the average minimum distance is greater or equal to 200 angstroms. In certain methods, the average minimum distance is about 200 angstroms.

In certain methods, the receptors possess physiochemical properties that prevent the cell surface activating receptor and the cell surface blocking receptor from being spaced at a distance less than an average minimum distance.

In certain aspects, the receptors have physiochemical properties that prevent the receptors from being spaced at a distance less than the average minimum distance. The physiochemical properties may include, for example, opposite charges engineered by design on the receptor sequences, leading to attraction, compared to neutral or similar charges. The physiochemical properties may also or alternatively include, for example, steric effects, non-covalent interactions, and/or van der Waals interactions.

In certain aspects, the immune cell includes a spacer operably associated with the cell surface activating receptor and the cell surface blocking receptor, wherein the spacer is configured to maintain the cell surface activating receptor and the cell surface blocking receptor spaced apart by at least an average minimum distance on the immune cell surface.

In certain methods, each receptor has a ligand binding domain (LBD), a hinge, a transmembrane domain, and an intracellular domain (ICD).

The spacer may covalently or non-covalently link the receptors such that the receptors are separated by a known spacing. The spacer may comprise a C- or N-terminal fusion. The receptors may be linked to the spacer via the LBD or ICD of each receptor. The receptors may be linked to the spacer at their respective hinge. The spacer may comprise one or more moieties that allow non-covalent binding of the receptors at their respective hinge. The spacer may comprise, for example, two moieties that are independently fused to the LBD, ICD, or hinge of each receptor. The receptors may be linked via a spacer that comprises a non-covalent interacting motif that mediates protein-protein interaction, such as leucine zipper. The receptors may be covalently attached via the spacer, and the spacer may comprise a cleavable linker such as a disulfide linker.

DETAILED DESCRIPTION

Figure 1:
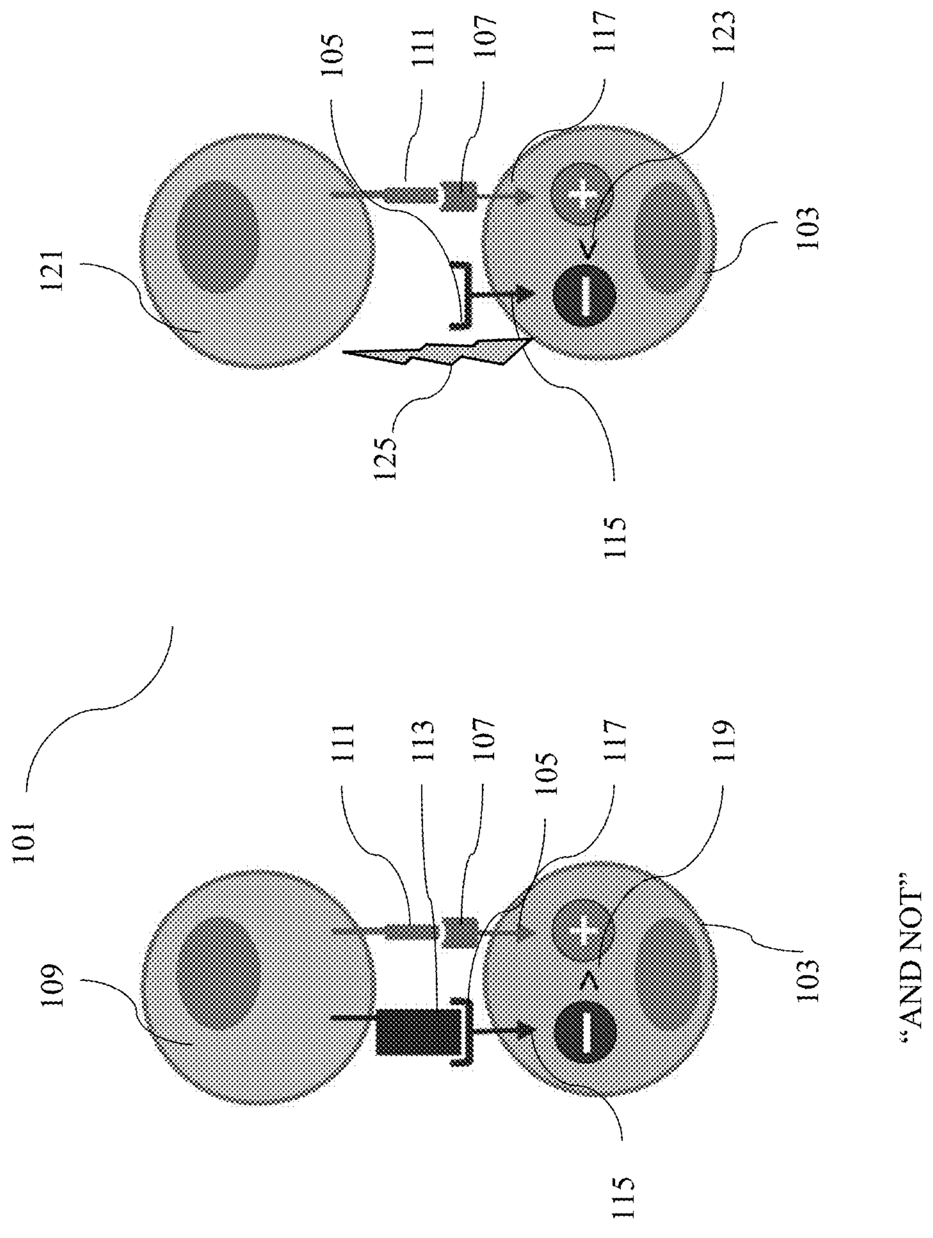
FIG. 1 shows a schematic of the immune cells expressing activating and blocking receptors.

The present disclosure provides engineered immune cells featuring "AND NOT" Boolean logic by expressing engineered activating and blocking receptors. The cells are designed such that when the activating receptors bind to cognate activating ligands on a target cell, they produce an activating signal. If the strength of the activating signal crosses a threshold, it causes a cytotoxic response by the immune cell, killing the cell expressing the cognate ligands. The second of these receptors is a blocking receptor, which is designed to bind to a cognate blocking ligand on the surface of another cell, thereby activating the receptor and causing it to trigger a blocking signal that blocks the activating signal, which prevents the cytotoxic response. The "AND NOT" Boolean logic engineered into the immune cells of the present disclosure makes them ideal for use as therapeutic agents.

Thus, in an exemplary method of the disclosure, a patient diagnosed with a medical condition, such as cancer, is treated with engineered immune cells that target and kill the patient's cancer cells while preserving their normal, healthy cells. One or more cellular samples may be taken from the patient, such as from a blood draw or tumor biopsy. Target cells, such as tumor cells, are identified in the sample. The identified target cells are assayed to determine the levels of expression of one or more cell-surface ligands. This may include, for example, assessing RNA expression profiles for various cell-surface receptors or using antibody probes that bind to certain cell surface receptors. Assaying target cells may determine, for example, that target cells do not express a certain cell surface ligand due to a loss of heterozygosity.

Then, immune cells, such as T cells, are harvested from the patient. These cells are caused to express engineered activating and blocking receptors. The blocking receptor is designed to bind to a blocking ligand expressed on healthy cells of the patient. This blocking ligand may be chosen because it is lost from cancer cells, e.g., due to loss of heterozygosity. The activating receptor is designed to bind to an activating ligand that is expressed on both healthy cells and cancer cells of the patient.

After the engineered immune cells are proliferated, the cells are administered to the patient. The immune cells are designed such that when an immune cell encounters a cancer cell in the patient's body, the activating receptors bind to activating ligands on the cancer cell. This triggers a cytotoxic immune response by the immune cell that kills the cancer cell. When the immune cell encounters a healthy cell the activating and blocking receptors bind to activating and blocking ligands on the healthy cell. Binding of the blocking receptors to blocking ligands inhibits and blocks the cytotoxic immune response triggered by the activating receptors binding to activating ligands. In this way, the engineered immune cells are designed to limit deleterious effects on non-target cells.

FIG. 1 shows a schematic of this "AND NOT" Boolean logic in the immune cells of the present disclosure. In FIG. 1, the immune cells 103 comprise a blocking receptor 105 and an activating receptor 107. A non-target cell 109 expresses an activating ligand 111 and blocking ligand 113. When the immune cell 103 contacts the non-target cell, the activating receptor 107 binds to the activating ligand 111 triggering an activating signal 117. Concurrently, the blocking receptor 105 binds to the blocking ligand 113, triggering a blocking signal 115. As shown schematically, when the immune cell 103 contacts a non-target cell, the strength of blocking signal is greater than the activating signal 119. Binding both blocking ligands and activating ligands causes the "AND NOT" state in the immune cell. The signal from the blocking receptors blocks the activating signal. As such, the activating signal cannot pass the threshold to trigger a cytotoxic response, which prevents a deleterious effect on the non-target cell expressing both ligands.

Conversely, a target cell 121, such as a tumor cell, expresses a blocking ligand 111, but does not express an activating ligand, or expresses an activating ligand at a lower level compared to the non-target cell 109. Thus, when the immune cell 103 contacts the target cell 121, the activating receptor 107 binds to the activating ligand 111, triggering an activating signal 117. As shown schematically, when the immune cell 103 contacts a non-target cell, the strength of the activating signal is greater than the blocking signal 123.

When the strength of the activating signal crosses an activation threshold, the immune cell produces a cytotoxic response 125 that kills the target cell 121.

Generally, the cognate antigens chosen for the activating receptors are expressed on both target cells, such as tumor cells, and non-target cells. The selected blocking ligands are expressed only by non-target cells, or expressed at lower levels by target cells compared to non-target cells. In this way, when the engineered immune cells contact target cells, the activating receptors bind to the activating ligands, which leads to the cytotoxic response. In contrast, when the engineered immune cells contact non-target cells, the blocking and activating receptors bind to their cognate blocking and activating ligands. This completes the "AND NOT" Boolean logic, thereby blocking the cytotoxic response. This scheme provides the general means by which the engineered immune cells safely kill target cells while limiting effects on non-target cells.

Engineered immune cells have been used as cancer therapies, such as immunotherapies. Traditionally, engineered immune cells have been designed to target molecular targets such as neo-antigens. Neo-antigens are a class of somatic mutant proteins that are mutated during somatic growth of tumors. They provide ideal targets for immune cell therapies because they comprise variants not found on non-target, healthy cells of a patient. However, very few cancers express neo-antigens. Thus, different targets must be pursued to treat most types of cancer using engineered immune cells. However, in prior immune cell therapies that lacked the blocking receptors of the present disclosure, when the immune cells targeted antigens expressed by healthy and non-health cells, severe adverse effects arose due to non-target activity. In cancer immunology, this phenomenon is known as on-target, off-tumor recognition.

The engineered immune cells and receptors of the present disclosure provide greater flexibility in choice of molecular target. The efficacy of the blocking receptor ensures that non-target effects are limited. Thus, the immune cells of the present disclosure can be designed to target widely expressed, cell surface molecules as the activating ligand. Exemplary ligands include a cell adhesion molecule, a cell-cell signaling molecule, an extracellular domain, a molecule involved in chemotaxis, a glycoprotein, a G protein-coupled receptor, a transmembrane, a receptor for a neurotransmitter or a voltage gated ion channel.

Activating receptors of the present disclosure may be configured to target activating ligands that are encoded by genes with essential cellular functions. Advantageously, this can prevent antigen escape, increasing the long-term efficacy of the engineered immune cells as a therapeutic. By selecting activating ligands encoded by genes with essential cellular functions, loss or escape of the ligand, such as through aneuploidy in cancer cells, is less likely. Thus, the activating ligand may be encoded by a gene that is haplo-insufficient, i.e., loss of copies of the gene encoding the ligand are not tolerated by the cell and lead to cell death, or a disadvantageous mutant phenotype. In fact, the engineered immune cells of the present disclosure may be designed to target activating ligands expressed on all cells of patient.

Advantageously, because the immune cells of the present disclosure can be engineered to use widely-expressed activating ligands, several problems can be avoided. For example, prior engineered immune cells often targeted minimally expressed antigens, such as certain neo-antigens. Thus, to ensure an adequate activating signal, prior immune cells were engineered with activating receptors that had very high expression or affinities for their activating ligands.

However, merely increasing the density or affinity of receptors is inadequate to ensure efficacy. High receptor affinity can lead to proportionally severe, toxic effects on non-target cells. It can also hinder an engineered immune cell from disassociating from a target cell, which limits the ability of the immune cell to subsequently bind to and kill other target cells. Further, high affinity can cause receptors to be continually activated. This chronic activation can lead to immune cell exhaustion, reduced generation and persistence, increasing differentiation to undesired phenotypes, and activation-induced immune cell death. Increasing density can lead to similar effects through ligand-independent, tonic signaling.

Use of widely expressed activating ligands, made safe through the use of a blocking receptor, allows the engineered immune cells of the present disclosure to avoid these potential issues.

The blocking receptor can be designed to bind to a cell surface molecule not expressed on the surface of the target cell, or expressed at sufficiently low levels on a target cell. Thus, where the engineered immune cells are used to treat cancer, the blocking ligand may be chosen based on the loss of heterozygosity (LOH) of the target cancer cells, i.e., the cancer cells no longer express the ligand due to a loss of genetic material from one of the homologous chromosomes. Exemplary genes whose expression is frequently lost in cancer cells, for example due to LOH, include, HLA class I alleles, minor histocompatibility antigens (MiHAs), and Y chromosome genes (in males where the homologous chromosome is the X chromosome).

As will be discussed, the immune cells of the present disclosure possess several features that leverage the general nature of the "AND NOT" Boolean logic, to provide effective, target-specific effects while minimizing deleterious non-target effects.

Reduced Activator Expression

Surprisingly, the engineered immune cells of the present disclosure, which express activating and blocking receptors, can be designed to exhibit reduced surface expression of activating receptors when they contact non-target cells.

Figure 2:
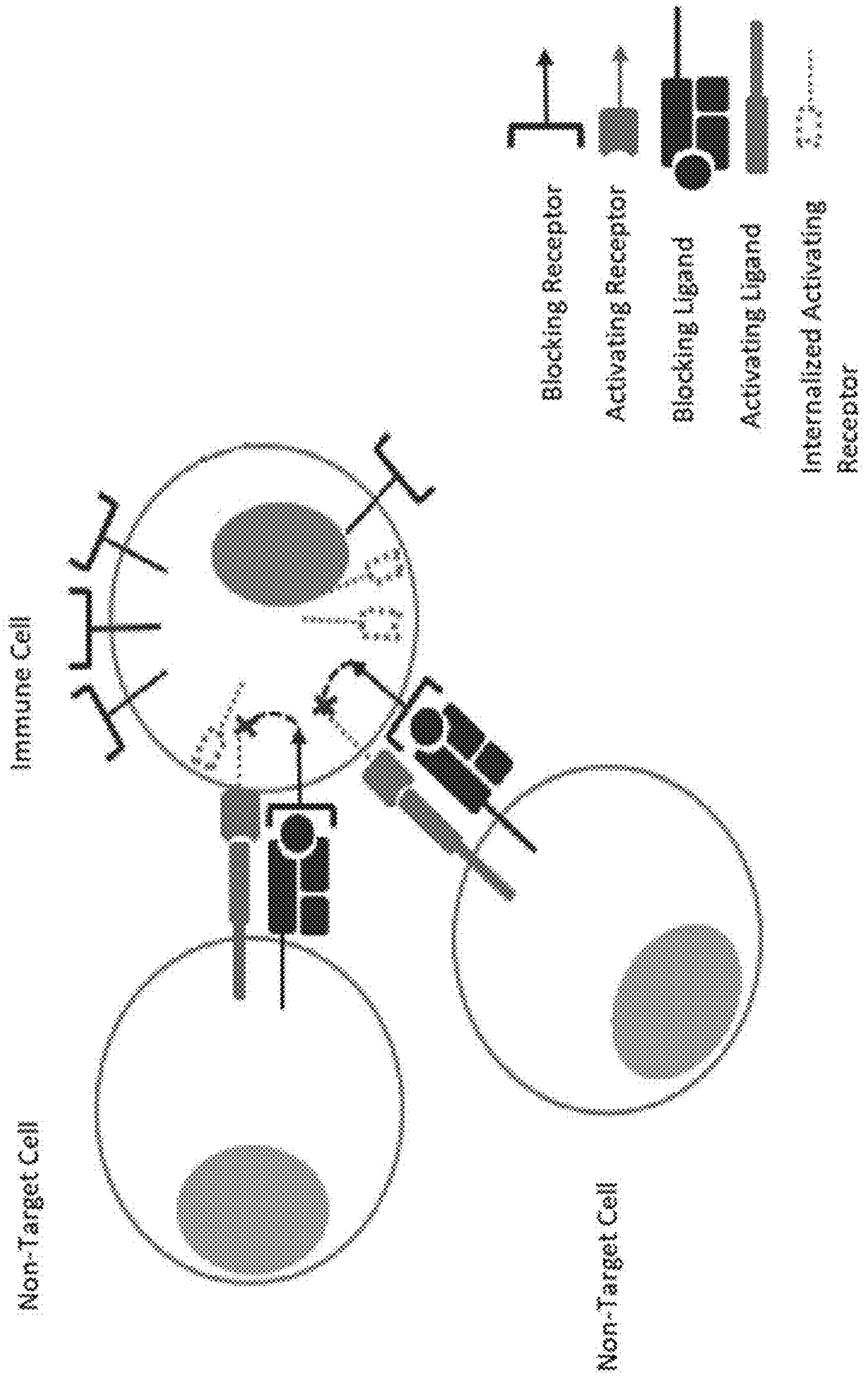
FIGS. 2-3 show reduced surface expression of activating receptors and reversibility of reduced surface expression of activating receptors.

This ability to reduce surface expression is shown schematically in FIG. 2. When an engineered immune cell contacts non-target cells, the blocking receptors and activating receptors bind to their cognate activating ligands and blocking ligands expressed on the non-target cell. As explained, this causes the blocking signal to inhibit the activating signal. Further, activation of the blocking receptors causes reduced surface expression of the activating receptors. The activating receptors may be internalized, such that they are no longer on the surface of the immune cell and able to interact with activating ligands. As a result, the threshold to trigger a cytotoxic response by the immune cell is raised. Thus, the immune cells may temporarily exhibit a reduced propensity to kill cells, which can increase the therapeutic window of the cells.

Figure 3:
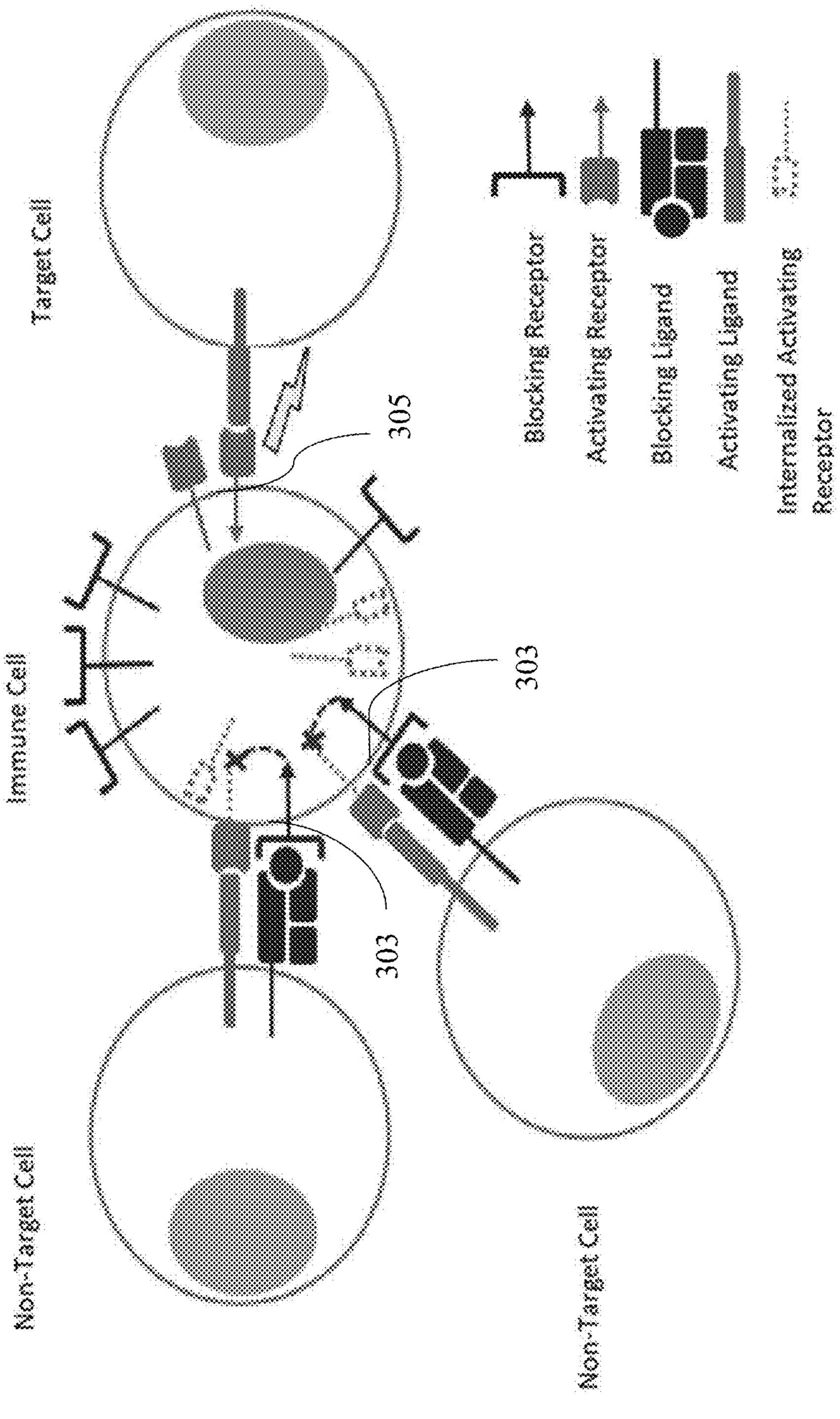

As shown in FIG. 3, when the immune cell contacts a target cell, this reduced surface expression of the activating receptor does not occur and/or is reversed. Thus, when the immune cell encounters a target cell, the activating receptors bind to activating ligands. This provides the activating signal, but also causes the immune cell to reverse the reduced surface expression of the activating receptors. When the activating receptors are expressed on the surface of the immune cell at higher numbers, the activation threshold to trigger the cytotoxic response is reduced. Thus, immune cells in contact with target cells may temporarily exhibit an increased propensity to kill cells.

In certain immune cells of the disclosure, the reduced and/or regained expression of the activating receptor can be localized to a region of the immune cell surface proximate to a target or non-target cell. Thus, returning to FIG. 3, when the immune cell contacts a non-target cells, reduction of the activating receptors occurs in regions 303 proximate to the non-target cells. This can desensitize the immune cell in the regions 303 proximate to each non-target cell, which raises the activation threshold to trigger the cytotoxic response. Similarly, the immune cell can contact a target cell, and reduced surface expression of the activating receptor is reversed and/or does not occur in a region(s) 305 proximate to the target cell(s). This allows the region 305 proximate to the target cell to experience a local activation signal sufficient to trigger a localized cytotoxic response.

Advantageously, these localized responses can occur as an immune cell simultaneously and/or sequentially contacts target and non-target cells. Thus, as shown in FIG. 3, the immune cells can provide an activating signal localized to a region 305 proximate to a target cell, while also modulating expression of the activating receptor to reduce the activation threshold in the same region. Simultaneously, the immune cell can provide localized blocking signals and localized, reduced expression of the blocking receptor.

Reducing surface expression of the activating receptors. when not in contact with target cells. confers several advantages to the immune cells of the present disclosure. For example, if an immune cell circulates away from target cells, such as in a tumor, the immune cell is presumably more likely to contact non-target cells. By reducing the surface expression of the activating receptor in response to a lack of target cells, the immune cell increases its activation threshold, which can temporarily reduce the propensity of the immune cell to trigger a cytotoxic response. This designed feature of the engineered immune cells acts as a "safe mode", which enhances the safety and protective effects provided by the "AND NOT" Boolean logic, and further limits deleterious effects caused by the immune cells.

Further, while in this "safe mode", fewer activating receptors are available to activate. Thus, the immune cells of the present disclosure are less likely to experience chronic activation or ligand-independent tonic signaling. As a result, the immune cells are less susceptible to exhaustion, differentiation, and activation-induced immune cell death, while concurrently exhibiting high generation and persistence.

An additional and important feature of this reduced expression is that it does not extend to the engineered blocking receptors. Only the engineered activating receptors experience appreciable amounts of reduced expression. This ensures the safety profile of the immune cells of the present disclosure is maintained.

Thus, the present disclosure provides an engineered immune cell with an activating receptor and blocking receptor expressed on a surface of the engineered immune cell, wherein binding of the activating receptor to an activating ligand on a target cell promotes a cytotoxic response by the engineered immune cell, and binding of the blocking receptor to a blocking ligand causes the engineered immune cell to exhibit reduced surface expression of the activating receptor.

The present disclosure also provides a method for treating a cancer that includes providing an engineered immune cell to a patient, wherein the engineered immune cell comprises an activating receptor and a blocking receptor, each expressed on a surface of the engineered immune cell. When the engineered immune cell encounters a tumor cell of the patient, the activating receptor binds to an activating ligand on the tumor cell while the blocking receptor remains unbound, thereby promoting a cytotoxic response by the engineered immune cell that results in a cytotoxic effect on the tumor cell. When the engineered immune cell encounters a normal cell of the patient the blocking receptor binds to a blocking ligand on the normal cell and causes the engineered immune cell to exhibit reduced surface expression of the activating receptor, thereby causing a signal from the blocking receptor to dominate a signal from the activating receptor and prevent the cytotoxic response by the engineered immune cell.

Micro-Clusters

A further advantageous feature of the engineered immune cells disclosed herein is that the cells and receptors can be designed such that the activating and blocking receptors form micro-clusters on the surface of the immune cell. This ability to form micro-clusters provides an engineered immune cell with the ability to sense its proximity to target/non-target cells and provide an appropriate, localized response.

Figure 20:
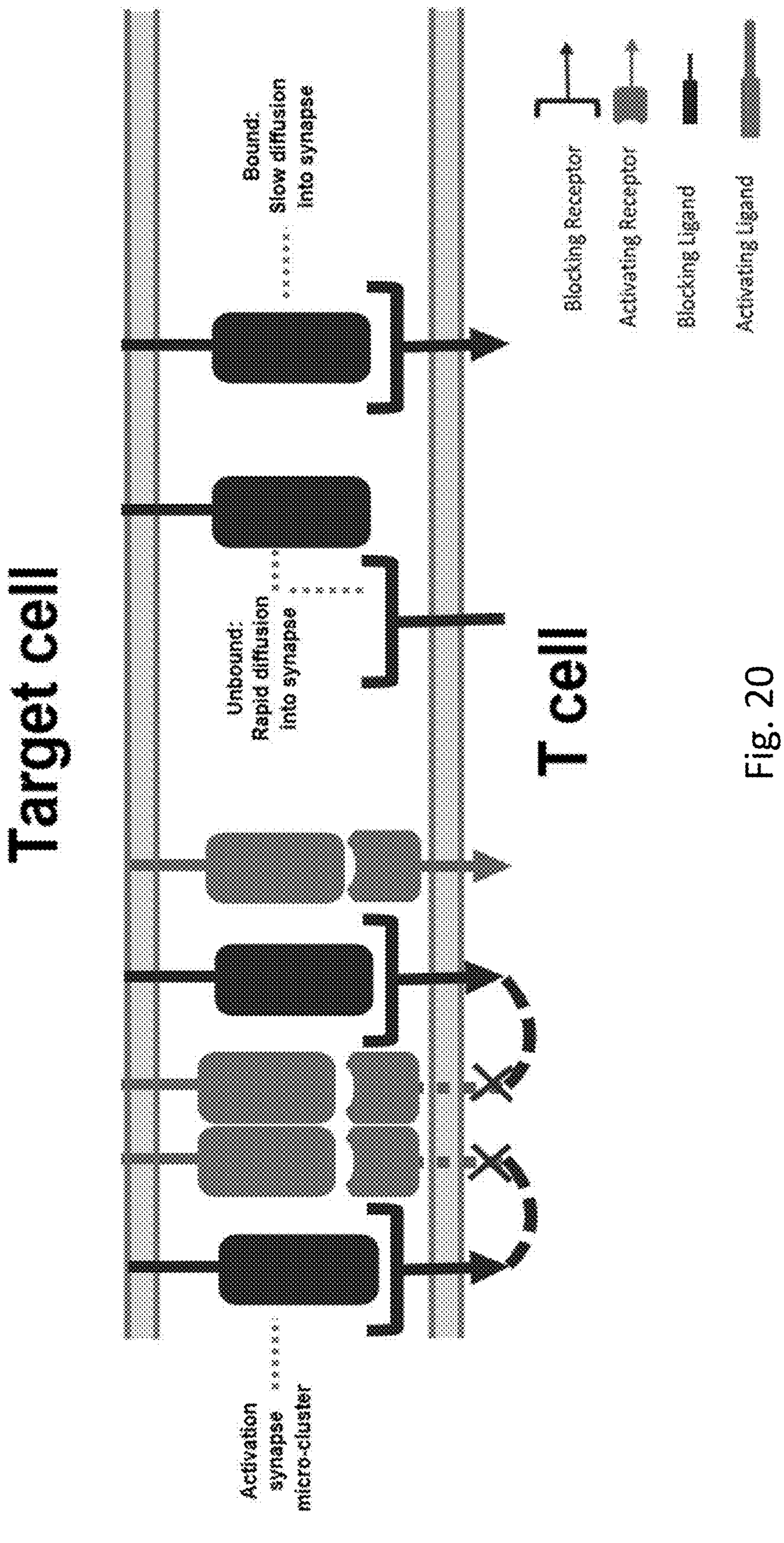
FIG. 20 shows a schematic of micro-clustering.

FIG. 20 shows a schematic of the micro-clustering behavior. When an immune cell encounters a target or non-target cell, its activating/blocking receptors bind to cognate ligands on the encountered cell(s). Cross-talk between these bound receptors and unbound receptors on the surface of the immune cell causes the unbound receptors to diffuse to a region on the immune cell surface proximate to the encountered cell(s). When the receptors diffuse into this region, they form a micro-cluster in which the ligand binding domains of the receptors locate in an activation synapse between the immune cell and the encountered cell(s).

Forming a micro-cluster with both activating and blocking receptors ensures that, when the blocking receptors are activated in the presence of an appropriate ligand on a non-target cell, the blocking signal is triggered proximate to the activation signal. This ensures that the blocking receptors can provide a localized inhibitory effect on the activation signal, thereby protecting the non-target cell. Thus, the micro-clusters enhance the "AND NOT" Boolean logic conferred by the activating and blocking receptors.

Advantageously, the engineered immune cells can be configured such that the activating and/or blocking ligands on target and/or non-target cells to experience a similar clustering effect on the surface of the encountered cell(s). Unbound activating and blocking ligands diffuse into an area on the target/non-target cell surface proximate to the immune cell, and become available for binding to a cognate receptor in the activation synapse.

Receptors are held in place on the surface of the immune cell by binding to cognate ligands in the activation synapse. This ensures that the receptors remain confined to a micro-cluster while the immune cell is in contact with a target/non-target cell. Maintaining the receptors within a micro-cluster helps assure that adequate numbers of activating and/or blocking receptors are within a region proximate to an encountered cell(s) to provide the requisite activating or blocking signal. It also increases the relative strength of both the activating and blocking receptors, which widens the therapeutic window of the immune cells of the disclosure.

The ability of the receptors to form micro-clusters also enhances the localized, reduced expression of the activating receptors when an immune cell encounters a non-target cell. By bringing activating and blocking receptors in close proximity, e.g., within the confines of a micro-cluster, the effect of cross-talk between the receptors is increased. This cross-talk leads to localized, reduced expression of the activating receptors in the micro-cluster.

Thus, the present disclosure provides an engineered immune cell comprising activating and blocking receptors on a surface of the engineered immune cell. When the engineered immune cell encounters a tumor cell, a first plurality of the activating receptors diffuse into a first region on the surface of the engineered immune cell and form a first micro-cluster proximal to the tumor cell that promotes a cytotoxic response by the engineered immune cell that results in cytotoxic effects on the tumor cell. When the engineered immune cell encounters a normal cell, a second plurality of the activating and blocking receptors diffuse into a second region on the surface of the engineered immune cell and form a second micro-cluster proximal to the normal cell, wherein the blocking receptors in the second micro-cluster inhibit cytotoxic effects on the normal cell.

The present disclosure also includes a method for treating cancer, the method comprising providing an engineered immune cell to a patient, the engineered immune cell comprising activating and blocking cell-surface receptors. When the engineered immune cell encounters a normal cell, a first plurality of the activating and blocking receptors collect into a micro-cluster within a region of the cell-surface of the engineered immune cell proximal to the normal cell. Binding of one of the blocking receptors in the micro-cluster to a blocking ligand on the normal cell inhibits breakup of the micro-cluster. The engineered immune cell kills tumor cells that exhibit an activating ligand bound by the activating receptor and do not exhibit the blocking ligand such that the blocking receptor remains unbound.

Multiplex and Localized Signaling

Figure 21:
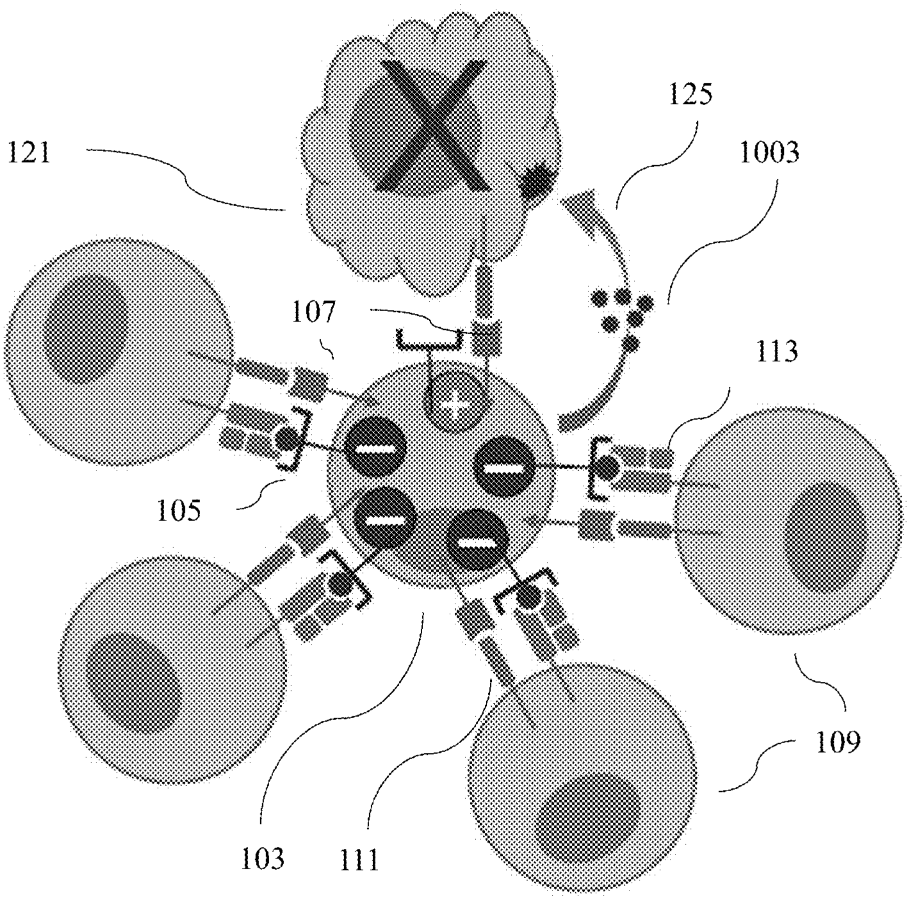
FIG. 21 shows a schematic of multiplex and localized signaling by the activating and blocking receptors.

The engineered immune cells of the present disclosure have been designed to exhibit multiplex and localized activity. A shown in FIG. 21 an engineered immune cell 103 can simultaneously contact both target cells 121 and non-target cells 109. On regions of the immune cell 103 surface proximate to a non-target cell, the activating receptors 107 and blocking receptors 105 bind to activating ligands 111 and blocking ligands 113 on the non-target cell. As a result, a localized blocking signal inhibits a cytotoxic response 125 by the immune cell on the proximate non-target cell. Simultaneously or sequentially, the immune cell 103 can contact a target cell 121. The activating receptor 107 binds to the activating ligand 111 on the target cell 121. This causes a localized cytotoxic response 125, which may release cytotoxic granules 2103. The cytotoxic response only targets the target cell 121. The localized inhibition of the cytotoxic response in areas proximate to the non-target cells 109 protects them from an undesired immune response.

Thus, the present disclosure provides an engineered immune cell that includes activating and blocking receptors on the surface of the cell. When the engineered immune cell encounters a tumor cell and a healthy cell, a first region of the activating and blocking receptors form proximal to the healthy cell and blocking receptors in the first region inhibit cytotoxic effects on the healthy cell. Simultaneously, a second region of the activating and blocking receptors form proximal to the tumor cell and promotes a cytotoxic response by the engineered immune cell that exhibits cytotoxic effects on the tumor cell.

The present disclosure also provides a method for treating cancer that includes providing an engineered immune cell to a patient. The engineered immune cell has activating and blocking cell-surface receptors. When the engineered immune cell encounters a tumor cell and a healthy cell of the patient, a first set of the activating and blocking receptors collect into a first cell-surface region of the engineered immune cell proximal to the healthy cell in which the blocking receptors inhibit cytotoxic effects of the engineered immune cell on the healthy. Simultaneously, a second set of the activating and blocking receptors collect into a second cell-surface region of the engineered immune cell proximal to the tumor cell in which the activating receptors promote a cytotoxic response by the engineered immune cell that kills the tumor cell.

Dominant Blocking Receptors

The engineered immune cells of the present disclosure can be configured to have blocking receptors that produce a blocking signal that can overwhelm and fully inhibit the activating signal from the activating receptors.

Figure 22:
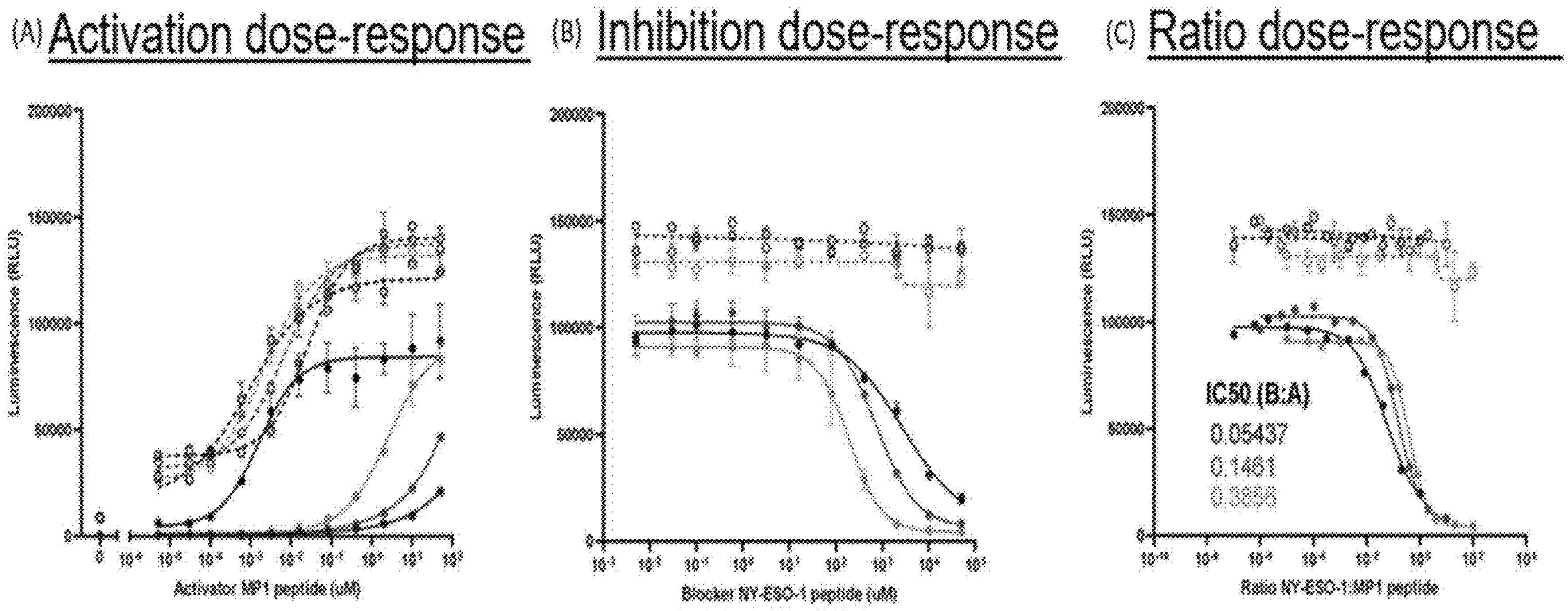
FIG. 22 provides experimental results showing that activity of the blocking receptors is ligand-dependent.

As shown in FIG. 22, which is explained in greater detail below, the cells can be designed to express activating and blocking receptors that, when expressed at equivalent concentrations, it takes less blocking antigen relative activating antigen to inhibit the activating signal. Thus, each blocking receptor can inhibit the activating signal of one or more activating receptors. This means that the blocking signal from a single blocking receptor can dominate and inhibit the activating signal from a single activating receptor. This helps solidify the safety profile of the "AND NOT" Boolean logic used by the immune cells of the present disclosure.

Figure 23:
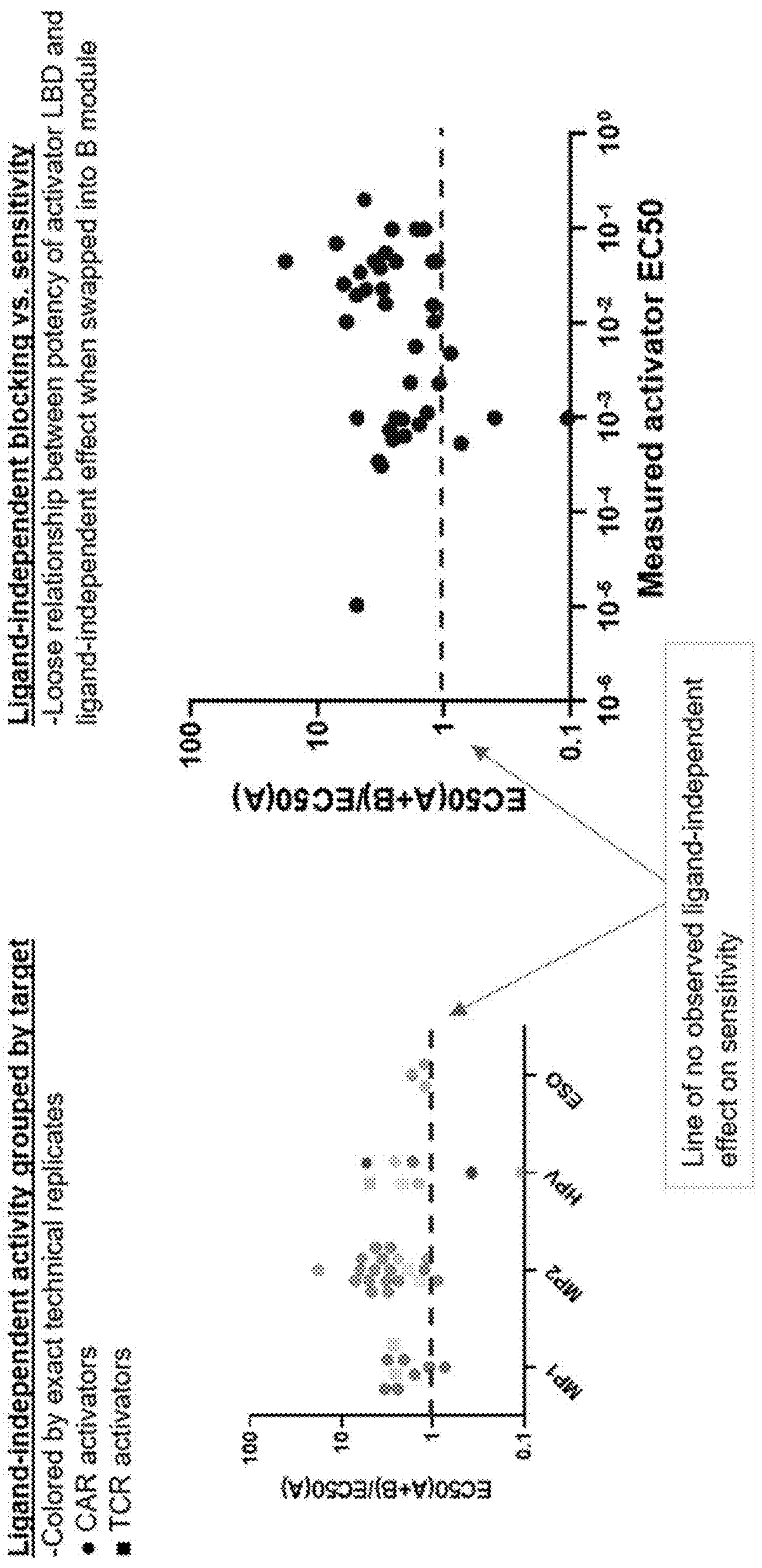
FIG. 23 provides experimental results showing that the blocking receptors cause minimum ligand-independent inhibition of the activating receptors.

As shown in FIG. 23, the blocking receptors can be engineered to provide minimal ligand-independent blocking activity on the activating receptors. As a corollary, the blocking receptors can provide overwhelmingly ligand-dependent activity.

Thus, the immune cells of the present disclosure may include blocking receptors that provide, for example, a less than 10× shift in the $EC_{50}$ of the activating receptors when the immune cells are contacted with the activating ligand in the absence of the blocking ligand. The immune cells of the present disclosure can provide a less than 3× shift in the $EC_{50}$ of the activating receptors when the immune cells are contacted with the activating ligand in the absence of the blocking ligand.

Since the blocking receptors of the present disclosure can provide an overwhelmingly ligand-dependent, dominate blocking signal, the levels of activating ligand and blocking ligand expressed on a non-target cell can be used to inform the appropriate levels of activating and blocking receptor expressed by the engineered immune cells of the present disclosure. The dominate blocking signal provides assurance that ligand quantity can be used as a proxy to inform the levels of activating and blocking receptors that should be expressed in order to assure sufficient inhibition. Moreover, the ligand-dependent nature of the blocking signal means that the expression of the blocking receptor will require little to no adjustment to prevent unintended increases to the $EC_{50}$ of the activating receptors in the absence of the blocking ligand.

Thus, the present disclosure provides methods for producing engineered immune cells that express activating and blocking receptors based on a ratio of a quantity of activating ligands to a quantity of blocking ligands that are expressed in a normal, non-tumor cell of a patient. The activating and blocking receptors may be expressed at a ratio based upon the ratio of the quantity of activating ligands to the quantity of blocking ligands expressed by the normal cell.

The present disclosure also provides an engineered immune cell with an activating receptor on a surface of the engineered immune cell. Binding of the activating receptor to an activating ligand on a target cell causes the activating receptor to trigger an activating signal that promotes a cytotoxic response by the engineered immune cell. The cell also has a blocking receptor. Binding of the blocking receptor to a blocking ligand on a target cell causes the blocking receptor to trigger an inhibitory signal stronger than the activating signal such that the inhibitory signal dominates and blocks the activating signal from the activating receptor, thereby preventing a localized cytotoxic response by the engineered immune cell.

The disclosure further includes a method for treating cancer, the method comprising providing an engineered immune cell to a patient. The engineered immune cell comprises an activating receptor and a blocking receptor, each expressed on a surface of the engineered immune cell. When the engineered immune cell encounters a tumor cell, the activating receptor binds to an activating ligand on the tumor cell and the activating receptor triggers an activating signal in the engineered immune cell that promotes a cytotoxic response by the engineered immune cell that results in a cytotoxic effect on the tumor cell. When the engineered immune cell encounters a normal cell, the activating receptor binds to the activating ligand on the normal cell and the blocking receptor binds to a blocking ligand on the normal cell. This leads to the activating receptor triggering an activating signal in the engineered immune cell and the blocking receptor triggering an inhibitory signal in the engineered immune cell that is stronger than the activating signal, such that the inhibitory signal dominates and blocks the activating signal from the activating receptor, thereby preventing a localized cytotoxic response by the engineered immune cell.

Modulating Activating and Blocking Signals of Receptors

The present disclosure also provides strategies for engineering receptors in a manner that modulates receptor signal strength to ensure strong activation signals and sufficient blocking signals.

Figure 24:
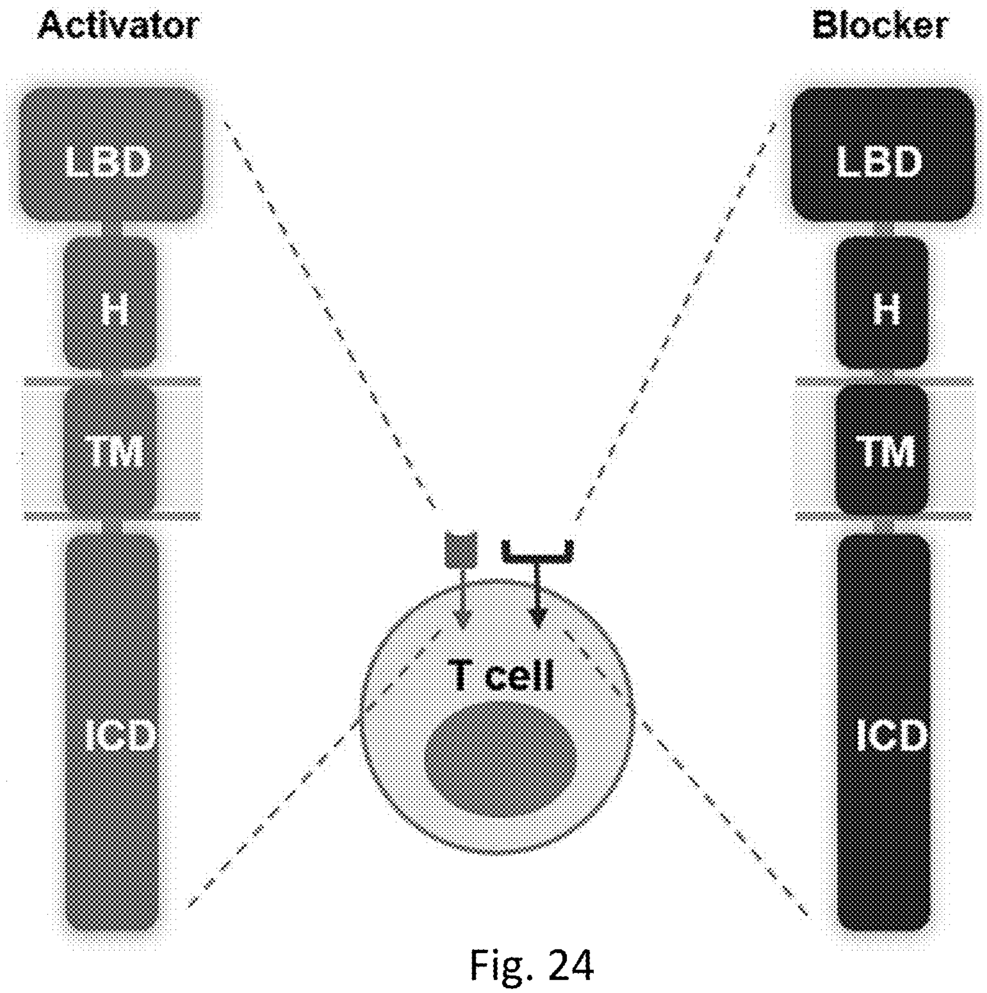
FIG. 24 provides a schematic of the activating and blocking receptors.

FIG. 24 shows a schematic of the blocking and activating receptors of the present disclosure. In general, each type of receptor can comprise four parts, the ligand binding domain ("LBD"), the hinge ("H"), the transmembrane domain ("TM"), and the intracellular domain ("ICD"). Each of these four parts can have an impact on the structure-activity relationship of each receptor. By altering these parts, the behavior of each receptor can be finely tuned to exhibit desired activity. For example, altering these parts can cause the receptors to exhibit varying specificity and affinity for cognate ligands, strengths of activating and/or blocking signals, levels of cross-talk between receptors, and/or receptor surface expression.

The hinge is an extracellular domain between a receptor's extracellular ligand binding domain and transmembrane domain and/or intracellular domain. Surprisingly, the Inventors of the present disclosure have found that, for the activating receptor, a wide variety of hinge lengths and sequences are tolerated. Thus, changes to the activating receptor hinge can provide relatively little change to the structure activity relationship of the activating receptor. For example, changes to the hinge were shown to cause only minimal contributions to the activating receptors' $EC_{50}$, baseline signaling, and maximum signaling.

In contrast, the Inventors of the present disclosure have found that modifications to the hinge can be used to modulate the activity of the blocking receptor, including increases in the surface expression of the blocking receptor and blocking signal strength. Thus, a feature of the present disclosure is that the blocking receptor can be designed using interchangeable hinges that connect an extracellular ligand binding domain to a transmembrane domain and/or an intracellular domain.

Figure 25:
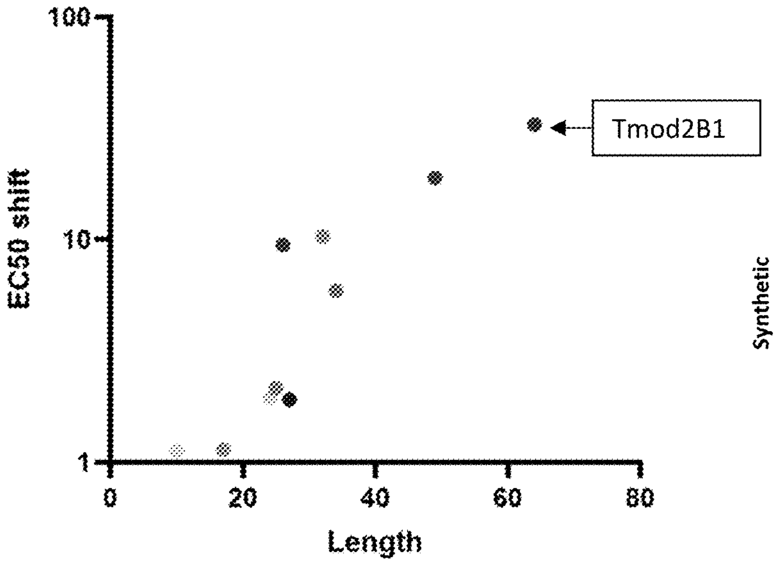
FIG. 25 provides experimental results for the effect the hinge of the blocking receptor has on blocking strength.

The hinges can be designed to have different lengths and flexibilities. As shown in FIG. 24, flexible hinges inure blocking receptors with a greater blocking strength compared to rigid hinges. However, a greater change to blocking strength can be provided by changing the length of the hinge. As shown in FIG. 25, lengthening a hinge from about 25 amino acids to about 35 amino acids confers a significant increase in blocker strength. This increase becomes more dramatic, as the hinge length approaches 65 amino acids in length. As also shown in FIG. 25, the relative flexibility/rigidity of a hinge also impacts the strength of a blocker. Although, this impact is reduced compared to that provided by the hinge length.

Thus, the blocking receptors can be designed with longer and/or more flexible hinges to increase the strength of the blocking receptor's signal or surface expression. In contrast, the blocking receptor can be engineered with shorter and/or more rigid hinges to decrease the strength of the blocking receptor's signal or surface expression. The blocking receptor can be configured to use a hinge selected from a group of hinges that have a known impact on the $EC_{50}$ of the activating ligand for the activating receptor to cause the immune cell to trigger a cytotoxic response. This allows pairs of blocking and activating receptors to be chosen or engineered to exhibit a desired level of activation/inhibition.

Advantageously, as the activating receptor can tolerate a wide variety of hinges, the activating receptors can be engineered with hinges that interact with a blocking receptor at the structural level. Different activator hinges may provide varying levels of interaction with a specific blocker. Thus, various activator hinges can be tested with a particular blocking receptor to determine the identity of activating receptor hinges that lead to increased blocking by a particular blocking receptor. Such testing may include, for example, changing the hinge of an activating receptor and measuring the blocking receptor strength, i.e., the $IC_{50}$, of a particular blocking receptor when a particular activating receptor hinge is used.

Figure 26:
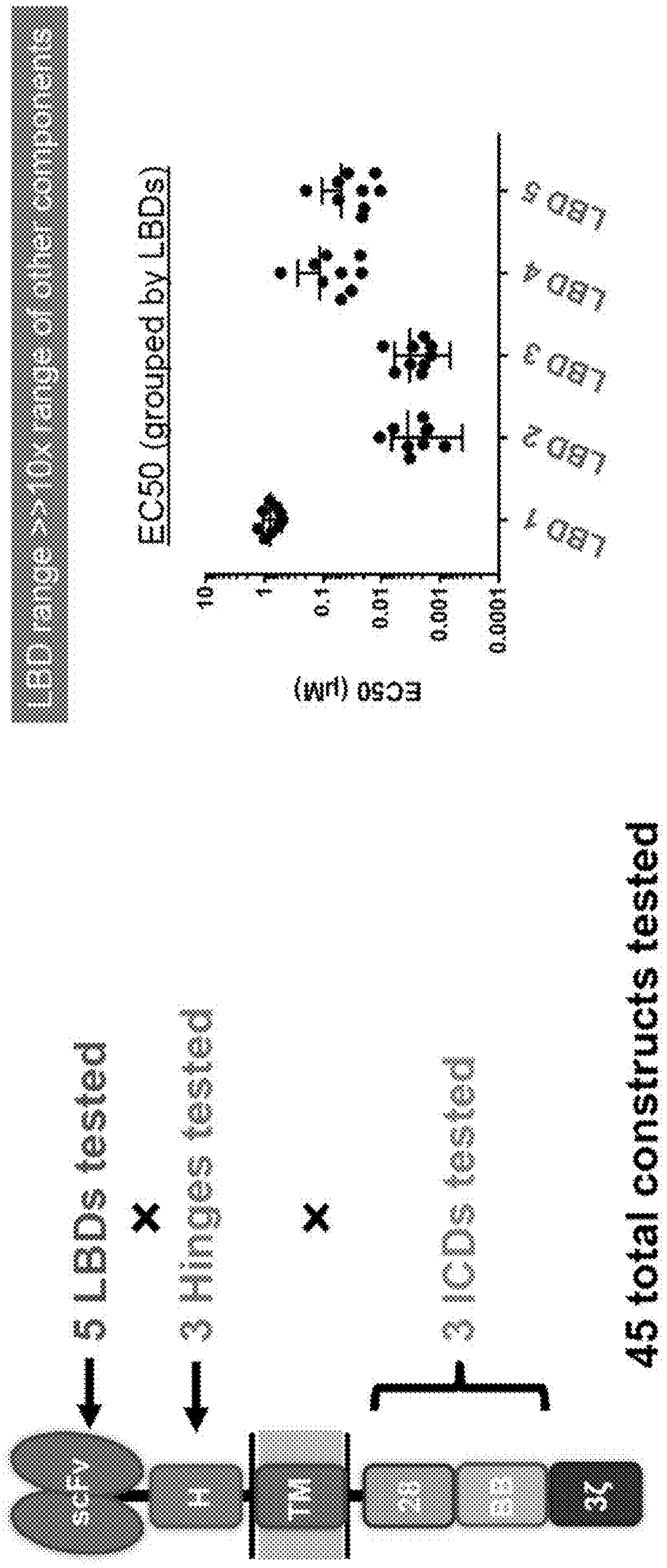
FIG. 26 provides experimental results showing that the identity of the ligand binding domain of the activating receptor drives the activity of the receptor.

The Inventors of the present disclosure found that the identity of the ligand binding domain of the engineered activating receptors has the greatest impact on the structure activity relationship of the receptors. As shown in FIG. 26, different ligand binding domains, which all bind to the same activating ligand, provide effects on the receptors' $EC_{50}$ that differ by orders of magnitude. In contrast, the identity of the hinge and/or intracellular domain provides a smaller impact on the receptors' $EC_{50}$.

Figure 27:
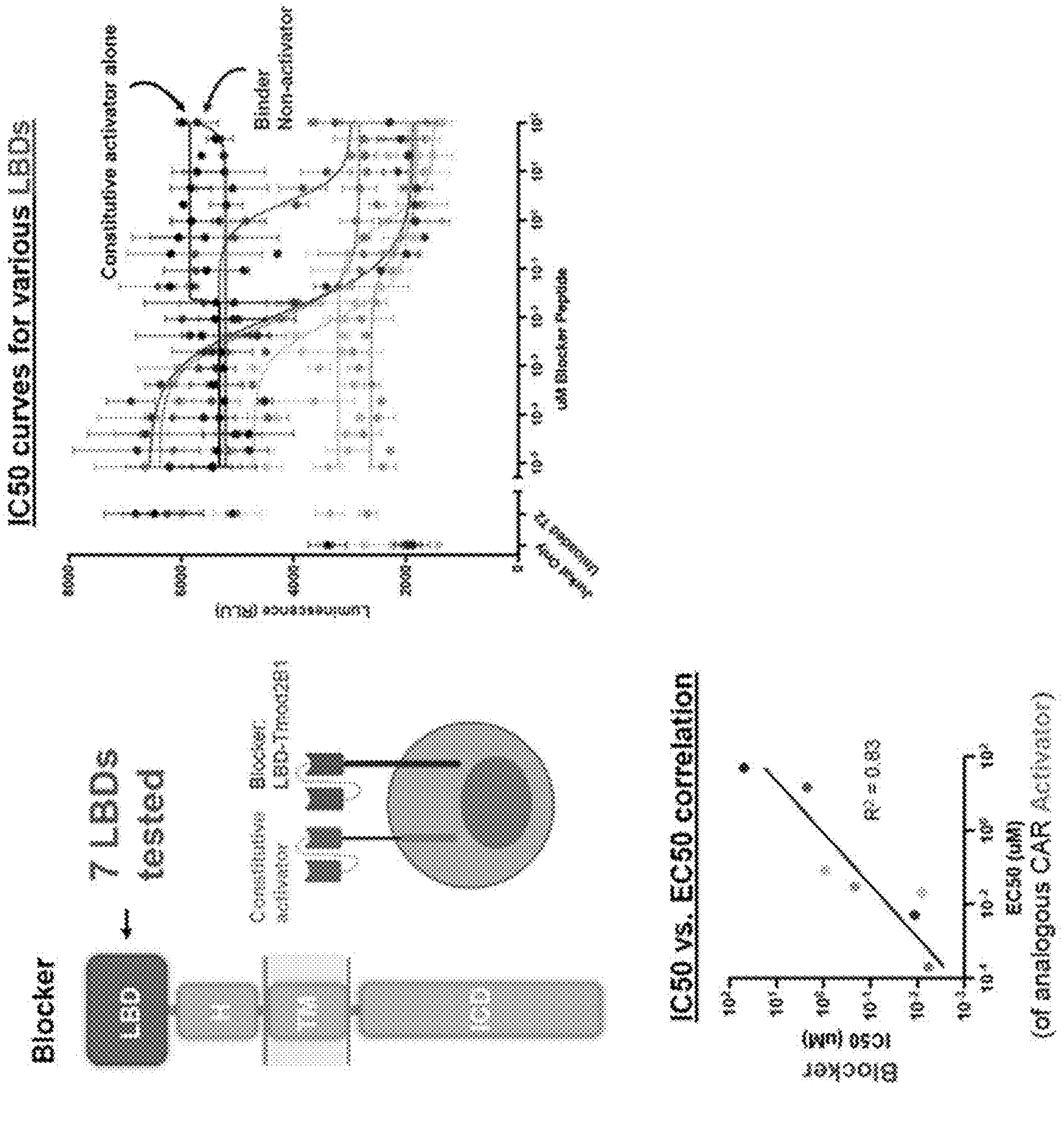
FIG. 27 provides experimental results showing the effect the ligand binding domain has on the blocking receptor.

As with the LBD of the activating receptor, the identity of the blocking receptor LBD can have large effects on the $IC_{50}$ of the engineered immune cells of the present disclosure. This is shown in FIG. 27, where several different ligand binding domains were tested for their effect on the $IC_{50}$ of engineered immune cells. Interestingly, the Inventors of the present disclosure found that when a ligand binding domain was switched between an activating receptor and blocking receptor, the LBD provided a correlative effect on the $IC_{50}$ and $EC_{50}$ of an immune cell.

Figure 32:
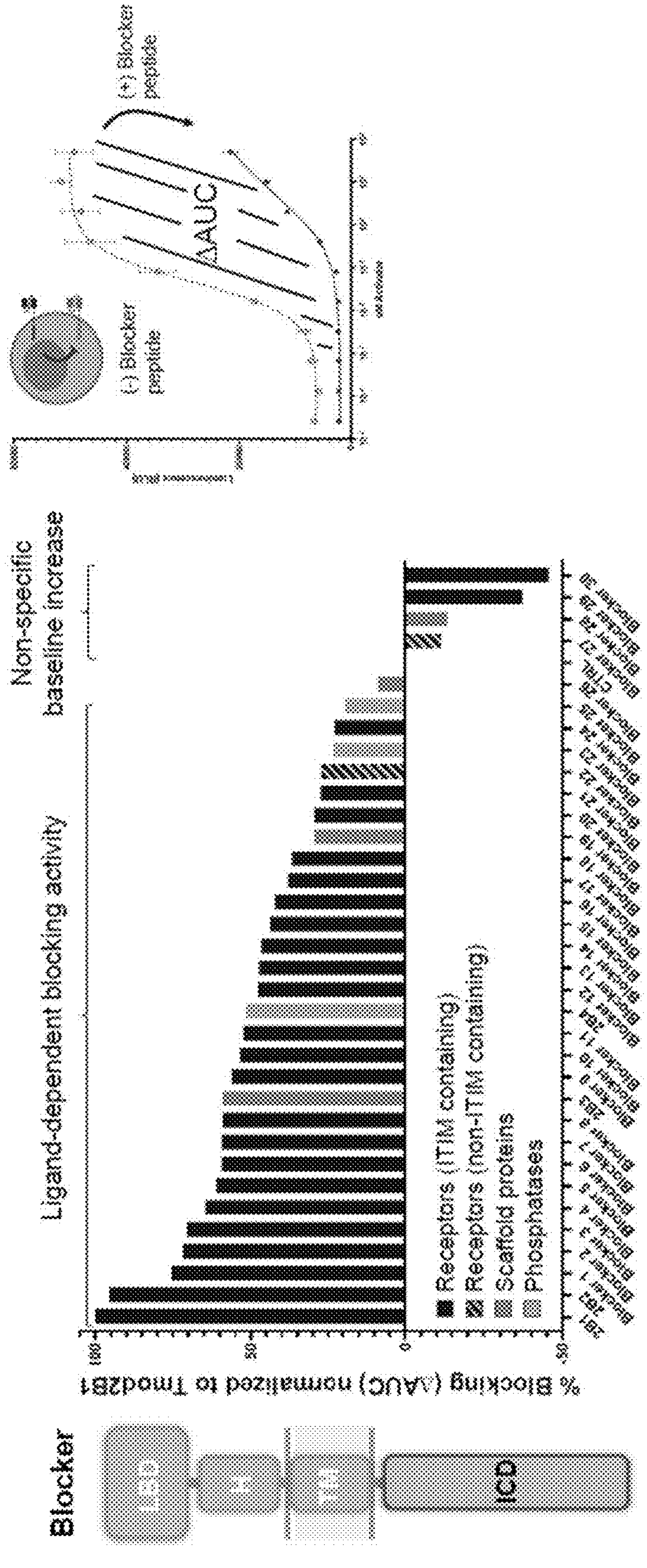
FIG. 32 provides experimental results showing the effect the intracellular domain has on the strength of the blocking receptor signal.

The Inventors of the present disclosure found that a wide variety of commonly used intracellular domains have relatively minimal impacts on the $EC_{50}$ of the activating receptor. Conversely, the Inventors discovered that the intracellular domain of the blocking receptor can have large effects on the strength of the blocking signal. Thus, the intracellular domain of the blocking receptor can be changed to modulate the strength of the blocking signal to ensure adequate inhibition. As shown in FIG. 32, changing the intracellular domain of the blocking receptor can have wide ranging effects on the strength of the blocking signal.

Receptor Cross-Talk

The present disclosure also provides engineered immune cells in which the activity of the activating and blocking receptors is modulated via cross-talk between the receptors.

Figure 33:
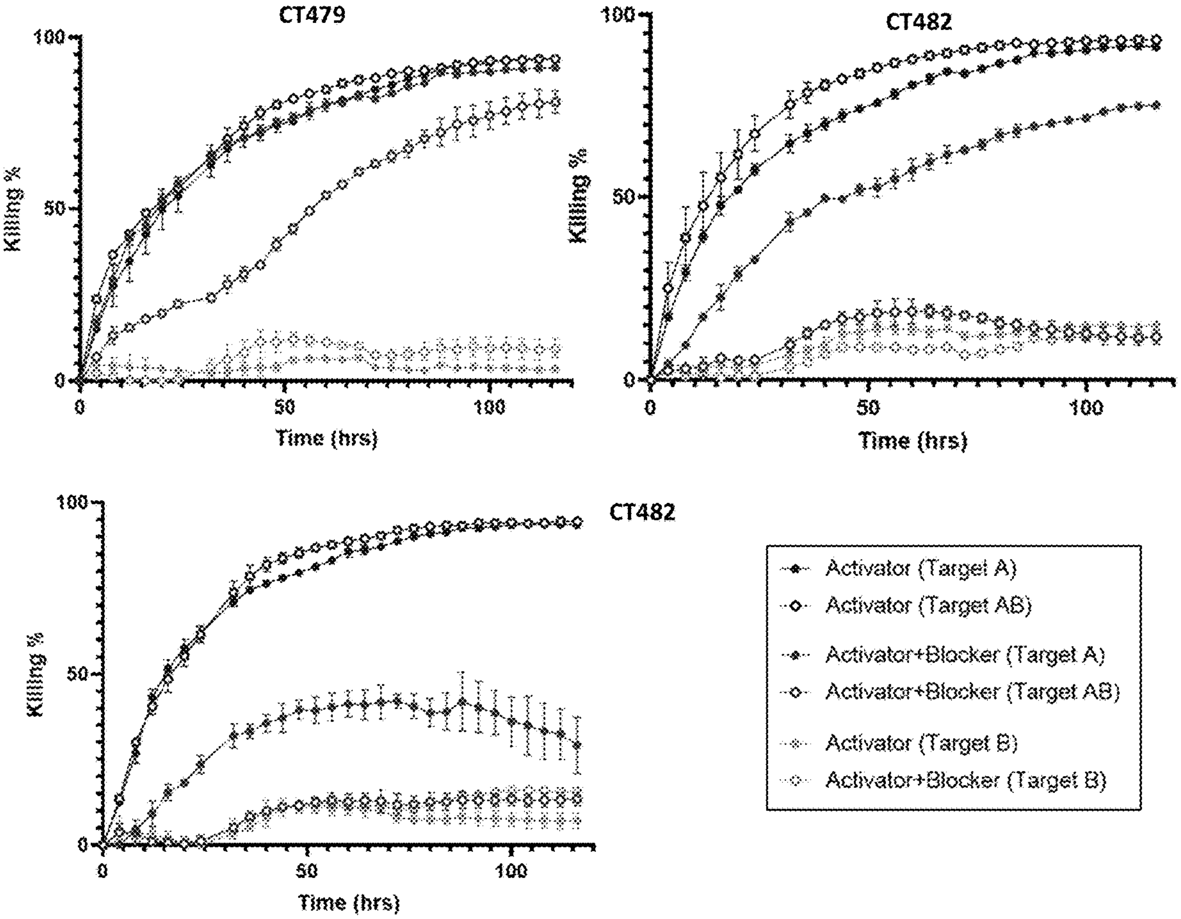
FIGS. 33-34 provide experimental results that indicate cross-talk between receptors.
Figure 34:
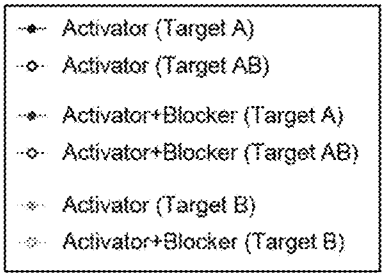
Figure 34:
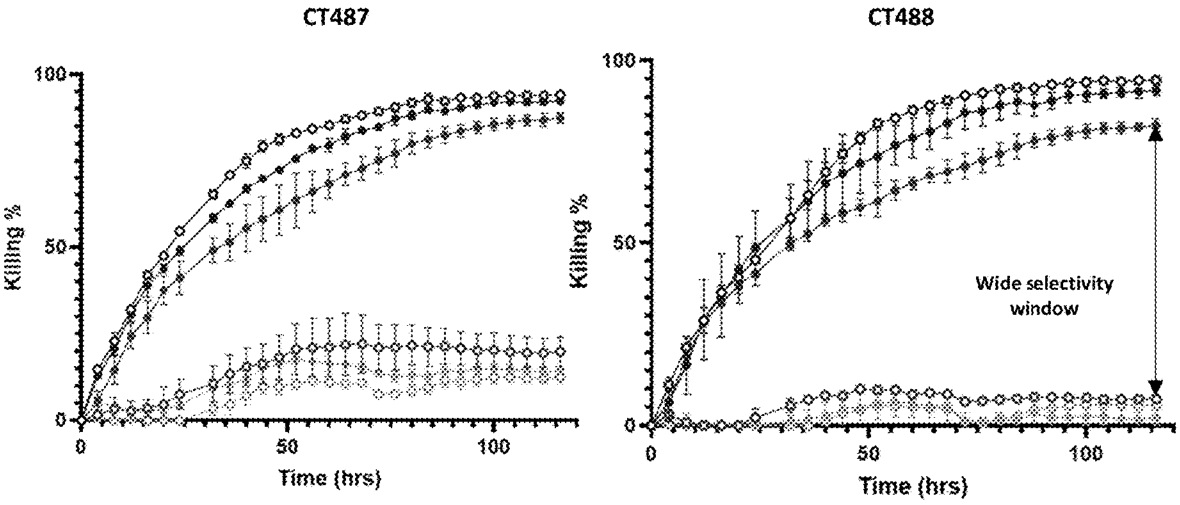

FIGS. 33-34 show the impact receptor cross-talk can have on the ability of the blocking receptor to inhibit the activation signal. Engineered immune cells were created with one of five different activating receptors. Though the activating receptors differed between the cell lines, each targeted the same activating ligand, epidermal growth factor receptor (EGFR), using a different antibody. As shown by the five graphs at the bottom in FIGS. 33-34, each of the different activating receptors provided the immune cells with equivalent abilities to kill target cells. Then, immune cells were created that had one of the five activating receptors and the same blocking receptor. Addition of the blocker caused some of the immune cells, like CT486, to exhibit a significant decrease in the cells' ability to kill target cells. The blocking receptors also provided varying effects in the ability of the immune cells to inhibit the activating signal in the presence of non-target cells.

This disparity in behavior between different activating receptors and a blocking receptor can be attributed to cross-talk between the receptors.

Thus, the present disclosure provides an engineered immune cell that includes an activating receptor that triggers a cytotoxic signal that promotes a cytotoxic response of the engineered immune cell when the activating receptor binds to an activating ligand of a target cell, a blocking receptor that sends an interfering signal that inhibits the cytotoxic response of the engineered immune cell when the blocking receptor binds a blocking ligand, and cross-talk between the activating receptor and the blocking receptor that affects an activation threshold for the cytotoxic response.

The disclosure also includes a method for treating cancer, the method includes providing an engineered immune cell to a patient. The engineered immune cell comprises an activating receptor and a blocking receptor, each expressed on a surface of the engineered immune cell. The activating receptor triggers a cytotoxic signal that promotes a cytotoxic response of the engineered immune cell when the activating receptor binds to an activating ligand of a target cell. The blocking receptor sends an interfering signal that inhibits the cytotoxic response of the engineered immune cell when the blocking receptor binds a blocking ligand. Cross-talk between the activating receptor and the blocking receptor affects an activation threshold for the cytotoxic response.

Modulating Receptor Proximity

The Inventors of the present disclosure made the surprising discovery that the strength of the blocking signal can increase as the distance between activating and blocking receptors decreases, and that when the receptors are separated by a particular average minimum distance, the blocking signal provides a maximum inhibitory effect on an activating receptor. Thus, the present disclosure provides engineered immune cells, and methods of making using engineered immune cells, with activating and blocking receptors spaced apart by at least a minimum average distance on the immune cell surface. The present Inventors also discovered that when activating and blocking receptors are within a certain, close proximity to one another, the activation of the blocking receptor may cause the blocking receptor to invert and provide an activating signal.

In certain engineered immune cells of the present disclosure, this average minimum distance is between about 100 to 200, 200 to 300, 300 to 400, 400 to 500, 500 to 600, 600 to 700, 700 to 800, 800 to 900, or 900 to 1000 angstroms.

Figure 35:
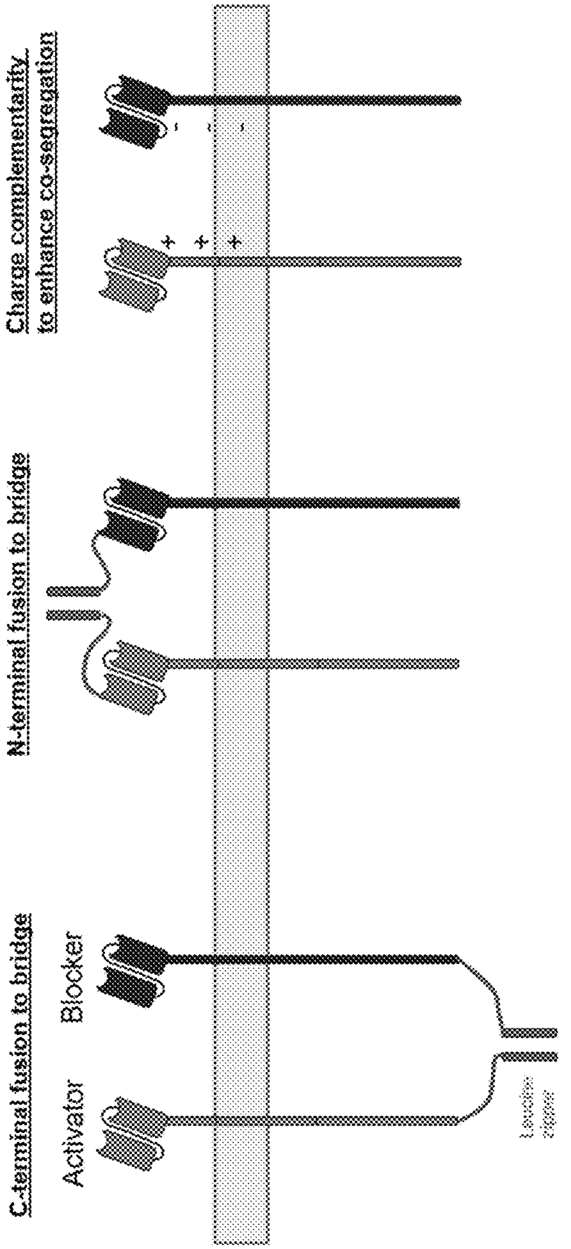
FIG. 35 shows various ways to control the distance between activating and blocking receptors.

As shown in FIG. 35, the Inventors devised several strategies to ensure that the activating and blocking receptors are spaced at a distance to ensure a high blocking signal strength. For example, the receptors can be attached via a C-terminal or N-terminal bridge. Alternatively or in addition, the receptors can be designed to have substituent groups or amino acids with opposing charges to enforce spacing between receptors. Bulky substituent groups or amino acids can also be used to cause steric effects that prevent the receptors from diffusing too close to one another.

Thus, the present disclosure provides engineered immune cells with activating and blocking receptors that possess physiochemical properties that maintain an average minimum distance between the receptors on the cell surface. Physiochemical properties may include, for example, opposing charges on each of the cell surface activating receptor and the cell surface blocking receptor, non-covalent interactions, van der Walls interactions, and/or steric effects.

The present disclosure also or alternatively provides engineered immune cells that have a spacer operably associated with an activating and blocking receptor on the cell surface that is configured to maintain an average minimum distance between the receptors on the cell surface. The spacer may covalently or non-covalently link the activating and blocking receptors. The spacer may include C- or N-terminal fusion that links the receptors. The spacer may alternatively or in addition include two moieties that allow non-covalent binding between the LBD, ICD, and/or hinge of each receptor. The spacer may also or alternatively include a non-covalent interacting motif that mediates protein-protein interaction, such as a leucine zipper.

The distance between the activating and blocking receptors may be controlled by using a spacer that includes a linker. Any linker may be used, and many fusion protein linker formats are known. For example, the linker may be flexible or rigid. Non-limiting examples of rigid and flexible linkers are provided in Chen et al. (Adv Drug Deliv Rev. 2013; 65(10):1357-1369).

Non-limiting exemplary rigid linkers include alpha helix-forming linkers with the sequence of $(EAAAK)_n$ and $(EAAAK)_nA$, wherein n=1-10. Another exemplary rigid linker is a proline rich linker having the sequence $(XP)_n$ where X is any amino acid and is preferably selected from A, G, and E and n=1-10, and glycine-serine linkers with a high ratio of serine to glycine.

The ligand binding domains described herein may be linked to each other in a random or specified order. The ligand binding domains described herein may be linked to each other in any orientation of N to C terminus.

Optionally, a short oligo- or polypeptide linker, for example, between 2 and 40 amino acids (e.g., 2, 3, 4, 5, 6, 7, 8, 9, or 10 amino acids) in length may form the linkage between the domains. The linker is a peptide of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 amino acid residues.

Non-limiting examples of amino acids found in linkers include Gly, Ser, Glu, Gin, Ala, Leu, Iso, Lys, Arg, Pro, and the like.

The linker may be [(Gly)n1Ser]n2, where n1 and n2 may be any number (e.g. n1 and n2 may independently be 1, 2, 4, 5, 6, 7, 8, 9, 10 or more than 10). The linker may be flexible polypeptide linker that is a Gly/Ser linker and comprises the amino acid sequence (Gly-Gly-Ser), (Gly-Gly-Gly-Ser), or (Gly-Gly-Gly-Gly-Ser) which can be repeated n times, where n is a positive integer equal to or greater than 1. For example, n=1, n=2, n=3, n=4, n=5, n=6, n=7, n=8, n=9 and n=10. The linker may include multiple repeats of (Gly Gly Ser), (Gly Ser) or (Gly Gly Gly Ser). Also included within the scope of the invention are linkers described in WO2012/138475 (incorporated herein by reference). In some embodiments, the flexible polypeptide linkers include, but are not limited to, GGS, GGGGS (SEQ ID NO: 226), GGGGS GGGGS (SEQ ID NO: 227), GGGGS GGGGS GGGGS (SEQ ID NO: 228), GGGGS GGGGS GGGGS GG (SEQ ID NO: 229) or GGGGS GGGGS GGGGS GGGGS (SEQ ID NO: 230). In some embodiments, the linkers include multiple repeats of (Gly Gly Ser), (Gly Ser) or (Gly Gly Gly Ser (SEQ ID NO: 231)).

The linker sequence may comprise a long linker (LL) sequence. The long linker sequence may comprise GGGGS, repeated four times. Such a linker may be used to link intracellular domains in a TCR alpha fusion protein of the disclosure. The long linker sequence may comprise GGGGS, repeated three times. The linker sequence may comprise a short linker (SL) sequence. The short linker sequence may comprise GGGGS. A glycine-serine doublet can be used as a suitable linker. Alternatively, domains are fused directly to each other via peptide bonds without use of a linker.

By reducing the G:S ratio in a Gly-Ser linker, the linker can be made more rigid.

The strength of the blocking signal may be the strongest when the activating and blocking receptors are separated by a distance of 0-1000 angstroms. The strength of the blocking signal may be the strongest when the activating and blocking receptors are separated by a distance of 0-50 angstroms, 50-100 angstroms, 100-200 angstroms, 200-300 angstroms, 300-400 angstroms, 400-500 angstroms, 500-600 angstroms, 600-700 angstroms, 700-800 angstroms, 800-900 angstroms, or 900-1000 angstroms. Preferably, the distance is about 200 angstroms.

Thus, the present disclosure provides an engineered immune cell with an activating receptor on the cell surface that triggers a cytotoxic signal that promotes a cytotoxic response of the engineered immune cell when the activating receptors binds to a first ligand on a target cell; and a blocking receptor on the cell surface that sends an interfering signal that inhibits the cytotoxic response of the engineered immune cell when the blocking receptor binds a second ligand of the target cell. Proximity of the blocking receptor to the activating receptor effects an activation threshold for the cytotoxic response, and the activating and blocking receptors physiochemical properties favoring interaction with one another, such that the receptors are spaced apart at an average distance on the immune cell surface.

The present disclosure also provides a method for treating cancer that includes providing an engineered immune cell to a patient, wherein the engineered immune cell comprises an activating receptor and a blocking receptor, each expressed on a surface of the engineered immune cell. The activating receptor triggers a cytotoxic signal that promotes a cytotoxic response of the engineered immune cell when the activating receptor binds a first ligand of a target cell, and the blocking receptor sends an interfering signal that inhibits the cytotoxic response of the engineered immune cell when the blocking receptor binds a second ligand of the target cell. Proximity of the blocking receptor to the activating receptor affects an activation threshold for the cytotoxic response, and the activating and blocking receptors physiochemical properties favoring interaction with one another, such that the receptors are spaced apart at an average distance on the immune cell surface.

The present disclosure also provides a method of producing an engineered immune cell that includes producing an engineered immune cell that expresses activating receptors and blocking receptors based on a determined distance between the receptors, wherein an activation threshold for a cytotoxic response by the immune cell is maximized when the receptors are separated on the cell surface by the determined average distance.

Receptor Types

The present disclosure provides immune cells comprising activating and blocking receptors, which may independently comprise a chimeric antigen receptor (CAR) a T cell receptor (TCR) or a combination of components from CARs or TCRs.

Figure 28:
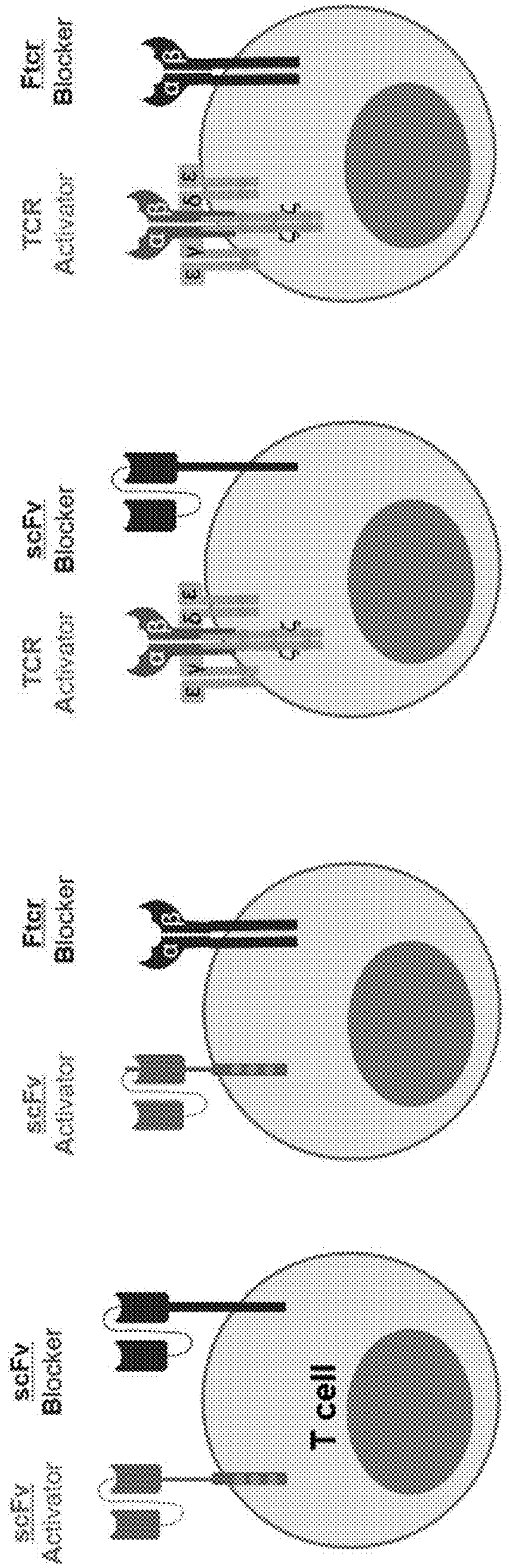
FIG. 28 shows combinations of various CAR- and TCR-based activating and blocking receptors.
Figure 29:
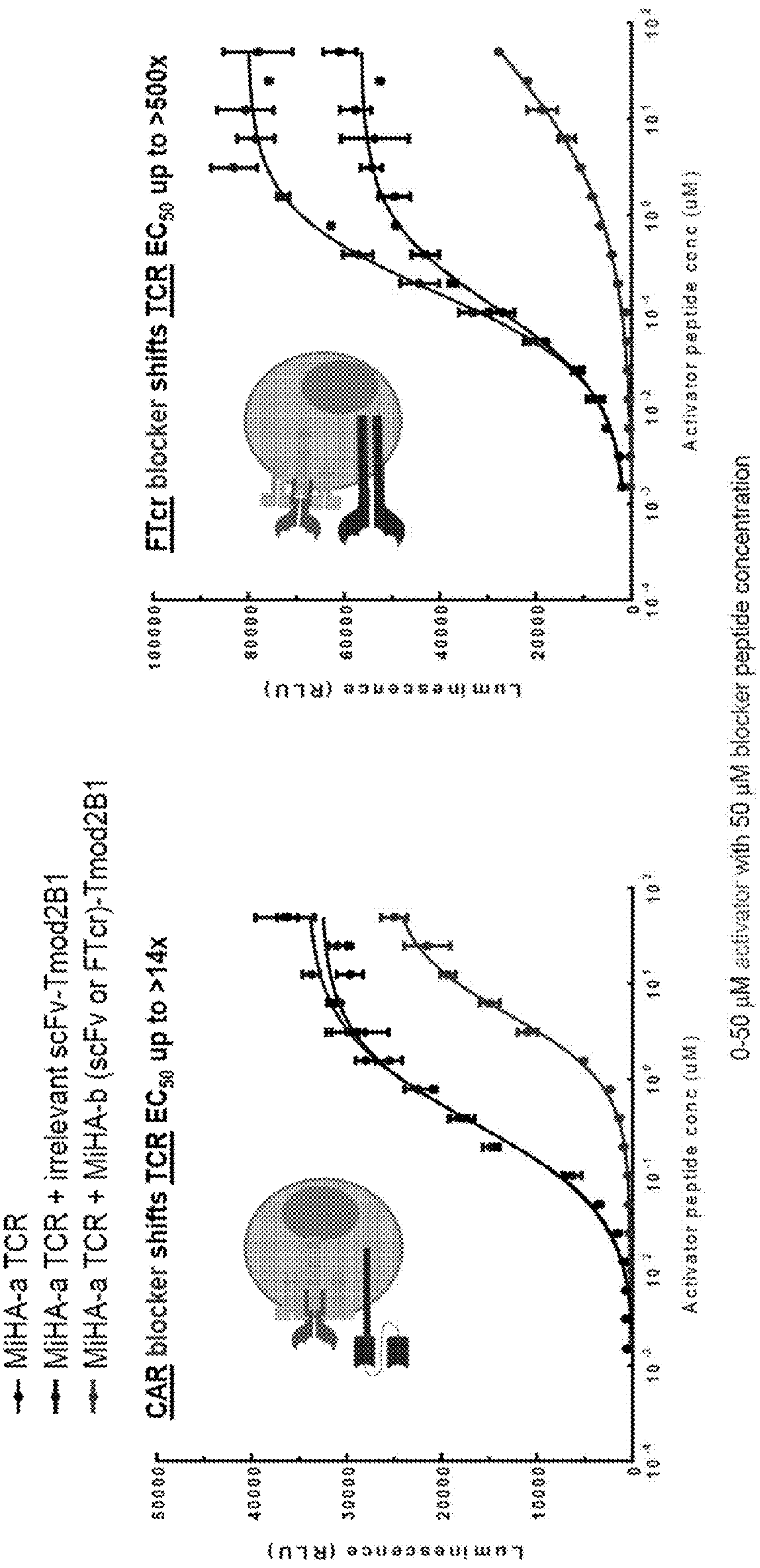
FIG. 29 provides experimental results showing that a CAR-based blocking receptor can inhibit a TCR-based activating receptor.

As shown in FIG. 28, the immune cells of the present disclosure can use receptors that comprise various combinations of TCRs and CARs. For example, as shown in FIG. 29, both a blocking CAR and blocking TCR can effectively inhibit the activation signal of a TCR-based activating receptor.

Moreover, the receptors of the present disclosure can effectively use components of both CARs and TCRs to achieve desired receptor activity.

Figure 30:
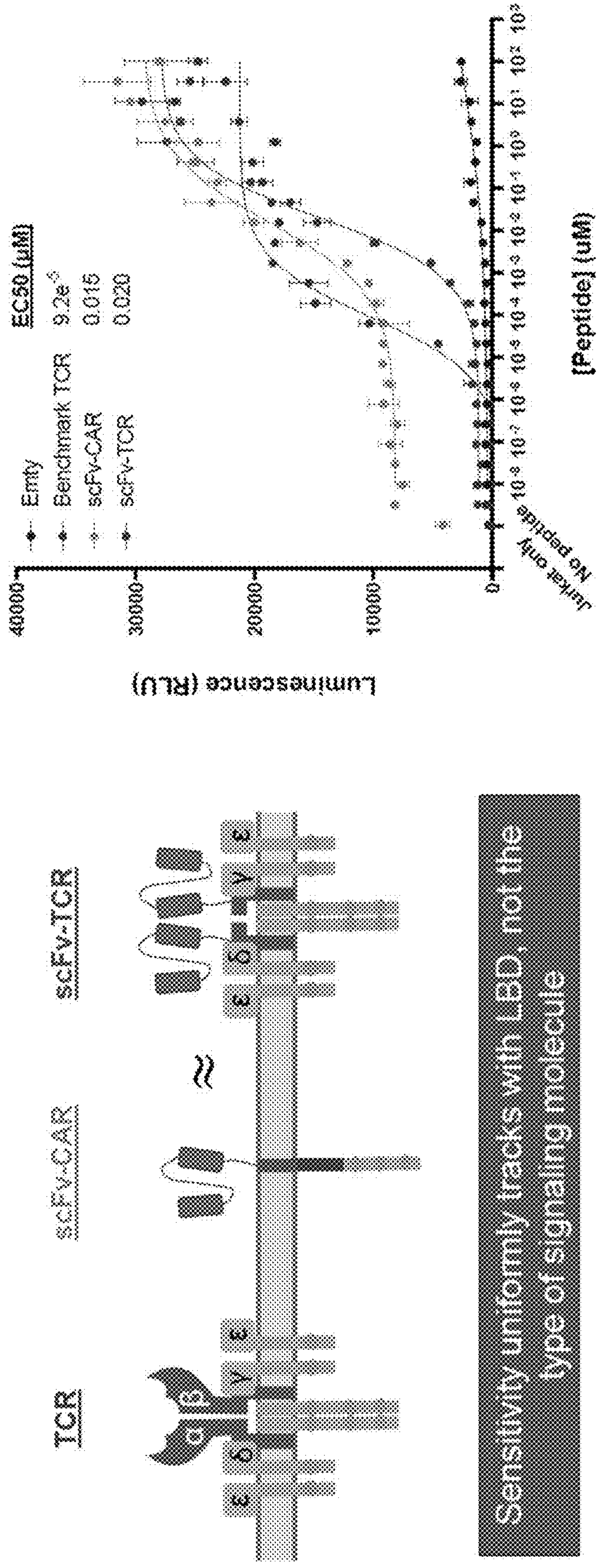
FIG. 30 provides experimental results showing that a CAR ligand binding domain can be used with a TCR activating receptor intracellular domain.

As shown in FIG. 30, the ligand binding domain of a CAR activating receptor can be used with the intracellular domain of a TCR activating receptor, and still provide a target-specific activation signal.

Figure 31:
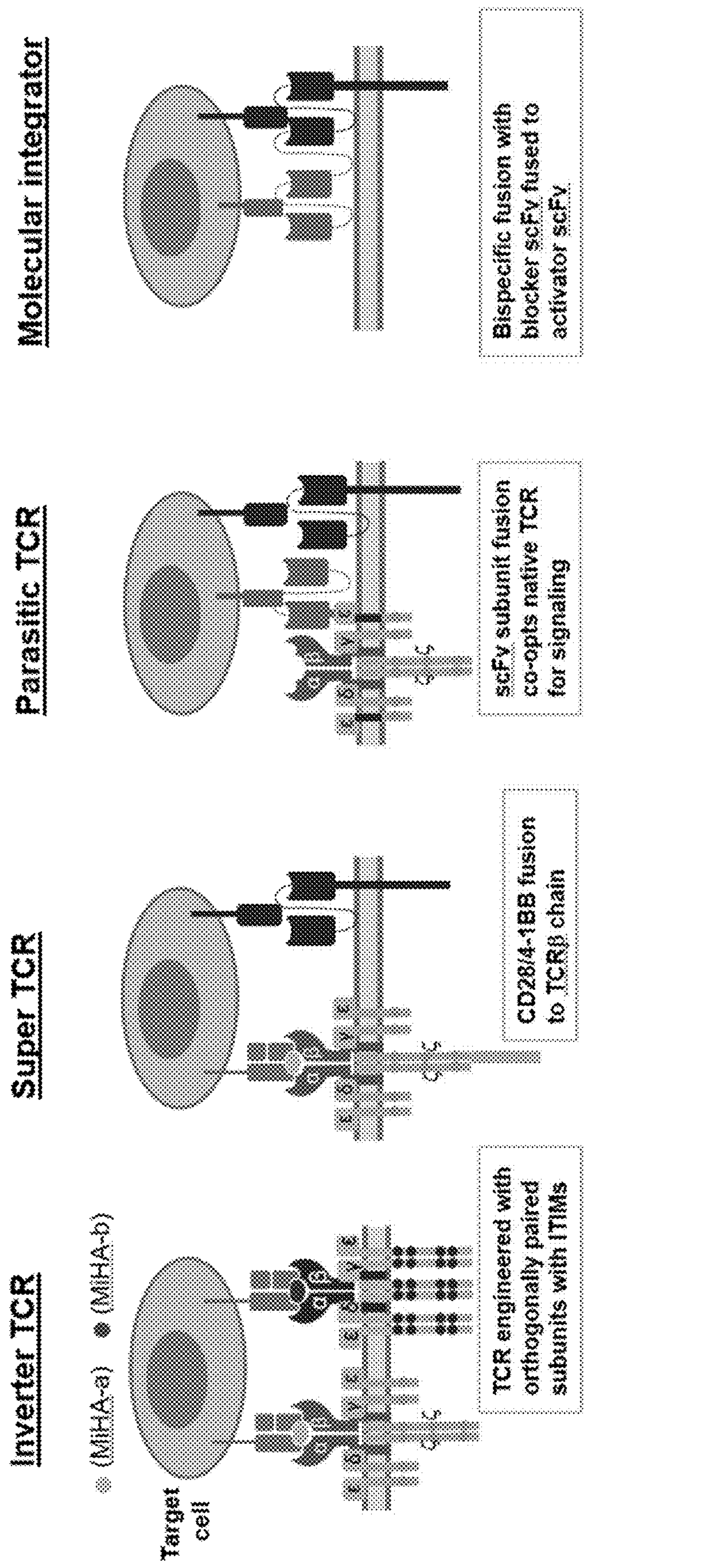
FIG. 31 shows different receptors that can be created in accordance with the present disclosure.

As shown in FIG. 31, the various components of TCRs and CARs can be interchanged to provide receptors with activities beyond blocking and activating receptors. For example, the components can be used to create Inverter TCRs, Super TCRs, Parasitic TCRs, and Molecular Integrators.

In some embodiments, one or more of the blocking receptor and activating receptor comprise a CAR. All CAR architectures are envisaged as within the scope of the instant disclosure.

The CARs of the present disclosure comprise an extracellular hinge region. Incorporation of a hinge region can affect cytokine production from CAR-T cells and improve expansion of CAR-T cells in vivo. Exemplary hinges can be isolated or derived from IgD and CD8 domains, for example IgG1, CD8a, or CD28, such as those disclosed by the Inventors of the present disclosure in PCT International Application No. PCT/US2020/045250 and PCT/US2021/030149, which are incorporated herein by reference in their entirety.

For example, exemplary hinges used in the receptors disclosed herein, which are isolated or derived from CDSa or CD28 include a CDSa hinge comprising an amino acid sequence having at least 80% identity, at least 90% identity, at least 95% identity, at least 99% identity or is identical to a sequence of SEQ ID NOS: 1 or 3 or encoded by SEQ ID NO: 4.

The CARs of the present disclosure can be designed to comprise a transmembrane domain that is fused to the hinge of the CAR. The transmembrane domain may be naturally associated with one of the domains of the CAR, such as the hinge or intracellular domain. For example, a CAR comprising a CD28 co-stimulatory domain might also use a CD28 transmembrane domain. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or synthetic source. When the source is natural, the domain may be derived from any membrane-bound or transmembrane protein. Transmembrane regions may be isolated or derived from (i.e., comprise at least the transmembrane region(s) of) the alpha, beta, or zeta chain of the T-cell receptor, CD28, CD3 epsilon, CD45, CD4, CD5, CD8, CD9, CD16, CD22, CD33, CD37, CD64, CD80, CD86, CD134, CD137, CD154, or from an immunoglobulin such as IgG4.

Alternatively, the transmembrane domain may be synthetic, in which case it can comprise predominantly hydrophobic residues such as leucine and valine. Certain transmembrane domains may comprise a triplet of phenylalanine, tryptophan and valine found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker. The CARs may comprise a CD28 transmembrane domain or an IL-2Rbeta transmembrane domain, such as those disclosed by the present Inventors in PCT International Application No. PCT/US2020/045250 and PCT/US2021/030149, incorporated herein by reference.

For example, the CD28 transmembrane domain may comprise an amino acid sequence having at least 80% identity, at least 90% identity, at least 95% identity, at least 99% identity or is identical to a sequence of SEQ ID NO: 5. The CD28 transmembrane domain may be encoded by a nucleotide sequence having at least 80% identity, at least 90% identity, at least 95% identity, at least 99% identity or is identical to SEQ ID NO: 6. An exemplary IL-2R beta transmembrane domain as disclosed here may comprise an amino acid sequence having at least 80% identity, at least 90% identity, at least 95% identity, at least 99% identity or is identical to SEQ ID NO: 7. In some aspects, an exemplary IL-2Rbeta transmembrane domain is encoded by a nucleotide sequence having at least 80% identity, at least 90% identity, at least 95% identity, at least 99% identity or is identical to a sequence of SEQ ID NO: 8.

The intracellular signaling domains of CARs used as parts of the activating or blocking receptors are responsible for activation of at least one of the normal effector functions of the immune cell in which the CAR has been placed. The term “effector function” refers to a specialized function of a cell. Effector functions of a regulatory T cell, for example, include the suppression or downregulation of induction or proliferation of effector T cells. Thus, the term “intracellular signaling domain” refers to the portion of a protein which transduces the effector function signal and directs the cell to perform a specialized function.

While usually an entire intracellular signaling domain can be employed, in many cases it is not necessary to use the entire domain. To the extent that a truncated portion of the intracellular signaling domain is used, such truncated portion may be used in place of the intact chain as long as it transduces the effector function signal. In some cases, multiple intracellular domains can be combined to achieve the desired functions of CAR-T cells of the instant disclosure. The term intracellular signaling domain is thus meant to include any truncated portion of one or more intracellular signaling domains sufficient to transduce the effector function signal.

Examples of intracellular signaling domains for use in the CARs of the instant disclosure include the cytoplasmic sequences of the T cell receptor (TCR) and co-receptors that act in concert to initiate signal transduction following antigen receptor engagement, as well as any derivative or variant of these sequences and any synthetic sequence that has the same functional capability. In certain receptors of the disclosure, the intracellular activation domain ensures that there is T cell receptor (TCR) signaling necessary to activate the effector functions of the CAR-T cell.

The CAR intracellular domains of the instant disclosure may comprise at least one cytoplasmic activation domain. The at least one cytoplasmic activation domain can be a CD247 molecule (CD3ζ) activation domain, a stimulatory killer immunoglobulin-like receptor (KIR) KIR2DS2 activation domain, or a DNAX-activating protein of 12 kDa (DAP12) activation domain, such as those disclosed by the present inventors in PCT International Application No. PCT/US2020/045250 and PCT/US2021/030149, which are incorporated by reference.

For example, the CD3z activation domain comprises an amino acid sequence having at least 80% identity, at least 90% identity, at least 95% identity, at least 99% identity or is identical to SEQ ID NO: 9 and/or encoded by a nucleotide sequence having at least 80% identity, at least 90% identity, at least 95% identity, at least 99% identity or is identical to a sequence of SEQ ID NO: 10.

It is known that signals generated through a TCR alone can be insufficient for full activation of a T cell, and that a secondary or co-stimulatory signal may be also required. Thus, T cell activation can be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory or inhibitory manner. Exemplary cytoplasmic signaling sequences are disclosed by the present Inventors in PCT International Application No. PCT/US2020/045250, which is incorporated by reference.

Primary cytoplasmic signaling sequences that act in a stimulatory manner may contain signaling motifs which are known as immunoreceptor tyrosine-based activation motifs or ITAMs. In certain receptors of the disclosure, the cytoplasmic signaling domain contains 1, 2, 3, 4, or 5 ITAMs.

In certain receptors of the disclosure, the cytoplasmic domain comprises a CD3ζ activation domain. The CD3ζ activation domain may comprise a single ITAM, two ITAMs, or three ITAMs.

Further examples of ITAM containing primary cytoplasmic signaling sequences that can be used in the CARs of the instant disclosure include those derived from TCRζ, FcRγ, FcRβ, CD3γ, CD3δ, CD3ε, CD3ζ, CD5, CD22, CD79a, CD79b, and CD66d. It is particularly preferred that cytoplasmic signaling molecule in the CAR of the instant invention comprises a cytoplasmic signaling sequence derived from CD3ζ.

In certain receptors of the disclosure, the cytoplasmic domain of the CAR may comprise the CD3ζ signaling domain by itself or combined with any other desired cytoplasmic domain(s). For example, the cytoplasmic domain of the CAR can comprise a CD3ζ chain portion and a co-stimulatory domain.

For example, the CD3z activation domain may comprise a single ITAM and comprises an amino acid sequence having at least 80% identity, at least 90% identity, at least 95% identity, at least 99% identity or is identical to a sequence of SEQ ID NO: 11 and/or encoded by a nucleotide sequence having at least 80% identity, at least 90% identity, at least 95% identity, at least 99% identity or is identical to SEQ ID NO: 12.

The co-stimulatory domain refers to a portion of a CAR comprising the intracellular domain of a costimulatory molecule. A costimulatory molecule is a cell surface molecule, other than an antigen receptor or its ligands, that is required for an efficient response of lymphocytes to an antigen. In receptors of the disclosure, the costimulatory domain is selected from the group consisting of IL2Rβ, Fc Receptor gamma (FcRγ), Fc Receptor beta (FcRβ), CD3g molecule gamma (CD37), CD36, CD3F, CD5 molecule (CD5), CD22 molecule (CD22), CD79a molecule (CD79a), CD79b molecule (CD79b), carcinoembryonic antigen related cell adhesion molecule 3 (CD66d), CD27 molecule (CD27), CD28 molecule (CD28), TNF receptor superfamily member 9 (4-1BB), TNF receptor superfamily member 4 (OX40), TNF receptor superfamily member 8 (CD30), CD40 molecule (CD40), programmed cell death 1 (PD-1), inducible T cell costimulatory (ICOS), lymphocyte function-associated antigen-1 (LFA-1), CD2 molecule (CD2), CD7 molecule (CD7), TNF superfamily member 14 (LIGHT), killer cell lectin like receptor C2 (NKG2C) and CD276 molecule (B7-H3) c-stimulatory domains, or functional fragments thereof.

The cytoplasmic domains within the cytoplasmic signaling portion of the CARs of the instant disclosure may be linked to each other in a random or specified order. Optionally, a short oligo- or polypeptide linker, for example between 2 and 10 amino acids in length may form the linkage. A glycine-serine doublet provides an example of a suitable linker.

The intracellular domains of CARs of the instant disclosure may include at least one co-stimulatory domain. The co-stimulatory domain may be isolated or derived from CD28.

An exemplary CD28 co-stimulatory domain comprises an amino acid sequence having at least 80% identity, at least 90% identity, at least 95% identity, at least 99% identity or is identical to a sequence of SEQ ID NO: 13 and/or encoded by a nucleotide sequence having at least 80% identity, at least 90% identity, at least 95% identity, at least 99% identity or is identical to a sequence of SEQ ID NO: 14.

The intracellular domain of the CARs of the instant disclosure may include an interleukin-2 receptor beta-chain (IL-2Rbeta or IL-2R-beta) cytoplasmic domain. The IL-2Rbeta domain may be truncated. The IL-2Rbeta cytoplasmic domain may comprise one or more STAT5-recruitment motifs, which may be outside the IL-2Rbeta cytoplasmic domain.

An exemplary IL-2Rbeta intracellular domain may comprise an amino acid sequence having at least 80% identity, at least 90% identity, at least 95% identity, at least 99% identity or is identical to a sequence of SEQ ID NO: 15 and/or encoded by a nucleotide sequence having at least 80% identity, at least 90% identity, at least 95% identity, at least 99% identity or is identical to a sequence of SEQ ID NO: 16.

Exemplary STAT5-recruitment motifs are provided by Passerini et al., (2008) STAT5-signaling cytokines regulate the expression of FOXP3 in CD4+CD25+ regulatory T cells and CD4+CD25+ effector T cells, *International Immunology*, Vol. 20, No. 3, pp. 421-431, and by Kagoya et al., (2018) A novel chimeric antigen receptor containing a JAK-STAT signaling domain mediates superior antitumor effects. Nature Medicine doi:10.1038/nm.4478, which are each incorporated herein by reference.

An exemplary STAT-recruitment motif used herein may consist of SEQ ID NO: 17.

In certain blocking receptors of the disclosure, the inhibitory signal is transmitted through the intracellular domain of the receptor. Thus, the blocking receptor may comprise an inhibitory intracellular domain.

The inhibitory intracellular domain may comprise an immunoreceptor tyrosine-based inhibitory motif (ITIM). The inhibitory intracellular domain comprising an ITIM can be isolated or derived from an immune checkpoint inhibitor such as CTLA-4 and PD-1. CTLA-4 and PD-1 are immune inhibitory receptors expressed on the surface of T cells, and play a pivotal role in attenuating or terminating T cell responses.

"ITIM" refers to a conserved sequence of amino acids with a consensus sequence provided in SEQ ID NO: 274. Exemplary ITIMs include, those having sequences of SEQ ID NOS: 67, 68, 69, and 70. In some embodiments, the intracellular domain comprises a sequence at least 95% identical to SEQ ID NOS: 71, 72, 73, 74, 75, or 76.

Inhibitory domains can also be isolated from human tumor necrosis factor related apoptosis inducing ligand (TRAIL) receptor and CD200 receptor 1.

The inhibitory domain may comprise an intracellular domain, a transmembrane or a combination thereof. Alternatively, the inhibitory domain comprises an intracellular domain, a transmembrane domain, a hinge region or a combination thereof. The inhibitory domain may contain an immunoreceptor tyrosine-based inhibitory motif (ITIM). The inhibitory domain comprising an ITIM can be isolated or derived from an immune checkpoint inhibitor such as CTLA-4 and PD-1.

Inhibitory domains can be isolated from human tumor necrosis factor related apoptosis inducing ligand (TRAIL) receptor and CD200 receptor 1. The inhibitory domain may be isolated or derived from a human protein, for example a human TRAIL receptor, CTLA-4, or PD-1 protein. In some embodiments, the TRAIL receptor comprises TR10A, TR10B or TR10D.

Endogenous TRAIL is expressed as a 281-amino acid type II trans-membrane protein, which is anchored to the plasma membrane and presented on the cell surface. TRAIL is expressed by natural killer cells, which, following the establishment of cell-cell contacts, can induce TRAIL-dependent apoptosis in target cells. Physiologically, the TRAIL-signaling system was shown to be essential for immune surveillance, for shaping the immune system through regulating T-helper cell 1 versus T-helper cell 2 as well as "helpless" CD8+ T-cell numbers, and for the suppression of spontaneous tumor formation.

The inhibitory domain may comprise an intracellular domain isolated or derived from a CD200 receptor. The cell surface glycoprotein CD200 receptor 1 (Uniprot ref. Q8TD46) represents another example of an inhibitory intracellular domain of the present invention. This inhibitory receptor for the CD200/OX2 cell surface glycoprotein limits inflammation by inhibiting the expression of proinflammatory molecules including TNF-alpha, interferons, and inducible nitric oxide synthase (iNOS) in response to selected stimuli.

The inhibitory domain may be isolated or derived from killer cell immunoglobulin like receptor, three Ig domains and long cytoplasmic tail 2 (KIR3DL2), killer cell immunoglobulin like receptor, three Ig domains and long cytoplasmic tail 3 (KIR3DL3), leukocyte immunoglobulin like receptor B1 (LIR1), programmed cell death 1 (PD1), Fc gamma receptor IIB (FcgRIIB), killer cell lectin like receptor K1 (NKG2D), CTLA-4, a domain containing a synthetic consensus ITIM, a ZAP70 SH2 domain (e.g., one or both of the N and C terminal SH2 domains), or ZAP70 KI_K369A (kinase inactive ZAP70).

The inhibitory domain may be isolated or derived from a human protein. The blocking receptor may comprise a cytoplasmic domain and transmembrane domain isolated or derived from the same protein. For example, an ITIM containing protein. The blocking receptor may comprise a cytoplasmic domain, a transmembrane domain, and an extracellular domain or a portion thereof isolated or derived isolated or derived from the same protein. The blocking receptor may comprise a hinge region isolated or derived from isolated or derived from the same protein as the intracellular domain and/or transmembrane domain.

In certain immune cells of the disclosure, one or more of the activating and blocking receptors comprise a T Cell Receptor (TCR).

A "TCR", sometimes also called a "TCR complex" or "TCR/CD3 complex" refers to a protein complex comprising a TCR alpha chain, a TCR beta chain, and one or more of the invariant CD3 chains (zeta, gamma, delta and epsilon), sometimes referred to as subunits.

The TCR alpha and beta chains can be disulfide-linked to function as a heterodimer to bind to peptide-MHC complexes. Once the TCR alpha/beta heterodimer engages peptide-MHC, conformational changes in the TCR complex in the associated invariant CD3 subunits are induced, which leads to their phosphorylation and association with downstream proteins, thereby transducing a primary stimulatory signal. In an exemplary TCR complex, the TCR alpha and TCR beta polypeptides form a heterodimer, CD3 epsilon and CD3 delta form a heterodimer, CD3 epsilon and CD3 gamma for a heterodimer, and two CD3 zeta form a homodimer.

The LBD of the activating or blocking receptors may be fused to an extracellular domain of a TCR subunit. The TCR subunit can be TCR alpha, TCR beta, CD3 delta, CD3 epsilon or CD3 gamma. Both the first and second ligand binding domains may be fused to the same TCR subunit in different TCR receptors. Alternatively, the first and second ligand binding domains are fused to different TCR subunits in different TCR receptors.

The LBD of the activating receptor and blocking receptor may each independently comprise an scFv domain or a Vo-only domain.

TCR subunits include TCR alpha, TCR beta, CD3 zeta, CD3 delta, CD3 gamma and CD3 epsilon. Any one or more of TCR alpha, TCR beta chain, CD3 gamma, CD3 delta or CD3 epsilon, or fragments or derivatives thereof, can be fused to one or more domains capable of providing a stimulatory signal of the disclosure, thereby enhancing TCR function and activity. Any one or more of TCR alpha, TCR beta chain, CD3 gamma, CD3 delta or CD3 epsilon, or fragments or derivative thereof, can be fused to an inhibitory intracellular domain of the disclosure.

The receptors of the present disclosure may comprise TCRs comprising a TCR variable domain. The TCR variable domain specifically binds to an antigen in the absence of a second TCR variable domain (a Vβ-only domain).

The TCRs may comprise additional elements besides the TCR variable domain, including additional amino acid sequences, additional protein domains (covalently associated, non-covalently associated or covalently and non-covalently associated with the TCR variable domain), fusion or non-covalent association of the TCR variable domain with other types of macromolecules (for example polynucleotides, polysaccharides, lipids, or a combination thereof), fusion or non-covalent association of the TCR variable domain with one or more small molecules, compounds, or ligands, or a combination thereof. Any additional element, as described, may be combined provided that the TCR variable domain is configured to specifically bind the epitope in the absence of a second TCR variable domain.

TCRs comprising a Vβ-only domain as described herein may comprise a single TCR chain (e.g. α, β, γ, or δ chain), or may comprise a single TCR variable domain (e.g. of α, β, γ, or δ chain). If a TCR is a single TCR chain, then the TCR chain comprises a transmembrane domain, a constant (or C domain) and a variable (or V domain), but does not comprise a second TCR variable domain. The TCRs may comprise or consist of a TCR α chain, a TCR β chain, a TCR γ chain or a TCR δ chain. The TCRs may be a membrane bound proteins. The TCRs may alternatively be membrane associated proteins.

The TCRs may use a surrogate a chain that lacks a Vα segment, which forms activation competent TCRs complexed with the six CD3 subunits. The TCRs may function independently of a surrogate a chain that lacks a Vα segment. For example, one or more TCRs may be fused to transmembrane (e.g., CD3ζ and CD28) and intracellular domain proteins (e.g., CD3ζ, CD28, and/or 4-1BB) that are capable of activating T cells in response to antigen.

TCRs may comprise one or more single TCR chains fused to the Vβ-only domain described herein. For example, the TCRs may comprise, or consist essentially of single α TCR chain, a single β TCR chain, a single γ TCR chain, or a single δ TCR chain fused to one or more Vβ-only domains.

The TCRs may engage antigens using complementarity determining regions (CDRs). Each TCR may contain three complement determining regions (CDR1, CDR2, and CDR3).

The first and/or second ligand binding Vβ-only domain may be a human TCR variable domain. Alternatively, the first and/or second Vβ-only domain may be a non-human TCR variable domain. The first and/or second Vβ-only domain may be a mammalian TCR variable domain. The first and/or second Vβ-only domain may be a vertebrate TCR variable domain.

Where Vβ-only domain is incorporated into a fusion protein, for example a fusion protein comprising a TCR subunit, and optionally, an additional stimulatory intracellular domain, the fusion protein may comprise a Vβ-only domain and any other protein domain or domains.

TCR receptors comprising transmembrane domains isolated or derived from any source are envisaged as within the scope of the fusion proteins of the disclosure.

The TCR transmembrane domain may be one that is associated with one of the other domains of the fusion protein, or isolated or derived from the same protein as one of the other domains of the fusion protein. The transmembrane domain and the second intracellular domain may be from the same protein, for example a TCR complex subunit such as TCR alpha, TCR beta, CD3 delta, CD3 epsilon or CD3 gamma. The extracellular domain (svd-TCR), the transmembrane domain and the second intracellular domain may be from the same protein, for example a TCR complex subunit such as TCR alpha, TCR beta, CD3 delta, CD3 epsilon or CD3 gamma.

The TCR extracellular domain (comprising one or more ligand binding domains, such as Vβ-only domain and scFv domains), the transmembrane domain and the intracellular domain(s) may be from different proteins. For example, the engineered svd-TCR may comprise a CD28 transmembrane domain with a CD28, 4-1BB and CD3ζ intracellular domain.

The TCR transmembrane domain may be derived from a natural or recombinant source. When the source is natural, the domain may be derived from any membrane-bound or transmembrane protein.

The transmembrane domain may be capable of signaling to the intracellular domain(s) whenever the TCR complex is bound to a target. A transmembrane domain of particular use in this receptors of the disclosure may include at least the transmembrane region(s) of the alpha, beta, or zeta chain of the TCR, CD3 delta, CD3 epsilon or CD3 gamma, CD28, CD3 epsilon, CD45, CD4, CD5, CD8, CD9, CD16, CD22, CD33, CD37, CD64, CD80, CD86, CD134, CD137, CD154.

The transmembrane domain can be attached to the extracellular region of the fusion protein, e.g., the antigen binding domain of the TCR alpha or beta chain, via a hinge, e.g., a hinge from a human protein. For example, in one embodiment, the hinge can be a human immunoglobulin (Ig) hinge, e.g., an IgG4 hinge, or a CD8a hinge. The hinge may be isolated or derived from CD8a or CD28.

For example, an exemplary hinge isolated or derived from CD8a hinge comprises an amino acid sequence having at least 80% identity, at least 90% identity, at least 95% identity, at least 99% identity or is identical to a sequence of SEQ ID NO: 1 and/or encoded by a nucleotide sequence having at least 80% identity, at least 90% identity, at least 95% identity, at least 99% identity or is identical to a sequence of SEQ ID NO: 2.

An exemplary CD28 hinge may comprise an amino acid sequence having at least 80% identity, at least 90% identity, at least 95% identity, at least 99% identity or is identical to SEQ ID NO: 3 and/or is encoded by a nucleotide sequence having at least 80% identity, at least 90% identity, at least 95% identity, at least 99% identity or is identical to a sequence of SEQ ID NO: 4.

The transmembrane domain may comprise a TCR alpha transmembrane domain, a TCR beta transmembrane domain, or a CD3 zeta transmembrane domain, such as those disclosed by the present Inventors in PCT International Application No. PCT/US2020/045250, which is incorporated by reference.

A transmembrane domain can include one or more additional amino acids adjacent to the transmembrane region, e.g., one or more amino acids associated with the extracellular region of the protein from which the transmembrane was derived (e.g., 1, 2, 3, 4, 5, 6, 7, 8, 9, 10 or up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 or up to 15 amino acids of the intracellular region).

The transmembrane domain can be selected or modified by amino acid substitution to avoid binding of such domains to the transmembrane domains of the same or different surface membrane proteins, e.g., to minimize interactions with other members of the receptor complex or to minimize interactions with other receptors. This can help, for example, to ensure that the receptors remain at a sufficient distance apart on the surface of the immune cell to prevent blocking receptor inversion.

When present, the transmembrane domain may be a natural TCR transmembrane domain, a natural transmembrane domain from a heterologous membrane protein, or an artificial transmembrane domain. The transmembrane domain may be a membrane anchor domain. Without limitation, a natural or artificial transmembrane domain may comprise a hydrophobic a helix of about 20 amino acids, often with positive charges flanking the transmembrane segment.

The transmembrane domain may have one transmembrane segment or more than one transmembrane segment. Prediction of transmembrane domains/segments may be made using publicly available prediction tools, e.g., TMHMM (Krogh et al., *Journal of Molecular Biology* 2001, 305(3):567-580) and TMpred (Hoppe-Seyler, *Hofmann & Stoffel Biol. Chem.* 1993; 347: 166), which are incorporated by reference. Non-limiting examples of membrane anchor systems include platelet derived growth factor receptor (PDGFR) transmembrane domain, glycosylphosphatidylinositol (GPI) anchor (added post-translationally to a signal sequence) and the like.

In certain aspects, transmembrane domain comprises a TCR alpha transmembrane domain. In some embodiments, the TCR alpha transmembrane domain comprises an amino acid sequence having at least 85% identity, at least 90% identity, at least 95% identity, at least 96% identity, at least 97% identity, at least 98% identity, at least 99% identity or is identical to a sequence of SEQ ID NO: 26 and/or is encoded by a nucleotide sequence having at least 80% identity, at least 90% identity, at least 95% identity, at least 99% identity or is identical to a sequence of SEQ ID NO: 27.

In some embodiments, the transmembrane domain comprises a TCR beta transmembrane domain. In some embodiments, the TCR beta transmembrane domain comprises an amino acid sequence having at least 85% identity, at least 90% identity, at least 95% identity, at least 96% identity, at least 97% identity, at least 98% identity, at least 99% identity or is identical to a sequence of SEQ ID NO: 28 or 35 and/or is encoded by a nucleotide sequence having at least 80% identity, at least 90% identity, at least 95% identity, at least 99% identity or is identical to a sequence of SEQ ID NO: 20 or 36.

In some embodiments, the transmembrane comprises a CD3 zeta transmembrane domain. In some embodiments, the CD3 zeta transmembrane domain comprises an amino acid sequence having at least 85% identity, at least 90% identity, at least 95% identity, at least 96% identity, at least 97% identity, at least 98% identity, at least 99% identity or is identical to a sequence of SEQ ID NO: 29.

In some embodiments, the CD3 zeta transmembrane domain comprises, or consists essentially of, SEQ ID NO: 29. The disclosure provides fusion proteins comprising an intracellular domain. An "intracellular domain," refers to an intracellular portion of a protein. The TCR intracellular domain may comprise one or more domains capable of providing a stimulatory signal to a transmembrane domain. The intracellular domain may comprise a first intracellular domain capable of providing a stimulatory signal and a second intracellular domain capable of providing a stimulatory signal. The intracellular domain may comprise a first, second and third intracellular domain capable of providing a stimulatory signal.

The intracellular domains capable of providing a stimulatory signal may be selected from the group consisting of a CD28 molecule (CD28) domain, a LCK proto-oncogene, Src family tyrosine kinase (Lck) domain, a TNF receptor superfamily member 9 (4-1B) domain, a TNF receptor superfamily member 18 (GITR) domain, a CD4 molecule (CD4) domain, a CD8a molecule (CD8a) domain, a FYN proto-oncogene, Src family tyrosine kinase (Fyn) domain, a zeta chain of T cell receptor associated protein kinase 70 (ZAP70) domain, a linker for activation of T cells (LAT) domain, lymphocyte cytosolic protein 2 (SLP76) domain, (TCR) alpha, TCR beta, CD3 delta, CD3 gamma and CD3 epsilon intracellular domains.

The TCR intracellular domain may comprise at least one intracellular signaling domain. An intracellular signaling domain generates a signal that promotes a function a cell, for example an immune effector function of a TCR containing cell, e.g., a TCR-expressing T cell. In certain methods and cells of the disclosure, the intracellular domain of the fusion proteins includes at least one intracellular signaling domain. For example, the intracellular domains of CD3 gamma, delta or epsilon comprise signaling domains.

The extracellular domain, transmembrane domain and intracellular domain may be isolated or derived from the same protein, for example T cell receptor (TCR) alpha, TCR beta, CD3 delta, CD3 gamma or CD3 epsilon.

Examples of intracellular domains for use in fusion proteins of the disclosure include the cytoplasmic sequences of the TCR alpha, TCR beta, CD3 zeta, and 4-1BB, and the intracellular signaling co-receptors that act in concert to initiate signal transduction following antigen receptor engagement, as well as any derivative or variant of these sequences and any recombinant sequence that has the same functional capability.

The intracellular signaling domain may comprise a primary intracellular signaling domain. Exemplary primary intracellular signaling domains include those derived from the proteins responsible for primary stimulation, or antigen dependent stimulation.

In some embodiments, the stimulatory domain comprises a CD28 intracellular domain. In some embodiments, the CD28 intracellular domain comprises an amino acid sequence having at least 85% identity, at least 90% identity, at least 95% identity, at least 96% identity, at least 97% identity, at least 98% identity, at least 99% identity or is identical to a sequence of SEQ ID NO: 37 and/or is encoded by a nucleotide sequence having at least 80% identity, at least 90% identity, at least 95% identity, at least 99% identity or is identical to a sequence of SEQ ID NO: 30.

In some embodiments, the stimulatory domain comprises a 4-IBB intracellular domain. In some embodiments, the 4-IBB intracellular domain comprises an amino acid sequence having at least 85% identity, at least 90% identity, at least 95% identity, at least 96% identity, at least 97% identity, at least 98% identity, at least 99% identity or is identical to a sequence of SEQ ID NO: 39 and/or is encoded by a nucleotide sequence having at least 80% identity, at least 90% identity, at least 95% identity, at least 99% identity or is identical to a sequence of SEQ ID NO: 40.

An intracellular signaling domain is generally responsible for activation of at least one of the normal effector functions of the immune cell in which the fusion protein has been introduced. The term "effector function" refers to a specialized function of a cell. Effector function of a T cell, for example, may be cytolytic activity or helper activity including the secretion of cytokines.

Thus, "intracellular signaling domain" refers to the portion of a protein which transduces the effector function signal and directs the cell to perform a specialized function. While in some cases the entire intracellular signaling domain can be employed, in many cases it is not necessary to use the entire intracellular signaling domain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

The intracellular domain may comprise the entirety or a portion of a CD3 delta intracellular domain, a CD3 epsilon intracellular domain, a CD3 gamma intracellular domain, or a CD3 zeta intracellular domain, such as those disclosed by the present inventors in PCT International Application No. PCT/US2020/045250, which is incorporated by reference.

The intracellular domain may comprise a TCR alpha intracellular domain or a TCR beta intracellular domain, such as those disclosed by the present inventors in PCT International Application No. PCT/US2020/045250, incorporated by reference.

The intracellular signaling domain may comprise at least one stimulatory intracellular domain. The intracellular signaling domain may comprise a primary intracellular signaling domain, such as a CD3 delta, CD3 gamma and CD3 epsilon intracellular domain, and one additional stimulatory intracellular domain, for example a co-stimulatory domain. The intracellular signaling domain may comprise a primary intracellular signaling domain, such as a CD3 delta, CD3 gamma and CD3 epsilon intracellular domain, and two additional stimulatory intracellular domains.

An exemplary CD3 delta intracellular domain may comprise, for example, an amino acid sequence having at least 85% identity, at least 90% identity, at least 95% identity, at least 96% identity, at least 97% identity, at least 98% identity, at least 99% identity or is identical to a sequence of SEQ ID NO: 30 and/or is encoded by a nucleotide sequence having at least 80% identity, at least 90% identity, at least 95% identity, at least 99% identity or is identical to a sequence of SEQ ID NO: 31.

An exemplary CD3 epsilon intracellular domain may comprise, for example, an amino acid sequence having at least 85% identity, at least 90% identity, at least 95% identity, at least 96% identity, at least 97% identity, at least 98% identity, at least 99% identity or is identical to a sequence of SEQ ID NO: 32 and/or is encoded by a nucleotide sequence having at least 80% identity, at least 90% identity, at least 95% identity, at least 99% identity or is identical to a sequence of SEQ ID NO: 19.

An exemplary CD3 gamma intracellular domain may comprise, for example, an amino acid sequence having at least 85% identity, at least 90% identity, at least 95% identity, at least 96% identity, at least 97% identity, at least 98% identity, at least 99% identity or is identical to a sequence of SEQ ID NO: 22 and/or is encoded by a nucleotide sequence having at least 80% identity, at least 90% identity, at least 95% identity, at least 99% identity or is identical to a sequence of SEQ ID NO: 9.

Exemplary co-stimulatory intracellular signaling domains include those derived from proteins responsible for co-stimulatory signals, or antigen independent stimulation.

The term "co-stimulatory molecule" refers to the cognate binding partner on a T-cell that specifically binds with a co-stimulatory ligand, thereby mediating a co-stimulatory response by the T-cell, such as, but not limited to, proliferation. Co-stimulatory molecules are cell surface molecules other than antigen receptors. Co-stimulatory molecules and their ligands are required for an efficient immune response. Co-stimulatory molecules include, but are not limited to an MHC class I molecule, BTLA, a Toll ligand receptor, as well as DAP10, DAP12, CD30, LIGHT, OX40, CD2, CD27, CDS, ICAM-1, LFA-1 (CD11a/CD18) 4-1BB (CD137, TNF receptor superfamily member 9), and CD28 molecule (CD28).

A "co-stimulatory domain", sometimes referred to as "a co-stimulatory intracellular signaling domain" can be the intracellular portion of a co-stimulatory protein. A co-stimulatory domain can be a domain of a co-stimulatory protein that transduces the co-stimulatory signal. A co-stimulatory protein can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, a ligand that specifically binds with CD83, CD4, and the like. The co-stimulatory domain can comprise the entire intracellular portion, or the entire native intracellular signaling domain, of the molecule from which it is derived, or a functional fragment thereof.

The stimulatory domain may comprise a co-stimulatory domain. The co-stimulatory domain may comprise a CD28 or 4-1BB co-stimulatory domain. CD28 and 4-1BB are well characterized co-stimulatory molecules required for full T cell activation and known to enhance T cell effector function. For example, CD28 and 4-1BB have been utilized in chimeric antigen receptors (CARs) to boost cytokine release, cytolytic function, and persistence over the first-generation CAR containing only the CD3 zeta signaling domain. Likewise, inclusion of co-stimulatory domains, for example CD28 and 4-1BB domains, in engineered TCR can increase T cell effector function and specifically allow co-stimulation in the absence of co-stimulatory ligand, which is typically down-regulated on the surface of tumor cells.

The stimulatory domain may comprise or be derived from a CD28 intracellular domain or a 4-1BB intracellular domain, such as those disclosed by the present inventors in PCT International Application No. PCT/US2020/045250, which is incorporated herein by reference.

The disclosure provides inhibitory intracellular domains which can be fused to the transmembrane or intracellular domain of any of the TCR subunits to generate a blocking TCR.

The inhibitory intracellular domain may comprise an immunoreceptor tyrosine-based inhibitory motif (ITIM). The inhibitory intracellular domain comprising an ITIM can be isolated or derived from an immune checkpoint inhibitor such as CTLA-4 and PD-1.

Inhibitory domains can be isolated from human tumor necrosis factor related apoptosis inducing ligand (TRAIL) receptor and CD200 receptor 1.

The inhibitory domain may comprise an intracellular domain, a transmembrane domain or a combination thereof. The inhibitory domain may comprise an intracellular domain, a transmembrane domain, a hinge region or a combination thereof. The inhibitory domain may comprise an immunoreceptor tyrosine-based inhibitory motif (ITIM). The inhibitory domain comprising an ITIM can be isolated or derived from an immune checkpoint inhibitor such as CTLA-4 and PD-1.

Inhibitory domains can be isolated from human tumor necrosis factor related apoptosis inducing ligand (TRAIL) receptor and CD200 receptor 1. The inhibitory domain can be isolated or derived from a human protein, for example a human TRAIL receptor, CTLA-4, or PD-1 protein. In some embodiments, the TRAIL receptor comprises TR10A, TR10B or TR10D.

Endogenous TRAIL is expressed as a 281-amino acid type II trans-membrane protein, which is anchored to the plasma membrane and presented on the cell surface. TRAIL is expressed by natural killer cells, which, following the establishment of cell-cell contacts, can induce TRAIL-dependent apoptosis in target cells. Physiologically, the TRAIL-signaling system was shown to be essential for immune surveillance, for shaping the immune system through regulating T-helper cell 1 versus T-helper cell 2 as well as "helpless" CD8+ T-cell numbers, and for the suppression of spontaneous tumor formation.

The inhibitory domain may comprise an intracellular domain isolated or derived from a CD200 receptor. The cell surface glycoprotein CD200 receptor 1 (Uniprot ref: Q8TD46) represents another example of an inhibitory intracellular domain of the present invention. This inhibitory receptor for the CD200/OX2 cell surface glycoprotein limits inflammation by inhibiting the expression of proinflammatory molecules including TNF-alpha, interferons, and inducible nitric oxide synthase (iNOS) in response to selected stimuli.

The inhibitory domain may be isolated or derived from killer cell immunoglobulin like receptor, three Ig domains and long cytoplasmic tail 2 (KIR3DL2), killer cell immunoglobulin like receptor, three Ig domains and long cytoplasmic tail 3 (KIR3DL3), leukocyte immunoglobulin like receptor B1 (LIR1), programmed cell death 1 (PD1), Fc gamma receptor IIB (FcgRIIB), killer cell lectin like receptor K1 (NKG2D), CTLA-4, a domain containing a synthetic consensus ITIM, a ZAP70 SH2 domain (e.g., one or both of the N and C terminal SH2 domains), or ZAP70 KI_K369A (kinase inactive ZAP70).

The inhibitory domain can be isolated or derived from a human protein.

The blocking receptor may comprise a cytoplasmic domain and transmembrane domain isolated or derived from the same protein, for example an ITIM containing protein. The blocking receptor may comprise a cytoplasmic domain, a transmembrane domain, and an extracellular domain or a portion thereof isolated or derived isolated or derived from the same protein, for example an ITIM containing protein. The blocking receptor may comprise a hinge region isolated or derived from isolated or derived from the same protein as the intracellular domain and/or transmembrane domain, for example an ITIM containing protein.

The blocking receptor may be a TCR comprising an inhibitory domain (an inhibitory TCR). The inhibitory TCR may comprise an inhibitory intracellular domain and/or an inhibitory transmembrane domain. The inhibitory intracellular domain can be fused to the intracellular domain of any one or more subunits of the TCR complex, including TCR alpha, TCR beta, CD3 delta, CD3 gamma or CD3 epsilon, or a portion of any thereof. The inhibitory intracellular domain can be fused to the transmembrane domain of TCR alpha, TCR beta, CD3 delta, CD3 gamma or CD3 epsilon.

The blocking receptor may comprise a hinge, transmembrane domain, and/or an intracellular domain derived from leukocyte immunoglobulin like receptor B1 (LILRBI). The blocking receptor may comprise the intracellular domain of the protein phosphoprotein membrane anchor with glycosphingolipid microdomains 1 (PAG1) or a functional variant thereof, and optionally hinge, a transmembrane domain, and/or one or more further intracellular domains. The transmembrane domain may be the transmembrane domain of PAG1. The hinge, transmembrane domain, and/or a further intracellular domain may be from leukocyte immunoglobulin like receptor B1 (LILRB1), PAG1 or a combination thereof. Examples of such blocking receptors have been disclosed by the Inventors of the present disclosure in U.S. Provisional Application Nos. 63/018,881 and 62/946,888 and PCT/US2021/030149, which are herein incorporated by reference in its entirety.

In some embodiments of the receptors having one or more domains isolated or derived from LILRB1, the one or more domains of LILRB1 comprise an amino acid sequence that is at least 80%, at least 90%, at least 95%, at least 96%, at least 97%, at least 98%, at least 99% or is identical to a sequence or subsequence of SEQ ID NO: 65, 77, 78, 79, 80, 81, 82, 83, 84, or 85 and/or is encoded by a polynucleotide sequence that is at least 80%, at least 90%, at least 95%, at least 96%, at least 97%, at least 98%, at least 99% or is identical to a sequence or subsequence of SEQ ID NO: 66.

In various embodiments, an blocking receptor is provided, comprising a polypeptide, wherein the polypeptide comprises one or more of: an LILRB1 hinge domain or functional fragment or variant thereof; an LILRB1 transmembrane domain or a functional variant thereof; and an LILRB1 intracellular domain or an intracellular domain comprising at least one, or at least two immunoreceptor tyrosine-based inhibitory motifs (ITIMs), wherein each ITIM is independently selected from and/or includes a sequence of SEQ ID NOS: 67, 68, 69, 70, 71, 72, 73, 74, 75, or 76.

Assays

Provided herein are assays that can be used to measure the activity of the engineered receptors and immune cells disclosed herein.

Receptor activity may be assayed using a cell line engineered to express a reporter of receptor activity such as a luciferase reporter. Exemplary cell lines include Jurkat T cells, although any suitable cell line known in the art may be used. For example, Jurkat cells expressing a luciferase reporter under the control of an NFAT promoter can be used as effector cells. Expression of luciferase by this cell line reflects TCR-mediated signaling.

Nuclear factor of activated T cells (NFAT) is a family of transcription factors shown to be important in immune response. The NFAT transcription factor family consists of five members NFATc1, NFATc2, NFATc3, NFATc4, and NFAT5. NFAT plays a role in regulating inflammation. As used herein, an NFAT promoter is a promoter that is regulated (i.e., activated or repressed) when NFAT is expressed in a cell. NFAT target promoters are described in Badran, B. M. et al., (2002) *J. Biological Chemistry*, Vol. 277: 47136-47148, incorporated herein by reference, and contain NFAT consensus sequences such as GGAAA.

The reporter cells can be transfected with each of the various fusion protein constructs, combinations of fusion protein constructs or controls described herein. Expression of the fusion proteins in reporter cells can be confirmed by using fluorescently labeled MHC tetramers, for example Alexa Fluor 647-labeled NY-ESO-1-MHC tetramer, to detect expression of the fusion protein.

To assay the activity of engineered receptors, target cells can be loaded with activating or blocking ligands prior to exposure to the cells comprising the reporter and the engineered receptor(s). For example, target cells can be loaded with ligands at least 12, 14, 16, 18, 20, 22 or 24 hours prior to exposure to immune cells. Exemplary target cells include A375 cells, although any suitable cells known in the art may be used. In some cases, target cells can be loaded with serially diluted concentrations of a ligand, such as NY-ESO-1 peptide. The immune cells can then be cocultured with target cells for a suitable period of time, for example 6 hours. Luciferase is then measured by luminescence reading after co-culture. Luciferase luminescence can be normalized to maximum and minimum intensity to allow comparison of activating peptide concentrations for each engineered receptor construct.

Provided herein are methods of determining the relative $EC_{50}$ of engineered receptors of the disclosure. As used herein, "$EC_{50}$" refers to the concentration of an inhibitor or agent to cause half the maximal response (or binding). Binding of the ligand, or probe to the engineered receptor can be measured by staining with labeled peptide or labeled peptide-MHC complex, for example MHC:NY-ESO-1 pMHC complex conjugated with fluorophore. $EC_{50}$ can be obtained by nonlinear regression curve fitting of reporter signal with peptide titration. Probe binding and $EC_{50}$ can be normalized to the levels of benchmark TCR without a fusion protein, e.g. NY-ESO-1 (clone 1G4).

Methods of assessing the effects of receptor activation on gene expression are known in the art, and include the use of reporter genes, whose expression can be quantified. Reporter genes can be used for identifying potentially transfected or transduced cells and for evaluating the functionality of regulatory sequences.

In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene. See, e.g., Ui-Tei et al., 2000 *FEBS Letters* 479: 79-82, which is incorporated herein by reference.

Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription. In exemplary embodiments, an NFAT promoter operably linked to a reporter gene is used to evaluate the expression of the receptors of the disclosure on NFAT signaling.

Exemplary assays have been disclosed by the present Inventors in PCT International Application Nos. PCT/US2019/037038, PCT/US2020/045250, PCT/US2020/045228, PCT/US2020/045373, and PCT/CA2016/051421, and U.S. Provisional Application Nos. 62/946,888, 62/934,419, 63/076,123, 63/068,244, 63/068,249, 63/068,245, 63/068,246, 63/065,324, and 63/037,975, which are each incorporated herein by reference.

Immune Cells

An immune cell can be a cell involved in the innate or adaptive (acquired) immune systems. Exemplary innate immune cells include phagocytic cells such as neutrophils, monocytes and macrophages, Natural Killer (NK) cells, polymophonuclear leukocytes such as neutrophils eosinophils and basophils and mononuclear cells such as monocytes, macrophages and mast cells. Immune cells with roles in acquired immunity include lymphocytes such as T-cells and B-cells. An engineered immune cell of the present disclosure can be derived from an innate immune cell and/or can be a modified innate immune cell.

A T cell is a type of lymphocyte that originates from a bone marrow precursor that develops in the thymus gland. There are several distinct types of T-cells which develop upon migration to the thymus, which include, helper CD4+ T-cells, cytotoxic CD8+ T cells, memory T cells, regulatory CD4+ T-cells and stem memory T-cells. Different types of T cells can be distinguished by the ordinarily skilled artisan based on their expression of markers. Methods of distinguishing between T cell types will be readily apparent to the ordinarily skilled artisan.

The present disclosure also comprises methods of producing and modifying the engineered immune cells disclosed herein. The engineered immune cells of the present disclosure can be derived from any naturally occurring immune cell.

Methods of producing the disclosed immune cells may comprise introducing polynucleotide encoding the activating and blocking receptors into cells, optionally using vectors. The resulting cells express the polynucleotide encoding the receptors.

Methods transforming populations of immune cells, such as T cells, with vectors will be readily apparent to the person of ordinary skill in the art. For example, CD3+ T cells can be isolated from PBMCs using a CD3+ T cell negative isolation kit (Miltenyi), according to manufacturer's instructions. T cells can be cultured at a density of 1×10^6 cells/mL in X-Vivo 15 media supplemented with 5% human A/B serum and 1% Pen/strep in the presence of CD3/28 Dynabeads (1:1 cell to bead ratio) and 300 Units/mL of IL-2 (Miltenyi). After 2 days, T cells can be transduced with viral vectors, such as lentiviral vectors using methods known in the art. In some embodiments, the viral vector is transduced at a multiplicity of infection (MOI) of 5. Cells can then be cultured in IL-2 or other cytokines such as combinations of IL-7/15/21 for an additional 5 days prior to enrichment.

Methods of isolating and culturing other populations of immune cells, such as B cells, or other populations of T cells, will be readily apparent to the person of ordinary skill in the art. Although this method outlines a potential approach it should be noted that these methodologies are rapidly evolving. For example, high levels of viral transduction of peripheral blood mononuclear cells can be achieved after 5 days of growth to generate a >99% CD3+ highly transduced cell population.

In some embodiments, the first and second receptors are encoded by a single vector. Methods of encoding multiple polypeptides using a single vector will be known to persons of ordinary skill in the art, and include, inter alia, encoding multiple polypeptides under control of different promoters, or, if a single promoter is used to control transcription of multiple polypeptides, use of sequences encoding internal ribosome entry sites (IRES) and/or self-cleaving peptides. Exemplary self-cleaving peptides include T2A, P2A, E2A and F2A self-cleaving peptides. In some embodiments, the T2A self-cleaving peptide comprises a sequence of EGRGSLLTCGDVEENPGP (SEQ ID NO: 271). In some embodiments, the P2A self-cleaving peptide comprises a sequence of ATNFSLLKQAGDVEENPGP (SEQ ID NO: 192). In some embodiments, the E2A self-cleaving peptide comprises a sequence of QCTNYALLKLAGDVESNPGP (SEQ ID NO: 272). In some embodiments, the F2A selfcleaving peptide comprises a sequence of VKQTLNFDLLKLAGDVESNPGP (SEQ ID NO: 273).

Methods of activating and culturing populations immune cells comprising the receptors, polynucleotides, or vectors of the disclosure will be readily apparent to the person of ordinary skill in the art.

Whether prior to or after genetic modification, the immune cells of the present disclosure can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041, 10,040,846; and U.S. Pat. Appl. Pub. No. 2006/0121005, each of which are incorporated herein by reference.

Immune cells of the instant disclosure can be expanded and activated in vitro. Generally, the immune cells of the instant disclosure are expanded in vitro by contact with a surface having an attached agent that stimulates a CD3/TCR complex associated signal and a ligand that stimulates a co-stimulatory molecule on the surface of the immune cells. Immune cell populations may be stimulated as described herein, such as by contact with an anti-CD3 antibody. For co-stimulation of an accessory molecule on the surface of the immune cells, a ligand that binds the accessory molecule can be used. For example, a population of T cells can be contacted with an anti-CD3 antibody and an anti-CD28 antibody, under conditions appropriate to stimulate proliferation of the T cells. In order to stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besangon, France) can be used as can other methods commonly known in the art, such as in Berg et al., *Transplant Proc.* 30(8):3975-3977, 1998; Haanen et al., *J. Exp. Med.* 190(9):13191328, 1999; and Garland et al., *J. Immunol Meth.* 227(1-2):53-63, 1999, each of which is incorporated herein by reference.

The primary stimulatory signal and the co-stimulatory signal for an immune cell of the disclosure may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. The agent providing the co-stimulatory signal may be bound to a cell surface and the agent providing the primary activation signal is in solution or coupled to a surface. Both agents can be in solution. The agents may be in soluble form, and then cross-linked to a surface, such as a cell expressing Fc receptors or an antibody or other binding agent which will bind to the agents. U.S. Patent Application Publication Nos. 2004/0101519 and 2006/0034810, which are incorporated herein by reference, disclose artificial antigen presenting cells (aAPCs) that are contemplated for use in activating and expanding immune cells of the present invention.

The two agents may be immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof, and both agents are co-immobilized to the same bead in equivalent molecular amounts.

In certain methods of the disclosure, a 1:1 ratio of each antibody bound to the beads for CD4+ immune cell expansion and growth is used. The ratio of CD3:CD28 antibody bound to the beads may range from 100:1 to 1:100, and all integer values there between. In one aspect of the present disclosure, more anti-CD28 antibody is bound to the particles than anti-CD3 antibody, i.e., the ratio of CD3:CD28 is less than one. In certain methods of the disclosure, the ratio of anti CD28 antibody to anti CD3 antibody bound to the beads is greater than 2:1.

Ratios of particles to cells from 1:500 to 500:1, and any integer values in between, may be used to stimulate immune cells, such as T cells, or other target cells. As those of ordinary skill in the art can readily appreciate, the ratio of particles to cells may depend on particle size relative to the target cell. For example, small sized beads may only bind a few cells, while larger beads can bind many.

In certain methods of the disclosure, the ratio of cells to particles ranges from 1:100 to 100:1, and any integer values in-between, can be used to stimulate the immune cells. In certain methods of the disclosure, the ratio comprises 1:9 to 9:1 and any integer values in between. In certain methods, a ratio of 1:1 cells to beads may be used. One of skill in the art will appreciate that a variety of other ratios may be suitable for use in the present invention. In particular, the ratios used will vary depending on particle size and on cell size and type.

In further methods of the present disclosure, the immune cells, such as T cells, are combined with agent-coated beads, the beads and the cells are subsequently separated, and then the cells are cultured. Alternatively, prior to culture, the agent-coated beads and cells are not separated, but are cultured together. The beads and cells may initially be concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached to contact the immune cells. The cells (for example, CD4+ T cells) and beads (for example, DYNABEADS CD3/CD28 T paramagnetic beads at a ratio of 1:1) are combined in a buffer. Again, those of ordinary skill in the art can readily appreciate any cell concentration may be used. In certain methods, it may be desirable to significantly decrease the volume in which particles and cells are mixed together (i.e., increase the concentration of cells), to ensure maximum contact of cells and particles. For example, a concentration of about 2 billion cells/ml can be used. Alternatively, greater than 100 million cells/ml can be used. A concentration of cells of 10, 15, 20, 25, 30, 35, 40, 45, or 50 million cells/ml can be used. A concentration of cells from 75, 80, 85, 90, 95, or 100 million cells/ml can be used. Concentrations of 125 or 150 million cells/ml can be used. In certain methods, cells are cultured at a density of $1\times10^6$ cells/mL.

The mixture may be cultured for several hours (about 3 hours) to about 14 days or any hourly integer value in between. The beads and immune cells may be cultured together for 2-3 days. Conditions appropriate for immune cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-7, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of immune cells. The media may comprise XVIVO-15 media supplemented with 5% human A/B serum, 1% penicillin/streptomycin (pen/strep) and 300 Units/ml of IL-2 (Miltenyi).

The engineered immune cells can be maintained under conditions necessary to support growth, for example, an appropriate temperature (e.g., 37° C.) and atmosphere (e.g., air plus 5% CO2).

Immune cells comprising receptors of the present disclosure may be autologous. Prior to expansion and genetic modification, a source of immune cells can obtained from a subject, such as a human patient. Immune cells, such as T cells, can be obtained from a number of sources, including peripheral blood mononuclear cells, bone marrow, lymph node tissue, cord blood, thymus tissue, tissue from a site of infection, ascites, pleural effusion, spleen tissue, and tumors.

In certain methods of the disclosure, any number of immune cell lines available in the art, may be used. Immune cells can be obtained from a unit of blood collected from a subject using any number of techniques known to the skilled artisan, such as Ficoll™ separation.

Cells from the circulating blood of an individual can be obtained by apheresis. The apheresis product typically contains lymphocytes, including T cells, monocytes, granulocytes, B cells, other nucleated white blood cells, red blood cells, and platelets. Cells collected by apheresis may be washed to remove the plasma fraction and to place the cells in an appropriate buffer or media for subsequent processing steps. The cells can be washed with phosphate buffered saline (PBS). The wash solution may lack calcium and magnesium or may lack many, if not all, divalent cations. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca2+-free, Mg2+-free PBS, PlasmaLyte A, or other saline solution with or without buffer. Alternatively, the undesirable components of the apheresis sample may be removed and the cells directly resuspended in culture media.

Immune cells, such as T cells, can be isolated from peripheral blood lymphocytes by lysing the red blood cells and depleting the monocytes, for example, by centrifugation through a PERCOLL™ gradient or by counterflow centrifugal elutriation. Specific subpopulations of immune cells, such as T cells, B cells, or CD4+ T cells can be further isolated by positive or negative selection techniques. For example, T cells can be isolated by incubation with anti-CD4-conjugated beads, for a time period sufficient for positive selection of the desired T cells.

Enrichment of an immune cell population, such as a T cell population, by negative selection can be accomplished with a combination of antibodies directed to surface markers unique to the negatively selected cells. One method is cell sorting and/or selection via negative magnetic immune-adherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of immune cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads.

The cells may be incubated on a rotator for varying lengths of time at varying speeds at either 2-10° C. or at room temperature.

T cells for stimulation, or PBMCs from which immune cells such as T cells are isolated, can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

Exemplary immune cells and methods for producing the same include those that have been disclosed by the present Inventors in PCT International Application Nos.

PCT/US2019/037038, PCT/US2020/045250, PCT/US2020/045228, PCT/US2020/045373, and PCT/CA2016/051421, and U.S. Provisional Application Nos. 62/946,888, 62/934,419, 63/076,123, 63/068,244, 63/068,249, 63/068,245, 63/068,246, 63/065,324, and 63/037,975, which are each incorporated herein by reference.

Target Ligands

The disclosure provides receptors comprising extracellular ligand binding domains. The ligand may be an antigen and the ligand binding domain may be an antigen binding domain.

Any suitable ligand binding domain is envisaged as within the scope of the receptors described herein.

The ligand binding domain of the activating or blocking receptors may comprise an antigen binding domain comprises an antibody fragment, a Vβ only domain, a linear antibody, a single-chain variable fragment (scFv), or a single domain antibody (sdAb).

The receptors may each comprise two polypeptides each having a part of a ligand-binding domain (e.g. cognates of a heterodimeric LDB, such as a TCRα/β- or Fab-based LBD). The disclosure further provides receptors having two polypeptides, each having a part of a ligand-binding domain (e.g. cognates of a heterodimeric LDB, such as a TCRα/β- or Fab-based LBD) and one part of the ligand binding domain is fused to a hinge or transmembrane domain, while the other part of the ligand binding domain has no intracellular domain. Further variations include receptors where each polypeptide has a hinge domain, and where each polypeptide has a hinge and transmembrane domain. Some receptors may not have a hinge domain.

The ligand binding domain of the receptors may comprise a Fab fragment of an antibody.

Receptors of the present disclosure may comprise a first polypeptide that comprises an antigen-binding fragment of the heavy chain of an antibody and an intracellular domain, and a second polypeptide of the receptor comprises an antigen-binding fragment of the light chain of the antibody. Alternatively, the first polypeptide may comprise an antigen-binding fragment of the light chain of the antibody and the intracellular domain, and the second polypeptide comprises an antigen-binding fragment of the heavy chain of the antibody.

The blocking and/or activating receptors may comprise an extracellular fragment of a T cell receptor (TCR).

Any macromolecule, including virtually all proteins or peptides, can serve as an antigen for the receptors described herein. Antigens can be derived from recombinant or genomic DNA. Any DNA, which comprises a nucleotide sequence or a partial nucleotide sequence encoding a protein that elicits an immune response, encodes an antigen. An antigen need not be encoded solely by a full-length nucleotide sequence of a gene. An antigen need not be encoded by a gene. An antigen can be generated synthesized or can be derived from a biological sample, or might be macromolecule besides a polypeptide. Such a biological sample can include, but is not limited to a tissue sample, a tumor sample, a cell or a fluid with other biological components.

In the engineered receptors of the present disclosure, the antigen-binding domain may specifically bind to a target selected from etiolate receptor, αvββ integrin, BCMA, B7-H3, B7-H6, CAIX, CD19, CD20, CD22, CD30, CD33, CD37, CD44, CD44v6, CD44v7/8, CD70, CD123, CD138, CD171, CEA, DLL4, EGP-2, EGP-40, CSPG4, EGFR, ErbB2 (HER2), ErbB3 (Her3), ErbB4 (Her4), EGFRvIII, EPCAM, EphA2, EpCAM, FAP, FBP, fetal acetylcholine receptor, Fzd7, GD2, GD3, Glypican-3 (GPC3), h5T4, IL-11R, IL13R-a2, KDR, κ light chain, λ light chain, LeY, LI CAM, MAGE-A1, mesothelin, MHC presented peptides, MUC1, MUC16, NCAM, NKG2D ligands, Notch1, Notch2/3, NYESO-1, PRAME, PSCA, PSMA, Survivin, TAG-72, TEMs, TERT, VEGFR2, and ROR1.

The antigen-binding domain may specifically bind peptide MHC (pMHC) as the antigen. Exemplary pMHC antigens include, but are not limited to, MAGE-A3 pMHC (e.g., FLWGPRALV and MPKVAELVHFL peptides), HPV E6 pMHC (e.g., TIHDIILECV peptide), HPV E7 pMHC (e.g., YMLDLQPET peptide) and NY-ESO-1 pMHC (e.g., LLEFYLAMPFA or SLLMWITQV peptides).

The antigen-binding domain may specifically bind to a target selected from CD33, CD38, a human leukocyte antigen (HLA), an organ specific antigen, a blood-brain barrier specific antigen, an Epithelial-mesenchymal transition (EMT) antigen, E-cadherin, cytokeratin, Opioid-binding protein/cell adhesion molecule (OPCML), HYLA2, Deleted in Colorectal Carcinoma (DCC), Scaffold/Matrix attachment region-binding protein 1 (SMAR1), cell surface carbohydrate and mucin type O-glycan.

The antigen-binding domain of the blocking receptor may specifically bind to an antigen from a gene with high, homogeneous surface expression across tissues. High, homogeneous surface expression across tissues allows the blocking receptor to deliver a large, even inhibitory signal. The antigen may be encoded by a gene that is absent or polymorphic in in many tumors.

Methods of distinguishing the differential expression of blocking ligands (e.g., antigens) between target and non-target cells can be used in methods and systems of the invention. For example, the presence or absence of blocking ligands in nontarget and target cells can be assayed by immunohistochemistry with an antibody that binds to the inhibitor ligand, followed by microscopy or FACS, RNA expression profiling of target cells and non-target cells, or DNA sequencing of non-target and target cells to determine if the genomic locus of the blocking ligand comprises mutations in either the target or non-target cells.

Homozygous deletions in primary tumors are rare and small, and therefore unlikely to yield blocking ligand candidates. For example, in an analysis of 2218 primary tumors across 21 human cancer types, the top 4 candidates were CDKN2A, RB1, PTEN and N3PB2. However, CDKN2A (P16) was deleted in only 5% homozygous deletion across all cancers. Homozygous HLA-A deletions were found in less than 0.2% of cancers in Cheng et al., Nature Comm. 8:1221 (2017), incorporated herein by reference. In contrast, deletion of a single copy of gene in cancer cells due to loss of hemizygosity occurs far more frequently.

Thus, the blocking ligand may comprise an allele of a gene that is lost in target cells due to loss of heterozygosity, and the target cells may comprise cancer cells. Cancer cells undergo frequent genome rearrangements, including duplication and deletions. These deletions can lead to the deletion of one copy of one or more genes in the cancer cells.

Loss of heterozygosity (LOH) refers to a genetic change, whereby one of the two alleles in the genome of a cell or cells is deleted, leaving a single mono-allelic (hemizygous) locus.

The blocking ligand may comprise an HLA class I allele. The major histocompatibility complex (MHC) class I is a gene complex that encodes proteins that display antigens to cells of the immune system, triggering immune response. The Human Leukocyte Antigens (HLAs) corresponding to MHC class I are HLA-A, HLA-B and HLA-C.

The blocking ligand may comprise an HLA class I allele. The blocking ligand may comprise an allele of HLA class I that is lost in a target cell through LOH. HLA-A is a group of human leukocyte antigens (HLA) of the major histocompatibility complex (MHC) that are encoded by the HLA-A locus. HLA-A is one of three major types of human MHC class I cell surface receptors. The receptor is a heterodimer comprising a heavy a chain and smaller β chain. The α chain is encoded by a variant of HLA-A, while the β chain (β2-microglobulin) is an invariant. There are several thousand variant HLA-A alleles, all of which fall within the scope of the instant disclosure.

The blocking ligand may comprise an HLA-B allele. The HLA-B gene has many possible variations (alleles). Hundreds of versions (alleles) of the HLA-B gene are known, each of which is given a particular number (such as HLAB27).

The blocking ligand may comprise an HLA-C allele. HLA-C belongs to the HLA class I heavy chain paralogues. This class I molecule is a heterodimer consisting of a heavy chain and a light chain (beta-2 microglobulin). Over one hundred HLA-C alleles have been described.

The HLA class I allele may have broad or ubiquitous RNA expression. The HLA class I allele may have a known, or generally high minor allele frequency. The HLA class I allele may not require a peptide-MHC antigen, for example when the HLA class I allele is recognized by a pan-HLA ligand binding domain.

The blocking ligand may comprise an HLA-A allele. The HLA-A allele may comprise HLA-A*02. Various single variable domains known in the art or disclosed herein that bind to and recognize HLA-A*02 are suitable for use in the present disclosure. Such scFvs include, for example and without limitation the following mouse and humanized scFv antibodies that bind HLA-A*02 in a peptide independent manner.

The blocking ligand (e.g., an antigen) may comprise a minor histocompatibility antigen (MiHA). The inhibitor ligand may comprise an allele of a MiHA that is lost in a target cell through LOH.

MiHAs are peptides derived from proteins that contain nonsynonymous differences between alleles and are displayed by common HLA alleles. The nonsynonymous differences can arise from SNPs, deletions, frameshift mutations or insertions in the coding sequence of the gene encoding the MiHA. Exemplary MiHAs can be about 9-12 amino acids in length and can bind to MHC class I and/or MHC class II proteins. Binding of the TCR to the MHC complex displaying the MiHA can activate T cells. The genetic and immunological properties of MiHAs will be known to the person of ordinary skill in the art. Candidate MiHAs are known peptides presented by known HLA class I alleles, are known to elicit T cell responses in the clinic (for example, in graft versus host disease, or transplant rejection), and allow for patient selection by simple SNP genotyping.

The MiHA may have broad or ubiquitous RNA expression. The MiHA may have high minor allele frequency. The MiHA may comprise a peptide derived from a Y chromosome gene.

The blocking ligand may comprise a Y chromosome gene, i.e. peptide encoded by a gene on the Y chromosome. The blocking ligand may comprise a peptide encoded by a Y chromosome gene that is lost in target cells through loss of Y chromosome (LoY). For example, about a third of the characterized MiHAs come from the Y chromosome. The Y chromosome contains over 200 protein coding genes, all of which are envisaged as within the scope of the instant disclosure.

As used herein, “loss of Y”, or “LoY” refers a genetic change that occurs at high frequency in tumors whereby part or all of the Y chromosome is deleted, leading to a loss of Y chromosome encoded gene(s).

Loss of Y chromosome is known to occur in certain cancers. For example, there is a reported 40% somatic loss of Y chromosome in renal clear cell cancers (Arseneault et al., Sci. Rep. 7: 44876 (2017)). Similarly, clonal loss of the Y chromosome was reported in 5 out of 31 in male breast cancer subjects in Wong et al., *Oncotarget* 6(42):44927-40 (2015), incorporated herein by reference. Loss of the Y chromosome in tumors from male patients has been described as a “consistent feature” of head and neck cancer patients, as in el-Naggar et al., *Am J Clin Pathol* 105(1): 102-8 (1996), incorporated herein by reference. Further, Y chromosome loss was associated with X chromosome disomy in four of seven male patients with gastric cancer in Saal et al., *Virchows Arch B Cell Pathol* (1993), incorporated herein by reference. Thus, Y chromosome genes can be lost in a variety of cancers, and can be used as blocking ligands with the engineered receptors of the instant disclosure targeting cancer cells.

The activating ligand may be a transferrin receptor (TFRC). Human transferrin receptor is described in NCBI record No. AAA61153.1, the contents of which are incorporated herein by reference.

The activating ligand may be a tumor specific antigen (TSA). The tumor specific antigen may be mesothelin (MSLN), CEACAM5 or EGFR. The TSA may be MSLN, CEA, EGFR, DLL4, CA125, GD2, ROR1 or HER2/NEU. The activating ligand may be a pan-HLA ligand, and the activating receptor ligand binding domain is a pan-HLA binding domain, i.e. a binding domain that binds to and recognizes an antigenic determinant shared among HLA I products, such as the HLA A, B and C loci. The activating ligand may also be another class I gene product; e.g., antigens encoded by HLA-E or F. Various single variable domains known in the art are suitable for use in embodiments. Such scFvs include, for example and without limitation the following mouse and humanized pan-HLA scFv antibodies. An exemplary pan-HLA ligand is W6/32, which recognizes a conformational epitope, reacting with HLA class I alpha3 and alpha2 domains. Further exemplary antibodies with broad HLA binding are known in the art and include HC-10 and TFL-006. Exemplary activating ligands and activating receptor ligand binding domains have been disclosed by the Inventors of the present disclosure in U.S. Provisional Application No. 63/018,881, which is herein incorporated by reference in its entirety.

Exemplary ligands and ligand binding domains of activating and blocking receptors include those that have been disclosed by the present Inventors in PCT International Application Nos. PCT/US2019/037038, PCT/US2020/045250, PCT/US2020/045228, PCT/US2020/045373, and PCT/CA2016/051421, and U.S. Provisional Application Nos. 62/946,888, 62/934,419, 63/076,123, 63/068,244, 63/068,249, 63/068,245, 63/068,246, 63/065,324, and 63/037,975, which are each incorporated herein by reference.

For example, in some embodiments of the immune cells of the disclosure, a first/activating ligand is EGFR or a peptide antigen thereof, and the first/activating ligand binding domain comprises a sequence of SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, or SEQ ID NO: 391, or a sequence having at least 90%, at least 95% or at least 99% identity thereto. In some embodiments, the first ligand binding domain comprises CDRs selected from SEQ ID NOs: 131-166.

In some embodiments, the activator ligand is EGFR or a peptide antigen thereof, and the activator ligand binding domain comprises an EGFR binding domain. In some embodiments, the EGFR ligand binding domain comprises an ScFv domain. In some embodiments, the EGFR ligand binding domain comprises a sequence of SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118 or SEQ ID NO: 391. In some embodiments, the EGFR ligand binding domain comprises a sequence at least 90%, at least 95% or at least 99% identical to SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118 or SEQ ID NO: 391. In some embodiments, the EGFR ligand binding domain is encoded by a sequence comprising SEQ ID NO: 103, SEQ ID NO: 104, SEQ ID NO: 107, SEQ ID NO: 109, SEQ ID NO: 111, SEQ ID NO: 113, SEQ ID NO: 115, SEQ ID NO: 117 or SEQ ID NO: 119. In some embodiments, the EGFR ligand binding domain is encoded by a sequence having at least 80% identity, at least 85% identity, at least 90% identity, at least 95% identity or at least 99% identity to a sequence of SEQ ID NO: 103, SEQ ID NO: 104, SEQ ID NO: 107, SEQ ID NO: 109, SEQ ID NO: 111, SEQ ID NO: 113, SEQ ID NO: 115, SEQ ID NO: 117 or SEQ ID NO: 119.

In some embodiments, the activator ligand is EGFR or a peptide antigen thereof, and the activator ligand binding domain comprises an EGFR ligand binding domain. In some embodiments, the EGFR ligand binding domain comprises a VH domain selected from the group consisting of SEQ ID NO: 120, SEQ ID NO: 122, SEQ ID NO: 124, SEQ ID NO: 126, SEQ ID NO: 128 and SEQ ID NO: 130. In some embodiments, the EGFR ligand binding domain comprises a VH selected from the group consisting of SEQ ID NO: 120, SEQ ID NO: 122, SEQ ID NO: 124, SEQ ID NO: 126, SEQ ID NO: 128 and SEQ ID NO: 130 or a sequence having at least 90%, at least 95% or at least 99% identity thereto. In some embodiments, the EGFR ligand binding domain comprises a VL domain selected from the group consisting of SEQ ID NO: 121, SEQ ID NO: 123, SEQ ID NO: 125, SEQ ID NO: 127, SEQ ID NO: 129 and SEQ ID NO: 131. In some embodiments, the EGFR ligand binding domain comprises a VH selected from the group consisting of SEQ ID NO: 121, SEQ ID NO: 123, SEQ ID NO: 125, SEQ ID NO: 127, SEQ ID NO: 129 and SEQ ID NO: 131 or a sequence having at least 90%, at least 95% or at least 99% identity thereto.

In some embodiments, the activator ligand is EGFR or a peptide antigen thereof, and the activator ligand binding domain is an EGFR ligand binding domain. In some embodiments, the EGFR ligand binding domain comprises CDRs selected from SEQ ID NOs: 131-166. In some embodiments, the EGFR ligand binding domain comprises a heavy chain CDR 1 (CDR HI) selected from the group consisting of SEQ ID NOs: 132-137. In some embodiments, the EGFR ligand binding domain comprises a heavy chain CDR 2 (CDR H2) selected from the group consisting of SEQ ID NOs: 138-143. In some embodiments, the EGFR ligand binding domain comprises a heavy chain CDR 3 (CDR H3) selected from the group consisting of SEQ ID NOs: 144-149. In some embodiments, the EGFR ligand binding domain comprises a light chain CDR 1 (CDR LI) selected from the group consisting of SEQ ID NOs: 150-155. In some embodiments, the EGFR ligand binding domain comprises a light chain CDR 2 (CDR L2) selected from the group consisting of SEQ ID NOs: 156-160. In some embodiments, the EGFR ligand binding domain comprises a light chain CDR 3 (CDR L3) selected from the group consisting of SEQ ID NOs: 161-166. In some embodiments, the EGFR ligand binding domain comprises a CDR HI selected from SEQ ID NOs: 132-137, a CDR H2 selected from SEQ ID NOs: 138-143, a CDR H3 selected from SEQ ID NOs: 144-149, a CDR LI selected from SEQ ID NOs: 150-155, a CDR L2 selected from SEQ ID NOs: 156-160, and a CDR L3 selected from SEQ ID NOs: 156-160.

In some embodiments of the immune cells of the disclosure, the first/activating ligand is MSLN or a peptide antigen thereof. In some embodiments, the first/activating ligand binding domain comprises a sequence of SEQ ID NO: 86, SEQ ID NO: 88, SEQ ID NO: 90 or SEQ P) NO: 92, or a sequence having at least 90%, at least 95% or at least 99% identity thereto. In some embodiments, the MSLN ligand binding domain is encoded by a sequence comprising SEQ ID NO: 87, SEQ ID NO: 89, SEQ ID NO: 91 or SEQ ID NO: 93. In some embodiments, the MSLN ligand binding domain is encoded by a sequence having at least 80% identity, at least 85% identity, at least 90% identity, at least 95% identity or at least 99% identity to a sequence of SEQ ID NO: 87, SEQ ID NO: 89, SEQ ID NO: 91 or SEQ ID NO: 93.

In some embodiments of the immune cells of the disclosure, the first/activating ligand is CEA or a peptide antigen thereof. In some embodiments, the first/activating ligand binding domain comprises SEQ ID NO: 94, SEQ ID NO: 96, SEQ ID NO: 98, SEQ ID NO: 100, SEQ ID NO: 282, SEQ ID NO: 284, or SEQ ID NO: 286, or a sequence having at least 90%, at least 95% or at least 99% identity thereto. In some embodiments, the first/activating ligand binding domain comprises CDRs selected from SEQ ID NOs: 294-302. In some embodiments, the CEA ligand binding domain is encoded by a sequence having at least 80% identity, at least 85% identity, at least 90% identity, at least 95% identity or at least 99% identity to a sequence of SEQ ID NO: 95, SEQ ID NO: 97, SEQ ID NO: 99, SEQ ID NO: 101, SEQ ID NO: 283, SEQ ID NO: 285 or SEQ ID NO: 287.

In some embodiments, the activator ligand is CEA or a peptide antigen thereof, and the activator ligand binding domain comprises a CEA binding domain. In some embodiments, the CEA ligand binding domain comprises a CDR-H1 of EFGMN (SEQ ID NO: 294), a CDR-H2 of WINTKTGEATYVEEFKG (SEQ ID NO: 295), a CDR-H3 of WDF AYYVEAMD Y (SEQ ID NO: 296) or WDFAHYFQTMDY (SEQ ID NO: 297), a CDR-L1 of KASQNVGTNV A (SEQ ID NO: 298) or KASAAVGTYVA (SEQ ID NO: 299), a CDR-L2 of SASYRYS (SEQ ID NO: 300) or SASYRKR (SEQ ID NO: 301), and a CDR-L3 of HQ YYTYPLFT (SEQ ID NO: 302) or sequences having at least 85% or at least 95% identity thereto. In some embodiments, a CEA ScFv comprises a CDR-H1 of EFGMN (SEQ ID NO: 294), a CDR-H2 of WINTKTGEATYVEEFKG (SEQ ID NO: 295), a CDR-H3 of WDF AYYVEAMD Y (SEQ ID NO: 296) or WDFAHYFQTMDY (SEQ ID NO: 297), a CDR-L1 of KASQNVGTNV A (SEQ ID NO: 298) or KASAAVGTYVA (SEQ ID NO: 299), a CDR-L2 of SASYRYS (SEQ ID NO: 300) or SASYRKR (SEQ ID NO: 301) and a CDR-L3 of HQ YYTYPLFT (SEQ ID NO: 302).

In some embodiments, a CEA binding domain comprises a CDR-H1 of EFGMN (SEQ ID NO: 294), a CDR-H2 of WINTKTGEATYVEEFKG (SEQ ID NO: 295), a CDR-H3 of WDFAYYVEAMDY (SEQ ID NO: 296), a CDR-L1 of KASQNVGTNV A (SEQ ID NO: 298), a CDR-L2 of SASYRYS (SEQ ID NO: 300) and a CDR-L3 of HQ YYTYPLFT (SEQ ID NO: 302). In some embodiments, a CEA ScFv comprises a CDR-H1 of EFGMN (SEQ ID NO: 294), a CDR-H2 of WINTKTGEATYVEEFKG (SEQ ID NO: 295), a CDR-H3 of WDFAYYVEAMDY (SEQ ID NO: 296), a CDR-L1 of KASAAVGTYVA (SEQ ID NO: 299), a CDR-L2 of SASYRKR, and a CDR-L3 of HQ YYTYPLFT (SEQ ID NO: 302). In some embodiments, a CEA binding domain comprises a CDR-H1 of EFGMN (SEQ ID NO: 294), a CDR-H2 of WINTKTGEAT YVEEFKG (SEQ IDNO: 295), a CDR-H3 of WDFAHYFQTMD Y (SEQ ID NO: 297), a CDR-L1 of KASAAVGTYVA (SEQ ID NO: 299), a CDR-L2 of SASYRKR, and a CDR-L3 of HQ YYTYPLFT (SEQ ID NO: 302).

In some embodiments, the activator ligand is CEA or a peptide antigen thereof, and the activator receptor is a CEA CAR In some embodiments, the CEA CAR comprises sequence at least 90%, at least 95% or at least 99% identical to SEQ ID NO: 288, SEQ ID NO: 290 or SEQ ID NO: 292. In some embodiments, the CEA CAR comprises or consists essentially of SEQ ID NO: 288, SEQ ID NO: 290 or SEQ ID NO: 292. In some embodiments, the CEA CAR is encoded by a sequence comprising or consisting essentially of SEQ ID NO: 289, SEQ ID NO: 291 or SEQ ID NO: 293. In some embodiments, the CEA CAR is encoded by a sequence having at least 80% identity, at least 85% identity, at least 90% identity, at least 95% identity or at least 99% identity to SEQ ID NO: 289, SEQ ID NO: 291 or SEQ ID NO: 293.

In some embodiments of the immune cells of the disclosure, the first/activating ligand is CD19 or a peptide antigen thereof, and the first ligand binding domain comprises SEQ ID NO: 275 or SEQ ID NO: 277, or a sequence having at least 90%, at least 95% or at least 99% identity thereto.

In some embodiments of the immune cells of the disclosure, the first/activating ligand is a pan-HLA ligand. In some embodiments, the first ligand binding domain comprises a sequence of SEQ ID NO: 167, SEQ ID NO: 169, SEQ ID NO: 171, SEQ ID NO: 173, SEQ ID NO: 175, or SEQ ID NO: 177, or a sequence having at least 90%, at least 95% or at least 99% identity thereto.

In some embodiments of the immune cells of the disclosure, the second/blocking ligand comprises HA-1. In some embodiments, and wherein the second/blocking ligand binding domain comprises a TCR alpha variable domain comprising SEQ ID NO: 199 or a sequence having at least 90%, at least 95%, or at least 99% identity thereto, and a TCR beta variable domain comprising SEQ ID NO: 200 or a sequence having at least 90%, at least 95%, or at least 99% identity thereto. In some embodiments, the second/blocking ligand binding domain comprises a TCR alpha variable domain comprising SEQ ID NO: 199, and a TCR beta variable domain comprising SEQ ID NO: 200.

In some embodiments of the immune cells of the disclosure, the second/blocking ligand comprises an HLA-A*02 allele. In some embodiments, the second/blocking ligand binding domain comprises any one of SEQ ID NOs: 53-64 or a sequence having at least 90%, at least 95%, or at least 99% identity thereto. In some embodiments, the second/blocking ligand binding domain comprises CDRs selected from SEQ ID NOs: 41-52.

In some embodiments of the inhibitory/blocking receptors of the disclosure, the extracellular ligand binding domain has a higher affinity for an HA-1 (H) peptide of VLHDDLLEA (SEQ ID NO: 191) than for an HA-1(R) peptide of VLRDDLLEA (SEQ ID NO: 266). In some embodiments, the inhibitory/blocking receptor is activated by the HA-1(H) peptide of VLHDDLLEA (SEQ ID NO: 191) and is not activated, or activated to a lesser extent, by the HA-1(R) peptide of VLRDDLLEA (SEQ ID NO: 266). In some embodiments, the extracellular ligand binding domain comprises a TCR alpha variable domain comprising SEQ ID NO: 199 or a sequence having at least 90%, at least 95%, or at least 99% identity thereto, and a TCR beta variable domain comprising SEQ ID NO: 200 or a sequence having at least 90%, at least 95%, or at least 99% identity thereto. In some embodiments, the extracellular ligand binding domain comprises a TCR alpha variable domain comprising SEQ ID NO: 199 and a TCR beta variable domain comprising SEQ ID NO: 200.

In some embodiments, the activator ligand is pan-HLA ligand, and the activator ligand binding domain comprises a pan-HLA ligand binding domain. In some embodiments, the pan-HLA ligand binding domain comprises an ScFv domain. In some embodiments, the pan-HLA ligand binding domain comprises a sequence of SEQ ID NO: 167, SEQ ID NO: 169, SEQ ID NO: 171, SEQ ID NO: 173, SEQ ID NO: 175, or SEQ ID NO: 177. In some embodiments, the pan-HLA ligand binding domain comprises a sequence at least 90%, at least 95% or at least 99% identical to SEQ ID NO: 167, SEQ ID NO: 169, SEQ ID NO: 171, SEQ ID NO: 173, SEQ ID NO: 175, or SEQ ID NO: 177. In some embodiments, the pan-HLA ligand binding domain is encoded by a sequence comprising SEQ ID NO: 168, SEQ ID NO: 170, SEQ ID NO: 172, SEQ ID NO: 174, SEQ ID NO: 176, or SEQ ID NO: 178. In some embodiments, the pan-HLA ligand binding domain is encoded by a sequence having at least 80% identity, at least 85% identity, at least 90% identity, at least 95% identity or at least 99% identity to a sequence of SEQ ID NO: 168, SEQ ID NO: 170, SEQ ID NO: 172, SEQ ID NO: 174, SEQ ID NO: 176, or SEQ ID NO: 178. [0181] In some embodiments, the activator ligand is CD19 molecule (CD19) or a peptide antigen thereof, and the activator ligand binding domain comprises a CD 19 ligand binding domain. In some embodiments, the CD 19 ligand binding domain comprises an ScFv domain. In some embodiments, the CD 19 ligand binding domain comprises a sequence at least 90%, at least 95% or at least 99% identical to SEQ ID NO: 275 or SEQ ID NO: 277. In some embodiments, the CD-19 ligand binding domain comprises a sequence of SEQ ID NO: 275 or SEQ ID NO: 277. In some embodiments, the CD19 ligand binding domain is encoded by a sequence comprising SEQ ID NO: 276, or SEQ ID NO: 278. In some embodiments, the CD19 ligand binding domain is encoded by a sequence having at least 80% identity, at least 85% identity, at least 90% identity, at least 95% identity or at least 99% identity to a sequence of SEQ ID NO: 276 or SEQ ID NO: 278.

In some embodiments, activator ligand is CD19 molecule (CD19) or a peptide antigen thereof, and the activator receptor is a CAR In some embodiments, the CD 19 CAR comprises a sequence at least 90%, at least 95% or at least 99% identical to SEQ ID NO: 279 or SEQ ID NO: 281. In some embodiments, the CD 19 CAR comprises or consists essentially of SEQ ID NO: 279 or SEQ ID NO: 281. In some embodiments, the CD19 CAR is encoded by a sequence having at least 80% identity, at least 85% identity, at least 90% identity, at least 95% identity or at least 99% identity to a sequence of SEQ ID NO: 280 or SEQ P) NO: 390. In some embodiments, the CD19 CAR is encoded by a sequence comprising or consisting essentially of SEQ ID NO: 280 or SEQ ID NO: 390.

In some embodiments, the one or more ligand comprises an HLA-A allele. In some embodiments the HLA-A allele comprises HLA-A*02. Various single variable domains known in the art or disclosed herein that bind to and recognize HLA-A* 02 are suitable for use in embodiments. Such scFvs include, for example and without limitation, the following mouse and humanized scFv antibodies that bind HLA-A* 02 in a peptide-independent way, which include binding domains having at least 80% identity, at least 85% identity, at least 90% identity, at least 95% identity or at least 99% identity to any one of SEQ ID NOS: 179-190.

In some embodiments, the scFv comprises the complementarity determined regions (CDRs) of any one of SEQ ID NOS: 41-52. In some embodiments, the scFv comprises a sequence at least 95% identical to any one of SEQ P) NOS: 41-52. In some embodiments, the scFv comprises a sequence identical to any one of SEQ ID NOS: 41-52. In some embodiments, the heavy chain of the antibody comprises the heavy chain CDRs of any one of SEQ ID NOS: 53-64, and wherein the light chain of the antibody comprises the light chain CDRs of any one of SEQ ID NOS: 53-64. In some embodiments, the heavy chain of the antibody comprises a sequence at least 95% identical to the heavy chain portion of any one of SEQ ID NOS: 53-64, and wherein the light chain of the antibody comprises a sequence at least 95% identical to the light chain portion of any one of SEQ ID NOS: 53-64. [0209] In some embodiments, the heavy chain of the antibody comprises a sequence identical to the heavy chain portion of any one of SEQ ID NOS: 53-64, and wherein the light chain of the antibody comprises a sequence identical to the light chain portion of any one of SEQ ID NOS: 53-64.

In some embodiments, a ligand as used herein comprises a minor histocompatibility antigen (MiHA). In some embodiments, the blocking ligand comprises an allele of a MiHA that is lost in a target cell through LOH. Exemplary, but non-limiting, examples of MiHAs that are envisaged as within the scope of the instant invention include those having the sequence of any one of SEQ ID NOS: 273, 303-325, 327-356, 358-389, 34, and 23-25.

Exemplary ligand binding domains that selectively bind to HA-1 variant H peptide (VLHDDLLEA (SEQ ID NO: 191)) include the sequences of SEQ ID NO: 194, 201, 202, 196, and 198. TCR alpha and TCR beta sequences in SEQ ID NO: 193 are separated by a P2A self-cleaving polypeptide of sequence ATNFSLLKQAGDVEENPGP (SEQ ID NO: 192) with an N terminal GSG linker.

In some embodiments, the TCR alpha and TCR beta variable domains separated by a self-cleaving polypeptide sequence comprise SEQ ID NO: 193, or a sequence having at least 90%, at least 95%, or at least 99% identity thereto. In some embodiments, the TCR alpha and TCR beta variable domains are encoded by a sequence of SEQ ID NO: 194, or a sequence having at least 80% identity, at least 90%, at least 95%, or at least 99% identity thereto. In some embodiments, the TCR alpha variable domain comprises SEQ ID NO: 199 or a sequence having at least 90%, at least 95%, or at least 99% identity thereto. In some embodiments, the TCR beta variable domain comprises SEQ ID NO: 200 or a sequence having at least 90%, at least 95%, or at least 99% identity thereto.

In some embodiments, the first or second ligand binding domain comprises a sequence of any one of SEQ ID NO: 210, SEQ ID NO: 212, SEQ ID NO: 214, SEQ ID NO: 216, SEQ ID NO: 218, SEQ ID NO: 220, SEQ ID NO: 222 Or SEQ ID NO: 224, or a sequence having at least 90%, at least 95% or at least 99% identity thereto.

It will be appreciated by the person of ordinary skill that first, activator ligand binding domains for the first receptor may be isolated or derived from any source known in the art, including, but not limited to, art recognized T cell receptors, chimeric antigen receptors and antibody binding domains.

Methods of Treatment

The present disclosure provides methods of treating a subject in need thereof, comprising administering to the subject a therapeutically effective amount of the engineered immune cells of the present disclosure.

The engineered immune cells of the present disclosure may be used to treat a subject that has cancer. The cancer may comprise a liquid tumor or a solid tumor. Exemplary liquid tumors include leukemias and lymphomas. Further cancers that are liquid tumors can be those that occur, for example, in blood, bone marrow, and lymph nodes, and can include, for example, leukemia, myeloid leukemia, lymphocytic leukemia, lymphoma, Hodgkin's lymphoma, melanoma, and multiple myeloma. Leukemias include, for example, acute lymphoblastic leukemia (ALL), acute myeloid leukemia (AML), chronic lymphocytic leukemia (CLL), chronic myelogenous leukemia (CML), and hairy cell leukemia. Exemplary solid tumors include sarcomas and carcinomas. Cancers can arise in virtually an organ in the body, including blood, bone marrow, lung, breast, colon, bone, central nervous system, pancreas, prostate and ovary. Further cancers that are solid tumors include, for example, prostate cancer, testicular cancer, breast cancer, brain cancer, pancreatic cancer, colon cancer, thyroid cancer, stomach cancer, lung cancer, ovarian cancer, Kaposi's sarcoma, skin cancer, squamous cell skin cancer, renal cancer, head and neck cancers, throat cancer, squamous carcinomas that form on the moist mucosal linings of the nose, mouth, throat, bladder cancer, osteosarcoma, cervical cancer, endometrial cancer, esophageal cancer, liver cancer, and kidney cancer. In some embodiments, the condition treated by the methods described herein is metastasis of melanoma cells, prostate cancer cells, testicular cancer cells, breast cancer cells, brain cancer cells, pancreatic cancer cells, colon cancer cells, thyroid cancer cells, stomach cancer cells, lung cancer cells, ovarian cancer cells, Kaposi's sarcoma cells, skin cancer cells, renal cancer cells, head or neck cancer cells, throat cancer cells, squamous carcinoma cells, bladder cancer cells, osteosarcoma cells, cervical cancer cells, endometrial cancer cells, esophageal cancer cells, liver cancer cells, or kidney cancer cells.

Treating cancer with the engineered immune cells of the present disclosure can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer with the engineered immune cells of the present disclosure can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer using the engineered immune cells of the present disclosure may result in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer with the engineered immune cells of the present disclosure can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer with the engineered immune cells of the present disclosure can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer with the engineered immune cells can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer with the engineered immune cells can result in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer with the engineered immune cells can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer with the engineered immune cells can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer with the engineered immune cells can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder with the engineered immune cells can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder with the engineered immune cells can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder with the engineered immune cells can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder with the engineered immune cells can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleomorphism.

Exemplary methods of treatment and conditions to be treated using the cells of the present invention including those that have been disclosed by the present Inventors in PCT International Application Nos. PCT/US2019/037038, PCT/US2020/045250, PCT/US2020/045228, PCT/US2020/045373, and PCT/CA2016/051421, and U.S. Provisional Application Nos. 62/946,888, 62/934,419, 63/076,123, 63/068,244, 63/068,249, 63/068,245, 63/068,246, 63/065,324, and 63/037,975, which are each incorporated herein by reference.

EXAMPLES

Example 1

Figure 4:
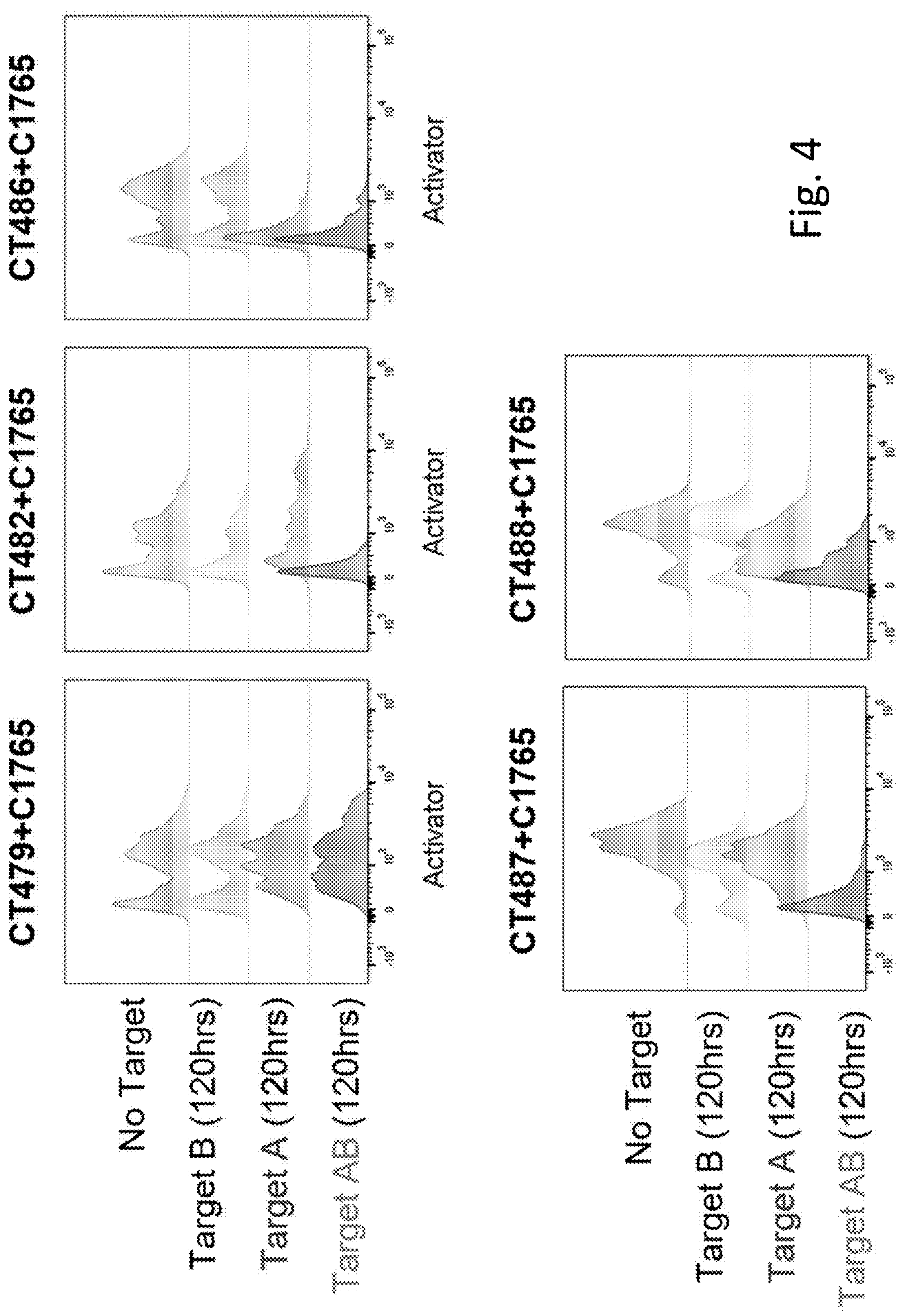
FIGS. 4-6 provide experimental results showing reduced expression of activating receptors.

FIG. 4 provides experimental results showing that, for the engineered immune cells of the present disclosure expressing activating and blocking receptors, surface levels of the activating receptor decrease when the immune cells are in the presence of non-target cells expressing both the activating and blocking ligand.

Figure 5:
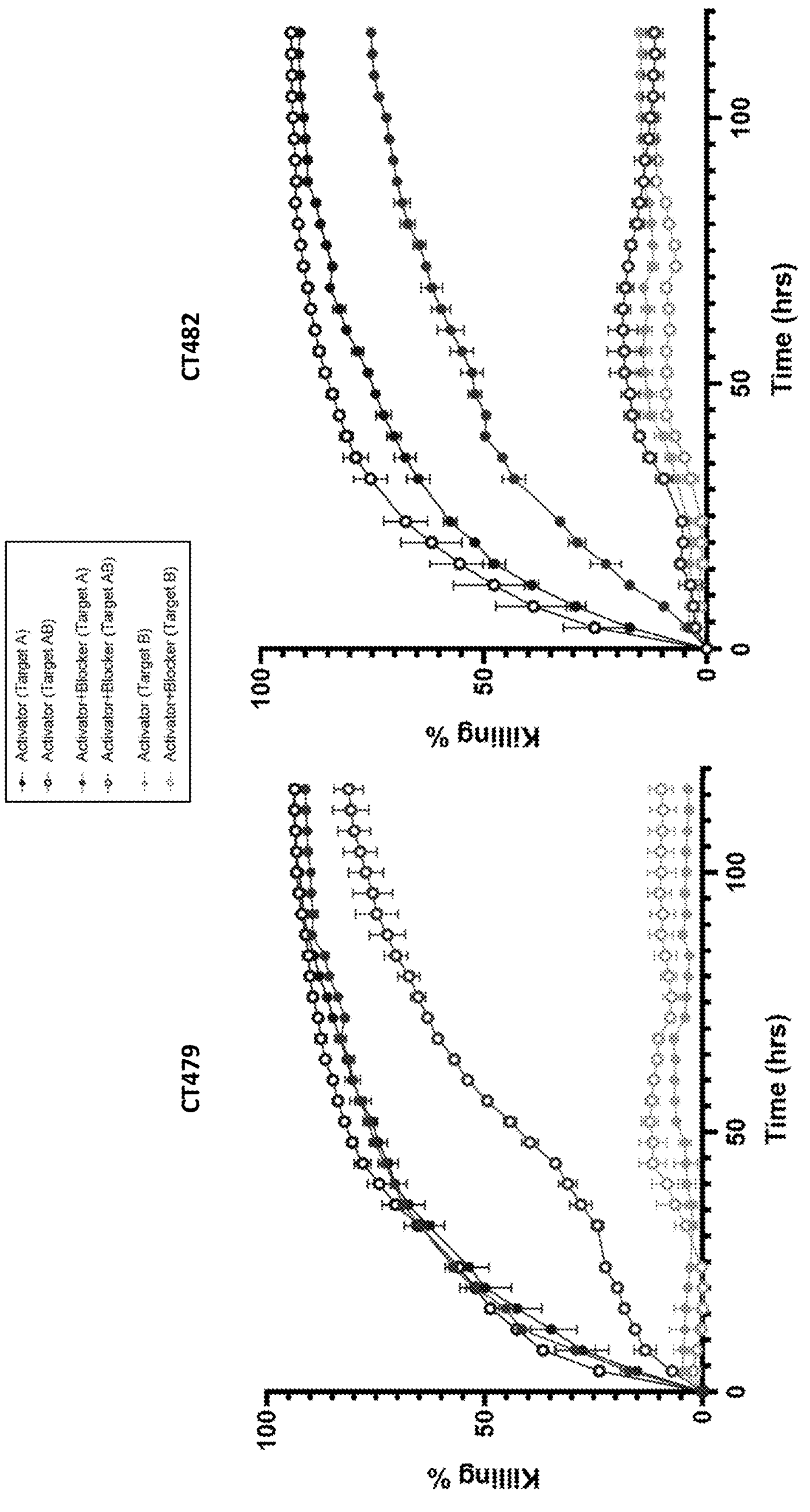
Figure 6:
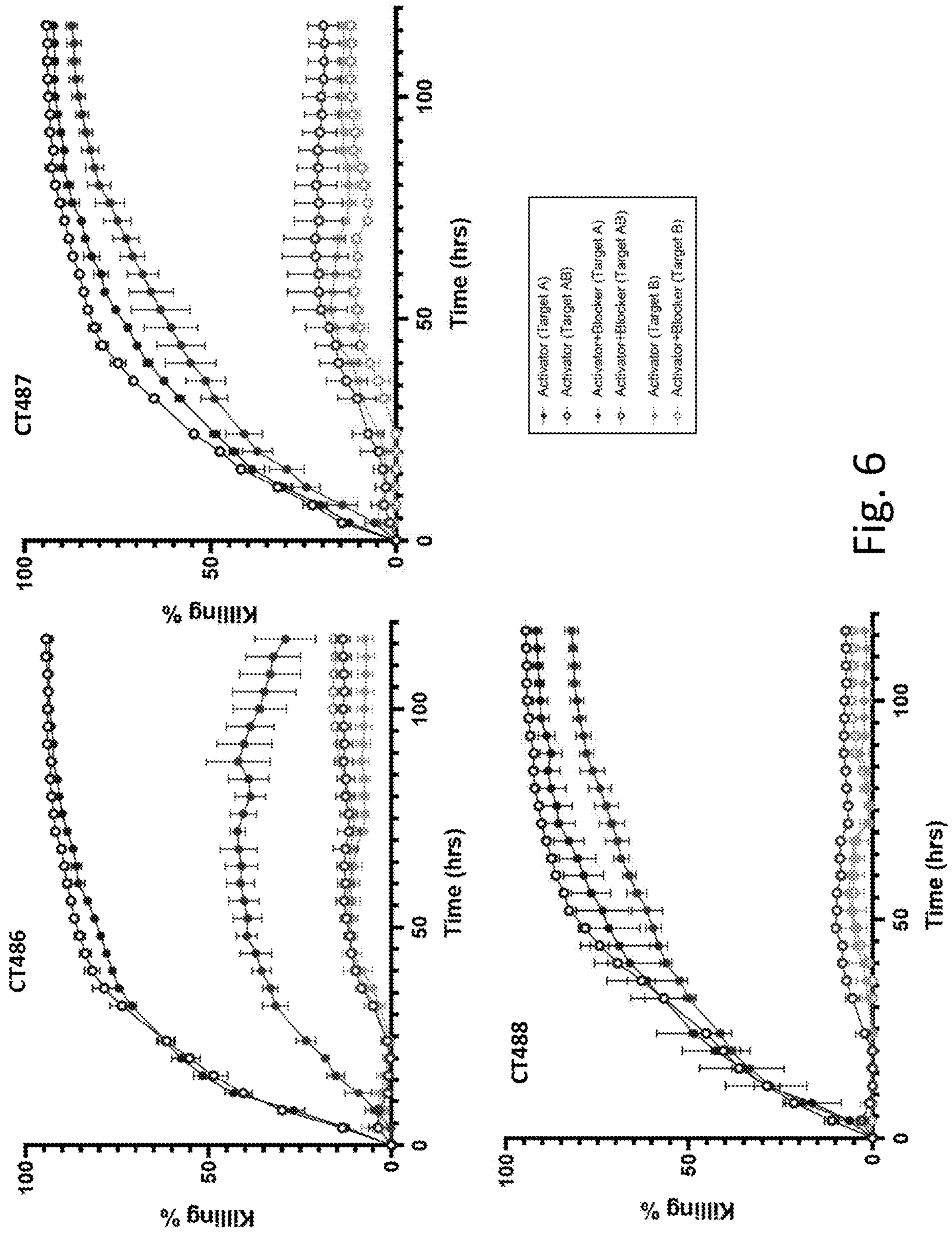
Figure 7:
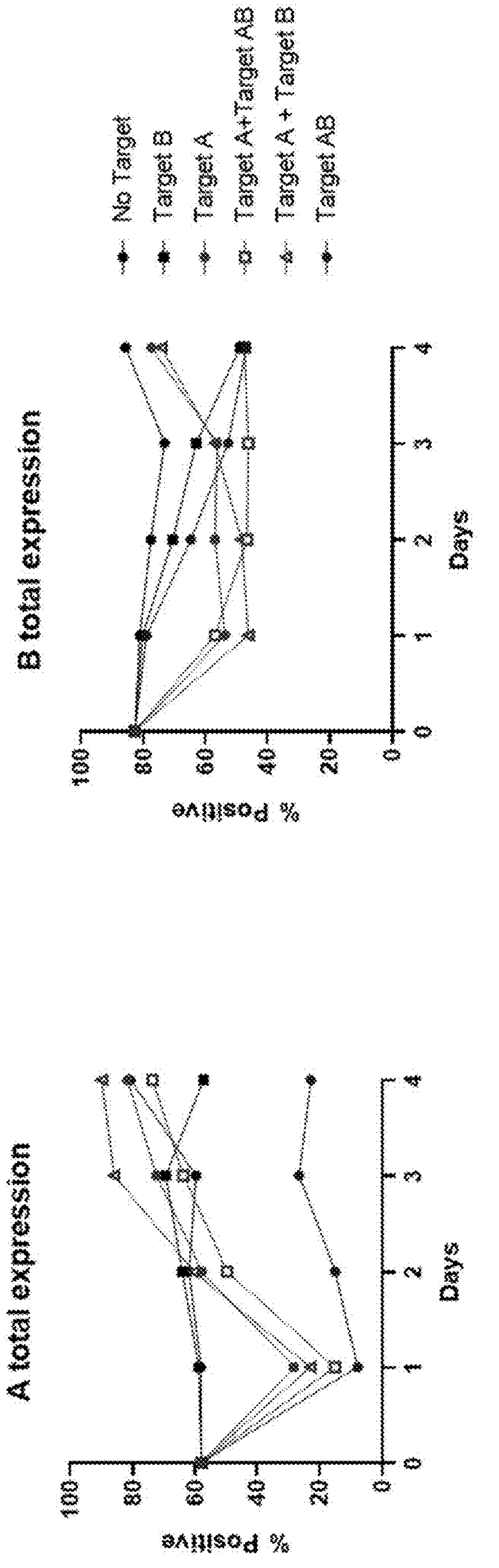
FIG. 7 provides experimental results showing reduced expression of activating receptors.
Figure 8:
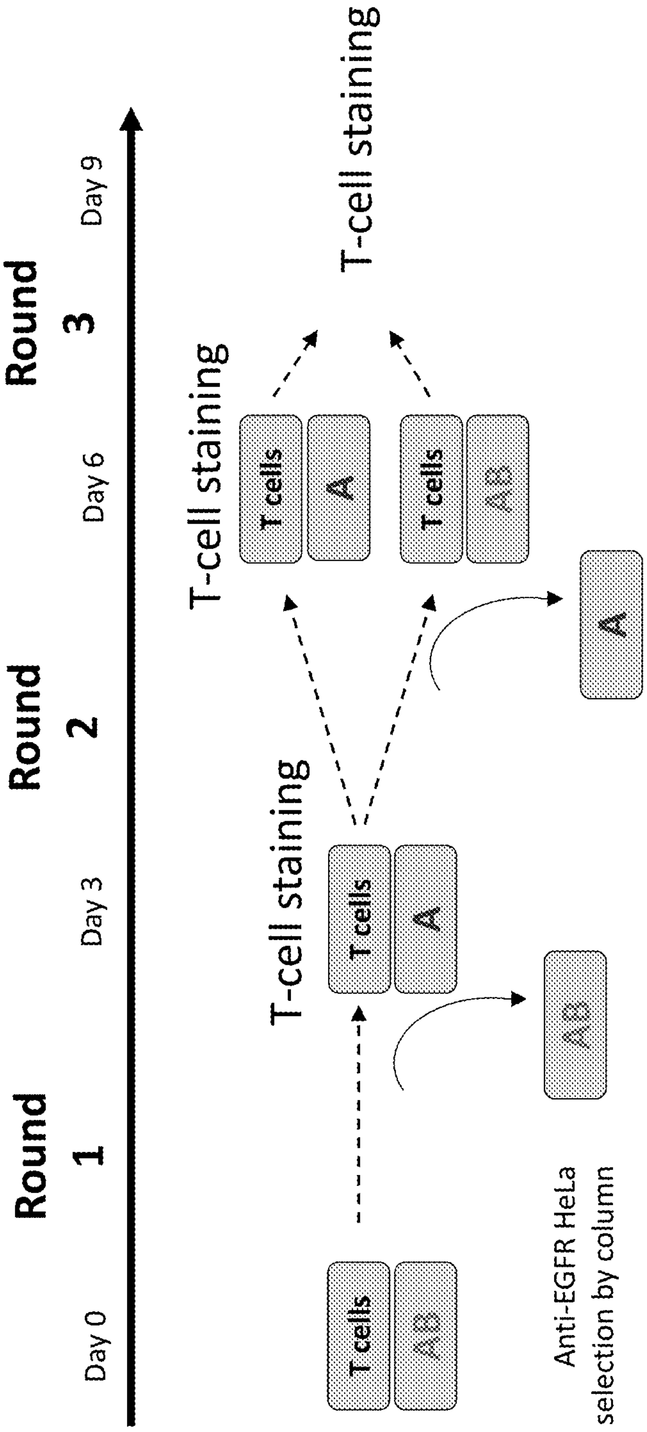
FIG. 8 shows a schematic for an experiment to show the reversibility of reduced expression of activating receptors.
Figure 9:
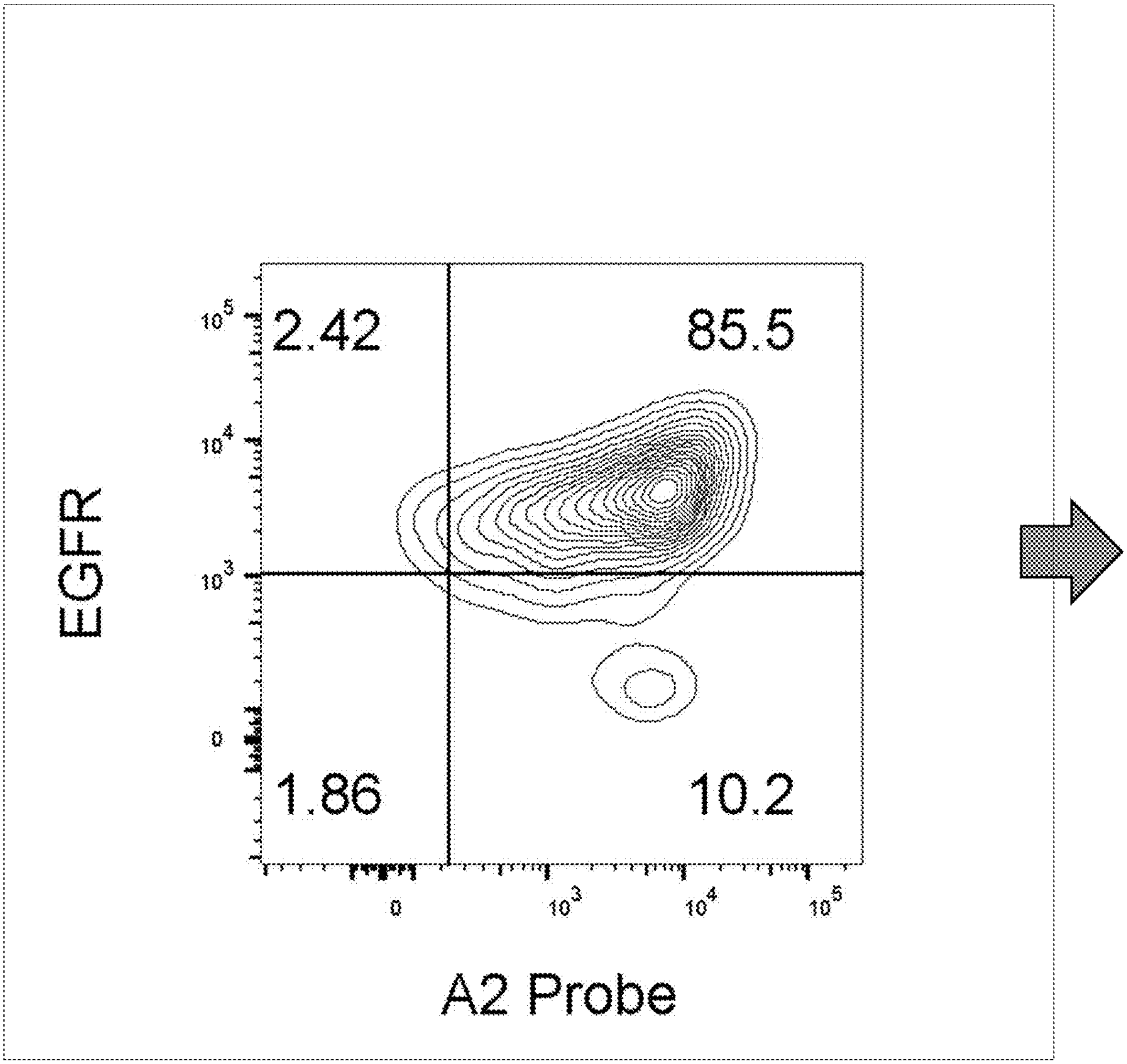
FIGS. 9-12 provide experimental results showing reversibly reduced expression of activating receptors.
Figure 10:
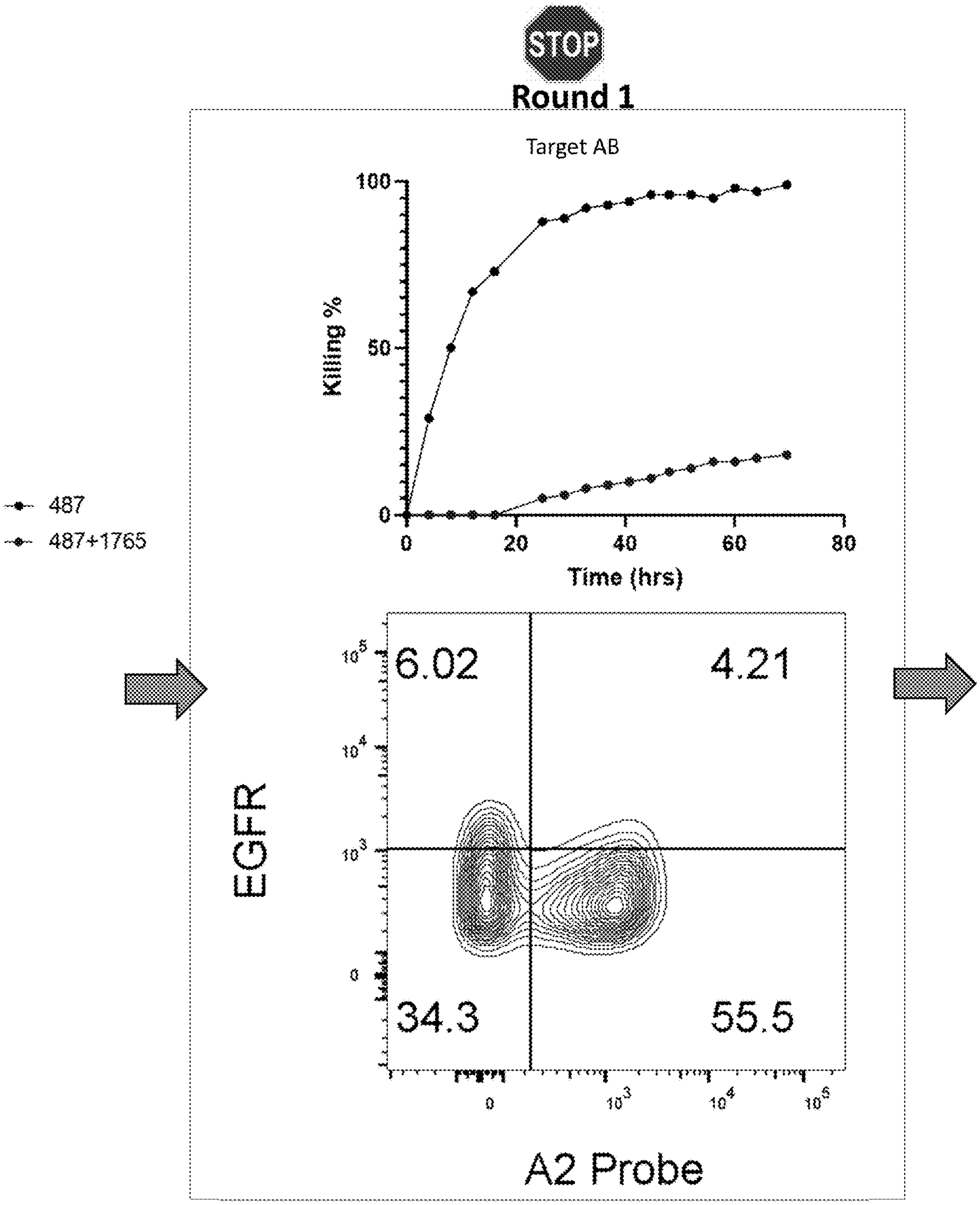
Figure 11:
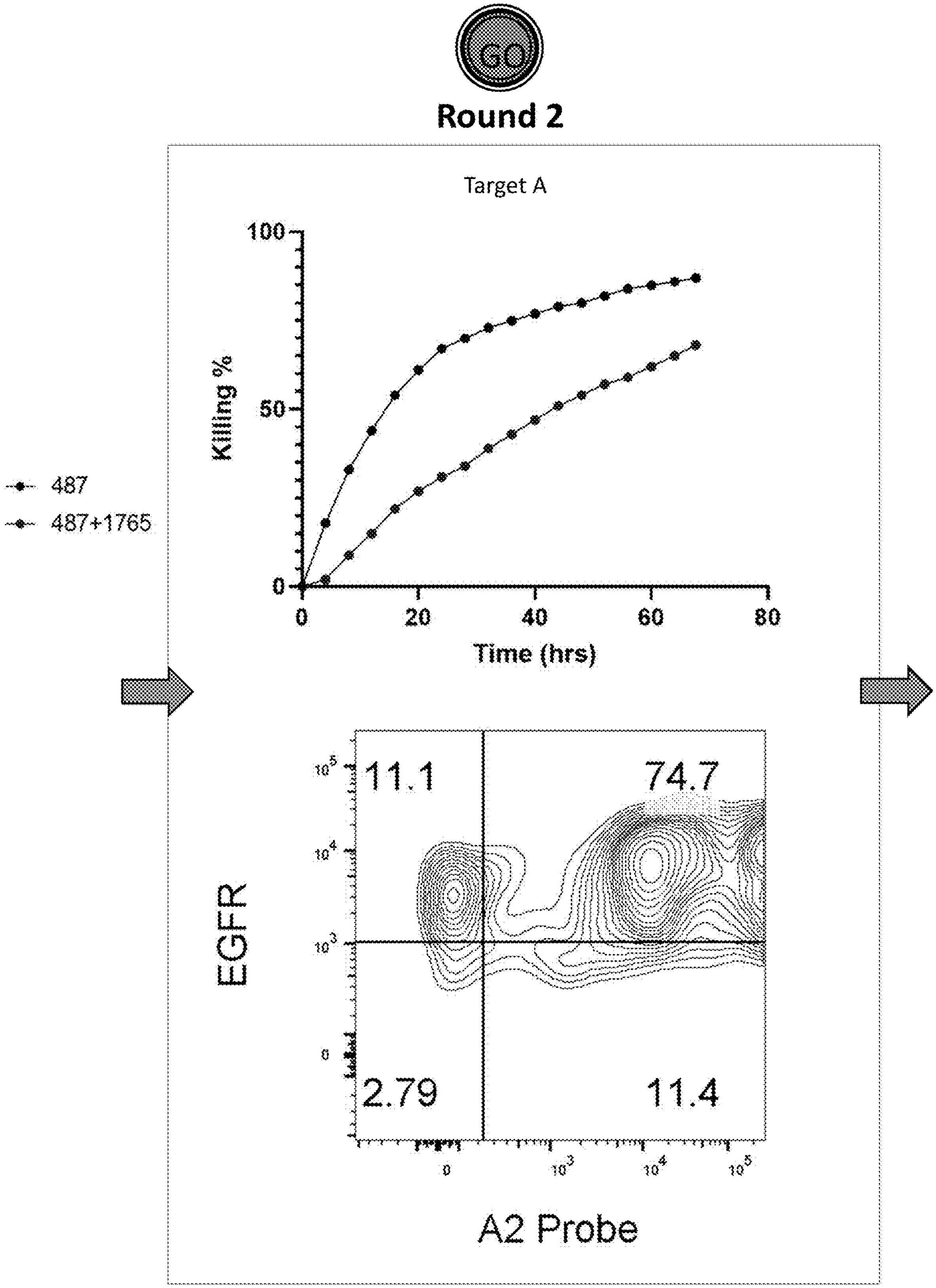
Figure 12:
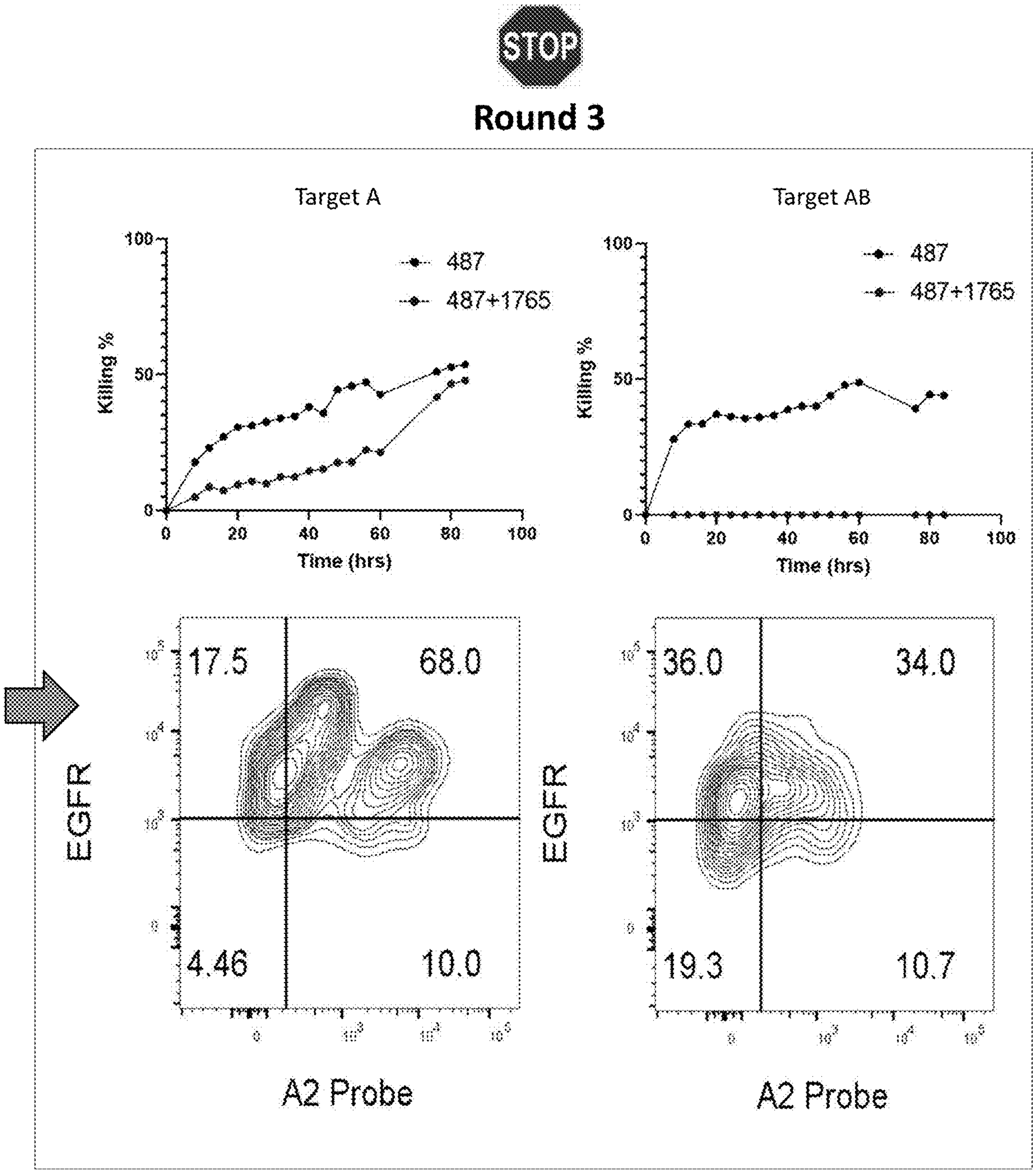
Figure 13:
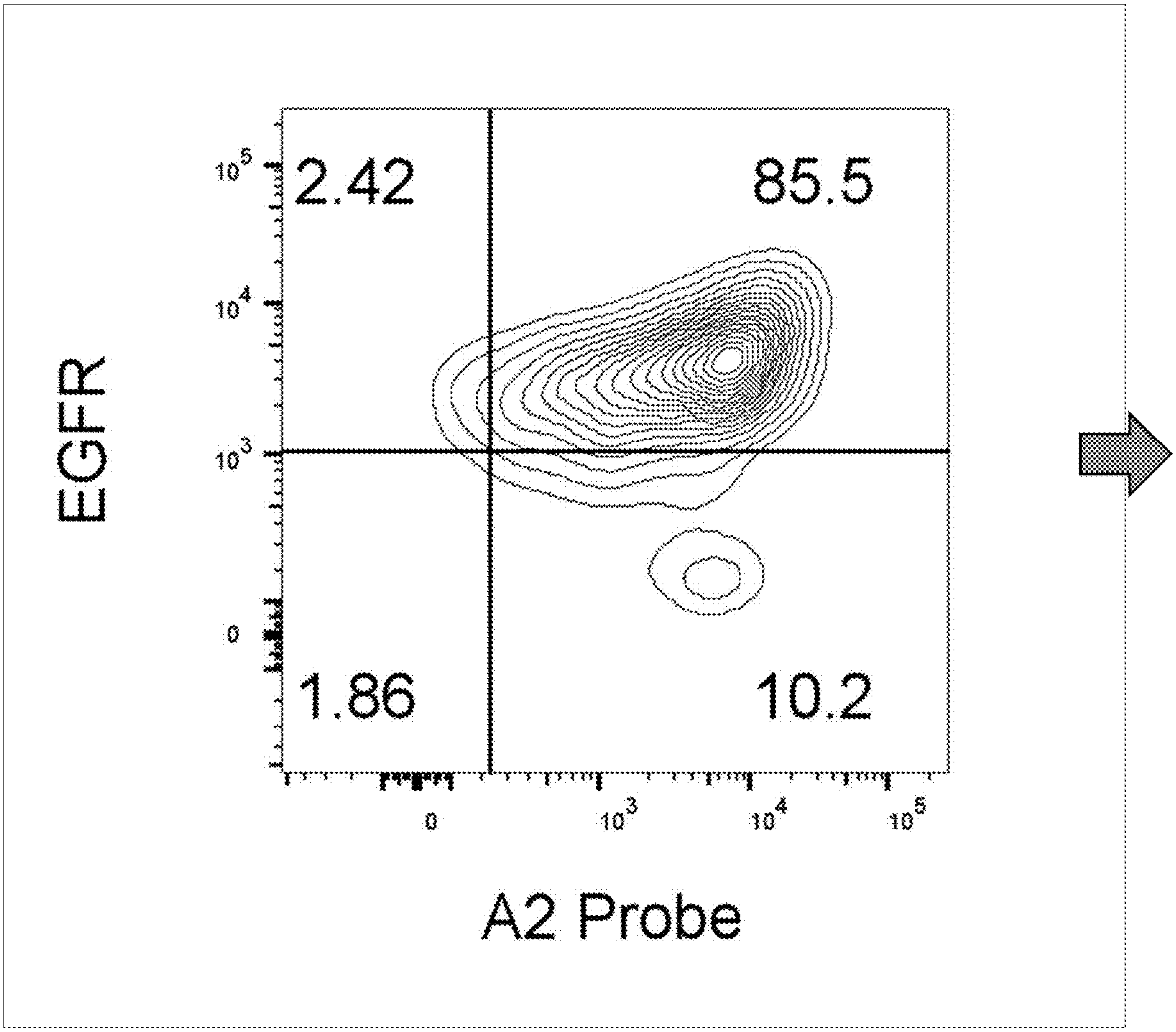
FIGS. 13-16 provide experimental results showing reversibly reduced expression of activating receptors.
Figure 14:
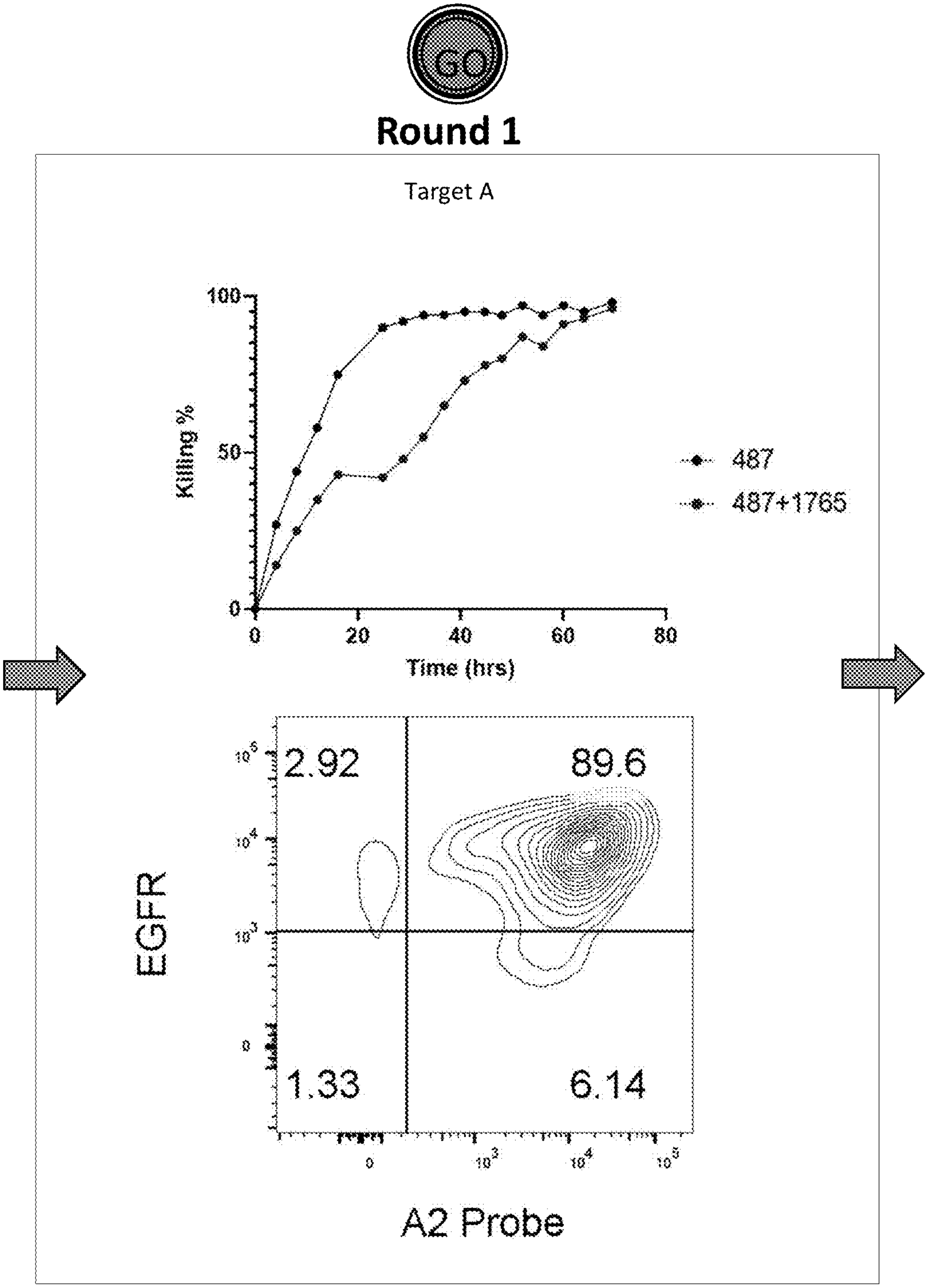
Figure 15:
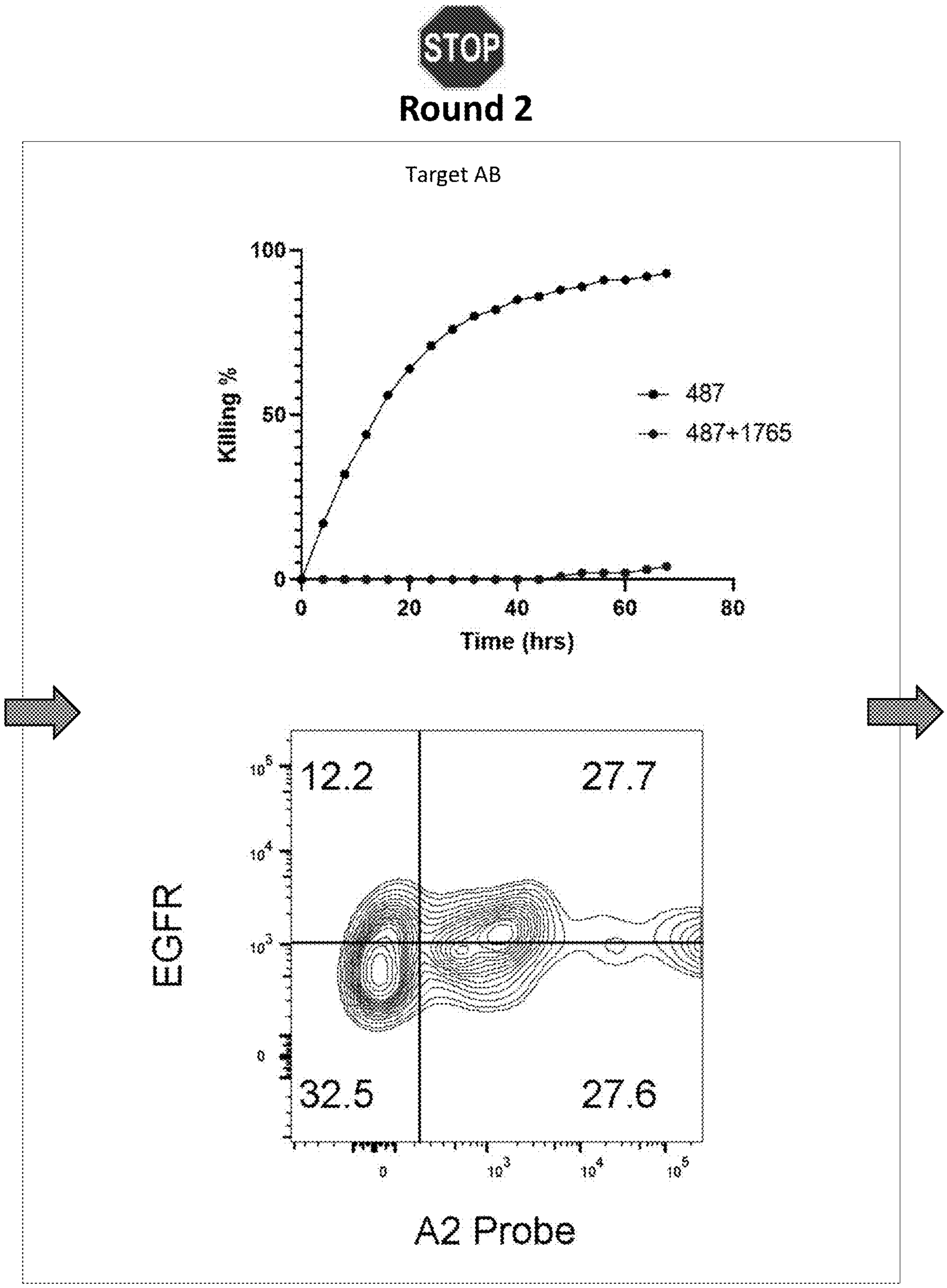
Figure 16:
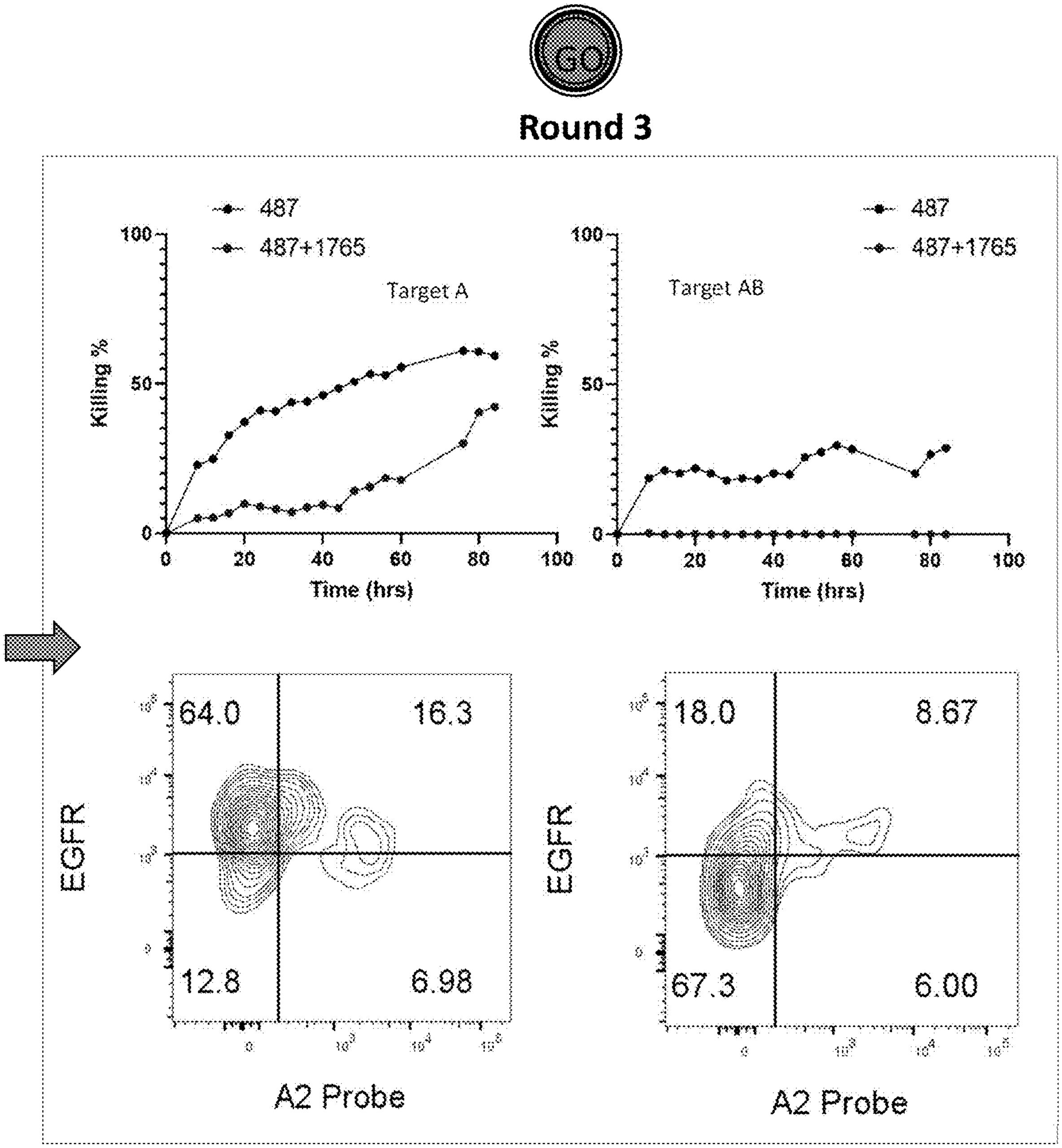

FIGS. 5-7 provides experimental results showing that this reduced surface expression of the activating receptors corresponds with the ability of the immune cells to kill other cells. Thus, advantageously, when the immune cells are in limited or no contact with target cells, their ability to kill is diminished, thereby reducing non-target effects.

Example 2

Another surprising facet of the immune cells of the present invention is that the reduced surface expression of the activating receptors only occurs when the immune cells contact non-target cells expressing both the activating and blocking ligands. This is shown in FIG. 7.

Example 3

FIGS. 8-16 provide an experimental protocol and results that indicate the reduced expression of activating receptors is reversible upon contact with target cells.

Example 4

Figure 17:
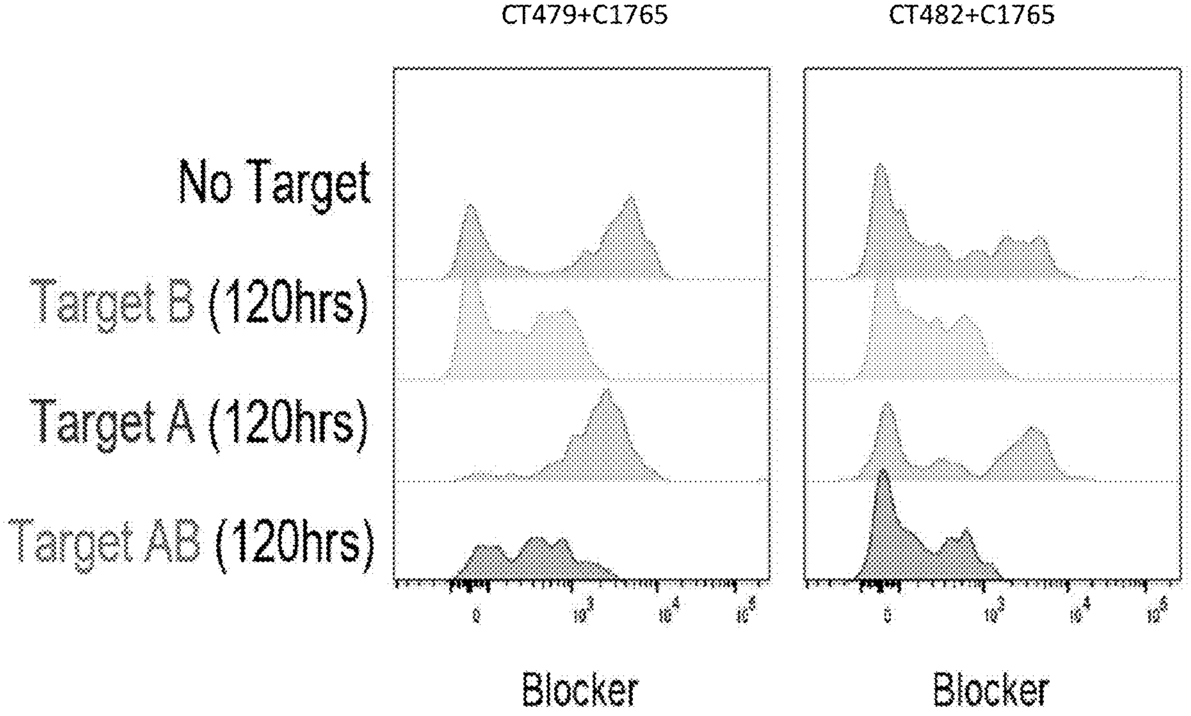
FIGS. 17-19 shows experimental results indicating that the blocking receptor does not undergo reduced surface expression in an appreciable amount in the presence of non-target cells.
Figure 18:
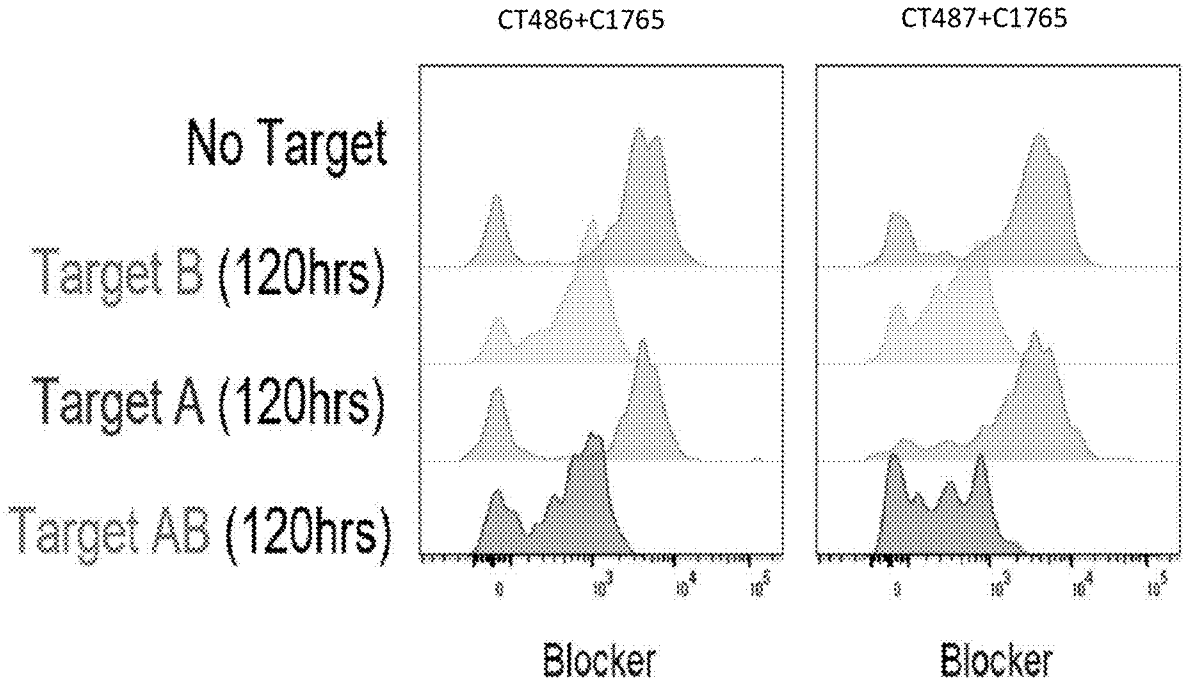
Figure 19:
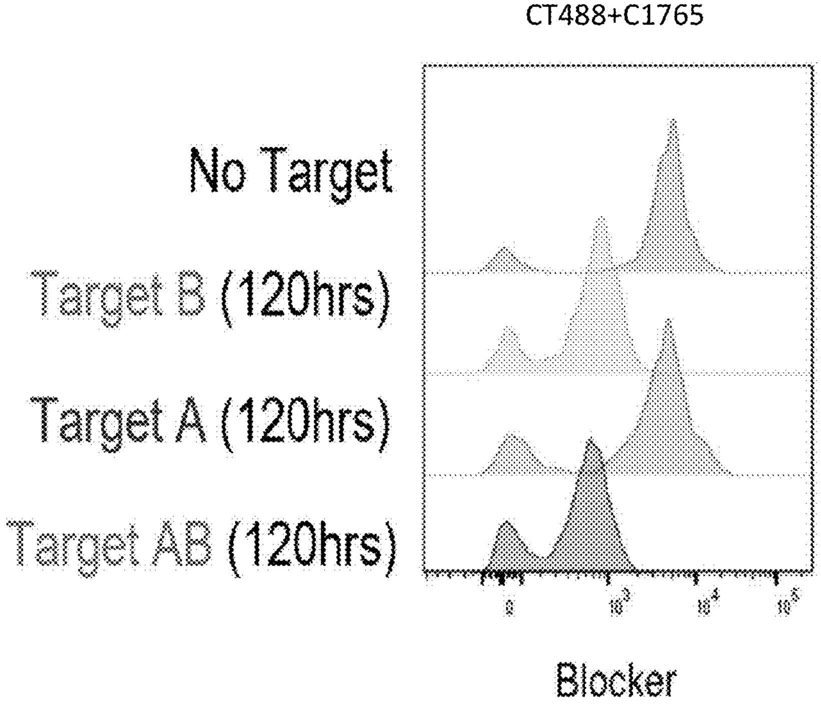

FIGS. 17-19 provide experimental results showing that, unlike the activating receptor, the blocking receptor does not undergo reduced surface expression in an appreciable amount in the presence of non-target cells.

Example 5

FIG. 22 shows experimental results indicating that the blocking receptor provides a blocking signal that dominates and inhibits the activating signal from the activating receptor.

Jurkat cells were transfected with either an activating receptor (MP1-CAR) for a MAGE-A3 activating ligand or the activating receptor and a blocking receptor (ESO-Tmod) for a NY-ESO-1 blocking ligand.

Panel A shows the NFAT-luciferase signal of Jurkat cells transfected with either the activator alone or in combination with the blocker, after 6 hours of co-culture with activator and blocker peptide-loaded T2 cells. The T2 cells were loaded with titrated amounts of activator MAGE-A3 peptide and a fixed amount of blocker NY-ESO-1 peptide concentration. This reveals the activation dose-response of the transfected cells.

Panel B shows the NFAT-luciferase signal of Jurkat cells transfected with either the activator alone or in combination with the blocker, after 6 hours of co-culture with activator and blocker peptide-loaded T2 cells. The T2 cells were loaded with titrated amounts of blocker NY-ESO-1 peptide and a fixed amount of activator MAGE-A3 peptide concentration above the Emax concentration (~0.1 μM). This reveals the inhibition dose-response of the transfected cells.

Panel C shows the NFAT-luciferase signal of Jurkat cells transfected with either the activator alone or in combination with the blocker, after 6 hours of co-culture with activator and blocker peptide-loaded T2 cells. The x-value blocker NY-ESO-1 peptide concentrations from panel B were normalized to the constant activator MAGE peptide concentrations used for each curve and plotted on the x-axis. The ratio of blocker peptide to activator peptide required for 50% blocking (IC50) are indicated for each curve. The B:A peptide ratio required is less than 1 indicating that, for this pair of activator CAR and blocker, similar (or fewer) blocker pMHC antigens may be sufficient on target cells to block activator pMHC antigens.

Since this ratio is less than 1, it can be inferred that the blocking signal dominates and inhibits the activating signal. Thus, a single blocking receptor can provide a blocking signal of sufficient strength to inhibit the activating signal of one or more activating receptors. As such, the quantity of activating and blocking ligands expressed by a non-target cell can form part of the basis for determining the appropriate relative amounts of activating and blocking receptors that should be expressed by an immune cell of the disclosure.

Example 6

FIG. 23 provides experimental results showing that the blocking receptors are ligand-dependent. For both CAR and TCR activating receptors, blocking receptors had minimal ligand-independent blocking activity. This impact is shown by the minimal effect on the $EC_{50}$ of the activating receptors by the blocking receptor in the presence/absence of the blocking ligand.

Example 7

FIG. 25 provides experimental results showing the relative impact hinge length and flexibility has on the strength of a blocking receptor as a function of the $EC_{50}$ of the activating receptor.

Example 8

FIG. 26 shows the large relative impact of the LBD on the activating receptor's structure activity relationship when compared with the effects provided by different hinges, transmembrane and intracellular domains. In this study, 45 separate activating receptors were created using various combinations of ligand binding domains, hinges, and intracellular domains. For each receptor one of five ligand binding domains that bind to the same activating ligand were selected. Despite all binding to the same target ligand, the identity of the ligand binding domain caused differences in the $EC_{50}$ of the activating receptors that spanned orders of magnitude. The ligand binding domain was shown to have greater than 10× the impact on the receptors' $EC_{50}$ compared to the hinge, transmembrane and intracellular domains.

Example 9

FIGS. 33-34 show the impact receptor cross-talk can have on the ability of the blocking receptor to inhibit the activation signal. Engineered immune cells were created with one of five different activating receptors. Though the activating receptors differed between the cells, each targeted the same activating ligand, epidermal growth factor receptor (EGFR), using a different LBD. As shown by five graph panels FIGS. 33-34, each of the different activating receptors provided the immune cells with equivalent abilities to kill target cells. Then, immune cells were created that had one of the five activating receptors and the same blocking receptor. Addition of the blocker caused some of the immune cells, like CT486-containing cells, to decrease their ability to kill target cells.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. An engineered immune cell comprising:

an activating receptor that triggers a cytotoxic signal that promotes a cytotoxic response of the engineered immune cell when the activating receptor binds a first ligand of a target cell; and a blocking receptor that sends an interfering signal that inhibits the cytotoxic response of the engineered immune cell when the blocking receptor binds a second ligand of the target cell, each receptor comprising an extracellular binding domain, a hinge, a transmembrane domain, and an intracellular domain and said blocking receptor comprising a hinge that comprises a peptide of at least 24 contiguous amino acids of SEQ ID NO: 84, said peptide derived from a leukocyte immunoglobulin-like receptor subfamily B member 1 (LILRB1), wherein cross-talk between the activating receptor and the blocking receptor affects an activation threshold for the cytotoxic response.

2. The immune cell of claim 1, wherein in the absence of the first and second ligands, the effect of the cross-talk on the activation threshold is minimized and/or reduced.

3. The immune cell of claim 1, wherein the effect of the cross-talk on the activation threshold increases with proximity of the activating receptor to the blocking receptor.

4. The immune cell of claim 3, wherein the activating receptor and blocking receptor are covalently linked together, or have physicochemical properties favoring interaction with one another such that the receptors are proximal to one another.

5. The immune cell of claim 1, wherein when the blocking receptor binds to the second ligand, the cross-talk between the blocking and activating receptors causes the immune cell to exhibit reduced surface expression of the activating receptor.

6. The immune cell of claim 1, wherein the immune cell comprises a plurality of the activating and blocking receptors, and when the immune cell contacts a target cell the plurality of the activating and blocking receptors diffuses into a region on the surface of the immune cell proximal to the target cell and forms a micro-cluster in which the effect of the cross-talk on the activation threshold is localized.

7. The immune cell of claim 1, wherein the cross-talk between the activating receptor and the blocking receptor prevents the blocking receptor from binding to the second ligand until the activating receptor binds to the first ligand.

8. A method for treating cancer, the method comprising:

providing an engineered immune cell to a patient, wherein the engineered immune cell comprises an activating receptor and a blocking receptor, each expressed on a surface of the engineered immune cell, wherein:

the activating receptor triggers a cytotoxic signal that promotes a cytotoxic response of the engineered immune cell when the activating receptor binds a first ligand of a target cell; and the blocking receptor sends an interfering signal that inhibits the cytotoxic response of the engineered immune cell when the blocking receptor binds a second ligand of the target cell, each receptor comprising an extracellular binding domain, a hinge, a transmembrane domain, and an intracellular domain and said blocking receptor comprising a hinge that comprises a peptide of at least 24 contiguous amino acids of SEQ ID NO: 84, said peptide derived from a leukocyte immunoglobulin-like receptor subfamily B member 1 (LILRB1), wherein cross-talk between the activating receptor and the blocking receptor affects an activation threshold for the cytotoxic response.

9. The method of claim 8, wherein in the absence of the second ligand, the effect of the cross-talk on the activation threshold is minimized and/or reduced.

10. The method of claim 8, wherein the effect of the cross-talk on the activation threshold increases with proximity of the activating receptor to the blocking receptor.

11. The method of claim 10, wherein the activating receptor and blocking receptor are linked together or have physicochemical properties favoring interaction with one another, such that the receptors are proximal to one another.

12. The method of claim 8, wherein when the blocking receptor binds to the second ligand, the cross-talk between the blocking and activating receptors causes the immune cell to exhibit reduced surface expression of the activating receptor.

13. The method of claim 8, wherein the immune cell comprises a plurality of the activating and blocking receptors, and when the immune cell contacts a target cell the plurality of the activating and blocking receptors diffuses into a region on the surface of the immune cell proximal to the target cell and forms a micro-cluster in which the effect of the cross-talk on the activation threshold is localized.

14. The method of claim 8, wherein the cross-talk between the activating receptor and the blocking receptor prevents the blocking receptor from binding to the second ligand until the activating receptor binds to the first ligand.

15. A method of producing an engineered immune cell, the method comprising:

determining an amount of cross-talk between an activating receptor and a blocking receptor for an engineered immune cell, wherein the amount of cross-talk between the activating receptor and the blocking receptor affects an activation threshold for the cytotoxic response; and producing an engineered immune cell that expresses different concentrations of activating receptors and blocking receptors based on the determined amount of cross-talk between the activating receptor and the blocking receptor, each receptor comprising an extracellular binding domain, a hinge, a transmembrane domain, and an intracellular domain and said blocking receptor comprising a hinge that comprises a peptide of at least 24 contiguous amino acids of SEQ ID NO: 84, said peptide derived from a leukocyte immunoglobulin-like receptor subfamily B member 1 (LILRB1).

16. The method of claim 15, wherein in the absence of cognate ligands for the activating and blocking receptors, the amount of the cross-talk is minimized and/or reduced.

17. The method of claim 15, wherein producing an engineered immune cell that expresses different concentrations of activating receptors and blocking receptors is further based on a ratio of a quantity of an activating ligand to a quantity of a blocking ligand that are expressed in non-tumor cells of a sample.

18. The method of claim 17, wherein the cross-talk between the activating receptor and the blocking receptor prevents the blocking receptor from binding to the blocking ligand until the activating receptor binds to the activating ligand.

19. The method of claim 15, wherein an amount of the cross-talk between the activating receptor and blocking receptor increases with proximity of the activating receptor to the blocking receptor.

20. The method of claim 19, wherein the activating receptor and blocking receptor are covalently linked, or have physicosochemical properties favoring interaction with one another such that the receptors are proximal to one another.

* * * * *